US006677148B1

(12) United States Patent
Narva et al.

(10) Patent No.: US 6,677,148 B1
(45) Date of Patent: *Jan. 13, 2004

(54) PESTICIDAL PROTEINS

(75) Inventors: Kenneth E. Narva, San Diego, CA (US); H. Ernest Schnepf, San Diego, CA (US); Mark Knuth, Poway, CA (US); Michael R. Pollard, Okemos, MI (US); Guy A. Cardineau, Poway, CA (US); George E. Schwab, Encinitas, CA (US); Tracy Ellis Michaels, Escondido, CA (US); Stacey Finstad Lee, San Diego, CA (US); Paula Diehl, Ramona, CA (US); Joanna Dojillo, San Diego, CA (US); Lisa Stamp, La Jolla, CA (US); Rod Herman, New Ross, IN (US)

(73) Assignee: Mycogen Corporation, Indianapolis, IN (US)

( * ) Notice: Subject to any disclaimer, the term of this patent is extended or adjusted under 35 U.S.C. 154(b) by 148 days.

This patent is subject to a terminal disclaimer.

(21) Appl. No.: 09/643,596

(22) Filed: Aug. 22, 2000

Related U.S. Application Data

(63) Continuation-in-part of application No. 09/378,088, filed on Aug. 20, 1999, now Pat. No. 6,372,480, which is a continuation-in-part of application No. 08/844,188, filed on Apr. 18, 1997, now Pat. No. 6,127,180, which is a continuation-in-part of application No. 08/633,993, filed on Apr. 19, 1996, now Pat. No. 6,083,499.

(51) Int. Cl.$^7$ ........................ C12N 15/62; C12N 15/32; C12N 15/82

(52) U.S. Cl. .................... 435/252.3; 435/419; 435/418; 536/23.4; 536/23.71; 800/302

(58) Field of Search .............................. 435/252.3, 419, 435/418; 536/23.4, 23.71; 800/302

(56) References Cited

U.S. PATENT DOCUMENTS

| | | | | |
|---|---|---|---|---|
| 5,723,758 A | | 3/1998 | Payne et al. | |
| 6,172,281 B1 | * | 1/2001 | Van Mellaert et al. ...... | 800/302 |

FOREIGN PATENT DOCUMENTS

| | | |
|---|---|---|
| WO | WO 00/24904 A1 | 5/2000 |

OTHER PUBLICATIONS

Hofte et al., "Insecticidal Crystal Proteins of *Bacillus thuringiensis,*" *Microbiological Reviews*, Jun. 1989, p. 242–255, vol. 53, No. 2.

* cited by examiner

*Primary Examiner*—Rebecca E. Prouty
(74) *Attorney, Agent, or Firm*—Saliwanchik, Lloyd & Saliwanchik

(57) ABSTRACT

The subject invention concerns new classes of pesticidally active proteins and the polynucleotide sequences that encode these proteins. In preferred embodiments, these pesticidal proteins have molecular weights of approximately 40–50 kDa and of approximately 10–15 kDa.

24 Claims, 8 Drawing Sheets

```
             1                                                        50
{149b145k}   ..........  .....GLYAA  TYLSLDDSGV  SLMNKNDDDI  DDYNLKWFLF
{167h245k}   ..........  .......HAA  TYLSLDDSGV  SLMNKNDDDI  DDYNLRWFLF
{80jj145k}   MLDTNKVYEI  SNLANGLYTS  TYLSLDDSGV  SLMSKKDEDI  DDYNLKWELF
Consensus    ----------  ----------  TYLSLDDSGV  SLM-K-D-DI  DDYNL-WELF

             51                                                      100
{149b145k}   PIDDDQYIIT  SYAANNCKVW  NVNNDKINVS  TYSSTNSIQK  WQIKANGSSY
{167h245k}   PIDDNQYIIT  SYAANNCKVW  NVNNDKINVS  TYSSTNSIQK  WQIKANASSY
{80jj145k}   PIDNNQYIIT  SYGANNCKVW  NVKNDKINVS  TYSSTNSVQK  WQIKAKDSSY
Consensus    PID--QYIIT  SY-ANNCKVW  NV-NDKINVS  TYSSTNS-QK  WQIKA--SSY

             101                                                     150
{149b145k}   VIQSDNGKVL  TAGTGQALGL  IRLTDESSNN  PNQQWNLTSV  QTIQLPQKPI
{167h245k}   VIQSNNGKVL  TAGTGQSLGL  IRLTDESPDN  PNQQWNLTPV  QTIQLPPKPT
{80jj145k}   IIQSDNGKVL  TAGVGQSLGI  VRLTDEFPEN  SNQQWNLTPV  QTIQLPQKPK
Consensus    -IQS-NGKVL  TAG-GQ-LG-  -RLTDE---N  -NQQWNLT-V  QTIQLP-KP-

             151                                                     200
{149b145k}   IDTKLKDYPK  YSPTGNIDNG  TSPQLMGWTL  VPCIMVNDPN  IDKNTQIKTT
{167h245k}   IDTKLKDYPK  YSQTGNIDKG  TPPQLMGWTL  IPCIMVNDPN  IDKNTQIKTT
{80jj145k}   IDEKLKDHPE  YSETGNINPK  TTPQLMGWTL  VPCIMVNDSK  IDKNTQIKTT
Consensus    ID-KLKD-P-  YS-TGNI---  T-PQLMGWTL  -PCIMVND-   IDKNTQIKTT
```

FIG. 1A

```
             201                                                        250
{149b145k}   PYYILKKYQY  WQRAVGSNVA  LRPHEKKSYT  YEWGTEIDQK  TTIINTLGFQ
{167h245k}   PYYILKKYQY  WQQAVGSNVA  LRPHEKKSYA  YEWGTEIDQK  TTIINTLGFQ
{80jj145k}   PYYIFKKYKY  WNLAKGSNVS  LLPHQKRSYD  YEWGTEKNQK  TTIINTVGLQ
Consensus    PYYI-KKY-Y  W--A-GSNV-  L-PH-K-SY-  YEWGTE--QK  TTIINT-G-Q

             251                                                        300
{149b145k}   INIDSGMKFD  IPEVGGGTDE  IKTQLNEELK  IEYSHETKIM  EKY.......
{167h245k}   INIDSGMKFD  IPEVGGGTDE  IKTQLNEELK  IEYSRETKIM  EKY.......
{80jj145k}   INIDSGMKFE  VPEVGGGTED  IKTQLTEELK  VEYSTETKIM  TKYQEHSEID
Consensus    INIDSGMKF-  -PEVGGGT -  IKTQL-EELK  -EYS-ETKIM  -KY-------

             301                                                        350
{149b145k}   ..........  ..........  ..........  ..........  ..........
{167h245k}   ..........  ..........  ..........  ..........  ..........
{80jj145k}   NPTNQPMNSI  GLLIYTSLEL  YRYNGTEIKI  MDIETSDHDT  YTLTSYPNHK
Consensus    ----------  ----------  ----------  ----------  ----------

             351                                          386
{149b145k}   ..........  ..........  ..........  ......
{167h245k}   ..........  ..........  ..........  ......
{80jj145k}   EALLLLTNHS  YEEVEEITKI  PKHTLIKLKK  HYFKK.
Consensus    ----------  ----------  ----------  ------
```

FIG. 1B

```
            1                                                50
S07711      MCDSKDNSGV SEKCGKKFTN YPLNTTPTSL NYNLPEISKK FYNLKNKY..
S07712      ~~~~~~~~~~ ~~~~~~~~~~ ~~~~~~~~~~ MRNLDFID.S FIPTEGKY..
ps149b1-45  ~~~~~~~~~~ ~~~~~~~~~~ ~~~~~~~~~~ ~~~~~~~~~~ MLDTNKVYEI
            51                                              100
S07711      SRNGYGLSKT EFPSSIENCP AKEYSIMYD. ..NKDPRFLI RFLLDDGRYI
S07712      IR.VMDFYNS EYPFCIHAPS APNGDIMTEI CSRENNQYFI FFPTDDGRVI
ps149b1-45  SNHANGLYAA TY.LSLDDSG VSLMNKNDDD IDDYNLKWFL .FPIDDDQYI
                                                        ------

            101                                             150
S07711      IADRDDGEVF DEAPIYLDNN NHPIISRHYT GEERQKFE.Q VGSGDYITGE
S07712      IANRHNGSVF .......TGE ATSVVSDIYT GSPLQFFR.E VKR....TME
ps149b1-45  ITS....YAA NNCKVWNVNN DKINVSTYSS TNSIQKWQIK ANGSSYVIQS
            ---A------
            151                                             200
S07711      QFFQFYTQNK TRVLSNCRAL DSRTILLSTA KIFPIYPPAS ETQLTAFV.N
S07712      TYY.LAIQNP ESA.TDVRAL EPHSHEL.PS RLY..YTNNI ENNSNILISN
ps149b1-45  DNGKVLTAGT GQALGLIRLT DESSNN.... ...PNQQWNL TSVQTIQLPQ

            201                                             250
S07711      SSFYAAAIPQ LPQTSLLENI PEPTSLDDSG VLPKDAVRAV KGSALLPCII
S07712      KEQIYLTLPS LPENEQYPKT PVLSGIDDIG ..PNQSEKSI IGSTLIPCIM
ps149b1-45  KPIIDTKLKD YPKYS..... ..PTGNIDNG TSPQ.....L MGWTLVPCIM
                                                         -----B---
            251                                             300
S07711      VHDPNLNNSD KMKFNTYYLL EYKEYWHQLW SQ .IIPAHQ TVKIQERTGI
S07712      VSD.FISLGE RMKTTPYYYV KHTQYWQSMW SA .LFPPGS KETKTEKSGI
ps149b1-45  VNDPNIDKNT QIKTTPYYIL KKYQYWQRAV GS VALRPHE KKSYTYEWGT
            ---
            301                                             350
S07711      SEVVQNSMIE DLNMYIGADF GMHFYLRSSG .....FKEQI TRGLNRPLSQ
S07712      TDTSQISMTD GINVSIGADF GLRFGNKTFG .....IKGGF TYDTKTQITN
ps149b1-45  EIDQKTTIIN TLGFQINIDS GMKFDIPEVG GGTDEIKTQL NEELKIEYSH
                            ---C---
            351                                             400
S07711      TTTQLGERVE EMEYYNSNDL DVRYVKYALA REFTLKRVNG EIVKN..WVA
S07712      TSQLLIETTY TREYTNTENF PVRYTGYVLA SEFTLHRSDG TQVNTIPWVA
ps149b1-45  ETKIMEKYQE QSEIDNPTDQ SMNSIGFLTI TSLELYRYNG SEIRIMQIQT
                                  -------D---------
            401                                             450
S07711      VDYRLAGIQS YPNAPITNPL TLTK..HTII RCENSYDGHI FKTPLIFKNG
S07712      LNDNYTTIAR YPHF.ASEPL LGNT..KIIT DDQN~~~~~~ ~~~~~~~~~~
ps149b1-45  SDNDTYNVTS YPNHQQALLL LTNHSYEEVE EITNIPKSTL KKLKKYYF~~

            451        466
S07711      EVIVKTNEEL IPKINQ
S07712      ~~~~~~~~~~ ~~~~~~
ps149b1-45  ~~~~~~~~~~ ~~~~~~
```

FIG. 4

```
             1                                                      50
   x14964    ~~~~~~~~~~ ~~~~~~~~~~ ~~~~~~~~~~ ~~~~~~~~~~ ~~~~~~~~~~
 x14964-2    ATGTGCGATT CAAAAGACAA TTCTGGCGTT TCAGAAAAAT GCGGAAAGAA
ps149b1-45   ~~~~~~~~~~ ~~~~~~~~~~ ~~~~~~~~~~ ~~~~~~~~~~ ~~~~~~~~~~

             51                                                    100
   x14964    ~~~~~~~~~~ ~~~~~~~~~~ .......... .......ATG AGAAATTTGG
 x14964-2    ATTTACTAAT TACCCGCTAA ATACTACTCC TACAAGCCTA AATTATAACC
ps149b1-45   ~~~~~~~~~~ ~~~~~~~~~~ ~~~~~~~~~~ ~~~~~~~~~~ ~~~~~~~~~~

             101                                                   150
   x14964    ATTTTATTGA TTCTTTTATA CCCACAGAAG GAAAGTACAT TCGCGTTATG
 x14964-2    TTCCAGAAAT ATCAAAAAAA TTTTATAACC TTAAGAATAA ATATTCACGG
ps149b1-45   ~~~~~~~~~~ ~ATGTTAGAT ACTAATAAAG TTTATGAAAT AAGCAATCAT

             151                                                   200
   x14964    GATTTTTATA ATAGCGAGTA TCCTTTCTGT ATACATGCAC CCTCAGCCCC
 x14964-2    AATGGTTATG GTTTATCAAA AACCGAATTT CCTTCAAGTA TCGAAAATTG
ps149b1-45   GCTAATGGAC TATATGCAGC AACTTATTTA AGTTTAGATG ATTCAGGTGT

             201                                                   250
   x14964    TAATGGGGAT ATCATGACAG AAATCTGTAG CAGAGAAAAT AATCAATATT
 x14964-2    CCCAGCTAAA GAATATTCAA TAATGTATGA TAATAAAGAT CCTCGATTCT
ps149b1-45   TAGTTTAATG AATAAAAATG ATGATGATAT TGATGATTAT AACTTAAAAT

             251                                                   300
   x14964    TTATTTTTTT TCCTACTGAT GATGGTCGAG TAATTATTGC AAATAGGCAT
 x14964-2    TGATTCGGTT TTTATTAGAT GATGGTAGAT ATATTATTGC AGATAGAGAC
ps149b1-45   GGTTTTTATT TCCTATTGAT GATGATCAAT ATATTATTAC AAGCTATGCA
                               GAT GATGrTmrAk wwATTATTrC A
                               GAT GATGrTmrAT ATATTATTrC A
                      45kD5':  GAT RATRATCAAT ATATTATTAC

             301                                                   350
   x14964    AATGGGTCCG TTTTTACCGG AGAAGCCACA AGTGTAGTAT CAGATATCTA
 x14964-2    GATGGAGAAG TTTTTGATGA AGCACCTATT TATTTGGATA ATAACAATCA
ps149b1-45   GCAAATAATT GTAAAGTTTG GAATGTTAAT AATGATAAAA TAAATGTTTC

             351                                                   400
   x14964    T......... .......... .......... .......... .......ACT
 x14964-2    CCCTATCATA AGTAGACATT ATACCGGAGA AGAGAGACAA AAGTTTGAGC
ps149b1-45   G......... .......... .......... .......... ..........

             401                                                   450
   x14964    GGTAGCCCAT TACAGTTTTT TAGAGAGGTC AAAAGAACTA TGGAAACTTA
 x14964-2    AGGTAGGTAG TGGAGATTAT ATTACGGGAG AGCAATTTTT TCAATTCTAT
ps149b1-45   .......... .......ACT TATTCTTCAA CAAATTCAAT ACAAAAATGG

             451                                                   500
   x14964    TTATTTAGCG ATACAAAATC CTGAATCCGC AACAGATGTG AGAGCTCTAG
 x14964-2    ACACAAAACA AAACACGTGT ATTGTCAAAT TGTAGGGCGC TTGACAGTAG
ps149b1-45   CAAATAAAAG CTAATGGTTC TTCATATGTA ATACAAAGTG ATAATGGAAA
```

FIG. 5A

```
           501                                                550
   x14964  AACCGCATTC CCATGAGCTG CCATCTCGCC TTTATTACAC TAACAATATT
 x14964-2  GACAATATTA CTATCTACTG CAAAAATCTT CCCAATTTAC CCTCCAGCTT
ps149b1-45 AGTCTTAACA GCAGGAACCG GTCAAGCTCT TGGATTGATA CGTTTAACTG

           551                                                600
   x14964  GAAAATAATA GCAACATATT AATTTCTAAT ..AAGGAACA AATATATTTA
 x14964-2  CTGAAACTCA ACTA.ACAGC TTTCGTTAAT ..AGTTCATT TTATGCTGCG
ps149b1-45 ATGAATCCTC AAATAATCCC AATCAACAAT GGAATTTAAC TTCTGTACAA

           601                                                650
   x14964  ACCTTGCCTT CACTTCCAGA AAACGAGCAA TACCCTAAAA CTCCAGTATT
 x14964-2  GCAATTCCTC AATTACCCCA AACATCCTTA CTTGAGAATA TTCCTGAGCC
ps149b1-45 ACAATTCAAC TTCCACAAAA ACCTATAATA GATACAAAAT TAAAAGATTA

           651                                                700
   x14964  AAGCGGTATC GATGAT.... ..ATAGGACC TAATCAATCA GAGAAATCAA
 x14964-2  TACTAGTCTC GATGATTCTG GAGTATTACC AAAAGATGCA GTAAGAGCAG
ps149b1-45 TCCCAAATAT TCACCAACTG GAAATATAGA TAATGGAACA TCTCCTCAAT

           701                                                750
   x14964  TAATAGGAAG TACTCTTATC CCATGTATAA TGGTTTCGGA TTTTA...TT
 x14964-2  TTAAAGGAAG TGCGCTATTA CCTTGTATAA TAGTACATGA TCCTAATTTA
ps149b1-45 TAATGGGATG GACATTAGTA CCTTGTATTA TGGTAAATGA TCCAAATATA
                GGAwG krCdyTwdTm CCwTGTATwA TrGTwhmkGA T
                GGAwG kACwyTwrTm CCwTGTATwA TGGTwwmkGA T
                GGAwG krCryTAdTA CCTTGTATwA TrGTAmATGA T
                GGAwG kACryTAdTA CCTTGTATwA TGGTAmATGA T
                GGATG GACATTAYTA CCTTG: 45kD3'rc:
           751                                                800
   x14964  AGTTTGGGGG AGAGAATGAA AACCACTCCA TATTATTATG TAAAGCACAC
 x14964-2  AACAATTCCG ATAAAATGAA ATTTAATACC TACTATCTTT TAGAATATAA
ps149b1-45 GATAAAAATA CTCAAATTAA AACTACTCCA TATTATATTT TAAAAAAATA

           801                                                850
   x14964  TCAATATTGG CAAAGCATGT GGTCCGCGCT CTTTCCACCC GGCTCTAAAG
 x14964-2  AGAATACTGG CATCAATTAT GGTCACAAAT TATACCTGCT CATCAAACTG
ps149b1-45 TCAATATTGG CAACGAGCAG TAGGAAGTAA TGTAGCTTTA CGTCCACATG

           851                                                900
   x14964  AGACAAAAAC TGAGAAATCA GGTATCACTG ACACTTCTCA AATAAGTATG
 x14964-2  TAAAAATACA GGAACGAACA GGAATATCTG AAGTTGTACA AAATAGCATG
ps149b1-45 AAAAAAAATC ATA.TACTTA TGAATGGGGC ACAGAAATAG ATCAAAAAAC

           901                                                950
   x14964  ACTGACGGGA TTAATGTTTC AATCGGAGCA GATTTCGGAT TAAGGTTTGG
 x14964-2  ATTGAAGATT TAAATATGTA TATTGGAGCA GATTTTGGCA TGCATTTTTA
ps149b1-45 AACAATTATA AATACATTAG GATTTCAAAT CAATATAGAT TCAGGAATGA
```

FIG. 5B

```
             951                                                1000
   x14964    AAATAAAACG TTTGGAATTA AGGGGGGGTT CACCTATGAT ACAAAGACTC
 x14964-2    TTTGAGATCT AGCGGATTTA AGGAACAAAT AACAAGGGGG CTAAATAGGC
ps149b1-45   AATTTGATAT ACCAGAAGTA GGTGGAGGTA CAGATGAAAT AAAAACACAA

             1001                                               1050
   x14964    AAATAACTAA TACCTCCCAA TTGTTA.ATA GAAACAACTT ATACTAGAGA
 x14964-2    CTTTATCCCA AACGACCACT CAGTTA.GGA GAAAGAGTAG AAGAAATGGA
ps149b1-45   CTAAATGAAG AATTAAAAAT AGAATATAGT CATGAAACTA AAATAATGGA

             1051                                               1100
   x14964    ATACACAAAT ACAGAAAATT TTCCTGTTAG ATATACAGGC TATGTTTTAG
 x14964-2    GTATTATAAT TCTAATGATT TGGATGTTAG ATATGTGAAA TACGCATTGG
ps149b1-45   AAAATATCAA GAACAATCTG AAATAGATAA TCCAACTGAT CAATCAATGA

             1101                                               1150
   x14964    CGTCAGAATT TACTTTACAT CGTAGTGATG GAACTCAGGT TAATACGATC
 x14964-2    CTAGAGAATT CACACTAAAA CGCGTTAATG GTGAAATTGT AAAAAATTGG
ps149b1-45   ATTCTATAGG ATTTCTTACT ATTACTTCCT TAGAATTATA TAGATATAAT

             1151                                               1200
   x14964    CCATGGGTTG CTTTAAACGA TAACTATACA ACAATAGCAA GATATCCACA
 x14964-2    GTTGCTGTAG ATTATCGATT GGCAGGTATA CAATCGTATC CTAATGCACC
ps149b1-45   GGCTCAGAAA TTCGTATAAT GCAAATTCAA ACCTCAGATA ATGATACTTA

             1201                                               1250
   x14964    TTTTGCAAGT GAACCTTTAC TAGGAAATAC AAAGATTATT ACAGATGATC
 x14964-2    TATAACTAAT CCACTTACGC TAACAAAACA TACAATTATT CGATGTGAAA
ps149b1-45   TAATGTTACT TCTTATCCAA ATCATCAACA AGCTTTATTA CTTCTTACAA

             1251                                               1300
   x14964    AAAACTAA~~ ~~~~~~~~~~ ~~~~~~~~~~ ~~~~~~~~~~ ~~~~~~~~~~
 x14964-2    ATAGTTACGA TGGACACATA TTTAAAACAC CTTTAATCTT TAAAAATGGT
ps149b1-45   ATCATTCATA TGAAGAAGTA GAAGAAATAA CAAATATTCC TAAAAGTACA

             1301                                               1350
   x14964    ~~~~~~~~~~ ~~~~~~~~~~ ~~~~~~~~~~ ~~~~~~~~~~ ~~~~~~~~~~
 x14964-2    GAAGTTATTG TAAAAACGAA TGAAGAATTA ATACCTAAAA TTAACCAGTG
ps149b1-45   CTAAAAAAAT TAAAAAAATA TTATTTTTAA ~~~~~~~~~~ ~~~~~~~~~~

             1351
   x14964    ~
 x14964-2    A
ps149b1-45   ~
```

PESTICIDAL PROTEINS

CROSS-REFERENCE TO A RELATED APPLICATION

This application is a continuation-in-part of U.S. Ser. No. 09/378,088, filed Aug. 20, 1999 now U.S. Pat. No. 6,372, 480, which is a continuation-in-part of Ser. No. 08/844,188, filed Apr. 18, 1997 now U.S. Pat. No. 6,127,180, which is a continuation-in-part of Ser. No. 08/633,993, filed Apr. 19, 1996, which issued as U.S. Pat. No. 6,083,499 on Jul. 4, 2000.

BACKGROUND OF THE INVENTION

Coleopterans are a significant group of agricultural pests which cause extensive damage to crops each year. Examples of coleopteran pests include corn rootworm and alfalfa weevils.

The alfalfa weevil, *Hypera postica*, and the closely related Egyptian alfalfa weevil, *Hypera brunneipennis*, are the most important insect pests of alfalfa grown in the United States, with 2.9 million acres infested in 1984. An annual sum of 20 million dollars is spent to control these pests. The Egyptian alfalfa weevil is the predominant species in the southwestern U.S., where it undergoes aestivation (i.e., hibernation) during the hot summer months. In all other respects, it is identical to the alfalfa weevil, which predominates throughout the rest of the U.S.

The larval stage is the most damaging in the weevil life cycle. By feeding at the alfalfa plant's growing tips, the larvae cause skeletonization of leaves, stunting, reduced plant growth, and, ultimately, reductions in yield. Severe infestations can ruin an entire cutting of hay. The adults, also foliar feeders, cause additional, but less significant, damage.

Approximately 10 million acres of U.S. corn are infested with corn rootworn species complex each year. The corn rootworm species complex includes the northern corn rootworm, *Diabrotica barberi*, the southern corn rootworm, *D. undecimpunctata howardi*, and the western corn rootworm, *D. virgifera virgifera*. The soil-dwelling larvae of these Diabrotica species feed on the root of the corn plant, causing lodging. Lodging eventually reduces corn yield and often results in death of the plant. By feeding on cornsilks, the adult beetles reduce pollination and, therefore, detrimentally affect the yield of corn per plant. In addition, adults and larvae of the genus Diabrotica attack cucurbit crops (cucumbers, melons, squash, etc.) and many vegetable and field crops in commercial production as well as those being grown in home gardens.

Control of corn rootworm has been partially addressed by cultivation methods, such as crop rotation and the application of high nitrogen levels to stimulate the growth of an adventitious root system. However, chemical insecticides are relied upon most heavily to guarantee the desired level of control. Insecticides are either banded onto or incorporated into the soil. Problems associated with the use of some chemical insecticides are environmental contamination and the development of resistance among the treated insect populations.

The soil microbe *Bacillus thuringiensis* (*B.t.*) is a Gram-positive, spore-forming bacterium characterized by parasporal protein inclusions, which can appear microscopically as distinctively shaped crystals. Certain strains of *B.t.* produce proteins that are toxic to specific orders of pests. Certain *B.t.* toxin genes have been isolated and sequenced, and recombinant DNA-based *B.t.* products have been produced and approved for use. In addition, with the use of genetic engineering techniques, new approaches for delivering these *B.t.* endotoxins to agricultural environments are under development, including the use of plants genetically engineered with endotoxin genes for insect resistance and the use of stabilized intact microbial cells as *B.t.* endotoxin delivery vehicles (Gaertner, F. H., L. Kim [1988] *TIBTECH* 6:S4–S7). Thus, isolated *B.t.* endotoxin genes are becoming commercially valuable.

Commercial use of *B.t.* pesticides was originally limited to a narrow range of lepidopteran (caterpillar) pests. Preparations of the spores and crystals of *B. thuringiensis* subsp. kurstaki have been used for many years as commercial insecticides for lepidopteran pests. For example, *B. thuringiensis* var. kurstaki HD-1 produces a crystalline δ-endotoxin which is toxic to the larvae of a number of lepidopteran insects.

In recent years, however, investigators have discovered *B.t.* pesticides with specificities for a much broader range of pests. For example, other species of *B.t.*, namely israelensis and tenebrionis (a.k.a. *B.t.* M-7, a.k.a. *B.t. san diego*), have been used commercially to control insects of the orders Diptera and Coleoptera, respectively (Gaertner, F. H. [1989] "Cellular Delivery Systems for Insecticidal Proteins: Living and Non-Living Microorganisms," in *Controlled Delivery of Crop Protection Agents*, R. M. Wilkins, ed., Taylor and Francis, New York and London, 1990, pp. 245–255). See also Couch, T. L. (1980) "Mosquito Pathogenicity of *Bacillus thuringiensis* var. israelensis," *Developments in Industrial Microbiology* 22:61–76; Beegle, C. C., (1978) "Use of Entomogenous Bacteria in Agroecosystems," *Developments in Industrial Microbiology* 20:97–104. Krieg, A., A. M. Huger, G. A. Langenbruch, W. Schnetter (1983) *Z. ang. Ent.* 96:500–508, describe *Bacillus thuringiensis* var. tenebrionis, which is reportedly active against two beetles in the order Coleoptera. These are the Colorado potato beetle, *Leptinotarsa decemlineata*, and *Agelastica alni.*

Recently, new subspecies of *B.t.* have been identified, and genes responsible for active δ-endotoxin proteins have been isolated (Höfte, H., H. R. Whiteley [1989] *Microbiological Reviews* 52(2):242–255). Höfte and Whiteley classified *B.t.* crystal protein genes into four major classes. The classes were CryI (Lepidoptera-specific), CryII (Lepidoptera- and Diptera-specific), CryIII (Coleoptera-specific), and CryIV (Diptera-specific). The discovery of strains specifically toxic to other pests has been reported. (Feitelson, J. S., J. Payne, L. Kim [1992] *Bio/Technology* 10:271–275).

The 1989 nomenclature and classification scheme of H öfte and Whiteley for crystal proteins was based on both the deduced amino acid sequence and the host range of the toxin. That system was adapted to cover fourteen different types of toxin genes which were divided into five major classes. As more toxin-genes were discovered, that system started to become unworkable, as genes with similar sequences were found to have significantly different insecticidal specificities. A revised nomenclature scheme has been proposed which is based solely on amino acid identity (Crickmore et al. [1996] Society for Invertebrate Pathology, 29th Annual Meeting, 3rd International Colloquium on *Bacillus thuringiensis*, University of Cordoba, Cordoba, Spain, September 1–6, abstract). The mnemonic "cry" has been retained for all of the toxin genes except cytA and cytB, which remain a separate class. Roman numerals have been exchanged for Arabic numerals in the primary rank, and the parentheses in the tertiary rank have been removed. Current boundaries represent approximately 95% (tertiary rank), 75% (secondary rank), and 48% (primary rank) sequence identity. Many of the original names have been retained, with the noted exceptions, although a number have been reclassified. See also N. Crickmore, D. R. Zeigler, J. Feitelson, E. Schnepf, J. Van Rie, D. Lereclus, J. Baum, and D. H. Dean (1998), "Revisions of the Nomenclature for the *Bacillus thuringiensis* Pesticidal Crystal Proteins," *Microbiology and Molecular Biology Reviews* Vol. 62:807–813; and Crickmore, Zeigler, Feitelson, Schnepf, Van Rie, Lereclus, Baum, and Dean, "Bacillus thuringiensis toxin nomenclature" (1999) http://www.biols.susx.ac.uk/Home/Neil_Crickmore/Bt/index.html. That system uses the freely available software applications CLUSTAL W and PHYLIP. The NEIGHBOR application within the PHYLIP package uses an arithmetic averages (UPGMA) algorithm.

The cloning and expression of a *B.t.* crystal protein gene in *Escherichia coli* has been described in the published literature (Schnepf, H. E., H. R. Whiteley [1981] *Proc. Natl. Acad. Sci. USA* 78:2893–2897). U.S. Pat. No. 4,448,885 and U.S. Pat. No. 4,467,036 both disclose the expression of *B.t.* crystal protein in *E. coli.*

U.S. Pat. Nos. 4,797,276 and 4,853,331 disclose *B. thuringiensis* strain tenebrionis (a.k.a. M-7, a.k.a. *B.t. san diego*), which can be used to control coleopteran pests in various environments. U.S. Pat. No. 4,918,006 discloses *B.t.* toxins having activity against Dipterans. U.S. Pat. No. 4,849,217 discloses *B.t.* isolates which have activity against the alfalfa weevil. U.S. Pat. No. 5,208,077 discloses coleopteran-active *Bacillus thuringiensis* isolates. U.S. Pat. No. 5,632,987 discloses a 130 kDa toxin from PS80JJ1 as having activity against corn rootworm. WO 94/40162, which is related to the subject application, describes new classes of proteins that are toxic to corn rootworn. U.S. Pat. No. 5,151,363 and U.S. Pat. No. 4,948,734 disclose certain isolates of *B.t.* which have activity against nematodes.

U.S. Pat. No. 6,083,499 and WO 97/40162 disclose "binary toxins." The subject invention is distinct from mosquitocidal toxins produced by *Bacillus sphaericus.* See EP 454 485; Davidson et al. (1990), "Interaction of the *Bacillus sphaericus* mosquito larvicidal proteins," *Can. J. Microbio.* 36(12):870–8; Baumann et al. (1988), "Sequence analysis of the mosquitocidal toxin genes encoding 51.4- and 41.9-kilodalton proteins from *Bacillus sphaericus* 2362 and 2297," *J. Bacteriol.* 170:2045–2050; Oei et al. (1992), "Binding of purified *Bacillus sphaericus* binary toxin and its deletion derivatives to *Culex quinquefasciatus* gut: elucidation of functional binding domains," *Journal of General Microbiology* 138(7):1515–26.

BRIEF SUMMARY OF THE INVENTION

The subject invention concerns novel materials and methods for controlling non-mammalian pests. In a preferred embodiment, the subject invention provides materials and methods for the control of coleopteran pests. In more preferred embodiments, the materials and methods described herein are used to control corn rootworm—most preferably Western corn rootworm. Lepidopteran pests (including the European corn borer and Helicoverpa zea) can also be controlled by the pesticidal proteins of the subject invention.

The subject invention advantageously provides polynucleotides and pesticidal proteins encoded by the polynucleotides. In preferred embodiments, a 40–50 kDa protein and a 10–15 kDa protein are used together, with the proteins being pesticidal in combination. Thus, the two classes of proteins of the subject invention can be referred to as "binary toxins." As used herein, the term "toxin" or "pesticidal protein" includes either class of these proteins. The use of a 40–50 kDa protein with a 10–15 kDa protein is preferred but not necessarily required. One class of polynucleotide sequences as described herein encodes proteins which have a full-length molecular weight of approximately 40–50 kDa. In a specific embodiment, these proteins have a molecular weight of about 43–47 kDa. A second class of polynucleotides of the subject invention encodes pesticidal proteins of about 10–15 kDa. In a specific embodiment, these proteins have a molecular weight of about 13–14 kDa. It should be clear that each type of toxin/gene is an aspect of the subject invention. In a particularly preferred embodiment, a 40–50 kDa protein of the subject invention is used in combination with a 10–15 kDa protein. Thus, the proteins of the subject invention can be used to augment and/or facilitate the activity of other protein toxins.

The subject invention includes polynucleotides that encode the 40–50 kDa or the 10–15 kDa toxins, polynucleotides that encode portions or fragments of the full length toxins that retain pesticidal activity (preferably when used in combination), and polynucleotides that encode both types of toxins. Novel examples of fusion proteins (a 40–50 kDa protein and a 10–15 kDa protein fused together) and polynucleotides that encode them are also disclosed herein.

In some embodiments, *B.t.* toxins useful according to the invention include toxins which can be obtained from the novel *B.t.* isolates disclosed herein. It should be clear that, where 40–50 kDa and 10–15 kDa toxins, for example, are used together, one type of toxin can be obtained from one isolate and the other type of toxin can be obtained from another isolate.

The subject invention also includes the use of variants of the exemplified *B.t.* isolates and toxins which have substantially the same coleopteran-active properties as the specifically exemplified *B.t.* isolates and toxins. Such variant isolates would include, for example, mutants. Procedures for making mutants are well known in the microbiological art. Ultraviolet light and chemical mutagens such as nitrosoguanidine are used extensively toward this end.

In preferred embodiments, the subject invention concerns plants and plant cells having at least one isolated polynucleotide of the subject invention. Preferably, the transgenic plant cells express pesticidal toxins in tissues consumed by the target pests.

Alternatively, the *B.t.* isolates of the subject invention, or recombinant microbes expressing the toxins described herein, can be used to control pests. In this regard, the invention includes the treatment of substantially intact *B.t.* cells, and/or recombinant cells containing the expressed toxins of the invention, treated to prolong the pesticidal activity when the substantially intact cells are applied to the environment of a target pest. The treated cell acts as a protective coating for the pesticidal toxin.

The toxins of the subject invention are oral intoxicants that affect an insect's midgut cells upon ingestion by the target insect. Thus, by consuming recombinant host cells, for example, that express the toxins, the target insect thereby contacts the proteins of the subject invention, which are toxic to the pest. This results in control of the target pest.

BRIEF DESCRIPTION OF THE DRAWINGS

FIGS. 1A and 1B show three exemplary 43–47 kDa pesticidal toxins as well as a consensus sequence for these pesticidal toxins.

FIG. 4 shows protein alignments of the 51 and 42 kDa *Bacillus sphaericus* toxins and genes and the 45 kDa 149B1 toxin and gene.

FIGS. 5A–5C show nucleotide sequence alignments of the 51 and 42 kDa *Bacillus sphaericus* toxins and genes and the 45 kDa 149B1 toxin and gene.

BRIEF DESCRIPTION OF THE SEQUENCES

Figure 2:
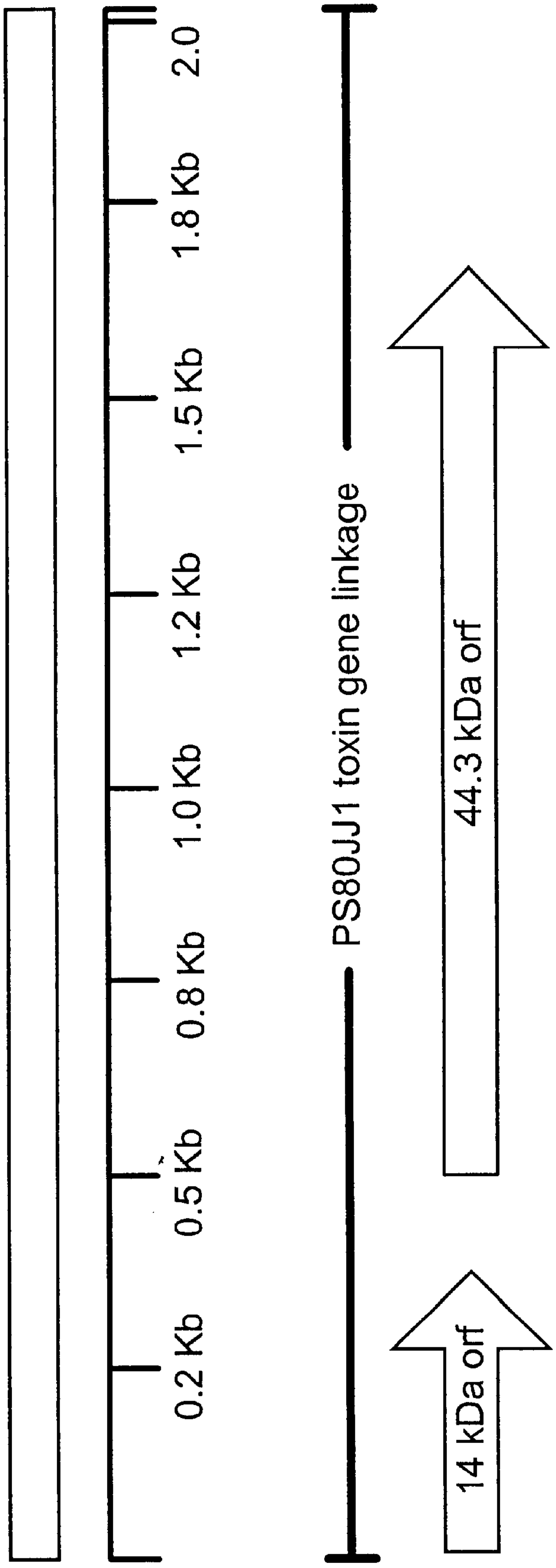
FIG. 2 shows the relationship of the 14 and 45 kDa sequences of PS80JJ1 (SEQ ID NOS. 31 and 10).

SEQ ID NO:1 is a 5-amino acid N-terminal sequence of the approximately 45 kDa toxin of 80JJ1.

SEQ ID NO:2 is a 25-amino acid N-terminal sequence of the approximately 45 kDa toxin of 80JJ1.

SEQ ID NO:3 is a 24-amino acid N-terminal sequence of the approximately 14 kDa toxin of 80JJ1.

SEQ ID NO:4 is the N-terminal sequence of the approximately 47 kDa toxin from 149B1.

SEQ ID NO:5 is a 50-amino acid N-terminal amino acid sequence for the purified approximately 14 kDa protein from PS149B1.

SEQ ID NO:6 is the N-terminal sequence of the approximately 47 kDa toxin from 167H2.

SEQ ID NO:7 is a 25-amino acid N-terminal sequence for the purified approximately 14 kDa protein from PS167H2.

SEQ ID NO:8 is an oligonucleotide probe for the gene encoding the PS80JJ1 44.3 kDa toxin and is a forward primer for PS149B1 and PS167H2 used according to the subject invention.

SEQ ID NO:9 is a reverse primer for PS149B1 and PS167H2 used according to the subject invention.

SEQ ID NO:10 is the nucleotide sequence of the gene encoding the approximately 45 kDa PS80JJ1 toxin.

SEQ ID NO:11 is the amino acid sequence for the approximately 45 kDa PS80JJ1 toxin.

SEQ ID NO:12 is the partial nucleotide sequence of the gene encoding the approximately 44 kDa PS149B1 toxin.

SEQ ID NO:13 is the partial amino acid sequence for the approximately 44 kDa PS149B1 toxin.

SEQ ID NO:14 is the partial nucleotide sequence of the gene encoding the approximately 44 kDa PS167H2 toxin.

SEQ ID NO:15 is the partial amino acid sequence for the approximately 44 kDa PS167H2 toxin.

SEQ ID NO:16 is a peptide sequence used in primer design according to the subject invention.

SEQ ID NO:17 is a peptide sequence used in primer design according to the subject invention.

SEQ ID NO:18 is a peptide sequence used in primer design according to the subject invention.

SEQ ID NO:19 is a peptide sequence used in primer design according to the subject invention.

SEQ ID NO:20 is a nucleotide sequence corresponding to the peptide of SEQ ID NO:16.

SEQ ID NO:21 is a nucleotide sequence corresponding to the peptide of SEQ ID NO:17.

SEQ ID NO:22 is a nucleotide sequence corresponding to the peptide of SEQ ID NO:18.

SEQ ID NO:23 is a nucleotide sequence corresponding to the peptide of SEQ ID NO:19.

SEQ ID NO:24 is a reverse primer based on the reverse complement of SEQ ID NO:22.

SEQ ID NO:25 is a reverse primer based on the reverse complement of SEQ ID NO:23.

SEQ ID NO:26 is a forward primer based on the PS80JJ1 44.3 kDa toxin.

SEQ ID NO:27 is a reverse primer based on the PS80JJ1 44.3 kDa toxin.

SEQ ID NO:28 is a generic sequence representing a new class of toxins according to the subject invention.

SEQ ID NO:29 is an oligonucleotide probe used according to the subject invention.

SEQ ID NO:30 is the nucleotide sequence of the entire genetic locus containing open reading frames of both the 14 and 45 kDa PS80JJ1 toxins and the flanking nucleotide sequences.

SEQ ID NO:31 is the nucleotide sequence of the PS80JJ1 14 kDa toxin open reading frame.

SEQ ID NO:32 is the deduced amino acid sequence of the 14 kDa toxin of PS80JJ1.

SEQ ID NO:33 is a reverse oligonucleotide primer used according to the subject invention.

SEQ ID NO:34 is the nucleotide sequence of the entire genetic locus containing open reading frames of both the 14 and 44 kDa PS167H2 toxins and the flanking nucleotide sequences.

SEQ ID NO:35 is the nucleotide sequence of the gene encoding the approximately 14 kDa PS167H2 toxin.

SEQ ID NO:36 is the amino acid sequence for the approximately 14 kDa PS167H2 toxin.

SEQ ID NO:37 is the nucleotide sequence of the gene encoding the approximately 44 kDa PS167H2 toxin.

SEQ ID NO:38 is the amino acid sequence for the approximately 44 kDa PS167H2 toxin.

SEQ ID NO:39 is the nucleotide sequence of the entire genetic locus containing open reading frames of both the 14 and 44 kDa PS149B1 toxins and the flanking nucleotide sequences.

SEQ ID NO:40 is the nucleotide sequence of the gene encoding the approximately 14 kDa PS149B1 toxin.

SEQ ID NO:41 is the amino acid sequence for the approximately 14 kDa PS149B1 toxin.

SEQ ID NO:42 is the nucleotide sequence of the gene encoding the approximately 44 kDa PS149B1 toxin.

SEQ ID NO:43 is the amino acid sequence for the approximately 44 kDa PS149B1 toxin.

SEQ ID NO:44 is a maize-optimized gene sequence encoding the approximately 14 kDa toxin of 80JJ1.

SEQ ID NO:45 is a maize-optimized gene sequence encoding the approximately 44 kDa toxin of 80JJ1.

SEQ ID NO:46 is the DNA sequence of a reverse primer used in Example 15, below.

SEQ ID NO:47 is the DNA sequence of a forward primer (see Example 16).

SEQ ID NO:48 is the DNA sequence of a reverse primer (see Example 16).

SEQ ID NO:49 is the DNA sequence of a forward primer (see Example 16).

SEQ ID NO:50 is the DNA sequence of a reverse primer (see Example 16).

SEQ ID NO:51 is the DNA sequence from PS131W2 which encodes the 14 kDa protein.

SEQ ID NO:52 is the amino acid sequence of the 14 kDa protein of PS131W2.

SEQ ID NO:53 is a partial DNA sequence from PS131W2 for the 44 kDa protein.

SEQ ID NO:54 is a partial amino acid sequence for the 44 kDa protein of PS131W2.

SEQ ID NO:55 is the DNA sequence from PS158T3 which encodes the 14 kDa protein.

SEQ ID NO:56 is the amino acid sequence of the 14 kDa protein of PS158T3.

SEQ ID NO:57 is a partial DNA sequence from PS158T3 for the 44 kDa protein.

SEQ ID NO:58 is a partial amino acid sequence for the 44 kDa protein of PS158T3.

SEQ ID NO:59 is the DNA sequence from PS158X10 which encodes the 14 kDa protein.

SEQ ID NO:60 is the amino acid sequence of the 14 kDa protein of PS158X10.

SEQ ID NO:61 is the DNA sequence from PS185FF which encodes the 14 kDa protein.

SEQ ID NO:62 is the amino acid sequence of the 14 kDa protein of PS185FF.

SEQ ID NO:63 is a partial DNA sequence from PS185FF for the 44 kDa protein.

SEQ ID NO:64 is a partial amino acid sequence for the 44 kDa protein of PS185FF.

SEQ ID NO:65 is the DNA sequence from PS185GG which encodes the 14 kDa protein.

SEQ ID NO:66 is the amino acid sequence of the 14 kDa protein of PS185GG.

SEQ ID NO:67 is the DNA sequence from PS185GG for the 44 kDa protein.

SEQ ID NO:68 is the amino acid sequence for the 44 kDa protein of PS185GG.

SEQ ID NO:69 is the DNA sequence from PS185L12 which encodes the 14 kDa protein.

SEQ ID NO:70 is the amino acid sequence of the 14 kDa protein of PS185L12.

SEQ ID NO:71 is the DNA sequence from PS185W3 which encodes the 14 kDa protein.

SEQ ID NO:72 is the amino acid sequence of the 14 kDa protein of PS185W3.

SEQ ID NO:73 is the DNA sequence from PS186FF which encodes the 14 kDa protein.

SEQ ID NO:74 is the amino acid sequence of the 14 kDa protein of PS186FF.

SEQ ID NO:75 is the DNA sequence from PS187F3 which encodes the 14 kDa protein.

SEQ ID NO:76 is the amino acid sequence of the 14 kDa protein of PS187F3.

SEQ ID NO:77 is a partial DNA sequence from PS187F3 for the 44 kDa protein.

SEQ ID NO:78 is a partial amino acid sequence for the 44 kDa protein of PS187F3.

SEQ ID NO:79 is the DNA sequence from PS187G1 which encodes the 14 kDa protein.

SEQ ID NO:80 is the amino acid sequence of the 14 kDa protein of PS187G1.

SEQ ID NO:81 is a partial DNA sequence from PS187G1 for the 44 kDa protein.

SEQ ID NO:82 is a partial amino acid sequence for the 44 kDa protein of PS187G1.

SEQ ID NO:83 is the DNA sequence from PS187L14 which encodes the 14 kDa protein.

SEQ ID NO:84 is the amino acid sequence of the 14 kDa protein of PS187L14.

SEQ ID NO:85 is a partial DNA sequence from PS187L14 for the 44 kDa protein.

SEQ ID NO:86 is a partial amino acid sequence for the 44 kDa protein of PS187L14.

SEQ ID NO:87 is the DNA sequence from PS187Y2 which encodes the 14 kDa protein.

SEQ ID NO:88 is the amino acid sequence of the 14 kDa protein of PS187Y2.

SEQ ID NO:89 is a partial DNA sequence from PS187Y2 for the 44 kDa protein.

SEQ ID NO:90 is a partial amino acid sequence for the 44 kDa protein of PS187Y2.

SEQ ID NO:91 is the DNA sequence from PS201G which encodes the 14 kDa protein.

SEQ ID NO:92 is the amino acid sequence of the 14 kDa protein of PS201G.

SEQ ID NO:93 is the DNA sequence from PS201HH which encodes the 14 kDa protein.

SEQ ID NO:94 is the amino acid sequence of the 14 kDa protein of PS201HH.

SEQ ID NO:95 is the DNA sequence from PS201L3 which encodes the 14 kDa protein.

SEQ ID NO:96 is the amino acid sequence of the 14 kDa protein of PS201L3.

SEQ ID NO:97 is the DNA sequence from PS204C3 which encodes the 14 kDa protein.

SEQ ID NO:98 is the amino acid sequence of the 14 kDa protein of PS204C3.

SEQ ID NO:99 is the DNA sequence from PS204G4 which encodes the 14 kDa protein.

SEQ ID NO:100 is the amino acid sequence of the 14 kDa protein of PS204G4.

SEQ ID NO:101 is the DNA sequence from PS204I11 which encodes the 14 kDa protein.

SEQ ID NO:102 is the amino acid sequence of the 14 kDa protein of PS204I11.

SEQ ID NO:103 is the DNA sequence from PS204J7 which encodes the 14 kDa protein.

SEQ ID NO:104 is the amino acid sequence of the 14 kDa protein of PS204J7.

SEQ ID NO:105 is the DNA sequence from PS236B6 which encodes the 14 kDa protein.

SEQ ID NO:106 is the amino acid sequence of the 14 kDa protein of PS236B6.

SEQ ID NO:107 is the DNA sequence from PS242K10 which encodes the 14 kDa protein.

SEQ ID NO:108 is the amino acid sequence of the 14 kDa protein of PS242K10.

SEQ ID NO:109 is a partial DNA sequence from PS242K10 for the 44 kDa protein.

SEQ ID NO:110 is a partial amino acid sequence for the 44 kDa protein of PS242K10.

SEQ ID NO:111 is the DNA sequence from PS246P42 which encodes the 14 kDa protein.

SEQ ID NO:112 is the amino acid sequence of the 14 kDa protein of PS246P42.

SEQ ID NO:113 is the DNA sequence from PS69Q which encodes the 14 kDa protein.

SEQ ID NO:114 is the amino acid sequence of the 14 kDa protein of PS69Q.

SEQ ID NO:115 is the DNA sequence from PS69Q for the 44 kDa protein.

SEQ ID NO:116 is the amino acid sequence for the 44 kDa protein of PS69Q.

SEQ ID NO:117 is the DNA sequence from KB54 which encodes the 14 kDa protein.

SEQ ID NO:118 is the amino acid sequence of the 14 kDa protein of KB54.

SEQ ID NO:119 is the DNA sequence from KR1209 which encodes the 14 kDa protein.

SEQ ID NO:120 is the amino acid sequence of the 14 kDa protein of KR1209.

SEQ ID NO:121 is the DNA sequence from KR1369 which encodes the 14 kDa protein.

SEQ ID NO:122 is the amino acid sequence of the 14 kDa protein of KR1369.

SEQ ID NO:123 is the DNA sequence from KR589 which encodes the 14 kDa protein.

SEQ ID NO:124 is the amino acid sequence of the 14 kDa protein of KR589.

SEQ ID NO:125 is a partial DNA sequence from KR589 for the 44 kDa protein.

SEQ ID NO:126 is a partial amino acid sequence for the 44 kDa protein of KR589.

SEQ ID NO:127 is a polynucleotide sequence for a gene designated 149B1-15-PO, which is optimized for expression in Zea mays. This gene encodes an approximately 15 kDa toxin obtainable from PS149B1 that is disclosed in WO 97/40162.

SEQ ID NO:128 is a polynucleotide sequence for a gene designated 149B1-45-PO, which is optimized for expression in Zea mays. This gene encodes an approximately 45 kDa toxin obtainable from PS149B1 that is disclosed in WO 97/40162.

SEQ ID NO:129 is a polynucleotide sequence for a gene designated 80JJ1-15-PO7, which is optimized for expression in maize. This is an alternative gene that encodes an approximately 15 kDa toxin.

SEQ ID NO:130 is an amino acid sequence for a toxin encoded by the gene designated 80JJ1-15-PO7.

SEQ ID NO:131 is an oligonucleotide primer (15kfor1) used according to the subject invention (see Example 20).

SEQ ID NO:132 is an oligonucleotide primer (45krev6) used according to the subject invention (see Example 20).

SEQ ID NO:133 is the DNA sequence from PS201L3 which encodes the 14 kDa protein.

SEQ ID NO:134 is the amino acid sequence of the 14 kDa protein of PS201L3.

SEQ ID NO:135 is a partial DNA sequence from PS201L3 for the 44 kDa protein.

SEQ ID NO:136 is a partial amino acid sequence for the 44 kDa protein of PS201L3.

SEQ ID NO:137 is the DNA sequence from PS187G1 which encodes the 14 kDa protein.

SEQ ID NO:138 is the amino acid sequence of the 14 kDa protein of PS187G1.

SEQ ID NO:139 is the DNA sequence from PS187G1 which encodes the 44 kDa protein.

SEQ ID NO:140 is the amino acid sequence of the 44 kDa protein of PS187G1.

SEQ ID NO:141 is the DNA sequence from PS201HH2 which encodes the 14 kDa protein.

SEQ ID NO:142 is the amino acid sequence of the 14 kDa protein of PS201HH2.

SEQ ID NO:143 is a partial DNA sequence from PS201HH2 for the 44 kDa protein.

SEQ ID NO:144 is a partial amino acid sequence for the 44 kDa protein of PS201HH2.

SEQ ID NO:145 is the DNA sequence from KR1369 which encodes the 14 kDa protein.

SEQ ID NO:146 is the amino acid sequence of the 14 kDa protein of KR1369.

SEQ ID NO:147 is the DNA sequence from KR1369 which encodes the 44 kDa protein.

SEQ ID NO:148 is the amino acid sequence of the 44 kDa protein of KR1369.

SEQ ID NO:149 is the DNA sequence from PS137A which encodes the 14 kDa protein.

SEQ ID NO:150 is the amino acid sequence of the 14 kDa protein of PS137A.

SEQ ID NO:151 is the DNA sequence from PS201V2 which encodes the 14 kDa protein.

SEQ ID NO:152 is the amino acid sequence of the 14 kDa protein of PS201V2.

SEQ ID NO:153 is the DNA sequence from PS207C3 which encodes the 14 kDa protein.

SEQ ID NO:154 is the amino acid sequence of the 14 kDa protein of PS207C3.

SEQ ID NO:155 is an oligonucleotide primer (F1new) for use according to the subject invention (see Example 22).

SEQ ID NO:156 is an oligonucleotide primer (R1new) for use according to the subject invention (see Example 22).

SEQ ID NO:157 is an oligonucleotide primer (F2new) for use according to the subject invention (see Example 22).

SEQ ID NO:158 is an oligonucleotide primer (R2new) for use according to the subject invention (see Example 22).

SEQ ID NO:159 is an approximately 58 kDa fusion protein.

SEQ ID NO:160 is a fusion gene encoding the protein of SEQ ID NO:159.

SEQ ID NO:161 is primer 45 kD5' for use according to the subject invention (see Example 27).

SEQ ID NO:162 is primer 45 kD3'rc for use according to the subject invention (see Example 27).

SEQ ID NO:163 is primer 45 kD5'01 for use according to the subject invention (see Example 27).

SEQ ID NO:164 is primer 45 kD5'02 for use according to the subject invention (see Example 27).

SEQ ID NO:165 is primer 45 kD3'03 for use according to the subject invention (see Example 27).

SEQ ID NO:166 is primer 45 kD3'04 for use according to the subject invention (see Example 27).

DETAILED DISCLOSURE OF THE INVENTION

The subject invention concerns two new classes of polynucleotide sequences as well as the novel pesticidal proteins encoded by these polynucleotides. In one embodiment, the proteins have a full-length molecular weight of approximately 40–50 kDa. In specific embodiments exemplified herein, these proteins have a molecular weight of about 43–47 kDa. In a second embodiment, the pesticidal proteins have a molecular weight of approximately 10–15 kDa. In specific embodiments exemplified herein, these proteins have a molecular weight of about 13–14 kDa.

In preferred embodiments, a 40–50 kDa protein and a 10–15 kDa protein are used together, and the proteins are pesticidal in combination. Thus, the two classes of proteins of the subject invention can be referred to as "binary toxins." As used herein, the term "toxin" includes either class of pesticidal proteins. The subject invention concerns polynucleotides which encode either the 40–50 kDa or the 10–15 kDa toxins, polynucleotides which encode portions or fragments of the full length toxins that retain pesticidal activity when used in combination, and polynucleotide sequences which encode both types of toxins. In a preferred embodiment, these toxins are active against coleopteran pests, more preferably corn rootworn, and most preferably Western corn rootworm. Lepidopteran pests can also be targeted.

Certain specific toxins are exemplified herein. For toxins having a known amino acid sequence, the molecular weight is also known. Those skilled in the art will recognize that the apparent molecular weight of a protein as determined by gel electrophoresis will sometimes differ from the true molecular weight. Therefore, reference herein to, for example, a 45 kDa protein or a 14 kDa protein is understood to refer to proteins of approximately that size even if the true molecular weight is somewhat different.

The subject invention concerns not only the polynucleotides that encode these classes of toxins, but also the use of these polynucleotides to produce recombinant hosts which express the toxins. In a further aspect, the subject invention concerns the combined use of an approximately 40–50 kDa toxin of the subject invention together with an approximately 10–15 kDa toxin of the subject invention to achieve highly effective control of pests, including coleopterans such as corn rootworm. For example, the roots of one plant can express both types of toxins.

Thus, control of pests using the isolates, toxins, and genes of the subject invention can be accomplished by a variety of methods known to those skilled in the art. These methods include, for example, the application of *B.t.* isolates to the pests (or their location), the application of recombinant microbes to the pests (or their locations), and the transformation of plants with genes which encode the pesticidal toxins of the subject invention. Microbes for use according to the subject invention may be, for example, *B.t., E. coli*, and/or Pseudomonas. Recombinant hosts can be made by those skilled in the art using standard techniques. Materials necessary for these transformations are disclosed herein or are otherwise readily available to the skilled artisan. Control of insects and other pests such as nematodes and mites can also be accomplished by those skilled in the art using standard techniques combined with the teachings provided herein.

The new classes of toxins and polynucleotide sequences provided here are defined according to several parameters. One critical characteristic of the toxins described herein is pesticidal activity. In a specific embodiment, these toxins have activity against coleopteran pests. Anti-lepidopteran-active toxins are also embodied. The toxins and genes of the subject invention can be further defined by their amino acid and nucleotide sequences. The sequences of the molecules within each novel class can be identified and defined in terms of their similarity or identity to certain exemplified sequences as well as in terms of the ability to hybridize with, or be amplified by, certain exemplified probes and primers. The classes of toxins provided herein can also be identified based on their immunoreactivity with certain antibodies and based upon their adherence to a generic formula.

It should be apparent to a person skilled in this art that genes encoding pesticidal proteins according to the subject invention can be obtained through several means. The specific genes exemplified herein may be obtained from the isolates deposited at a culture depository as described herein. These genes, and toxins, of the subject invention can also be constructed synthetically, for example, by the use of a gene synthesizer.

The sequence of three exemplary 45 kDa toxins are provided as SEQ ID NOS:11, 43, and 38. In preferred embodiments, toxins of this class have a sequence which conforms to the generic sequence presented as SEQ ID NO:28. In preferred embodiments, the toxins of this class will conform to the consensus sequence shown in FIG. 1.

With the teachings provided herein, one skilled in the art could readily produce and use the various toxins and polynucleotide sequences of the novel classes described herein.

Microorganisms useful according to the subject invention have been deposited in the permanent collection of the Agricultural Research Service Patent Culture Collection (NRRL), Northern Regional Research Center, 1815 North University Street, Peoria, Ill. 61604, USA. The culture repository numbers of the deposited strains are as follows:

| Culture | Repository No. | Deposit Date |
|---|---|---|
| *B.t.* strain PS80JJ1 | NRRL B-18679 | July 17, 1990 |
| *B.t.* strain PS149B1 | NRRL B-21553 | March 28, 1996 |
| *B.t.* strain PS167H2 | NRRL B-21554 | March 28, 1996 |
| *E. coli* NM522(pMYC2365) | NRRL B-21170 | Jan. 5, 1994 |
| *E. coli* NM522(pMYC2382) | NRRL B-21329 | Sept. 28, 1994 |
| *E. coli* NM522(pMYC2379) | NRRL B-21155 | Nov. 3, 1993 |
| *E. coli* NM522(pMYC2421) | NRRL B-21555 | March 28, 1996 |
| *E. coli* NM522(pMYC2427) | NRRL B-21672 | March 26, 1997 |
| *E. coli* NM522(pMYC2429) | NRRL B-21673 | March 26, 1997 |
| *E. coli* NM522(pMYC2426) | NRRL B-21671 | March 26, 1997 |
| *B.t.* strain PS185GG | NRRL B-30175 | Aug. 19, 1999 |
| *B.t.* strain PS187G1 | NRRL B-30185 | Aug. 19, 1999 |
| *B.t.* strain PS187Y2 | NRRL B-30187 | Aug. 19, 1999 |
| *B.t.* strain PS201G | NRRL B-30188 | Aug. 19, 1999 |
| *B.t.* strain PS201HH2 | NRRL B-30190 | Aug. 19, 1999 |
| *B.t.* strain PS242K10 | NRRL B-30195 | Aug. 19, 1999 |
| *B.t.* strain PS69Q | NRRL B-30175 | Aug. 19, 1999 |
| *B.t.* strain KB54A1-6 | NRRL B-30197 | Aug. 19, 1999 |
| *B.t.* strain KR589 | NRRL B-30198 | Aug. 19, 1999 |
| *B.t.* strain PS185L12 | NRRL B-30179 | Aug. 19, 1999 |
| *B.t.* strain PS185W3 | NRRL B-30180 | Aug. 19, 1999 |
| *B.t.* strain PS187L14 | NRRL B-30186 | Aug. 19, 1999 |
| *B.t.* strain PS186FF | NRRL B-30182 | Aug. 19, 1999 |
| *B.t.* strain PS131W2 | NRRL B-30176 | Aug. 19, 1999 |
| *B.t.* strain PS158T3 | NRRL B-30177 | Aug. 19, 1999 |
| *B.t.* strain PS158X10 | NRRL B-30178 | Aug. 19, 1999 |
| *B.t.* strain PS185FF | NRRL B-30182 | Aug. 19, 1999 |
| *B.t.* strain PS187F3 | NRRL B-30184 | Aug. 19, 1999 |
| *B.t.* strain PS201L3 | NRRL B-30189 | Aug. 19, 1999 |
| *B.t.* strain PS204C3 | NRRL B-30191 | Aug. 19, 1999 |
| *B.t.* strain PS204G4 | NRRL B-18685 | July 17, 1990 |
| *B.t.* strain PS204I11 | NRRL B-30192 | Aug. 19, 1999 |
| *B.t.* strain PS204J7 | NRRL B-30193 | Aug. 19, 1999 |
| *B.t.* strain PS236B6 | NRRL B-30194 | Aug. 19, 1999 |
| *B.t.* strain PS246P42 | NRRL B-30196 | Aug. 19, 1999 |
| *B.t.* strain KR1209 | NRRL B-30199 | Aug. 19, 1999 |
| *B.t.* strain KR1369 | NRRL B-30200 | Aug. 19, 1999 |
| *B.t.* strain MR1506 | NRRL B-30298 | June 1, 2000 |
| *B.t.* strain MR1509 | NRRL B-30330 | Aug. 8, 2000 |
| *B.t.* strain MR1510 | NRRL B-30331 | Aug. 8, 2000 |
| *P.f.* strain MR1607 | NRRL B-30332 | Aug. 8, 2000 |

The PS80JJ1 isolate is available to the public by virtue of the issuance of U.S. Pat. No. 5,151,363 and other patents.

A further aspect of the subject invention concerns novel isolates and the toxins and genes obtainable from these isolates. Novel isolates have been deposited and are included in the above list. These isolates have been deposited under conditions that assure that access to the cultures will be available during the pendency of this patent application to one determined by the Commissioner of Patents and Trademarks to be entitled thereto under 37 CFR 1.14 and 35 U.S.C. 122. The deposits are available as required by foreign patent laws in countries wherein counterparts of the subject application, or its progeny, are filed. However, it should be understood that the availability of a deposit does not constitute a license to practice the subject invention in derogation of patent rights granted by governmental action.

Further, the subject culture deposits will be stored and made available to the public in accord with the provisions of the Budapest Treaty for the Deposit of Microorganisms, i.e., they will be stored with all the care necessary to keep them viable and uncontaminated for a period of at least five years after the most recent request for the furnishing of a sample of a deposit, and in any case, for a period of at least 30 (thirty) years after the date of deposit or for the enforceable life of any patent which may issue disclosing the cultures. The depositor acknowledges the duty to replace the deposit (s) should the depository be unable to furnish a sample when requested, due to the condition of the deposit(s). All restrictions on the availability to the public of the subject culture deposits will be irrevocably removed upon the granting of a patent disclosing them.

Following is a table which provides characteristics of certain *B.t.* isolates that are useful according to the subject invention.

TABLE 1

Description of *B.t.* strains toxic to coleopterans

| Culture | Crystal Description | Approx. MW (kDa) | Serotype | NRRL Deposit | Deposit Date |
|---|---|---|---|---|---|
| PS80JJ1 | multiple attached | 130, 90, 47, 37, 14 | 4a4b, sotto | B-18679 | July 17, 1990 |
| PS149B1 | | 130, 47, 14 | | B-21553 | March 28, 1996 |
| PS167H2 | | 70, 47, 14 | | B-23554 | March 28, 1996 |

Other isolates of the subject invention can also be characterized in terms of the shape and location of toxin inclusions.

Toxins, genes, and probes. The polynucleotides of the subject invention can be used to form complete "genes" to encode proteins or peptides in a desired host cell. For example, as the skilled artisan would readily recognize, some of the polynucleotides in the attached sequence listing are shown without stop codons. Also, the subject polynucleotides can be appropriately placed under the control of a promoter in a host of interest, as is readily known in the art.

As the skilled artisan would readily recognize, DNA typically exists in a double-stranded form. In this arrangement, one strand is complementary to the other strand and vice versa. As DNA is replicated in a plant (for example) additional, complementary strands of DNA are produced. The "coding strand" is often used in the art to refer to the strand that binds with the anti-sense strand. The mRNA is transcribed from the "anti-sense" strand of DNA. The "sense" or "coding" strand has a series of codons (a codon is three nucleotides that can be read three-at-a-time to yield a particular amino acid) that can be read as an open reading frame (ORF) to form a protein or peptide of interest. In order to express a protein in vivo, a strand of DNA is typically transcribed into a complementary strand of mRNA which is used as the template for the protein. Thus, the subject invention includes the use of the exemplified polynucleotides shown in the attached sequence listing and/or the complementary strands. RNA and PNA (peptide nucleic acids) that are functionally equivalent to the exemplified DNA are included in the subject invention.

Toxins and genes of the subject invention can be identified and obtained by using oligonucleotide probes, for example. These probes are detectable nucleotide sequences which may be detectable by virtue of an appropriate label or may be made inherently fluorescent as described in International Application No. WO 93/16094. The probes (and the polynucleotides of the subject invention) may be DNA, RNA, or PNA. In addition to adenine (A), cytosine (C), guanine (G), thymine (T), and uracil (U; for RNA molecules), synthetic probes (and polynucleotides) of the subject invention can also have inosine (a neutral base capable of pairing with all four bases; sometimes used in place of a mixture of all four bases in synthetic probes). Thus, where a synthetic, degenerate oligonucleotide is referred to herein, and "n" is used generically, "n" can be G, A, T, C, or inosine. Ambiguity codes as used herein are in accordance with standard IUPAC naming conventions as of the filing of the subject application (for example, R means A or G, Y means C or T, etc.) As is well known in the art, if the probe molecule and nucleic acid sample hybridize by forming a strong bond between the two molecules, it can be reasonably assumed that the probe and sample have substantial homology/similarity/identity. Preferably, hybridization is conducted under stringent conditions by techniques well-known in the art, as described in, for example, Keller, G. H., M. M. Manak (1987) *DNA Probes*, Stockton Press, New York, N.Y., pp. 169–170. For example, as stated therein, high stringency conditions can be achieved by first washing with 2×SSC (Standard Saline Citrate)/0.1% SDS (Sodium Dodecyl Sulfate) for 15 minutes at room temperature. Two washes are typically performed. Higher stringency can then be achieved by lowering the salt concentration and/or by raising the temperature. For example, the wash described above can be followed by two washings with 0.1×SSC/0.1% SDS for 15 minutes each at room temperature followed by subsequent washes with 0.1×SSC/0.1% SDS for 30 minutes each at 55° C. These temperatures can be used with other hybridization and wash protocols set forth herein and as would be known to one skilled in the art (SSPE can be used as the salt instead of SSC, for example). The 2×SSC/0.1% SDS can be prepared by adding 50 ml of 20×SSC and 5 ml of 10% SDS to 445 ml of water. 20×SSC can be prepared by combining NaCl (175.3 g/0.150 M), sodium citrate (88.2 g/0.015 M), and water to 1 liter, followed by adjusting pH to 7.0 with 10 N NaOH. 10% SDS can be prepared by dissolving 10 g of SDS in 50 ml of autoclaved water, diluting to 100 ml, and aliquotting.

Detection of the probe provides a means for determining in a known manner whether hybridization has occurred. Such a probe analysis provides a rapid method for identifying toxin-encoding genes of the subject invention. The nucleotide segments which are used as probes according to the invention can be synthesized using a DNA synthesizer and standard procedures. These nucleotide sequences can also be used as PCR primers to amplify genes of the subject invention.

Hybridization characteristics of a molecule can be used to define polynucleotides of the subject invention. Thus the subject invention includes polynucleotides (and/or their complements, preferably their full complements) that hybridize with a polynucleotide exemplified herein (such as the DNA sequences included in SEQ ID NOs:46–166).

As used herein "stringent" conditions for hybridization refers to conditions which achieve the same, or about the same, degree of specificity of hybridization as the conditions employed by the current applicants. Specifically, hybridization of immobilized DNA on Southern blots with $^{32}$P-labeled gene-specific probes was performed by standard methods (Maniatis, T., E. F. Fritsch, J. Sambrook [1982] *Molecular Cloning: A Laboratory Manual*, Cold Spring Harbor Laboratory, Cold Spring Harbor, N.Y.). In general, hybridization and subsequent washes were carried out under stringent conditions that allowed for detection of target sequences (with homology to the PS80JJ1 toxin genes, for example). For double-stranded DNA gene probes, hybridization was carried out overnight at 20–25° C. below the melting temperature (Tm) of the DNA hybrid in 6×SSPE, 5×Denhardt's solution, 0.1% SDS, 0.1 mg/ml denatured DNA. The melting temperature is described by the following formula (Beltz, G. A., K. A. Jacobs, T. H. Eickbush, P. T. Cherbas, and F. C. Kafatos [1983] *Methods of Enzymology*, R. Wu, L. Grossman and K. Moldave [eds.] Academic Press, New York 100:266–285):

Tm=81.5° C.+16.6 Log[Na+]+0.41(%G+C)−0.61(%formamide)−600/length of duplex in base pairs.

Washes are typically carried out as follows:

(1) Twice at room temperature for 15 minutes in 1×SSPE, 0.1% SDS (low stringency wash).

(2) Once at Tm−20° C. for 15 minutes in 0.2×SSPE, 0.1% SDS (moderate stringency wash).

For oligonucleotide probes, hybridization was carried out overnight at 10–20° C. below the melting temperature (Tm) of the hybrid in 6×SSPE, 5×Denhardt's solution, 0.1% SDS, 0.1 mg/ml denatured DNA. Tm for oligonucleotide probes was determined by the following formula:

Tm(° C.)=2(number T/A base pairs)+4(number G/C base pairs)

(Suggs, S. V., T. Miyake, E. H. Kawashime, M. J. Johnson, K. Itakura, and R. B. Wallace [1981] *ICN-UCLA Symp. Dev. Biol. Using Purified Genes*, D. D. Brown [ed.], Academic Press, New York, 23:683–693).

Washes were typically carried out as follows:

(1) Twice at room temperature for 15 minutes 1×SSPE, 0.1% SDS (low stringency wash).

(2) Once at the hybridization temperature for 15 minutes in 1×SSPE, 0.1% SDS (moderate stringency wash).

Toxins obtainable from isolates PS149B1, PS167H2, and PS80JJ1 have been characterized as having have at least one of the following characteristics (novel toxins of the subject invention can be similarly characterized with this and other identifying information set forth herein):

(a) said toxin is encoded by a nucleotide sequence which hybridizes under stringent conditions with a nucleotide sequence selected from the group consisting of: DNA which encodes SEQ ID NO:2, DNA which encodes SEQ ID NO:4, DNA which encodes SEQ ID NO:6, SEQ ID NO:8, SEQ ID NO:10, DNA which encodes SEQ ID NO:11, SEQ ID NO:12, DNA which encodes SEQ ID NO:13, SEQ ID NO:14, DNA which encodes SEQ ID NO:15, DNA which encodes SEQ ID NO:16, DNA which encodes SEQ ID NO:17, DNA which encodes SEQ ID NO:18, DNA which encodes SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, DNA which encodes a pesticidal portion of SEQ ID NO:28, SEQ ID NO:37, DNA which encodes SEQ ID NO:38, SEQ ID NO:42, and DNA which encodes SEQ ID NO:43;

(b) said toxin immunoreacts with an antibody to an approximately 40–50 kDa pesticidal toxin, or a fragment thereof, from a *Bacillus thuringiensis* isolate selected from the group consisting of PS80JJ1 having the identifying characteristics of NRRL B-18679, PS149B1 having the identifying characteristics of NRRL B-21553, and PS167H2 having the identifying characteristics of NRRL B-21554;

(c) said toxin is encoded by a nucleotide sequence wherein a portion of said nucleotide sequence can be amplified by PCR using a primer pair selected from the group consisting of SEQ ID NOs:20 and 24 to produce a fragment of about 495 bp, SEQ ID NOs:20 and 25 to produce a fragment of about 594 bp, SEQ ID NOs:21 and 24 to produce a fragment of about 471 bp, and SEQ ID NOs:21 and 25 to produce a fragment of about 580 bp;

(d) said toxin comprises a pesticidal portion of the amino acid sequence shown in SEQ ID NO:28;

(e) said toxin comprises an amino acid sequence which has at least about 60% homology with a pesticidal portion of an amino acid sequence selected from the group consisting of SEQ ID NO:11, SEQ ID NO:13, SEQ ID NO:15, SEQ ID NO:38, and SEQ ID NO:43;

(f) said toxin is encoded by a nucleotide sequence which hybridizes under stringent conditions with a nucleotide sequence selected from the group consisting of DNA which encodes SEQ ID NO:3, DNA which encodes SEQ ID NO:5, DNA which encodes SEQ ID NO:7, DNA which encodes SEQ ID NO:32, DNA which encodes SEQ ID NO:36, and DNA which encodes SEQ ID NO:41;

(g) said toxin immunoreacts with an antibody to an approximately 10–15 kDa pesticidal toxin, or a fragment thereof, from a *Bacillus thuringiensis* isolate selected from the group consisting of PS80JJ1 having the identifying characteristics of NRRL B-18679, PS149B1 having the identifying characteristics of NRRL B-21553, and PS167H2 having the identifying characteristics of NRRL B-21554;

(h) said toxin is encoded by a nucleotide sequence wherein a portion of said nucleotide sequence can be amplified by PCR using the primer pair of SEQ ID NO:29 and SEQ ID NO:33; and (i) said toxin comprises an amino acid sequence which has at least about 60% homology with an amino acid sequence selected from the group consisting of SEQ ID NO:3, SEQ ID NO:5, SEQ ID NO:7, pesticidal portions of SEQ ID NO:32, pesticidal portions of SEQ ID NO:36, and pesticidal portions of SEQ ID NO:41.

Modification of genes and toxins. The genes and toxins useful according to the subject invention include not only the specifically exemplified full-length sequences, but also portions and/or fragments (including internal and/or terminal deletions compared to the full-length molecules) of these sequences, variants, mutants, chimerics, and fusions thereof. Proteins of the subject invention can have substituted amino acids so long as they retain the characteristic pesticidal activity of the proteins specifically exemplified herein. "Variant" genes have nucleotide sequences which encode the same toxins or which encode toxins having pesticidal activity equivalent to an exemplified protein. As used herein, the term "equivalent toxins" refers to toxins having the same or essentially the same biological activity against the target pests as the exemplified toxins. As used herein, reference to "essentially the same" sequence refers to sequences which have amino acid substitutions, deletions, additions, or insertions which do not materially affect pesticidal activity. Fragments retaining pesticidal activity are also included in this definition. Fragments and equivalents which retain the pesticidal activity of the exemplified toxins would be within the scope of the subject invention.

Equivalent toxins and/or genes encoding these equivalent toxins can be derived from wild-type or recombinant *B.t.* isolates and/or from other wild-type or recombinant organisms using the teachings provided herein. Other Bacillus species, for example, can be used as source isolates.

Variations of genes may be readily constructed using standard techniques for making point mutations, for example. Also, U.S. Pat. No. 5,605,793, for example, describes methods for generating additional molecular diversity by using DNA reassembly after random fragmentation. Variant genes can be used to produce variant proteins; recombinant hosts can be used to produce the variant proteins. Fragments of full-length genes can be made using commercially available exonucleases or endonucleases according to standard procedures. For example, enzymes such as Bal31 or site-directed mutagenesis can be used to systematically cut off nucleotides from the ends of these genes. Also, genes which encode active fragments may be obtained using a variety of restriction enzymes. Proteases may be used to directly obtain active fragments of these toxins.

There are a number of methods for obtaining the pesticidal toxins of the instant invention. For example, antibodies to the pesticidal toxins disclosed and claimed herein can be used to identify and isolate other toxins from a mixture of proteins. Specifically, antibodies may be raised to the portions of the toxins which are most constant and most distinct from other *B.t.* toxins. These antibodies can then be used to specifically identify equivalent toxins with the characteristic activity by immunoprecipitation, enzyme linked immunosorbent assay (ELISA), or western blotting. Antibodies to the toxins disclosed herein, or to equivalent toxins, or to fragments of these toxins, can readily be prepared using standard procedures. The genes which encode these toxins can then be obtained from the source microorganism.

Because of the redundancy of the genetic code, a variety of different DNA sequences can encode the amino acid sequences disclosed herein. It is well within the skill of a person trained in the art to create these alternative DNA sequences encoding the same, or essentially the same, toxins. These variant DNA sequences are within the scope of the subject invention.

Certain toxins of the subject invention have been specifically exemplified herein. Since these toxins are merely exemplary of the toxins of the subject invention, it should be readily apparent that the subject invention comprises variant or equivalent toxins (and nucleotide sequences coding for equivalent toxins) having the same or similar pesticidal activity of the exemplified toxin. Equivalent toxins will have amino acid similarity (and/or homology) with an exemplified toxin. The amino acid identity will typically be greater than 60%, preferably greater than 75%, more preferably greater than 80%, even more preferably greater than 90%, and can be greater than 95%. Preferred polynucleotides and proteins of the subject invention can also be defined in terms of more particular identity and/or similarity ranges. For example, the identity and/or similarity can be 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% as compared to a sequence exemplified herein. Unless otherwise specified, as used herein percent sequence identity and/or similarity of two nucleic acids is determined using the algorithm of Karlin and Altschul (1990), *Proc. Natl. Acad. Sci. USA* 87:2264–2268, modified as in Karlin and Altschul (1993), *Proc. Natl. Acad. Sci. USA* 90:5873–5877. Such an algorithm is incorporated into the NBLAST and XBLAST programs of Altschul et al. (1990), *J. Mol. Biol.* 215:402–410. BLAST nucleotide searches are performed with the NBLAST program, score=100, wordlength=12, to obtain nucleotide sequences with the desired percent sequence identity. To obtain gapped alignments for comparison purposes, Gapped BLAST is used as described in Altschul et al. (1997), *Nucl. Acids Res.* 25:3389–3402. When utilizing BLAST and Gapped BLAST programs, the default parameters of the respective programs (NBLAST and XBLAST) are used. See http://www.ncbi.nih.gov. The scores can also be calculated using the methods and algorithms of Crickmore et al. as described in the Background section, above.

The amino acid homology will be highest in critical regions of the toxin which account for biological activity or are involved in the determination of three-dimensional configuration which ultimately is responsible for the biological activity. In this regard, certain amino acid substitutions are acceptable and can be expected if these substitutions are in regions which are not critical to activity or are conservative amino acid substitutions which do not affect the three-dimensional configuration of the molecule. For example, amino acids may be placed in the following classes: nonpolar, uncharged polar, basic, and acidic. Conservative substitutions whereby an amino acid of one class is replaced with another amino acid of the same type fall within the scope of the subject invention so long as the substitution does not materially alter the biological activity of the compound. Table 2 provides a listing of examples of amino acids belonging to each class.

TABLE 2

| Class of Amino Acid | Examples of Amino Acids |
|---|---|
| Nonpolar | Ala, Val, Leu, Ile, Pro, Met, Phe, Trp |
| Uncharged Polar | Gly, Ser, Thr, Cys, Tyr, Asn, Gln |
| Acidic | Asp, Glu |
| Basic | Lys, Arg, His |

In some instances, non-conservative substitutions can also be made. The critical factor is that these substitutions must not significantly detract from the biological activity of the toxin.

As used herein, reference to "isolated" polynucleotides and/or "purified" toxins refers to these molecules when they are not associated with the other molecules with which they would be found in nature; these terms would include their use in plants. Thus, reference to "isolated" and/or "purified" signifies the involvement of the "hand of man" as described herein.

Synthetic genes which are functionally equivalent to the toxins of the subject invention can also be used to transform hosts. Methods for the production of synthetic genes can be found in, for example, U.S. Pat. No. 5,380,831.

Transgenic hosts. The toxin-encoding genes of the subject invention can be introduced into a wide variety of microbial or plant hosts. In preferred embodiments, expression of the toxin gene results, directly or indirectly, in the intracellular production and maintenance of the pesticide proteins. When transgenic/recombinant/transformed host cells are ingested by the pests, the pests will ingest the toxin. This is the preferred manner in which to cause contact of the pest with the toxin. The result is a control (killing or making sick) of the pest. Alternatively, suitable microbial hosts, e.g.; Pseudomonas such as *P. fluorescens*, can be applied to the situs of the pest, where some of which can proliferate, and are ingested by the target pests. The microbe hosting the toxin gene can be treated under conditions that prolong the activity of the toxin and stabilize the cell. The treated cell, which retains the toxic activity, then can be applied to the environment of the target pest.

In preferred embodiments, recombinant plant cells and plants are used. Preferred plants (and plant cells) are corn and/or maize.

Where the *B.t.* toxin gene is introduced via a suitable vector into a microbial host, and said host is applied to the environment in a living state, certain host microbes should be used. Microorganism hosts are selected which are known to occupy the "phytosphere" (phylloplane, phyllosphere, rhizosphere, and/or rhizoplane) of one or more crops of interest. These microorganisms are selected so as to be capable of successfully competing in the particular environment (crop and other insect habitats) with the wild-type microorganisms, provide for stable maintenance and expression of the gene expressing the polypeptide pesticide, and, desirably, provide for improved protection of the pesticide from environmental degradation and inactivation.

A large number of microorganisms are known to inhabit the phylloplane (the surface of the plant leaves) and/or the rhizosphere (the soil surrounding plant roots) of a wide variety of important crops. These microorganisms include bacteria, algae, and fungi. Of particular interest are microorganisms, such as bacteria, e.g., genera Pseudomonas, Erwinia, Serratia, Klebsiella, Xanthomonas, Streptomyces, Rhizobium, Rhodopseudomonas, Methylophilius, Agrobacterium, Acetobacter, Lactobacillus, Arthrobacter, Azotobacter, Leuconostoc, and Alcaligenes; fungi, particularly yeast, e.g., genera Saccharomyces, Cryptococcus, Kluyveromyces, Sporobolomyces, Rhodotorula, and Aureobasidium. Of particular interest are such phytosphere bacterial species as *Pseudomonas syringae, Pseudomonas fluorescens, Serratia marcescens, Acetobacter xylinum, Agrobacterium tumefaciens, Rhodopseudomonas spheroides, Xanthomonas campestris, Rhizobium melioti, Alcaligenes entrophus*, and *Azotobacter vinlandii*; and phytosphere yeast species such as *Rhodotorula rubra, R. glutinis, R. marina, R. aurantiaca, Cryptococcus albidus, C. diffluens, C. laurentii, Saccharomyces rosei, S. pretoriensis, S. cerevisiae, Sporobolomyces roseus, S. odorus, Kluyveromyces veronae*, and *Aureobasidium pollulans*. Of particular interest are the pigmented microorganisms.

A wide variety of ways are available for introducing a *B.t.* gene encoding a toxin into the target host under conditions which allow for stable maintenance and expression of the gene. These methods are well known to those skilled in the art and are described, for example, in U.S. Pat. No. 5,135,867, which is incorporated herein by reference.

Treatment of cells. As mentioned above, *B.t.* or recombinant cells expressing a *B.t.* toxin can be treated to prolong the toxin activity and stabilize the cell. The pesticide microcapsule that is formed comprises the *B.t.* toxin within a cellular structure that has been stabilized and will protect the toxin when the microcapsule is applied to the environment of the target pest. Suitable host cells may include either prokaryotes or eukaryotes, normally being limited to those cells which do not produce substances toxic to higher organisms, such as mammals. However, organisms which produce substances toxic to higher organisms could be used, where the toxic substances are unstable or the level of application sufficiently low as to avoid any possibility of toxicity to a mammalian host. As hosts, of particular interest will be the prokaryotes and the lower eukaryotes, such as fungi.

The cell will usually be intact and be substantially in the proliferative form when treated, rather than in a spore form, although in some instances spores may be employed.

Treatment of the microbial cell, e.g., a microbe containing the *B.t.* toxin gene, can be by chemical or physical means, or by a combination of chemical and/or physical means, so long as the technique does not deleteriously affect the properties of the toxin, nor diminish the cellular capability of protecting the toxin. Examples of chemical reagents are halogenating agents, particularly halogens of atomic no. 17–80. More particularly, iodine can be used under mild conditions and for sufficient time to achieve the desired results. Other suitable techniques include treatment with aldehydes, such as glutaraldehyde; anti-infectives, such as zephiran chloride and cetylpyridinium chloride; alcohols, such as isopropyl and ethanol; various histologic fixatives, such as Lugol iodine, Bouin's fixative, various acids and Helly's fixative (See: Humason, Gretchen L., *Animal Tissue Techniques*, W. H. Freeman and Company, 1967); or a combination of physical (heat) and chemical agents that preserve and prolong the activity of the toxin produced in the cell when the cell is administered to the host environment. Examples of physical means are short wavelength radiation such as gamma-radiation and X-radiation, freezing, UV irradiation, lyophilization, and the like. Methods for treatment of microbial cells are disclosed in U.S. Pat. Nos. 4,695,455 and 4,695,462, which are incorporated herein by reference.

The cells generally will have enhanced structural stability which will enhance resistance to environmental conditions. Where the pesticide is in a proform, the method of cell treatment should be selected so as not to inhibit processing of the proform to the mature form of the pesticide by the target pest pathogen. For example, formaldehyde will crosslink proteins and could inhibit processing of the proform of a polypeptide pesticide. The method of treatment should retain at least a substantial portion of the bioavailability or bioactivity of the toxin.

Characteristics of particular interest in selecting a host cell for purposes of production include ease of introducing the *B.t.* gene into the host, availability of expression systems, efficiency of expression, stability of the pesticide in the host, and the presence of auxiliary genetic capabilities. Characteristics of interest for use as a pesticide microcapsule include protective qualities for the pesticide, such as thick cell walls, pigmentation, and intracellular packaging or formation of inclusion bodies; survival in aqueous environments; lack of mammalian toxicity; attractiveness to pests for ingestion; ease of killing and fixing without damage to the toxin; and the like. Other considerations include ease of formulation and handling, economics, storage stability, and the like.

Growth of cells. The cellular host containing the *B.t.* insecticidal gene may be grown in any convenient nutrient medium, preferably where the DNA construct provides a selective advantage, providing for a selective medium so that substantially all or all of the cells retain the *B.t.* gene. These cells may then be harvested in accordance with conventional ways. Alternatively, the cells can be treated prior to harvesting.

The *B.t.* cells of the invention can be cultured using standard art media and fermentation techniques. Upon completion of the fermentation cycle the bacteria can be harvested by first separating the *B.t.* spores and crystals from the fermentation broth by means well known in the art. The recovered *B.t.* spores and crystals can be formulated into a wettable powder, liquid concentrate, granules or other formulations by the addition of surfactants, dispersants, inert carriers, and other components to facilitate handling and application for particular target pests. These formulations and application procedures are all well known in the art.

Formulations. Formulated bait granules containing an attractant and spores and crystals of the *B.t.* isolates, or recombinant microbes comprising the genes obtainable from the *B.t.* isolates disclosed herein, can be applied to the soil. Formulated product can also be applied as a seed-coating or root treatment or total plant treatment at later stages of the crop cycle. Plant and soil treatments of *B.t.* cells may be employed as wettable powders, granules or dusts, by mixing with various inert materials, such as inorganic minerals (phyllosilicates, carbonates, sulfates, phosphates, and the like) or botanical materials (powdered corncobs, rice hulls, walnut shells, and the like). The formulations may include spreader-sticker adjuvants, stabilizing agents, other pesticidal additives, or surfactants. Liquid formulations may be aqueous-based or non-aqueous and employed as foams, gels, suspensions, emulsifiable concentrates, or the like. The ingredients may include rheological agents, surfactants, emulsifiers, dispersants, or polymers.

As would be appreciated by a person skilled in the art, the pesticidal concentration will vary widely depending upon the nature of the particular formulation, particularly whether it is a concentrate or to be used directly. The pesticide will be present in at least 1% by weight and may be 100% by weight. The dry formulations will have from about 1–95% by weight of the pesticide while the liquid formulations will generally be from about 1–60% by weight of the solids in the liquid phase. The formulations will generally have from about $10^2$ to about $10^4$ cells/mg. These formulations will be administered at about 50 mg (liquid or dry) to 1 kg or more per hectare.

The formulations can be applied to the environment of the pest, e.g., soil and foliage, by spraying, dusting, sprinkling, or the like.

Mutants. Mutants of the isolates of the invention can be made by procedures well known in the art. For example, an asporogenous mutant can be obtained through ethylmethane sulfonate (EMS) mutagenesis of an isolate. The mutants can be made using ultraviolet light and nitrosoguanidine by procedures well known in the art.

A smaller percentage of the asporogenous mutants will remain intact and not lyse for extended fermentation periods; these strains are designated lysis minus (−). Lysis minus strains can be identified by screening asporogenous mutants in shake flask media and selecting those mutants that are still intact and contain toxin crystals at the end of the fermentation. Lysis minus strains are suitable for a cell treatment process that will yield a protected, encapsulated toxin protein.

To prepare a phage resistant variant of said asporogenous mutant, an aliquot of the phage lysate is spread onto nutrient agar and allowed to dry. An aliquot of the phage sensitive bacterial strain is then plated directly over the dried lysate and allowed to dry. The plates are incubated at 30° C. The plates are incubated for 2 days and, at that time, numerous colonies could be seen growing on the agar. Some of these colonies are picked and subcultured onto nutrient agar plates. These apparent resistant cultures are tested for resistance by cross streaking with the phage lysate. A line of the phage lysate is streaked on the plate and allowed to dry. The presumptive resistant cultures are then streaked across the phage line. Resistant bacterial cultures show no lysis anywhere in the streak across the phage line after overnight incubation at 30° C. The resistance to phage is then reconfirmed by plating a lawn of the resistant culture onto a nutrient agar plate. The sensitive strain is also plated in the same manner to serve as the positive control. After drying, a drop of the phage lysate is placed in the center of the plate and allowed to dry. Resistant cultures showed no lysis in the area where the phage lysate has been placed after incubation at 30° C. for 24 hours.

Following are examples which illustrate procedures for practicing the invention. These examples should not be construed as limiting. All percentages are by weight and all solvent mixture proportions are by volume unless otherwise noted.

EXAMPLE 1

Culturing of *B.t.* Isolates of the Invention

A subculture of the *B.t.* isolates, or mutants thereof, can be used to inoculate the following medium, a peptone, glucose, salts medium.

| | |
|---|---|
| Bacto Peptone | 7.5 g/l |
| Glucose | 1.0 g/l |
| $KH_2PO_4$ | 3.4 g/l |
| $K_2HPO_4$ | 4.35 g/l |
| Salt Solution | 5.0 ml/l |
| $CaCl_2$ Solution | 5.0 ml/l |
| pH | 7.2 |
| Salts Solution (100 ml) | |
| $MgSO_4.7\ H_2O$ | 2.46 g |
| $MnSO_4.H_2O$ | 0.04 g |
| $ZnSO_4.7\ H_2O$ | 0.28 g |
| $FeSO_4.7\ H_2O$ | 0.40 g |
| $CaCl_2$ Solution (100 ml) | |
| $CaCl_2.2\ H_2O$ | 3.66 g |

The salts solution and $CaCl_2$ solution are filter-sterilized and added to the autoclaved and cooked broth at the time of inoculation. Flasks are incubated at 30° C. on a rotary shaker at 200 rpm for 64 hr.

The above procedure can be readily scaled up to large fermentors by procedures well known in the art.

The *B.t.* spores and/or crystals, obtained in the above fermentation, can be isolated by procedures well known in the art. A frequently-used procedure is to subject the harvested fermentation broth to separation techniques, e.g., centrifugation.

EXAMPLE 2

Activity of Sporulated *Bacillus thuringiensis* Cultures on Corn Rootworm

Liquid cultures of PS80JJ1, PS149B1 or PS167H2 were grown to sporulation in shake flasks and pelleted by centrifugation. Culture pellets were resuspended in water and assayed for activity against corn rootworm in top load bioassays as described above. The amounts of 14 kDa and 44.3 kDa proteins present in the culture pellets were estimated by densitometry and used to calculate specific activity expressed as $LC_{50}$. Activity of each native *B. thuringiensis* strain is presented in Table 3 (WCRW top load bioassay of *B.t.* strains).

TABLE 3

WCRW Top Load Bioassay of *B.t.* Strains

| *B.t.* strain | $LC_{50}$ ($\mu g/cm^2$)* | 95% CL | Slope |
|---|---|---|---|
| PS80JJ1 | 6 | 4–8 | 1.5 |
| PS167H2 | 6 | 4–9 | 1.6 |
| PS149B1 | 8 | 4–12 | 1.8 |
| CryB cell blank | 4% | N/A | N/A |
| Water blank | 4% | N/A | N/A |

*Percentage mortality at top dose is provided for controls

EXAMPLE 3

Protein Purification for 45 kDa 80JJ1 Protein

One gram of lyophilized powder of 80JJ1 was suspended in 40 ml of buffer containing 80 mM Tris-Cl pH 7.8, 5 mM EDTA, 100 $\mu$M PMSF, 0.5 $\mu$g/ml Leupeptin, 0.7 $\mu$g/ml Pepstatin, and 40 $\mu$g/ml Bestatin. The suspension was centrifuged, and the resulting supernatant was discarded. The pellet was washed five times using 35–40 ml of the above buffer for each wash. The washed pellet was resuspended in 10 ml of 40% NaBr, 5 mM EDTA, 100 $\mu$M PMSF, 0.5 $\mu$g/ml Leupeptin, 0.7 $\mu$g/ml Pepstatin, and 40 $\mu$g/ml Bestatin and placed on a rocker platform for 75 minutes. The NaBr suspension was centrifuged, the supernatant was removed, and the pellet was treated a second time with 40% NaBr, 5 mM EDTA, 100 $\mu$M PMSF, 0.5 $\mu$g/ml Leupeptin, 0.7 $\mu$g/ml Pepstatin, and 40 $\mu$g/ml Bestatin as above. The supernatants (40% NaBr soluble) were combined and dialyzed against 10 mM CAPS pH 10.0, 1 mM EDTA at 4° C. The dialyzed extracts were centrifuged and the resulting supernatant was removed. The pellet (40% NaBr dialysis pellet) was suspended in 5 ml of $H_2O$ and centrifuged. The resultant supernatant was removed and discarded. The washed pellet was washed a second time in 10 ml of $H_2O$ and centrifuged as above. The washed pellet was suspended in 1.5 ml of $H_2O$ and contained primarily three protein bands with apparent mobilities of approximately 47 kDa, 45 kDa, and 15 kDa when analyzed using SDS-PAGE. At this stage of purification, the suspended 40% NaBr dialysis pellet contained approximately 21 mg/ml of protein by Lowry assay.

The proteins in the pellet suspension were separated using SDS-PAGE (Laemlli, U. K. [1970] *Nature* 227:680) in 15% acrylamide gels. The separated proteins were then electrophoretically blotted to a PVDF membrane (Millipore Corp.) in 10 mM CAPS pH 11.0, 10% MeOH at 100 V constant. After one hour the PVDF membrane was rinsed in water briefly and placed for 3 minutes in 0.25% Coomassie blue R-250, 50% methanol, 5% acetic acid. The stained membrane was destained in 40% MeOH, 5% acetic acid. The destained membrane was air-dried at room temperature (LeGendre et al. [1989] *In A Practical Guide to Protein Purification For Microsequencing*, P. Matsudaira, ed., Academic Press, New York, N.Y.). The membrane was sequenced using automated gas phase Edman degradation (Hunkapillar, M. W., R. M. Hewick, W. L. Dreyer, L. E. Hood [1983] *Meth. Enzymol.* 91:399).

The amino acid analysis revealed that the N-terminal sequence of the 45 kDa band was as follows: Met-Leu-Asp-Thr-Asn (SEQ ID NO:1).

The 47 kDa band was also analyzed and the N-terminal amino acid sequence was determined to be the same 5-amino acid sequence as SEQ ID NO:1. Therefore, the N-terminal amino acid sequences of the 47 kDa peptide and the 45 kDa peptide were identical.

This amino acid sequence also corresponds to a sequence obtained from a 45 kDa peptide obtained from PS80JJ1 spore/crystal powders, using another purification protocol, with the N-terminal sequence as follows: Met-Leu-Asp-Thr-Asn-Lys-Val-Tyr-Glu-Ile-Ser-Asn-Leu-Ala-Asn-Gly-Leu-Tyr-Thr-Ser-Thr-Tyr-Leu-Ser-Leu (SEQ ID NO:2).

EXAMPLE 4

Purification of the 14 kDa Peptide of PS80JJ1

0.8 ml of the white dialysis suspension (approximately 21 mg/ml) containing the 47 kDa, 45 kDa, and 15 kDa peptides, was dissolved in 10 ml of 40% NaBr, and 0.5 ml of 100 mM EDTA were added. After about 18 hours (overnight), a white opaque suspension was obtained. This was collected by centrifugation and discarded. The supernatant was concentrated in a Centricon-30 (Amicon Corporation) to a final volume of approximately 15 ml. The filtered volume was washed with water by filter dialysis and incubated on ice, eventually forming a milky white suspension. The suspension was centrifuged and the pellet and supernatant were separated and retained. The pellet was then suspended in 1.0 ml water (approximately 6 mg/ml). The pellet contained substantially pure 15 kDa protein when analyzed by SDS-PAGE.

The N-terminal amino acid sequence was determined to be: Ser-Ala-Arg-Glu-Val-His-Ile-Glu-Ile-Asn-Asn-Thr-Arg-His-Thr-Leu-Gln-Leu-Glu-Ala-Lys-Thr-Lys-Leu (SEQ ID NO:3).

EXAMPLE 5

Bioassay of Protein

A preparation of the insoluble fraction from the dialyzed NaBr extract of 80JJ1 containing the 47 kDa, 45 kDa, and 15 kDa peptides was bioassayed against Western corn rootworm and were found to exhibit significant toxin activity.

EXAMPLE 6

Protein Purification and Characterization of PS149B1 45 kDa Protein

The P1 pellet was resuspended with two volumes of deionized water per unit wet weight, and to this was added nine volumes of 40% (w/w) aqueous sodium bromide. This and all subsequent operations were carried out on ice or at 4–6° C. After 30 minutes, the suspension was diluted with 36 volumes of chilled water and centrifuged at 25,000×g for 30 minutes to give a pellet and a supernatant.

The resulting pellet was resuspended in 1–2 volumes of water and layered on a 20–40% (w/w) sodium bromide gradient and centrifuged at 8,000×g for 100 minutes. The layer banding at approximately 32% (w/w) sodium bromide (the "inclusions", or INC) was recovered and dialyzed overnight against water using a dialysis membrane with a 6–8 kDa MW cut-off. Particulate material was recovered by centrifugation at 25,000×g, resuspended in water, and aliquoted and assayed for protein by the method of Lowry and by SDS-PAGE.

The resulting supernatant was concentrated 3- to 4-fold using Centricon-10 concentrators, then dialyzed overnight against water using a dialysis membrane with a 6–8 kDa MW cut-off. Particulate material was recovered by centrifugation at 25,000×g, resuspended in water, and aliquoted and assayed for protein by the method of Lowry and by SDS-PAGE. This fraction was denoted as P1.P2.

The peptides in the pellet suspension were separated using SDS-PAGE (Laemlli, U. K., supra) in 15% acrylamide gels. The separated proteins were then electrophoretically blotted to a PVDF membrane (Millipore Corp.) in 10 mM CAPS pH 11.0, 10% MeOH at 100 V constant. After one hour the PVDF membrane was rinsed in water briefly and placed for 3 minutes in 0.25% Coomassie blue R-250, 50% methanol, 5% acetic acid. The stained membrane was destained in 40% MeOH, 5% acetic acid. The destained membrane was air-dried at room temperature (LeGendre et al., supra). The membrane was sequenced using automated gas phase Edman degradation (Hunkapillar et al., supra).

Protein analysis indicated the presence of two major polypeptides, with molecular weights of 47 kDa and 14 kDa. Molecular weights were measured against standard polypeptides of known molecular weight. This process provides only an estimate of true molecular weight. The 47 kDa band from PS149B1 migrated on SDS-PAGE in a manner indistinguishable from the 47 kDa protein from PS80JJ1. Likewise, the 14 kDa band from PS149B1 migrated on SDS-PAGE in a manner indistinguishable from 14 kDa bands from PS167H2 and PS80JJ1. Apart from these two polypeptides, which were estimated to account for 25–35% (47 kDa) and 35–55% (15 kDa) of the Coomassie staining material respectively, there may be minor bands, including those of estimated MW at 46 kDa, 130 kDa, and 70 kDa.

Protein analysis indicated that fraction INC contained a single polypeptide with MW of 47 kDa, and that fraction P1.P2 contained a single polypeptide with MW of 14 kDa. These polypeptides were recovered in yields greater than 50% from P1.

The N-terminal amino acid sequence for the purified 47 kDa protein from PS149B1 is: Met-Leu-Asp-Thr-Asn-Lys-Val-Tyr-Glu-Ile-Ser-Asn-His-Ala-Asn-Gly-Leu-Tyr-Ala-Ala-Thr-Tyr-Leu-Ser-Leu (SEQ ID NO:4).

The N-terminal amino acid sequence for the purified 14 kDa protein from PS149B1 is: Ser-Ala-Arg-Glu-Val-His-Ile-Asp-Val-Asn-Asn-Lys-Thr-Gly-His-Thr-Leu-Gln-Leu-Glu-Asp-Lys-Thr-Lys-Leu-Asp-Gly-Gly-Arg-Trp-Arg-Thr-Ser- Pro-Xaa-Asn-Val-Ala-Asn-Asp-Gln-Ile-Lys-Thr-Phe-Val-Ala-Glu-Ser-Asn (SEQ ID NO:5).

EXAMPLE 7

Amino Acid Sequence for 45 kDa and 14 kDa Toxins of PS167H2

The N-terminal amino acid sequence for the purified 45 kDa protein from PS167H2 is: Met-Leu-Asp-Thr-Asn-Lys-Ile-Tyr-Glu-Ile-Ser-Asn-Tyr-Ala-Asn-Gly-Leu-His-Ala-Ala-Thr-Tyr-Leu-Ser-Leu (SEQ ID NO:6).

The N-terminal amino acid sequence for the purified 14 kDa protein from PS167H2 is: Ser-Ala-Arg-Glu-Val-His-Ile-Asp-Val-Asn-Asn-Lys-Thr-Gly-His-Thr-Leu-Gln-Leu-Glu-Asp-Lys-Thr-Lys-Leu (SEQ ID NO:7).

These amino acid sequences can be compared to the sequence obtained for the 47 kDa peptide obtained from 80JJ1 spore/crystal powders with the N-terminal sequence (SEQ ID NO:1) and to the sequence obtained for the 14 kDa peptide obtained from 80JJ1 spore/crystal powders with the N-terminal sequence (SEQ ID NO:3).

Clearly, the 45–47 kDa proteins are highly related, and the 14 kDa proteins are highly related.

EXAMPLE 8

Bioassay of Protein

The purified protein fractions from PS149B1 were bioassayed against western corn rootworm and found to exhibit significant toxin activity when combined. In fact, the combination restored activity to that noted in the original preparation (P1). The following bioassay data set presents percent mortality and demonstrates this effect.

TABLE 4

| Concentration ($\mu g/cm^2$) | PI | INC | P1.P2 | INC + P1.P2 |
|---|---|---|---|---|
| 300 | 88, 100, 94 | 19 | 13 | 100 |
| 100 | 94, 50, 63 | 31 | 38 | 94 |
| 33.3 | 19, 19, 44 | 38 | 13 | 50 |
| 11.1 | 13, 56, 25 | 12 | 31 | 13 |
| 3.7 | 0, 50, 0 | 0 | 31 | 13 |
| 1.2 | 13, 43, 12 | 0 | 12 | 19 |
| 0.4 | 6, 12, 6 | 25 | 19 | 6 |

EXAMPLE 9

Molecular Cloning, Expression, and DNA Sequence Analysis of a Novel δ-Endotoxin Gene From *Bacillus thuringiensis* Strain PS80JJ1

Total cellular DNA was prepared from *Bacillus thuringiensis* (*B.t.*) cells grown to an optical density, at 600 nm, of 1.0. Cells were pelleted by centrifugation and resuspended in protoplast buffer (20 mg/ml lysozyme in 0.3 M sucrose, 25 mM Tris-Cl [pH 8.0], 25 mM EDTA). After incubation at 37° C. for 1 hour, protoplasts were lysed by two cycles of freezing and thawing. Nine volumes of a solution of 0.1 M NaCl, 0.1% SDS, 0.1 M Tris-Cl were added to complete lysis. The cleared lysate was extracted twice with phenol:chloroform (1:1). Nucleic acids were precipitated with two volumes of ethanol and pelleted by centrifugation. The pellet was resuspended in TE buffer and RNase was added to a final concentration of 50 μg/ml. After incubation at 37° C. for 1 hour, the solution was extracted once each with phenol:chloroform (1:1) and TE-saturated chloroform. DNA was precipitated from the aqueous phase by the addition of one-tenth volume of 3 M NaOAc and two volumes of ethanol. DNA was pelleted by centrifugation, washed with 70% ethanol, dried, and resuspended in TE buffer.

An oligonucleotide probe for the gene encoding the PS80JJ1 45 kDa toxin was designed from N-terminal peptide sequence data. The sequence of the 29-base oligonucleotide probe was:

5'-ATG YTW GAT ACW AAT AAA GTW TAT GAA AT-3' (SEQ ID NO:8)

This oligonucleotide was mixed at four positions as shown. This probe was radiolabeled with $^{32}P$ and used in standard condition hybridization of Southern blots of PS80JJ1 total cellular DNA digested with various restriction endonucleases. Representative autoradiographic data from these experiments showing the sizes of DNA restriction fragments containing sequence homology to the 44.3 kDa toxin oligonucleotide probe of SEQ ID NO:8 are presented in Table 5.

TABLE 5

RFLP of PS80JJ1 cellular DNA fragments on Southern blots that hybridized under standard conditions with the 44.3 kDa toxin gene oligonucleotide probe (SEQ ID NO: 8)

| Restriction Enzyme | Approximate Fragment Size (kbp) |
|---|---|
| EcoRI | 6.0 |
| HindIII | 8.3 |
| KpnI | 7.4 |
| PstI | 11.5 |
| XbaI | 9.1 |

These DNA fragments identified in these analyses contain all or a segment of the PS80JJ1 45 kDa toxin gene. The approximate sizes of the hybridizing DNA fragments in Table 5 are in reasonable agreement with the sizes of a subset of the PS80JJ1 fragments hybridizing with a PS80JJ1 45 kDa toxin subgene probe used in separate experiments, as predicted (see Table 6, below).

A gene library was constructed from PS80JJ1 DNA partially digested with Sau3AI. Partial restriction digests were fractionated by agarose gel electrophoresis. DNA fragments 9.3 to 23 kbp in size were excised from the gel, electroeluted from the gel slice, purified on an Elutip-D ion exchange column (Schleicher and Schuell, Keene, N H), and recovered by ethanol precipitation. The Sau3AI inserts were ligated into BamHI-digested LambdaGem-11 (Promega, Madison, Wis.). Recombinant phage were packaged and plated on *E. coli* KW251 cells. Plaques were screened by hybridization with the oligonucleotide probe described above. Hybridizing phage were plaque-purified and used to infect liquid cultures of *E. coli* KW251 cells for isolation of DNA by standard procedures (Maniatis et al., supra).

Southern blot analysis revealed that one of the recombinant phage isolates contained an approximately 4.8 kbp XbaI-SacI band that hybridized to the PS80JJ1 toxin gene probe. The SacI site flanking the PS80JJ1 toxin gene is a phage vector cloning site, while the flanking XbaI site is located within the PS80JJ1 DNA insert. This DNA restriction fragment was subcloned by standard methods into pBluescript S/K (Stratagene, San Diego, Calif.) for sequence analysis. The resultant plasmid was designated pMYC2421. The DNA insert was also subcloned into pHTBlueII (an *E. coli/B. thuringiensis* shuttle vector comprised of pBluescript S/K [Stratagene, La Jolla, Calif.] and the replication origin from a resident *B.t.* plasmid [D. Lereclus et al. (1989) *FEMS Microbiology Letters* 60:211–218]) to yield pMYC2420.

An oligonucleotide probe for the gene encoding the PS80JJ1 14 kDa toxin was designed from N-terminal peptide sequence data. The sequence of the 28-base oligonucleotide probe was: 5' GW GAA GTW CAT ATW GAA ATW AAT AAT AC 3' (SEQ ID NO:29). This oligonucleotide was mixed at four positions as shown. The probe was radiolabelled with $^{32}P$ and used in standard condition hybridizations of Southern blots of PS80JJ1 total cellular and pMYC2421 DNA digested with various restriction endonucleases. These RFLP mapping experiments demonstrated that the gene encoding the 14 kDa toxin is located on the same genomic EcoRI fragment that contains the N-terminal coding sequence for the 44.3 kDa toxin.

To test expression of the PS80JJ1 toxin genes in *B.t.*, pMYC2420 was transformed into the acrystalliferous (Cry-) *B.t.* host, CryB (A. Aronson, Purdue University, West Lafayette, Ind.), by electroporation. Expression of both the approximately 14 and 44.3 kDa PS80JJ1 toxins encoded by pMYC2420 was demonstrated by SDS-PAGE analysis. Toxin crystal preparations from the recombinant CryB [pMYC2420] strain, MR536, were assayed and found to be active against western corn rootworm.

The PS80JJ1 toxin genes encoded by pMYC2421 were sequenced using the ABI373 automated sequencing system and associated software. The sequence of the entire genetic locus containing both open reading frames and flanking nucleotide sequences is shown in SEQ ID NO:30. The termination codon of the 14 kDa toxin gene is 121 base pairs upstream (5') from the initiation codon of the 44.3 kDa toxin gene (FIG. 2). The PS80JJ1 14 kDa toxin open reading frame nucleotide sequence (SEQ ID NO:31), the 44.3 kDa toxin open reading frame nucleotide sequence (SEQ ID NO:10), and the respective deduced amino acid sequences (SEQ ID NO:32 and SEQ ID NO:11) are novel compared to other toxin genes encoding pesticidal proteins.

Thus, the nucleotide sequence encoding the 14 kDa toxin of PS80JJ1 is shown in SEQ ID NO:31. The deduced amino acid sequence of the 14 kDa toxin of PS80JJ1 is shown in SEQ ID NO:32. The nucleotide sequences encoding both the 14 and 45 kDa toxins of PS80JJ1, as well as the flanking sequences, are shown in SEQ ID NO:30. The relationship of these sequences is shown in FIG. 2.

A subculture of *E. coli* NM522 containing plasmid pMYC2421 was deposited in the permanent collection of the Patent Culture Collection (NRRL), Regional Research Center, 1815 North University Street, Peoria, Ill. 61604 USA on Mar. 28, 1996. The accession number is NRRL B-21555.

EXAMPLE 10

RFLP and PCR Analysis of Additional Novel δ-Endotoxin Genes From *Bacillus thuringiensis* Strains PS149B1 and PS167H2

Two additional strains active against corn rootworm, PS149B1 and PS167H2, also produce parasporal protein crystals comprised in part of polypeptides approximately 14 and 45 kDa in size. Southern hybridization and partial DNA sequence analysis were used to examine the relatedness of these toxins to the 80JJ1 toxins. DNA was extracted from these *B.t.* strains as described above, and standard Southern hybridizations were performed using the 14 kDa toxin oligonucleotide probe (SEQ ID NO:29) and an approximately 800 bp PCR fragment of the 80JJ1 44.3 kDa toxin gene-encoding sequence. RFLP data from these experiments showing the sizes of DNA restriction fragments containing sequence homology to the 44.3 kDa toxin are presented in Table 6. RFLP data from these experiments showing the sizes of DNA restriction fragments containing sequence homology to the approximately 14 kDa toxin are presented in Table 7.

TABLE 6

RFLP of PS80JJ1, PS149B1, and PS167H2 cellular DNA fragments on Southern blots that hybridized with the approximately 800 bp PS80JJ1 44.3 kDa toxin subgene probe under standard conditions

| | Strain | | |
|---|---|---|---|
| | PS80JJ1 | PS149B1 | PS167H2 |
| Restriction enzyme | Approximate fragment size (kbp) | | |
| EcoRI | 6.4 | 5.7 | 2.6 |
| | 1.3 | 2.8 | |
| | 0.6 | | |
| HindIII | 8.2 | 6.2 | 4.4 |
| KpnI | 7.8 | 10.0 | 11.5 |

TABLE 6-continued

RFLP of PS80JJ1, PS149B1, and PS167H2 cellular DNA fragments on Southern blots that hybridized with the approximately 800 bp PS80JJ1 44.3 kDa toxin subgene probe under standard conditions

| | Strain | | |
|---|---|---|---|
| Restriction enzyme | PS80JJ1 | PS149B1 | PS167H2 |
| | Approximate fragment size (kbp) | | |
| PstI | 12.0 | 9.2 | 9.2 |
| | | | 8.2 |
| XbaI | 9.4 | 10.9 | 10.9 |
| SacI | 17.5 | 15.5 | 11.1 |
| | 13.1 | 10.5 | 6.3 |

Each of the three strains exhibited unique RFLP patterns. The hybridizing DNA fragments from PS149B1 or PS167H2 contain all or part of toxin genes with sequence homology to the PS80JJ1 44.3 kDa toxin.

TABLE 7

Restriction fragment length polymorphisms of PS80JJ1, PS149B1, and PS167H2 cellular DNA fragments on Southern blots that hybridized with the PS80JJ1 14 kDa toxin oligonucleotide probe under standard conditions

| | Strain | | |
|---|---|---|---|
| Restriction enzyme | PS80JJ1 | PS149B1 | PS167H2 |
| | Approximate fragment size (kbp) | | |
| EcoRI | 5.6 | 2.7 | 2.7 |
| HindIII | 7.1 | 6.0 | 4.7 |
| XbaI | 8.4 | 11.2 | 11.2 |

Each of the three strains exhibited unique RFLP patterns. The hybridizing DNA fragments from PS149B1 or PS167H2 contain all or part of toxin genes with sequence homology to the PS80JJ1 14 kDa toxin gene.

Portions of the toxin genes in PS149B1 or PS167H2 were amplified by PCR using forward and reverse oligonucleotide primer pairs designed based on the PS80JJ1 44.3 kDa toxin gene sequence. For PS149B1, the following primer pair was used:

Forward:

5'-ATG YTW GAT ACW AAT AAA GTW TAT GAA AT-3' (SEQ ID NO:8)

Reverse:

5'-GGA TTA TCT ATC TCT GAG TGT TCT TG-3' (SEQ ID NO:9)

For PS167H2, the same primer pair was used. These PCR-derived fragments were sequenced using the ABI373 automated sequencing system and associated software. The partial gene and peptide sequences obtained are shown in SEQ ID NO:12–15. These sequences contain portions of the nucleotide coding sequences and peptide sequences for novel corn rootworm-active toxins present in *B.t.* strains PS149B1 or PS167H2.

EXAMPLE 11

Molecular Cloning and DNA Sequence Analysis of Novel δ-Endotoxin Genes From *Bacillus thuringiensis* Strains PS149B1 and PS167H2

Total cellular DNA was extracted from strains PS149B1 and PS167H2 as described for PS80JJ1. Gene libraries of size-fractionated Sau3A partial restriction fragments were constructed in Lambda-Gem11 for each respective strain as previously described. Recombinant phage were packaged and plated on *E. coli* KW251 cells. Plaques were screened by hybridization with the oligonucleotide probe specific for the 44 kDa toxin gene. Hybridizing phage were plaque-purified and used to infect liquid cultures of *E. coli* KW251 cells for isolation of DNA by standard procedures (Maniatis et al., supra).

For PS167H2, Southern blot analysis revealed that one of the recombinant phage isolates contained an approximately 4.0 to 4.4 kbp HindIII band that hybridized to the PS80JJ1 44 kDa toxin gene 5' oligonucleotide probe (SEQ ID NO:8). This DNA restriction fragment was subcloned by standard methods into pBluescript S/K (Stratgene, San Diego, Calif.) for sequence analysis. The fragment was also subcloned into the high copy number shuttle vector, pHT370 (Arantes, O., D. Lereclus [1991] *Gene* 108:115–119) for expression analyses in *Bacillus thuringiensis* (see below). The resultant recombinant, high copy number bifunctional plasmid was designated pMYC2427.

The PS167H2 toxin genes encoded by pMYC2427 were sequenced using the ABI automated sequencing system and associated software. The sequence of the entire genetic locus containing both open reading frames and flanking nucleotide sequences is shown in SEQ ID NO:34. The termination codon of the 14 kDa toxin gene is 107 base pairs upstream (5') from the initiation codon of the 44 kDa toxin gene. The PS167H2 14 kDa toxin coding sequence (SEQ ID NO:35), the 44 kDa toxin coding sequence (SEQ ID NO:37), and the respective deduced amino acid sequences, SEQ ID NO:36 and SEQ ID NO:38, are novel compared to other known toxin genes encoding pesticidal proteins. The toxin genes are arranged in a similar manner to, and have some homology with, the PS80JJ1 14 and 44 kDa toxins.

A subculture of *E. coli* NM522 containing plasmid pMYC2427 was deposited in the permanent collection of the Patent Culture Collection (NRRL), Regional Research Center, 1815 North University Street, Peoria, Ill. 61604 USA on Mar. 26, 1997. The accession number is NRRL B-21672.

For PS149B1, Southern blot analysis using the PS80JJ1 44 kDa oligonucleotide 5' probe (SEQ ID NO:8) demonstrated hybridization of an approximately 5.9 kbp ClaI DNA fragment. Complete ClaI digests of PS149B1 genomic DNA were size fractionated on agarose gels and cloned into pHTBlueII. The fragment was also subcloned into the high copy number shuttle vector, pHT370 (Arantes, O., D. Lereclus [1991] *Gene* 108:115–119) for expression analyses in *Bacillus thuringiensis* (see below). The resultant recombinant, high copy number bifunctional plasmid was designated pMYC2429.

The PS149B1 toxin genes encoded by pMYC2429 were sequenced using the ABI automated sequencing system and associated software. The sequence of the entire genetic locus containing both open reading frames and flanking nucleotide sequences is shown in SEQ ID NO:39. The termination codon of the 14 kDa toxin gene is 108 base pairs upstream (5') from the initiation codon of the 44 kDa toxin gene. The PS149B1 14 kDa toxin coding sequence (SEQ ID NO:40), the 44 kDa toxin coding sequence (SEQ ID NO:42), and the respective deduced amino acid sequences, SEQ ID NO:41 and SEQ ID NO:43, are novel compared to other known toxin genes encoding pesticidal proteins. The toxin genes are arranged in a similar manner as, and have some homology with, the PS80JJ1 and PS167H2 14 and 44 kDa toxins. Together, these three toxin operons comprise a new family of pesticidal toxins.

A subculture of *E. coli* NM522 containing plasmid pMYC2429 was deposited in the permanent collection of the Patent Culture Collection (NRRL), Regional Research Center, 1815 North University Street, Peoria, Ill. 61604 USA on Mar. 26, 1997. The accession number is NRRL B-21673.

EXAMPLE 12

PCR Amplification for Identification and Cloning Novel Corn Rootworm-active Toxin The DNA and peptide sequences of the three novel approximately 45 kDa corn rootworm-active toxins from PS80JJ1, PS149B1, and PS167H2 (SEQ ID NOS. 12–15) were aligned with the Genetics Computer Group sequence analysis program Pileup using a gap weight of 3.00 and a gap length weight of 0.10. The sequence alignments were used to identify conserved peptide sequences to which oligonucleotide primers were designed that were likely to hybridize to genes encoding members of this novel toxin family. Such primers can be used in PCR to amplify diagnostic DNA fragments for these and related toxin genes. Numerous primer designs to various sequences are possible, four of which are described here to provide an example. These peptide sequences are:

Asp-Ile-Asp-Asp-Tyr-Asn-Leu (SEQ ID NO:16)

Trp-Phe-Leu-Phe-Pro-Ile-Asp (SEQ ID NO:17)

Gln-Ile-Lys-Thr-Thr-Pro-Tyr-Tyr (SEQ ID NO:18)

Tyr-Glu-Trp-Gly-Thr-Glu (SEQ ID NO:19).

The corresponding nucleotide sequences are:

5'-GATATWGATGAYTAYAAYTTR-3' (SEQ ID NO:20)

5'-TGGTTTTTRTTTCCWATWGAY-3' (SEQ ID NO:21)

5'-CAAATHAAAACWACWCCATATTAT-3' (SEQ ID NO:22)

5'-TAYGARTGGGGHACAGAA-3' (SEQ ID NO:23).

Forward primers for polymerase amplification in thermocycle reactions were designed based on the nucleotide sequences of SEQ ID NOs:20 and 21.

Reverse primers were designed based on the reverse complement of SEQ ID NOs:22 and 23:

5'-ATAATATGGWGTWGTTTTDATTTG-3' (SEQ ID NO:24)

5'-TTCTGTDCCCCAYTCRTA-3' (SEQ ID NO:25).

These primers can be used in combination to amplify DNA fragments of the following sizes (Table 8) that identify genes encoding novel corn rootworm toxins.

TABLE 8

Predicted sizes of diagnostic DNA fragments (base pairs) amplifiable with primers specific for novel corn rootworm-active toxins

| Primer pair (SEQ ID NO.) | DNA fragment size (bp) |
|---|---|
| 20 + 24 | 495 |
| 20 + 25 | 594 |
| 21 + 24 | 471 |
| 21 + 25 | 580 |

Similarly, entire genes encoding novel corn rootworm-active toxins can be isolated by polymerase amplification in thermocycle reactions using primers designed based on DNA sequences flanking the open reading frames. For the PS80JJ1 44.3 kDa toxin, one such primer pair was designed, synthesized, and used to amplify a diagnostic 1613 bp DNA fragment that included the entire toxin coding sequence. These primers are:

Forward: 5'-CTCAAAGCGGATCAGGAG-3' (SEQ ID NO:26)

Reverse: 5'-GCGTATTCGGATATGCTTGG-3' (SEQ ID NO:27).

For PCR amplification of the PS80JJ1 14 kDa toxin, the oligonucleotide coding for the N-terminal peptide sequence (SEQ ID NO:29) can be used in combination with various reverse oligonucleotide primers based on the sequences in the PS80JJ1 toxin gene locus. One such reverse primer has the following sequence:

5' CATGAGATTTATCTCCTGATCCGC 3' (SEQ ID NO:33).

When used in standard PCR reactions, this primer pair amplified a diagnostic 1390 bp DNA fragment that includes the entire 14 kDa toxin coding sequence and some 3' flanking sequences corresponding to the 121 base intergenic spacer and a portion of the 44.3 kDa toxin gene. When used in combination with the 14 kDa forward primer, PCR will generate a diagnostic 322 base pair DNA fragment.

EXAMPLE 13

Clone Dose-response Bioassays

The PS80JJ1 toxin operon was subcloned from pMYC2421 into pHT370 for direct comparison of bioactivity with the recombinant toxins cloned from PS149B1 and PS167H2. The resultant recombinant, high copy number bifunctional plasmid was designated pMYC2426.

A subculture of *E. coli* NM522 containing plasmid pMYC2426 was deposited in the permanent collection of the Patent Culture Collection (NRRL), Regional Research Center, 1815 North University Street, Peoria, Ill. 61604 USA on Mar. 26, 1997. The accession number is NRRL B-21671.

To test expression of the PS80JJ1, PS149B1 and PS167H2 toxin genes in *B.t.*, pMYC2426, pMYC2427 and pMYC2429 were separately transformed into the acrystalliferous (Cry-) *B.t.* host, CryB (A. Aronson, Purdue University, West Lafayette, Ind.), by electroporation. The recombinant strains were designated MR543 (CryB [pMYC2426]), MR544 (CryB [pMYC2427]) and MR546 (CryB [pMYC2429]), respectively. Expression of both the approximately 14 and 44 kDa toxins was demonstrated by SDS-PAGE analysis for each recombinant strain.

Toxin crystal preparations from the recombinant strains were assayed against western corn rootworm. Their diet was amended with sorbic acid and SIGMA pen-strep-ampho-B. The material was top-loaded at a rate of 50 $\mu$l of suspension per $cm^2$ diet surface area. Bioassays were run with neonate Western corn rootworm larvae for 4 days at approximately 25° C. Percentage mortality and top-load $LC_{50}$ estimates for the clones (pellets) are set forth in Table 9. A dH2O control yielded 7% mortality.

TABLE 9

| Sample | Percentage mortality at given protein concentration ($\mu g/cm^2$) | | |
|---|---|---|---|
| | 50 $\mu g/cm^2$ | 5 $\mu g/cm^2$ | 0.5 $\mu g/cm^2$ |
| MR543 pellet | 44% | 19% | 9% |
| MR544 pellet | 72% | 32% | 21% |
| MR546 pellet | 52% | 32% | 21% |

The amounts of 14 kDa and 44.3 kDa proteins present in the crystal preparations were estimated by densitometry and used to calculate specific activity expressed as $LC_{50}$. $LC_{50}$ estimates for the clones (pellets) are set forth in Table 10 (WCRW top load bioassay of *B.t.* clones).

TABLE 10

| WCRW Top Load Bioassay of *B.t.* Clones | | | | |
|---|---|---|---|---|
| *B.t.* Clone | *B.t.* Parental Strain | $LC_{50}$ ($\mu g/cm^2$)* | 95% CL | Slope |
| MR543 | PS80JJ1 | 37 | 17–366* | 0.79 |
| MR544 | PS167H2 | 10 | 6–14 | 1.6 |
| MR546 | PS149B1 | 8 | 4–12 | 1.5 |
| N/A | CzyB cell blank | 4% | N/A | N/A |
| N/A | Water blank | 4% | N/A | N/A |

*Percentage mortality at top dose is provided for controls
**90% CL

EXAMPLE 14

Mutational Analysis of the 14 and 44 kDa Polypeptides in the PS80JJ1 Binary Toxin Operon Binary toxin genes of the subject invention are, in their wild-type state, typically arranged in an operon wherein the 14 kDa protein gene is transcribed first, followed by that of the 45 kDa protein gene. These genes are separated by a relatively short, non-coding region. Representative ORFs are shown in SEQ ID NO:30, SEQ ID NO:34, and SEQ ID NO:39.

In order to investigate the contribution of the individual 14 and 44.3 kDa crystal proteins to corn rootworm activity, each gene in the PS80JJ1 operon was mutated in separate experiments to abolish expression of one of the proteins. The intact gene was then expressed in *B.t.* and recombinant proteins were tested for activity against corn rootworm.

First, the 44.3 kDa gene encoded on pMYC2421 was mutated by truncation at the EcoRI site at base position 387 of the open reading frame. This truncation and subsequent ligation with vector sequences resulted in an open reading frame encoding an approximately 24 kDa hypothetical fusion protein. The resulting operon encoding the intact 14 kDa gene and the truncated 45 kDa gene was subcloned into the high copy number shuttle vector, pHT370 (Arantes, O., D. Lereclus [1991] *Gene* 108:115–119) for expression analyses in *Bacillus thuringiensis*. The resulting plasmid, pMYC2424 was transformed into the acrystalliferous (Cry-) *B.t.* host, CryB (A. Aronson, Purdue University, West Lafayette, Ind.), by electroporation. The resulting recombinant strain was designated MR541. Only the 14 kDa PS80JJ1 protein was detectable by SDSPAGE analysis of sporulated cultures of MR541. Mortality was not observed for preparations of MR541 expressing only the 14 kDa PS80JJ1 protein in top-load bioassays against corn rootworm.

Next, the 14 kDa gene encoded on pMYC2421 was mutated by insertion of an oligonucleotide linker containing termination codons in all possible reading frames at the Nrul site at base position 11 of the open reading frame. The sequence of this linker is 5' TGAGTAACTAGATCTATTCAATTA 3'. The linker introduces a BglII site for confirmation of insertion by BglII restriction digestion. Plasmid clones containing the mutagenic linker were identified with BglII and sequenced for verification. The operon insert encoding the 14 kDa nonsense mutations was subcloned into pHT370, resulting in plasmid pMYC2425. This plasmid was transformed into CryB by electroporation to yield the recombinant *B.t.* strain MR542. Only the 44.3 kDa PS80JJ1 protein was expressed in sporulated cultures of MR542 as shown by SDSPAGE analysis. Mortality against corn rootworm was not observed for preparations of MR542 expressing only the 44.3 kDa PS80JJ1 protein.

EXAMPLE 15

Single Gene Heterologous Expression, Purification and Bioassay of the 14 and 44.3 kDa Polypeptides From PS149B1 in *Pseudomonas fluorescens*

The 14 kDa and 44.3 kDa polypeptide genes from PS149B1 were separately engineered into plasmid vectors by standard DNA cloning methods, and transformed into *Psuedomonas flourescens*. The recombinant *Pseudomonas fluorescens* strain expressing only the PS149B1 14 kDa gene was designated MR1253. The recombinant *Pseudomonas fluorescens* strain expressing only the PS149B1 44.3 kDa gene was designated MR1256.

MR1253 and MR1256 each individually expressing one of the two binary proteins were grown in 1 L fermentation tanks. A portion of each culture was then pelleted by centrifugation, lysed with lysozyme, and treated with DNAse I to obtain semi-pure protein inclusions. These inclusions were then solubilized in 50 mM Sodium Citrate (pH 3.3) by gentle rocking at 4° C. for 1 hour. The 14 kDa protein dissolved readily in this buffer whereas the 44.3 kDa protein was partially soluble. The solubilized fractions were then centrifuged at 15,000×g for 20 minutes; and the supernatants were retained.

The 14 kDa protein was further purified through ion-exchange chromatography. The solubilized 14 kDa protein was bound to a Econo-S column and eluted with a Sodium Chloride 0–1M gradient.

The chromatographically pure MR1253 (14 kDa protein) and the Sodium Citrate (pH3.3) solubilized preparation of MR1256 (45 kDa protein) were then tested for activity on corn rootworm individually or together at a molar ratio of 1 to 10 (45 kDa protein to 14 kDa protein). Observed mortality for each of the proteins alone was not above background levels (of the water/control sample) but 87% mortality resulted when they were combined in the above ratio (see Table 11).

TABLE 11

| Molar ratio (45 kD to 14 kD) | load volume | ug 45 kD/ well | ug 14 kD/ well | Total ug protein | CRW Mortality |
|---|---|---|---|---|---|
| 0 to 1 | 100 ul | 0 | 260 | 260 | 13 |
| 1 to 0 | 200 ul | 260 | 0 | 260 | 9 |
| 1 to 10 | 100 ul | 65 | 195 | 260 | 87 |
| water | 100 ul | 0 | 0 | 0 | 11 |

EXAMPLE 16

Identification of Additional Novel 14 kDa and 44.3 kDa Toxin Genes by Hybridization of Total *B.t.* Genomic DNA and by RFLP Total genomic DNA from each isolate was prepared using the Qiagen DNEasy 96 well tissue kit. DNA in 96-well plates was denatured prior to blotting by adding 10 ul of each DNA sample and 10 ul of 4 M NaOH to 80 ul sterile distilled water. Samples were incubated at 70° C. for one hour after which 100 ul of 20×SSC was added to each well. PS149B1 total genomic DNA was included with each set of 94 samples as a positive hybridization control, and cryb-total genomic DNA was included with each set of 94 samples as a negative hybridization control. Each set of 96 samples was applied to Magnacharge nylon membranes using two 48 well slot blot manifolds (Hoefer Scientific), followed by two washes with 10×SSC. Membranes were baked at 80° C. for one hour and kept dry until used. Membranes were prehybridized and hybridized in standard formamide solution (50% formamide, 5×SSPE, 5×Denhardt's solution, 2% SDS, 100 ug/ml single stranded DNA) at 42° C. Membranes were washed under two conditions: 2×SSC/0.1% SDS at 42° C. (low stringency) and 0.2×SSC/0.1% SDS at 65° C. (moderate to high stringency). Membranes were probed with an approximately 1.3 kilobase pair PCR fragment of the P5149B1 44.3 kDa gene amplified from pMYC2429 using forward primer SEQ ID NO:8 and a reverse primer with the sequence 5' GTAGAAGCAGAACAAGAAGGTATT 3' (SEQ ID NO:46). The probe was radioactively labeled using the Prime-it II kit (Stratagene) and 32-P-dCTP, purified on Sephadex columns, denatured at 94° C. and added to fresh hybridization solution. Strains containing genes with homology to the PS149B1 probe were identified by exposing membranes to X-ray film.

The following strains were identified by positive hybridization reactions: PS184M2, PS185GG, PS187G1, PS187Y2, PS201G, PS201HH2, PS242K10, PS69Q, KB54A1-6, KR136, KR589, PS185L12, PS185W3, PS185Z11, PS186L9, PS187L14, PS186FF, PS131W2, PS147U2, PS158T3, PS158X10, PS185FF, PS187F3, PS198H3, PS201H2, PS201L3, PS203G2, PS203J1, PS204C3, PS204G4, PS204I11, PS204J7, PS210B, PS213E8, PS223L2, PS224F2, PS236B6, PS246P42, PS247C16, KR200, KR331, KR625, KR707, KR959, KR1209, KR1369, KB2C-4, KB10H-5, KB456, KB42C17-13, KB45A43-3, KB54A33-1, KB58A10-3, KB59A54-4, KB59A54-5, KB53B7-8, KB53B7-2, KB60F5-7, KB60F5-11, KB59A58-4, KB60F5-15, KB61A18-1, KB65A15-2, KB65A15-3, KB65A15-7, KB65A15-8, KB65A15-12, KB65A14-1, KB3F-3, T25, KB53A71-6, KB65A11-2, KB68B57-1, KB63A5-3, and KB71A118-6.

Further identification and classification of novel toxin genes in preparations of total genomic DNA was performed using the $^{32}$P-labeled probes and hybridization conditions described above in this Example. Total genomic DNA was prepared as above or with Qiagen Genomic-Tip 20/G and Genomic DNA Buffer Set according to protocol for Gram positive bacteria (Qiagen Inc.; Valencia, Calif.) was used in southern analysis. For Southern blots, approximately 1–2 $\mu$g of total genomic DNA from each strain identified by slot blot analysis was digested with DraI and NdeI enzymes, electrophoresed on a 0.8% agarose gel, and immobilized on a supported nylon membrane using standard methods (Maniatis et al.). After hybridization, membranes were washed under low stringency (2×SSC/0.1% SDS at 42° C.) and exposed to film. DNA fragment sizes were estimated using BioRad Chemidoc system software. Restriction fragment length polymorphisms were used to (arbitrarily) classify genes encoding the 44 kDa toxin. These classifications are set forth in Table 12.

TABLE 12

| RFLP Class (45 & 14 kD) | Isolate Strain Name |
|---|---|
| A | 149B1 |
| A' | KR331, KR1209, KR1369 |
| B | 167H2, 242K10 |
| C | 184M2, 201G, 201HH2 |
| D | 185GG, 187Y2, 185FF1, 187F3 |
| E | 187G1 |
| F | 80JJ1, 186FF, 246P42 |
| G | 69Q |
| H | KB54A1-6 |
| I | KR136 |
| J | KR589 |
| K | 185L12, 185W3, 185Z11, 186L9, 187L14 |
| L | 147U2, 210B, KB10H-5, KB58A10-3, KB59A54-4, KB59A54-5, KB59A58-4, KB65A14-1 |
| M | 158T3, 158X10 |
| N | 201H2, 201L3, 203G2, 203J1, 204C3, 204G4, 204I11, 204J7, 236B6 |
| P | 223L2, 224F2 |
| P' | 247C16, KB45A43-3, KB53B7-8, KB53B7-2, KB61A18-1, KB3F-3, KB53A71-6, KB6SA11-2, KB68B57-1, KB63A5-3, KB71A118-6 |
| Q | 213E8, KB60F5-11, KB60F5-15 |
| R | KR959 |
| S | KB2C-4, KB46, KB42C17-13 |
| T | KB54A33-1, KB60F5-7 |
| U | T25 |
| V | KB65A15-2, KB65A15-3, KB65A15-7, KB65A15-8, KB65A15-12 |

EXAMPLE 17

DNA Sequencing of Additional Binary Toxin Genes

Degenerate oligonucleotides were designed to amplify all or part of the 14 and 44.3 kDa genes from *B.t.* strains identified by hybridization with the 149B1 PCR product described above. The oligonucleotides were designed to conserved sequence blocks identified by alignment of the 14 kDa or 44.3 kDa genes from PS149B1, PS167H2 and PS80JJ1. Forward primers for both genes were designed to begin at the ATG initiation codon. Reserve primers were designed as close to the 3' end of each respective gene as possible.

The primers designed to amplify the 14 kDa gene are as follows:

149DEG1 (forward):
5'-ATG TCA GCW CGY GAA GTW CAY ATT G-3'(SEQ ID NO: 47)
149DEG2 (reverse):
5'-GTY TGA ATH GTA TAH GTH ACA TG-3'(SEQ ID NO: 48)

These primers amplify a product of approximately 340 base pairs.

The primers designed to amplify the 44.3 kDa gene are as follows:

149DEG3 (forward):
5'-ATG TTA GAT ACW AAT AAA RTW TAT G -3'(SEQ ID NO: 49)
149DEG4 (reverse):
5'-GTW ATT TCT TCW ACT TCT TCA TAH GAA G-3' (SEQ ID NO: 50)

These primers amplify a product of approximately 1,100 base pairs.

The PCR conditions used to amplify gene products are as follows:

95° C., 1 min., one cycle

95° C., 1 min.

50° C., 2 min., this set repeated 35 cycles

72° C., 2 min.

72° C., 10 min., one cycle

PCR products were fractionated on 1% agarose gels and purified from the gel matrix using the Qiaexll kit (Qiagen). The resulting purified fragments were ligated into the pCR-TOPO cloning vector using the TOPO TA cloning kit (Invitrogen). After ligation, one half of the ligation reaction was transformed into XL10 Gold ultracompetant cells (Stratagene). Transformants were then screened by PCR with vector primers 1212 and 1233. Clones containing inserts were grown on the LB/carbenicillin medium for preparation of plasmids using the Qiagen plasmid DNA miniprep kit (Qiagen). Cloned PCR-derived fragments were then sequenced using Applied Biosystems automated sequencing systems and associated software. Sequences of additional novel binary toxin genes and polypeptides related to the holotype 14 and 44.3 kDa toxins from PS80JJ1 and PS149B1 are listed as SEQ ID NOS. 51–126. The section above, entitled "Brief Description of the Sequences," provides a further explanation of these sequences.

The 14 kDa-type toxins and genes from three additional *B.t.* strains, PS137A, PS201V2 and PS207C3, were also sequenced using the above procedures (with any differences noted below). PCR using the 149DEG1 (forward) and 149DEG2 (reverse) primers was performed. These primers amplify a product of approximately 340 base pairs. The PCR was performed with the following conditions:

1. 95° C., 3 min.
2. 94° C., 1 min.
3. 42° C., 2 min.
4. 72° C., 3 min.+5 sec./cycle
5. Steps 2 through 4 repeated 29 times PCR products were gel purified using the QiaQuick gel extraction kit (Qiagen), the purified fragment was ligated into the pCR-TOPO cloning vector using the TOPO-TA kit (Invitrogen), and subsequently transformed into XL10-Gold Ultracompetent *E. coli* cells (Strategene). Preparation of transformant DNA is described above. Sequences of the 14 kDa toxin gene for each of the three new strains were obtained as per above. The nucleotide and polypeptide sequences are provided in the attached Sequence Listing as follows: PS137A (SEQ ID NOs:149 and 150), PS201V2 (SEQ ID NOs:151 and 152), and PS207C3 (SEQ ID NOs:153 and 154).

EXAMPLE 18

PS149B1 Toxin Transgenes and Plant Transformation

Separate synthetic transgenes optimized for maize codon usage were designed for both the 14 and 44.3 kDa toxin components. The synthetic versions were designed to modify the guanine and cytosine codon bias to a level more typical for plant DNA. Preferred plant-optimized transgenes are described in SEQ ID NOs:127–128. The promoter region used for expression of both transgenes was the *Zea mays* ubiquitin promoter plus *Z. mays* exon 1 and *Z. mays* intron 1 (Christensen, A. H. et al. (1992) Plant Mol. Biol. 18:675–689). The transcriptional terminator used for both transgenes was the potato proteinase inhibitor II (PinII) terminator (An, G. et al. 1989 Plant Cell 1:115–22).

Phosphinothricin acetyltransferase (PAT) was used as the selectable marker for plant transformation. The phosphinothricin acetyltransferase gene (pat) was isolated from the bacterium *Streptomyces viridochromogenes* (Eckes P. et al., 1989). The PAT protein acetylates phosphinothricin, or its precursor demethylphosphinothricin, conferring tolerance to a chemically synthesized phosphinothricin such as the herbicide glufosinate-ammonium. Acetylation converts phosphinothricin to an inactive form that is no longer toxic to corn plants. Glufosinate ammonium is a broad spectrum, non-systemic, non-selective herbicide. Regenerating corn tissue or individual corn plants tolerant to glufosinate ammonium herbicide can be readily identified through incorporation of PAT into regeneration medium or by spray application of the herbicide to leaves.

The synthetic version of the pat gene was produced in order to modify the guanine and cytosine codon bias to a level more typical for plant DNA. The promoter for the pat gene is the CaMV promoter of the 35S transcript from cauliflower mosiac virus (Pietrzak et al., 1986). The transcriptional terminator is the CaMV 35 S terminator.

For transformation of maize tissue, a linear portion of DNA, containing both the PS149B1 14 and 44.3 kDa and pat selectable marker coding sequences, and the regulatory components necessary for expression, was excised from a complete plasmid. This linear portion of DNA, termed an insert, was used in the transformation process.

Maize plants containing PS149B1 14 kDa and 44.3 kDa transgenes were obtained by microprojectile bombardment using the Biolistics®Ò PDS-100He particle gun manufactured by Bio-Rad, essentially as described by Klein et al. (1987). Immature embryos isolated from corn ears harvested approximately 15 days after pollination were cultured on callus initiation medium for three to eight days. On the day of transformation, microscopic tungsten particles were coated with purified DNA and accelerated into the cultured embryos, where the insert DNA was incorporated into the cell chromosome. Six days after bombardment, bombarded embryos were transferred to callus initiation medium containing glufosinate (Bialaphos) as the selection agent. Healthy, resistant callus tissue was obtained and repeatedly transferred to fresh selection medium for approximately 12 weeks. Plants were regenerated and transferred to the greenhouse. A total of 436 regenerated plants were obtained. Leaf samples were taken for molecular analysis to verify the presence of the transgenes by PCR and to confirm expression of the foreign protein by ELISA. Plants were then subjected to a whole plant bioassay using western corn rootworm. Positive plants were crossed with inbred lines to obtain seed from the initial transformed plants. These plants were found to be resistant to damage by corn rootworm in both greenhouse and field trials.

EXAMPLE 19

Further Bioassays

Protein preparations from the strains identified on Example 16 were assayed for activity against western corn rootworm using the basic top load assay methods, as described in Example 13. The results are shown in Table 13.

TABLE 13

| Strain | $LC_{50}$ (ug/cm2) | 95% Cl |
|---|---|---|
| KB45A43-3 | 9.48 | 6.58–15.27 |
| 213'E'8 | 10.24 | 7.50–19.87 |
| KR707 | 11.17 | 8.27–22.54# |

TABLE 13-continued

| Strain | $LC_{50}$ (ug/cm2) | 95% Cl |
|---|---|---|
| 185GG | 11.53 | 7.51–16.81 |
| 187Y2 | 13.82 | 11.08–17.67 |
| 149B1 | 14.77 | 4.91–27.34 |
| 69Q | 27.52 | 117.28–14.77# |
| 167H2 | 31.38 | 19.35–47.60 |
| KB54A33-10 | 32.62 | 24.76–83.85 |
| 185Z11 | 34.47 | ND |
| KB60F5-7 | 34.67 | 19.15–124.29 |
| 242K10 | 34.73 | 21.08–58.25 |
| 201G | 34.90 | 13.20–355.18# |
| 204J7 | 38.57 | 29.83–48.82 |
| KB60F5-15 | 38.62 | 15.00–2.59E03 |
| 80JJ1 | 41.96 | 27.35–139.43 |
| 203J1 | 43.85 | 23.18–69.51 |
| KR589 | 47.28 | 29.83–230.71# |
| 201HH2 | 49.94 | 23.83–351.77 |
| KB60FS-11 | 51.84 | 19.38–1313.75# |
| 158X10 | 52.25 | 43.13–77.84# |
| KB58A10-3 | 53.77 | ND |
| 201L3 | 55.01 | 41.01–78.96 |
| 158T3 | 58.07 | 39.59–211.13 |
| 184M2 | 60.54 | 26.57–411.88 |
| 204G4 | 69.09 | 52.32–93.83 |
| KB59A58-4 | 70.35 | 48.90–144.90 |
| 201H2 | 71.11 | 52.40–130.35 |
| 203G2 | 81.93 | 57.13–226.33 |
| KB59A54-4 | 82.03 | 38.50–1.63E03 |
| 204I11 | 88.41 | 62.48–173.07 |
| 236B6 | 89.33 | 64.16–158.96 |
| KR1369 | 93.25 | 71.97–205.04# |
| KB63A5-3 | 94.52 | 51.56–542.46 |
| 204C3 | 125.45 | 85.26–427.67# |
| KR1209 | 128.14 | 91.57–294.56 |
| 185W3 | 130.61 | ND |
| KR625 | 160.36 | ND |
| 210B | 201.26 | 48.51–0.14E + 06# |
| KB10H-5 | 214.25 | 87.97–8.22E + 03 |
| KB68B57-1 | 264.30 | 48.51–8.95E + 04# |
| 223L2 | 3.81E + 02 | ND |
| KR136 | 7.83E + 02 | — |
| T25 | 1.30E + 03 | ND |
| KB61A18-1 | 2.58E + 03 | ND |
| 147U2 | 3.67E + 03 | ND |
| KR200 | 2.14E + 05 | ND |
| KB59A54-5 | 3.32E + 05 | ND |
| KB3F-3 | 4.07E + 05 | ND |
| 187G1(bs) | 3.50E + 07 | ND |
| MR559 | 20%** | n/a |
| KB42C17-13 | 26%** | n/a |
| 224F2 | 33%** | n/a |
| KR959 | 41%** | n/a |
| KB2C-4 | 42%** | n/a |
| 198H3 | 46%** | n/a |
| KR331 | 47%** | n/a |
| KB46 | 55%** | n/a |
| KB71A118-6 | 71%** | n/a |
| KB53B7-2 | 84%** | n/a |
| 187Y2 | ND | n/a |
| 185L12 | ND | ND |
| 186L9 | ND | n/a |
| KB54A1-6 | ND | n/a |
| 187L14 | ND | n/a |
| 187G1(b) | nt | nt |
| 187G1(s) | nt | nt |

EXAMPLE 20

Molecular Cloning, Expression, and DNA Sequence Analysis of a Novel Binary Endotoxin Gene from *Bacillus thuringiensis* Strain PS201L3

Genomic DNA from PS201L3 was prepared from cells grown in shake flask culture using a Qiagen Genomic-tip 500/G kit and Genomic DNA Buffer Set according to the protocol for Gram positive bacteria (Qiagen Inc.; Valencia, Calif.). A gene library was constructed from PS201L3 DNA partially digested with Sau3AI. Partial restriction digests were fractionated by agarose gel electrophoresis. DNA fragments 9.3 to 23 kbp in size were excised from the gel, electroeluted from the gel slice, purified on an Elutip-D ion exchange column (Schleicher and Schuell, Keene, N.H.), and recovered by ethanol precipitation. The Sau3AI inserts were ligated into BamHI-digested LambdaGem-11 (Promega, Madison, Wis.). Recombinant phage were packaged using Gigapack III XL Packaging Extract (Stratagene, La Jolla, Calif.) and plated on *E. coli* KW251 cells. Plaques were lifted onto Nytran Nylon Transfer Membranes (Schleicher & Schuell, Keene, N.H.) and probed with a $^{32}P$-dCTP labeled gene probe for binary toxin coding sequences. This gene probe was an approximately 1.0 kb PCR product amplified using genomic PS201L3 DNA template and oligonucleotides "15kfor1" and "45krev6."

| | |
|---|---|
| 15kfor1 (SEQ ID NO: 131) | ATGTCAGCTCGCGAAGTACAC |
| 45krev6 (SEQ ID NO: 132) | GTCCATCCCATTAATTGAGGAG |

The membranes were hybridized with the probe overnight at 65° C. and then washed three times with 1×SSPE and 0.1% SDS. Thirteen plaques were identified by autoradiography. These plaques were subsequently picked and soaked overnight in 1 mL SM Buffer+10 uL $CHCl_3$. Phage were plated for confluent lysis on KW251 host cells; 6 confluent plates were soaked in SM and used for large-scale phage DNA preparations. The purified phage DNA was digested with various enzymes and run on 0.7% agarose gels. The gels were transferred to Nytran Membranes by Southern blotting and probed with the same PCR-amplified DNA fragment as above. An approximately 6.0 kb hybridizing XbaI band was identified and subcloned into pHT370, an *E. coli/Bacillus thuringiensis* shuttle vector (Arantes, O., D. Lereclus [1991] *Gene* 108:115–119) to generate pMYC2476. XL10 Gold Ultracompetent *E. coli* cells (Stratagene) transformed with pMYC2476 were designated MR1506. PMYC2476 was subsequently transformed into acrytalliferous CryB cells by electroporation and selection on DM3+erythromycin (20 ug/mL) plates at 30° C. Recombinant CryB[pMYC2476] was designated MR561.

A subculture of MR1506 was deposited in the permanent collection of the Patent Culture Collection (NRRL), Regional Research Center, 1815 North University Street, Peoria, Ill. 61604 USA on Jun. 1, 2000. The accession number is B-30298.

*B.t.* strain MR561 was examined for expression of the PS201L3 binary toxin proteins by immunoblotting. Cells were grown in liquid NYS-CAA medium+erythromycin (10 ug/ml) overnight at 30° C. The culture was then pelleted by centrifugation and a portion of the cell pellet was resuspended and run on SDS-PAGE gels. Both 14 kDa and 44 kDa proteins were apparent by Western Blot analysis when probed with antibodies specific for either the PS149B1 14 kDa or 44 kDa toxins, respectively.

DNA sequencing of the toxin genes encoded on pMYC2476 was performed using an ABI377 automated sequencer. The DNA sequence for PS201L3 14 kDa gene is shown in SEQ ID NO:133. The deduced peptide sequence for PS201L3 14 kDa toxin is shown in SEQ ID NO:134. The DNA sequence for PS201L3 44 kDa gene is shown in SEQ ID NO:135. The deduced peptide sequence for PS201L3 44 kDa toxin is shown in SEQ ID NO:136.

The following table shows sequence similarity and identity of binary genes and proteins from 201IL3 and 149B1.

The program BESTFIT (part of the GCG software package) was used for these comparisons. BESTFIT uses the local homology algorithm of Smith and Waterman (*Advances in Applied Mathematics* 2: 482–489 (1981)).

TABLE 14

| 201L3 vs 149B1 | % similarity | % identity |
|---|---|---|
| 14 kDa nucleotide seq | — | 71.1 |
| 14 kDa peptide seq | 63.9 | 54.1 |
| 45 kDa nucleotide seq | — | 76.1 |
| 45 kDa peptide seq | 70.9 | 62.7 |

EXAMPLE 21

Molecular Cloning and DNA Sequence Analysis of Novel δ-Endotoxin Genes From *Bacillus thuringiensis* Strains PS187G1, PS201HH2 and KR1369

Total cellular DNA was prepared from *Bacillus thuringensis* strains PS187G1, PS201HH2 and KR1369 grown to an optical density of 0.5–1.0 at 600 nm visible light in Luria Bertani (LB) broth. DNA was extracted using the Qiagen Genomic-tip 500/G kit and Genomic DNA Buffer Set according to the protocol for Gram positive bacteria (Qiagen Inc.; Valencia, Calif.). PS187G1, PS201HH2 and KR1369 cosmid libraries were constructed in the SuperCos1 vector (Stratragene) using inserts of PS187G1, PS201HH2 and KR1369 total cellular DNA, respectively, partially digested with Nde II. XL1-Blue MR cells (Stratagene) were transfected with packaged cosmids to obtain clones resistant to carbenicillin and kanamycin. For each strain, 576 cosmid colonies were grown in 96-well blocks in 1 ml LB+carbenicillin (100 ug/ml)+kanamycin (50 ug/ml) at 37° C. for 18 hours and replica plated onto nylon filters for screening by hybridization.

A PCR amplicon containing approximately 1000 bp of the PS187G1, PS201HH2 or KR1369 14 kDa and 44 kDa toxin operon was amplified from PS187G1, PS201HH2 or KR1369 genomic DNA using primers designed to amplify binary homologs:

15kfor1: 5'-ATG TCA GCT CGC GAA GTA CAC-3' (SEQ ID NO: 131)
45krev6:
5'-GTC CAT CCC ATT AAT TGA GGA G-3' (SEQ ID NO: 132)

The DNA fragment was gel purified using QiaQuick extraction (Qiagen). The probe was radiolabeled with $^{32}P$-dCTP using the Prime-It II kit (Stratgene) and used in aqueous hybridization solution (6×SSPE, 5×Denhardt's solution, 0.1% SDS, 0.1 mg/ml denatured DNA) with the colony lift filters at 65° C. for 16 hours. The colony lift filters were briefly washed 1× in 0.5×SSC/0.1%SDS at room temperature followed by two additional washes for 10 minutes at 65° C. in 0.5×SSC/0.1%SDS. The filters were then exposed to X-ray film for 20 minutes (PS187G1 and PS201HH2) or for 1 hour (KR1369). One cosmid clone that hybridized strongly to the probe was selected for further analysis for each strain. These cosmid clones were confirmed to contain the approximately 1000 bp 14 kDa and 44 kDa toxin gene target by PCR amplification with the primers listed above. The cosmid clone of PS187G1 was designated as pMYC3106; recombinant *E. coli* XL1-Blue MR cells containing pMYC3106 are designated MR1508. The cosmid clone of PS201HH2 was designated as pMYC3107; recombinant *E. coli* XL1-Blue MR cells containing pMYC3107 are designated MR1509. The cosmid clone of KR1369 was designated as pMYC3108; recombinant *E. coli* XL1-Blue MR cells containing pMYC3108 are designated MR1510. Subcultures of MR1509 and MR1510 were deposited in the permanent collection of the Patent Culture Collection (NRRL),Regional Research Center, 1815 North University Street, Peoria, Ill. 61604 USA on Aug. 8, 2000. The accession numbers are NRRL B-30330 and NRRL-B 30331, respectively.

The PS187G1, PS201HH2 and KR1369 14 kDa and 44 kDa toxin genes encoded by pMYC3106, pMYC3107 and pMYC3108, respectively, were sequenced using the ABI377 automated sequencing system and associated software.

The PS187G1 14 kDa and 44 kDa nucleotide and deduced polypeptide sequences are shown as SEQ ID NOs:137–140. Both the 14 kDa and 44 kDa toxin gene sequences are complete open reading frames. The PS187G1 14 kDa toxin open reading frame nucleotide sequence, the 44 kDa toxin open reading frame nucleotide sequence, and the respective deduced amino acid sequences are novel compared to other toxin genes encoding pesticidal proteins.

The PS201HH2 14 kDa and 44 kDa nucleotide and deduced polypeptide sequences are shown as SEQ ID NOs:141–144. The 14 kDa toxin gene sequence is the complete open reading frame. The 44 kDa toxin gene sequence is a partial sequence of the gene. The PS201HH2 14 kDa toxin open reading frame nucleotide sequence, the 44 kDa toxin partial open reading frame nucleotide sequence, and the respective deduced amino acid sequences are novel compared to other toxin genes encoding pesticidal proteins.

The KR1369 14 kDa and 44 kDa nucleotide and deduced polypeptide sequences are shown as SEQ ID NOs:145–148. Both the 14 kDa and 44 kDa toxin gene sequences are complete open reading frames. The KR1369 14 kDa toxin open reading frame nucleotide sequence, the 44 kDa toxin open reading frame nucleotide sequence, and the respective deduced amino acid sequences are novel compared to other toxin genes encoding pesticidal proteins.

EXAMPLE 22

Construction and Expression of a Hybrid Gene Fusion Containing the PS149B1 14 kDa and 44 kDa Binary Toxin Genes Oligonucleotide primers were designed to the 5' and 3' ends of both the 14 kDa and 44 kDa genes from PS149B1. These oligonucleotides were designed to create a gene fusion by SOE-PCR ("Gene Splicing By Overlap Extension: Tailor-made Genes Using PCR," *Biotechniques* 8:528–535, May 1990). The two genes were fused together in the reverse order found in the native binary toxin operon (i.e. 44 kDa gene first, followed by the 14 kDa gene.)

The sequences of the olignucleotides used for SOE-PCR were the following:

F1 new:
AAATATTATTTTATGTCAGCACGTGAAGTACACATTG (SEQ ID NO: 155)
R1 new: tctctGGTACCttaTTAtgatttatgcccatatcgtgagg (SEQ ID NO: 156)
F2 new:
agagaCTAGTaaaaaggagataaccATGttagatactaataaag (SEQ ID NO: 157)

-continued

R2 new:
CGTGCTGACATAAAATAATATTTTTAATTTTTTTAGTGTACTTT
(SEQ ID NO: 158)

Oligo "F1new" was designed to direct amplification from the 5' end of the 14 kDa gene and hybridize to the 3' end of the 44 kDa gene. Oligo "R1new" was designed to direct amplification from the 3' end of the 14 kDa gene. This primer was designed with two stop codons in order to ensure termination of translation. It was also designed with a KpnI site for directional cloning into a plasmid expression vector for *Pseudomonas fluorescens*. Oligo "F2new" was designed to direct amplification from the 5' end of the 44 kDa gene. It also includes a ribosome binding sequence and a SpeI cloning site. Oligo "R2new" was designed to direct amplification from the 3' end of the 44 kDa gene and hybridize to the 5' end of the 14 kDa gene.

The two genes were first independently amplified from PS149B1 genomic DNA; the 14 kDa gene using "F1new" and "R1new," and the 44 kDa gene using "F2new" and "R2new." The products were then combined in one PCR tube and amplified together using "R1new" and "F2new." At this point, Herculase™ Enhanced Polymerase Blend (Stratagene, La Jolla, Calif.) was used at a 48° C. annealing temperature to amplify a 1.5 kb DNA fragment containing the gene fusion. This DNA fragment was subsequently digested using KpnI and SpeI, fractionated on agarose gels, and purified by electroelution. The plasmid vector was also digested with KpnI and SpeI, fractionated on agarose gels, purified by electroelution and treated with phosphatase. The vector and insert were then ligated together overnight at 14° C. Ligated DNA fragments were transformed into MB214 *P.f.* cells by electroporation and selection overnight on LB+ tetracycline (30 ug/mL) plates. Strains containing the gene fusion were identified by diagnostic PCR and sequenced for verification of successful gene splicing. One representative strain containing the cloned gene fusion was designated MR1607; the recombinant plasmid was designated pMYC2475.

A subculture of MR1607 was deposited in the permanent collection of the Patent Culture Collection (NRRL), Regional Research Center, 1815 North University Street, Peoria, Ill. 61604 USA on Aug. 8, 2000. The accession number is NRRL B-30332. MR1607 was grown and protein production was verified by SDS-PAGE and immunoblotting. A protein band at ~58 kDa representing the 44 kDa+14 kDa fusion product was identified when western blots were probed with antibodies specific to either the 14 kDa toxin or the 44 kDa toxin.

The sequence of the 58 kDa fusion protein is provided in SEQ ID NO:159. The DNA sequence for the gene fusion is provided in SEQ ID NO:160.

EXAMPLE 23

Binary Homologue Mixing Study

Growth of Homologue Strains.

Four strains were selected, one from each major binary toxin family—149B1 , 80JJ1, 201L3, and 167H2. In order to reduce time spent purifying individual toxin proteins, the following *Pseudomonas fluorescens* (*P.f.*) clones were grown instead: MR1253 (14 kDa of 149B1) and MR1256 (44 kDa of 149B1). Similarly, *B.t.* clones MR541 (expressing 14 kDa of 80JJ1), and MR542 (44 kDa of 80JJ1) were used. *B.t.* strains were grown as described in Example 1. Pellets were washed 3× with water and stored at −20° C. until needed. *P.f.* strains were grown in 10 L batches in Biolafitte fermenters using standard procedures. Pellets were stored at −80° C. until needed.

Extraction & Purification of Toxins.

Purification of 167H2, MR541, MR542, 201L3. Extractions of cell pellets were done using 100 mM sodium citrate buffer at pH's ranging from 3.0 to 5.5. In a typical extraction, pellets were extracted with a buffer volume 1/10 to 1/3× of the original culture volume. Pellets were suspended in the buffer and placed on a rocking platform at 4° C. for periods of time ranging from 2.5 hours to overnight. The extracts were centrifuged and supernatants were retained. This procedure was repeated with each strain until at least approximately 10 mg of each protein were obtained. SDS-PAGE confirmed the presence/absence of protein toxins in the extracts through use of the NuPAGE Bis/Tris gel system (Invitrogen). Samples were prepared according to the manufacturers instructions and were loaded onto 4–12% gels and the electrophoretograms were developed with MES running buffer. The exception to this procedure was the sample prep of all 201L3 samples. These samples were prepared by diluting ½× with BioRad's Laemmli sample buffer and heating at 95° C. for 4 minutes. Protein quantitation was done by laser scanning gel densitometry with BSA as a standard (Molecular Dynamics Personal Densitometer SI). Extracts were clarified by filtration through a 0.2 μm membrane filter and stored at 4° C.

Purification of MR1253 & MR1256. The recombinant proteins MR1253 and MR 1256, corresponding to the 14 and 44 kDa proteins of 149B1 respectively, were prepared as solubilized inclusions. Inclusion bodies were prepared using standard procedures. The inclusion bodies were solubilized in 1 mM EDTA, 50 mM sodium citrate, pH 3.5.

Purification of individual toxins, 167H2 & 201L3. All extracts known to contain either the 14, the 44 kDa, or both were combined. This combined extract was dialyzed against 100 mM sodium citrate, 150 mM NaCl, pH 4. Dialysis tubing was from Pierce (Snakeskin 10 k MWCO). Samples were usually dialyzed for approximately 6 hours and then again overnight in fresh buffer.

Extracts were then concentrated with either Centriprep 10 or Centricon Plus-20 (Biomax—5, 5000 NMWL) centrifugal filter devices (Millipore), quantitated for both the 14 kDa and 44 kDa proteins, and subjected to gel filtration chromatography.

In preparation for chromatography, all samples and buffers were filtered through a 0.2 μm filter and degassed. Samples were then applied to a HiPrep 26/60 Sephacryl S-100 gel filtration column which had been equilibrated with two bed volumes of the separation buffer, 100 mM sodium citrate, 150 mM NaCl, pH 4.0. Sample volumes ranged from 5–10 ml. An AKTA purifier 100 FPLC system (Amersham Pharmacia) controlled the runs. Chromatography was done at ambient temperature. Buffer flow through the column during the run was maintained at 0.7 ml/min. Proteins were detected by monitoring UV absorbance at 280 nm. Fractions were collected and stored at 4° C. Fractions containing either the 14 or 44 kDa protein were pooled and checked for purity by SDS-PAGE as described above.

For 167H2 samples, two large peaks were detected and were well separated from each other at the baseline. SDS-PAGE of fractions showed each peak represented one of the protein toxins.

In the 201L3 sample, three well defined peaks and one shoulder peak were detected. SDS-PAGE revealed that the first peak represented a 100 kDa protein plus an 80 kDa protein. The second peak represented the 44 kDa protein, while the shoulder peak was a 40 kDa protein. The third peak was the 14 kDa protein. Fractions with the 44 kDa from both samples were combined as were all fractions containing the 14 kDa.

The 149B1 proteins had been obtained individually from *Pf* clones MR1253 and MR1256 and, therefore, further purification was not necessary. Similarly, the 80JJ1 recombinants, MR541 and MR542 yielded the individual 14 and 44 kDa proteins thereby obviating further purification.

Sample Preparation for wCRW $LC_{50}$ Bioassay.

Dialysis. Samples of individual binary toxin proteins were dialyzed against 6 L of 20 mM sodium citrate, pH 4.0. The first dialysis proceeded for several hours, the samples were transferred to fresh buffer and alowed to dialyze overnight. Finally, the samples were transferred to fresh buffer and dialyzed several more hours. Sources of the protein samples were either the pooled gel-filtration fractions (167H2, 201L3), pellet extracts (MR541, MR542), or inclusion pellet extracts (MR1253, MR1256). All samples were filtered through 0.2 um membranes to sterilize.

Concentration. Samples were concentrated with Centricon Plus-20 (Biomax—5, 5000 NMWL) centrifugal filter devices (Millipore).

Quantitation. Samples were quantitated for protein as above. To meet the requirements of the $LC_{50}$ bioassay, a minimum of 6.3 mg of each toxin protein were needed at a concentration range of 0.316–1.36 mg/ml for the various combinations. If necessary, samples were concentrated as above, or were diluted with buffer (20 mM sodium citrate, pH 4.0) and requantitated.

Mixing of binaries/$LC_{50}$ bioassay. For each of the four strains, the 14 kDa was combined with an amount the 44 kDa of each strain to give a 1/1 mass ratio. The top dose was 50 ug/cm$^2$ for the mixtures, with the exception of mixtures with the 14 kDa protein of 203J1. Top doses of mixtures with this protein were only 44 ug/cm$^2$. For controls, each protein was submitted individually, as was the extract buffer, 20 mM sodium citrate, pH 4.0. Native combinations were also tested (i.e. 14 kDa+44 kDa of 149B1). All toxin combinations and buffer controls were evaluated three times by bioassay against Western corn rootworm, while individual toxins were tested once.

The results are reported below in Table 15 ($LC_{50}$ Results for Toxin Combinations) and Table 16 (Comparison of Potencies of Strains to 149B1).

TABLE 15

| Toxin combination | Top load, ul/well | $LC_{50}$ (ug/cm$^2$) |
|---|---|---|
| 80JJ1 14 + 80JJ1 44 | 96 | 28 (19–44 C.I.) |
| 167H2 44 | 159 | >Top dose |
| 201L3 44 | 172 | No dose response |
| 149B1 44 | 78 | No dose response |
| 167H2 14 + 167H2 44 | 161 | 19 (13–27 C.I.) |
| 80JJ1 44 | 97 | No dose response |
| 201L3 44 | 174 | 14 (10–22 C.I.) |
| 149B1 44 | 80 | No dose response |
| 201L3 14 + 201L3 44 | 193 | No dose response |
| 80JJ1 44 | 116 | No dose response |
| 167H2 44 | 180 | No dose response |
| 149B1 44 | 99 | No dose response |
| 149B1 14 + 149B1 44 | 45 | 10 (7–15 C.I.) |
| 80JJ1 44 | 63 | 11 (8–16 C.I.) |
| 167H2 44 | 126 | 8 (6–11 C.I.) |
| 201L3 44 | 139 | 18 (13–27 C.I.) |

TABLE 16

Comparison of potencies of strains to 149B1

| Toxin combination | Relative potency |
|---|---|
| 149B1 14 + 149B1 44 | To which all others are compared |
| 149B1 14 + 80JJ1 44 | 0.9 |
| 149B1 14 + 167H2 44 | 1.3 |
| 149B1 14 + 201L3 44 | 0.5 |
| 80JJ1 14 + 80JJ1 44 | 0.4 |
| 167H2 14 + 167H2 44 | 0.5 |
| 167H2 14 + 201L3 44 | 0.7 |

Figure 3:
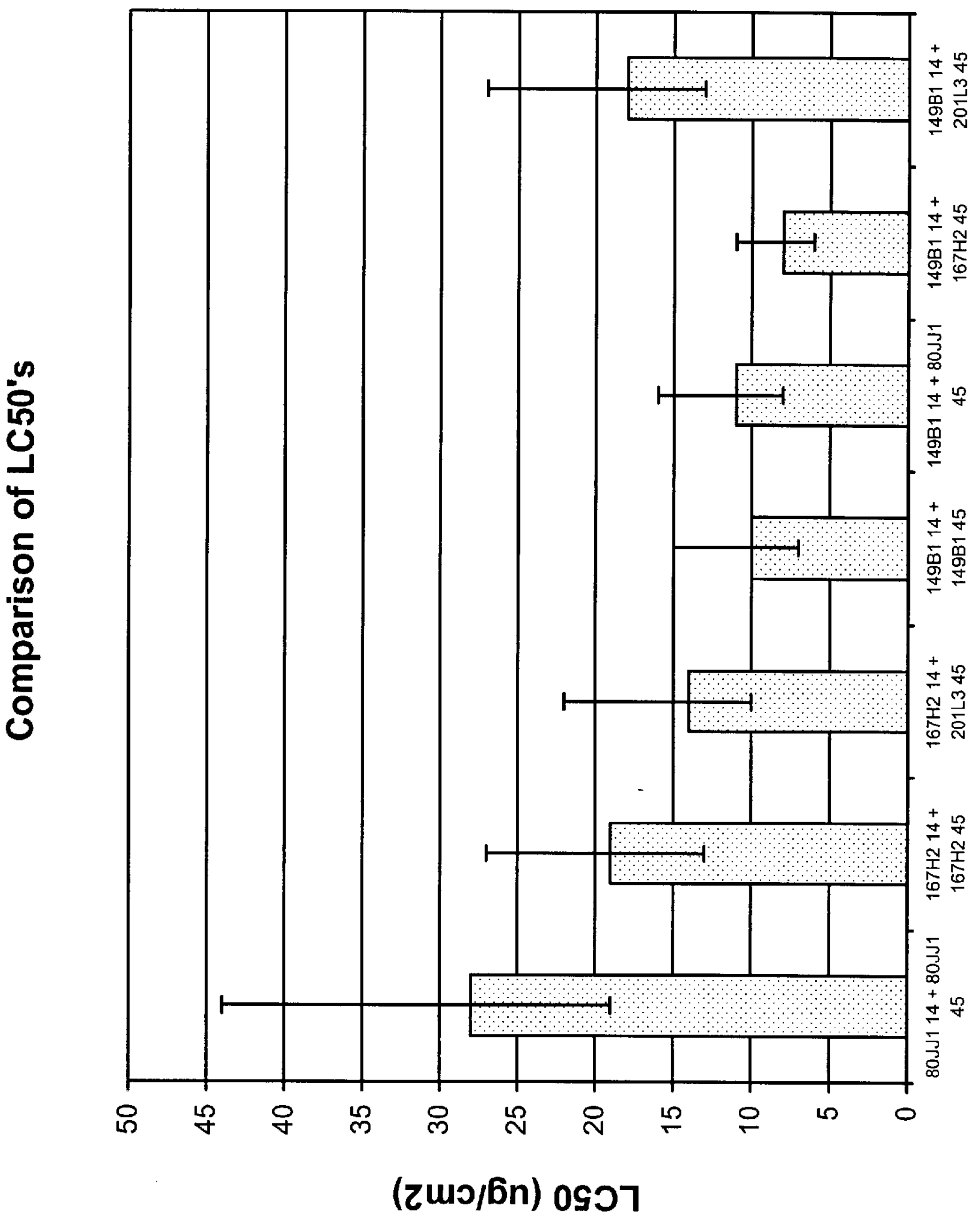
FIG. 3 shows a comparison of $LC_{50}$ values from the mixing study of Example 23.

The results are also displayed graphically in FIG. 3.

Native combinations were highly active against Western corn rootworm, except for 201L3. However, the 44 kDa of 201L3 was active when combined with either the 14 kDa of 167H2 or 149B1. Other active combinations were the 149B1 14 kDa with either 80JJ1 or 167H2 44 kDa, with the latter appearing to be more active than the native 149B1 mixture. No dose response was noted for either the individual proteins, or the buffer and water controls.

EXAMPLE 24

Control of Southern Corn Rootworm With PS149B1 14-kDa Protein

A powder containing approximately 50% (wt/wt) of a 14-kDa δ-endotoxin, originally discovered in *Bacillus thuringiensis* strain PS149B1, was isolated from recombinant *Pseudomonas fluorescens* strain (MR1253). This powder was evaluated for insecticidal activity using the following procedure.

Artificial insect diet (R. I. Rose and J. M. McCabe (1973), "Laboratory rearing techniques for rearing corn rootworm," *J. Econ. Entomol.* 66(2): 398–400) was dispensed at ~0.5 mL/well into 128-well bioassay trays (C-D International, Pitman, N.J.) to produce a surface area of ~1.5 cm2. Buffer (10-mM potassium phosphate, pH 7.5) suspensions of the 14-kDa protein powder were applied to the surface of the artificial insect diet at 50 μL/well, and the diet surface was allowed to dry. Buffer controls were also included in each test. A single neonate southern corn rootworn, *Diabrotica undecimpunctata howardi*, was placed in each well, and the wells were sealed with lids that were provided with the trays. The bioassays were held for 6 days at 28° C., after which time, the live larvae were weighed as a group for each treatment. Percent growth inhibition was calculated by subtracting the weight of live insects from each treatment from the weight of live, control insects, and then dividing by the control weight. This result was multiplied by 100 to convert the number to a percent. Growth inhibition was calculated for each of 5 tests that each contained 16 insects per treatment, and the growth inhibition was averaged across tests.

Results demonstrated that the 14-kDa protein inhibited growth of southern corn rootworms in a concentration-dependent manner. Table 17 shows southern corn rootworn growth inhibition with PS149B1 14-kDa protein.

TABLE 17

| Treatment | Concentration in μg ai/$cm^2$ | % Growth Inhibition |
|---|---|---|
| 14-kDa Protein | 1 | 32 |
| 14-kDa Protein | 3 | 55 |
| 14-kDa Protein | 9 | 78 |

ai = active ingredient

EXAMPLE 25

Control of European Corn Borer and Corn Earworm With PS149B1 Binary Toxin

A powder containing 54% of a 14-kDa δ-endotoxin, and another powder containing 37% of a 44-kDa δ-endotoxin, both originally discovered in *Bacillus thuringiensis* strain PS149B1, were isolated from recombinant *Pseudomonas fluorescens* strains MR1253 and MR1256, respectively. Mixtures of these powders were evaluated for insecticidal activity using the following procedure.

Artificial insect diet (R. I. Rose and J. M. McCabe (1973), "Laboratory rearing techniques for rearing corn rootworm," *J. Econ. Entomol.* 66(2): 398–400) was dispensed at ~0.5 mL/well into 128-well bioassay trays (C-D International, Pitman, N.J.) to, produce a surface area of ~1.5 cm2. Buffer (10-mM potassium phosphate, pH 7.5) suspensions of the protein powders were mixed, and were then applied to the surface of the artificial insect diet at 50 μL/well. The diet surface was allowed to dry. Buffer controls were also included in each test. A single neonate larvae was placed in each well, and the wells were sealed with lids that were provided with the trays. Tests were conducted with European corn borer, *Ostrinia nubilalis*, and corn earworm, *Helicoverpa zea* (both are lepidopterans). The bioassays were held for 6 days at 28° C., after which time, the live larvae were weighed as a group for each treatment. Percent growth inhibition was calculated by subtracting the weight of live insects in each treatment from the weight of live, control insects, and then dividing by the control weight. This result was multiplied by 100 to convert the number to a percent. Growth inhibition was calculated for each of 4 tests that each contained 14 to 16 insects per treatment, and the growth inhibition was averaged across tests.

Results demonstrated that the 14-kDa protein inhibited growth of European corn borers and corn earworms in a concentration-dependent manner. Table 18 shows corn earworm (CEW) and European corn borer (ECB) growth inhibition with PS149B1 protein mixtures.

TABLE 18

| 14-kDa protein + 44-kDa Protein | % Growth Inhibition | |
|---|---|---|
| Concentration in μg ai/$cm^2$ | CEW | ECB |
| 3.7 + 11 | 42 | 59 |
| 11 + 33 | 57 | 77 |
| 33 + 100 | 61 | 89 |

ai = active ingredient

EXAMPLE 26

Further Characterization of the 45 kDa Proteins and Primer Design for Identifying Additional Polynucleotides and Proteins The subject invention includes not only the specifically exemplified sequences. Portions of the subject genes and toxins can be used to identify other related genes and toxins. Thus, the subject invention includes polynucleotides that encode proteins or polypeptides comprising at least ten contiguous amino acids, for example, of any of the binary-type proteins or polypeptides included in the attached sequence listing and described herein. Other embodiments include polynucleotides that encode, for example, at least 20, 30, 40, 50, 60, 70, 80, 90, and 100 contiguous amino acids of a protein exemplified herein; these numbers also apply similarly to contiguous nucleotides of an exemplified polynucleotide. The proteins encoded by such polynucleotides are included in the subject invention. Likewise, polynucleotides comprising contiguous nucleotides (that code for proteins or polypeptides comprising peptides of these approximate sizes) are included in the subject invention.

While still very different, the "closest" toxins to those of the subject invention are believed to be the 51 and 42 kDa mosquitocidal proteins of *Bacillus sphaericus*. Attached as FIGS. 4 and 5 are protein alignments and nucleotide sequences alignments of the 51 and 42 kDa sphaericus toxins and genes and the 45 kDa 149B1 toxin and gene.

Two blocks of sequences are highlighted in the nucleotide alignment to which primers could be made. An exemplary PCR primer pair is included below, and in 5'-3' orientation (45 kD3'rc is shown as the complement). These primers have been successfully used to identify additional members of the 45 kDa binary family. Fully redundant sequences and a prophetic pair are also included below.

| | |
|---|---|
| 45kD5': | GAT RAT RAT CAA TAT ATT ATT AC (SEQ ID NO: 161). |
| 45kD3'rc: | CAA GGT ART AAT GTC CAT CC (SEQ ID NO: 162). |

The sequences would be useful as both the sequence written and as the reverse complement (03 and 04 are complementary to 45 kD3'rc, the exemplified reverse primer).

| | |
|---|---|
| 45kD5'01: | GAT GATGrTmrAk wwATTATTrC A (SEQ ID NO: 163). |
| 45kD5'02: | GAT GATGrTmrAT ATATTATTrC A (SEQ ID NO: 164). |
| 45kD3'03: | GGAwG krCdyTwdTm CCwTGTAT (SEQ ID NO: 165). |
| 45kD3'04: | GGAwG kACryTAdTA CCTTGTAT (SEQ ID NO: 166). |

Regarding the manner in which the sphaericus toxins were identified, a BLAST (Altschul et al. (1997), "Gapped BLAST and PSI-BLAST: a new generation of protein database search programs," Nucleic Acids Res. 25:3389–3402) database search using the 149B1 45 kDa protein found matches to the 42 kDa *B. sphaericus* crystal inclusion protein (expectation score $3*10^{-4}$) and the 51 kDa *B. sphaericus* crystal inclusion protein (expectation score $3*10^{-9}$).

An alignment of the 45 kDa 149B1 peptide sequence to the 42 kDa *B. sphaericus* crystal inclusion protein results in an alignment having 26% identity over 325 residues. The alignment score is 27.2 sd above the mean score of 100 randomized alignments. A similar analysis of the 45 kDa 149B1 peptide sequence to the 42 kDa *B. sphaericus* crystal inclusion protein results in an alignment having 29% identity over 229 residues. The alignment score is 23.4 sd above the mean score of 100 randomized alignments. Alignment scores>10 sd above the mean of random alignments have been considered significant (Lipman, D. J. and Pearson, W. R. (1985), "Rapid and sensitive similarity searches," *Science* 227:1435–1441; Doolittle, R. F. (1987), *Of URFs and ORFs: a primer on how to analyze derived amino acid sequences*, University Science Books, Mill Valley, Calif.).

For reference, the structurally similar Cry1Aa, Cry2Aa and Cry3Aa protein sequences were compared in the same way. Cry2Aa vs. Cry1Aa and Cry2Aa vs. Cry3Aa share 29% and 27% identity over 214 and 213 residues, respectively, with alignment scores 32.2 sd and 29.5 sd above the mean score of 100 randomized alignments. An alignment of the 149B1 45 kDa protein sequence and the Cry2Aa protein sequence resulted in an alignment score within 1 sd of the mean of 100 randomized alignments.

The following comparisons are also noted:

TABLE 19

| Comparison | Quality | Length | Ratio | Gaps | % Similarity | % Identity | Average Quality* |
|---|---|---|---|---|---|---|---|
| ps149b1-45.pep × s07712 | 189 | 325 | 0.612 | 12 | 35.135 | 26.351 | 39.4 ± 5.5 |
| ps149b1-45.pep × 07711 | 161 | 229 | 0.742 | 9 | 36.019 | 28.910 | 39.3 ± 5.2 |
| cry2aa1.pep × cry1aa1.pep | 182 | 214 | 0.888 | 6 | 37.688 | 28.643 | 43.5 ± 4.3 |
| cry3aa1.pep × cry2aa1.pep | 187 | 213 | 0.926 | 6 | 40.500 | 27.000 | 42.3 ± 4.9 |
| ps149b1-45.pep × cry2aa1.pep | 40 | 28 | 1.429 | 0 | 42.857 | 35.714 | 41.6 ± 5.6 |

*based on 100 randomizations

For further comparison purposes, and for further primer design, the following references are noted:

Oei et al. (1992), "Binding of purified *Bacillus sphaericus* binary toxin and its deletion derivatives to Culex quinquefasciatus gut: elucidation of functional binding domains," *Journal of General Microbiology* 138(7): 1515–26.

For the 51 kDa: 35-448 is active; 45-448 is not; 4-396 is active; 4-392 is not.

For the 42 kDa: 18-370 is active, 35-370 is not; 4-358 is active; 4-349 is not.

The work was done with GST fusions purified and cleaved with thrombin. All truncations were assayed with== of other intact subunit. All deletions had some loss of activity. P51deltaC56 binds, but doesn't internalize 42. P51delta N45 doesn't bind. Only 42 kDa+51 kDa are internalized. Both N-terminal and C-terminal non-toxic 42 kDa proteins failed to bind the 51 kDa protein or 51 kDa-receptor complex.

Davidson et al. (1990), "Interaction of the *Bacillus sphaericus* mosquito larvicidal proteins," *Can. J. Microbiol.* 36(12):870–8. N-termini of SDS-PAGE purified proteins obtained from *B. sphaericus*. S29 and N31 of 51 kDa and S9 of 42 kDa in 68–74 kDa complexes (unreduced). S9 and S29 of 51 and N31 of 42 from 51 kDa band (unreduced). In reduced gels the 45 kDa band had S29 and N31 of the 51 kDa and the 39 kDa band contained S9 of the 42 kDa protein.

Baumann et al. (1988), "Sequence analysis of the mosquitocidal toxin genes encoding 51.4- and 41.9-kilodalton proteins from *Bacillus sphaericus* 2362 and 2297," *J. Bacteriol.* 17:2045–2050. N-termini of 41.9 kDa at D5 from *B. sphaericus protease* and I11 from chymotrypsin; C-terminus following R349 with trypsin. Regions of enhanced similarity were identified that correspond to many of those above. Similar sequence blocks A through D between the 51 and 42 kDa proteins.

In summary, the sphaericus toxins discussed above are not meant to be included in the scope of the subject invention (in fact, they are specifically excluded). In that regard, divergent contiguous sequences, as exemplified in the alignments (FIGS. 4 and 5) discussed above, can be used as primers to identify unique toxins that are suggested but not specifically exemplified herein. However, the conserved contiguous sequences, as shown in the alignments, can also be used according to the subject invention to identify further novel 15/45 kDa-type binary toxins (active against corn rootworm and other pests).

EXAMPLE 27

Insertion and Expression of Toxin Genes in Plants

One aspect of the subject invention is the transformation of plants with polynucleotides of the subject invention that express proteins of the subject invention. The transformed plants are resistant to attack by the target pest.

The novel corn rootworm-active genes described here can be optimized for expression in other organisms. For example, maize optimized gene sequences encoding the 14 and 44 kDa PS80JJ1 toxins are disclosed in SEQ ID NO:44 and SEQ ID NO:45, respectively.

Genes encoding pesticidal toxins, as disclosed herein, can be inserted into plant cells using a variety of techniques which are well known in the art. For example, a large number of cloning vectors comprising a replication system in *E. coli* and a marker that permits selection of the transformed cells are available for preparation for the insertion of foreign genes into higher plants. The vectors comprise, for example, pBR322, pUC series, M13mp series, pACYC184, etc. Accordingly, the sequence encoding the *B.t.* toxin can be inserted into the vector at a suitable restriction site. The resulting plasmid is used for transformation into *E. coli*. The *E. coli* cells are cultivated in a suitable nutrient medium, then harvested and lysed. The plasmid is recovered. Sequence analysis, restriction analysis, electrophoresis, and other biochemical-molecular biological methods are generally carried out as methods of analysis. After each manipulation, the DNA sequence used can be cleaved and joined to the next DNA sequence. Each plasmid sequence can be cloned in the same or other plasmids. Depending on the method of inserting desired genes into the plant, other DNA sequences may be necessary. If, for example, the Ti or Ri plasmid is used for the transformation of the plant cell, then at least the right border, but often the right and the left border of the Ti or Ri plasmid T-DNA, has to be joined as the flanking region of the genes to be inserted.

The use of T-DNA for the transformation of plant cells has been intensively researched and sufficiently described in EP 120 516; Hoekema (1985) In: *The Binary Plant Vector*

*System*, Offset-durkkerij Kanters B. V., Alblasserdam, Chapter 5; Fraley et al., *Crit. Rev. Plant Sci.* 4:1–46; and An et al. (1985) *EMBO J.* 4:277–287.

Once the inserted DNA has been integrated in the genome, it is relatively stable there and, as a rule, does not come out again. It normally contains a selection marker that confers on the transformed plant cells resistance to a biocide or an antibiotic, such as kanamycin, G 418, bleomycin, hygromycin, or chloramphenicol, inter alia. The individually employed marker should accordingly permit the selection of transformed cells rather than cells that do not contain the inserted DNA.

A large number of techniques are available for inserting DNA into a plant host cell. Those techniques include transformation with T-DNA using *Agrobacterium tumefaciens* or *Agrobacterium rhizogenes* as transformation agent, fusion, injection, biolistics (microparticle bombardment), or electroporation as well as other possible methods. If Agrobacteria are used for the transformation, the DNA to be inserted has to be cloned into special plasmids, namely either into an intermediate vector or into a binary vector. The intermediate vectors can be integrated into the Ti or Ri plasmid by homologous recombination owing to sequences that are homologous to sequences in the T-DNA. The Ti or Ri plasmid also comprises the vir region necessary for the transfer of the T-DNA. Intermediate vectors cannot replicate themselves in Agrobacteria. The intermediate vector can be transferred into *Agrobacterium tumefaciens* by means of a helper plasmid (conjugation). Binary vectors can replicate themselves both in *E. coli* and in Agrobacteria. They comprise a selection marker gene and a linker or polylinker which are framed by the right and left T-DNA border regions. They can be transformed directly into Agrobacteria (Holsters et al. [1978] *Mol. Gen. Genet.* 163:181–187). The Agrobacterium used as host cell is to comprise a plasmid carrying a vir region. The vir region is necessary for the transfer of the T-DNA into the plant cell. Additional T-DNA may be contained. The bacterium so transformed is used for the transformation of plant cells. Plant explants can advantageously be cultivated with *Agrobacterium tumefaciens* or *Agrobacterium rhizogenes* for the transfer of the DNA into the plant cell. Whole plants can then be regenerated from the infected plant material (for example, pieces of leaf, segments of stalk, roots, but also protoplasts or suspension-cultivated cells) in a suitable medium, which may contain antibiotics or biocides for selection. The plants so obtained can then be tested for the presence of the inserted DNA. No special demands are made of the plasmids in the case of injection and electroporation. It is possible to use ordinary plasmids, such as, for example, pUC derivatives.

The transformed cells grow inside the plants in the usual manner. They can form germ cells and transmit the transformed trait(s) to progeny plants. Such plants can be grown in the normal manner and crossed with plants that have the same transformed hereditary factors or other hereditary factors. The resulting hybrid individuals have the corresponding phenotypic properties.

In a preferred embodiment of the subject invention, plants will be transformed with genes wherein the codon usage has been optimized for plants. See, for example, U.S. Pat. No. 5,380,831, which is hereby incorporated by reference. Also, advantageously, plants encoding a truncated toxin will be used. The truncated toxin typically will encode about 55% to about 80% of the full length toxin. Methods for creating synthetic *B.t.* genes for use in plants are known in the art.

EXAMPLE 28

Cloning of *B.t.* Genes Into Insect Viruses

A number of viruses are known to infect insects. These viruses include, for example, baculoviruses and entomopoxviruses. In one embodiment of the subject invention, genes encoding the insecticidal toxins, as described herein, can be placed within the genome of the insect virus, thus enhancing the pathogenicity of the virus. Methods for constructing insect viruses which comprise *B.t.* toxin genes are well known and readily practiced by those skilled in the art. These procedures are described, for example, in Merryweather et al. (Merryweather, A. T., U. Weyer, M. P. G. Harris, M. Hirst, T. Booth, R. D. Possee (1990) *J. Gen. Virol.* 71:1535–1544) and Martens et al. (Martens, J. W. M., G. Honee, D. Zuidema, J. W. M. van Lent, B. Visser, J. M. Vlak (1990) *Appl. Environmental Microbiol.* 56(9):2764–2770).

All patents, patent applications, provisional applications, and publications referred to or cited herein are incorporated by reference in their entirety to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application and the scope of the appended claims.

What is claimed is:

1. An isolated polynucleotide that encodes a fusion protein comprising a first amino acid sequence and a second amino acid sequence, wherein said first amino acid sequence is the amino acid sequence of an approximately 45 kDa polypeptide and said second amino acid sequence is the amino acid sequence of an approximately 15 kDa polypeptide, wherein said polypeptides are toxic to a rootworm pest that ingests said polypeptides, wherein a nucleotide sequence that codes for said first amino acid sequence hybridizes with the complement of the nucleic acid sequence of SEQ ID NO:10, and wherein a nucleotide sequence that codes for said second amino acid sequence hybridizes with the complement of the nucleic acid sequence of SEQ ID NO:31.

2. An isolated polynucleotide that encodes a fusion protein comprising a first amino acid sequence and a second amino acid sequence wherein said fusion protein is toxic to a rootworm pest that ingests said protein; wherein said first amino sequence is the amino sequence of an approximately 45 kDa polypeptide and said second amino acid sequence is the amino acid sequence of an approximately 15 kDa polypeptide; wherein a nucleotide sequence that codes for said first amino acid sequence hybridizes under stringent conditions with the complement of a nucleic acid sequence selected form the group consisting of SEQ ID NO:10, SEQ ID NO:42, and SEQ ID NO:45; and wherein a nucleotide sequences that codes for said second amino acid sequence hybridizes under stringent condition with the complement of nucleic acid sequence selected from the group consisting of SEQ ID NO:31, SEQ ID NO:40, and SEQ ID NO:44.

3. The polynucleotide according to claim 1 wherein said polynucleotide encodes a fusion protein comprising the amino acid sequence of SEQ ID NO:159.

4. The polynucleotide according to claim 1 wherein said polynucleotide comprises the nucleic acid sequence of SEQ ID NO:160.

5. The polynucleotide according to claim 2 wherein a nucleotide sequence that codes for said first amino acid sequence hybridizes under stringent conditions with the complement of the nucleic acid sequence of SEQ ID NO:10.

6. The polynucleotide according to claim 2 wherein a nucleotide sequence that codes for said second amino acid sequence hybridizes under stringent conditions with the complement of the nucleic acid sequence of SEQ ID NO:31.

7. The polynucleotide according to claim 2 wherein a nucleotide sequence that codes for said first amino acid sequence hybridizes under stringent conditions with the complement of the nucleic acid sequence of SEQ ID NO:42.

8. The polynucleotide according to claim 2 wherein a nucleotide sequence that codes for said second amino acid sequence hybridizes under stringent conditions with the complement of the nucleic acid sequence of SEQ ID NO:40.

9. The polynucleotide according to claim 2 wherein a nucleotide sequence that codes for said first amino acid sequence hybridizes under stringent conditions with the complement of the nucleic acid sequence SEQ ID NO:45.

10. The polynucleotide according to claim 2 wherein a nucleotide sequence that codes for said amino acid sequence hybridizes under stringent conditions with the complement of the nucleic acid sequence of SEQ ID NO:44.

11. The polynucleotide according to claim 2 wherein said polynucleotide comprises the nucleic acid sequence of SEQ ID NO:44.

12. The polynucleotide according of claim 2 wherein said polynucleotide comprises the nucleic acid sequence of SEQ ID NO:45.

13. The polynucleotide according to claim 2 wherein said first amino acid sequence is SEQ ID NO:11.

14. The polynucleotide according to claim 2 wherein said second amino acid sequence is SEQ ID NO:32.

15. The polynucleotide according to claim 2 wherein said first amino acid sequence is SEQ ID NO:43.

16. The polynucleotide according to claim 2 wherein said second amino acid sequence is SEQ ID NO:41.

17. The polynucleotide of claim 1 wherein said polynucleotide comprises a first segment and a second segment, wherein said first segment encodes said first amino acid sequence and said second segment encodes said second amino acid sequence, and wherein said second segment is 5' to said first segment.

18. The polynucleotide of claim 1 wherein said second amino acid sequence is at the carboxy terminus of said protein and said first amino acid sequence is at the amino terminus of said protein.

19. A transgenic host cell comprising a polynucleotide of claim 1, wherein said cell is selected from the group consisting of a plant cell and a bacterial cell.

20. The polynucleotide according to claim 2, wherein said first amino acid sequence is SEQ ID NO:11.

21. The polynucleotide according to claim 2 wherein said second amino acid sequence is SEQ ID NO:32.

22. The polynucleotide of claim 2 wherein said polynucleotide comprises a first segment and a second segment, wherein said first segment encodes said first amino aid sequence and said second segment encodes said second amino acid sequence, and wherein said second segment is 5' to said first segment.

23. The polynucleotide of claim 2 wherein said second amino acid sequence is at the carboxy terminus of said protein and said first amino acid sequence is at the amino terminus of said protein.

24. A transgenic host cell comprising a polynucleotide of claim 2, wherein said cell is selected from the group consisting of a plant cell and a bacterial cell.

* * * * *

UNITED STATES PATENT AND TRADEMARK OFFICE

CERTIFICATE OF CORRECTION

PATENT NO. : 6,677,148 B1
APPLICATION NO. : 09/643596
DATED : January 13, 2004
INVENTOR(S) : Kenneth E. Narva et al.

It is certified that error appears in the above-identified patent and that said Letters Patent is hereby corrected as shown below:

Column 2,
Line 54, "toxin-genes" should read -- toxin genes --.

Column 3,
Line 33, "corn rootworn." should read -- corn rootworm. --.

Column 19,
Line 5, "hosts, e.g.; Pseudomonas such" should read -- hosts, e.g., Pseudomonas such --.

Column 22,
Line 36, "$MgSO_4$.7 $H_2O$" should read -- $MgSO_4 \cdot 7H_2O$ --.
Line 37, "$MnSO_4$.$H_2O$" should read -- $MnSO_4 \cdot H_2O$ --.
Line 38, "$ZnSO_4$.7 $H_2O$" should read -- $ZnSO_4 \cdot 7H_2O$ --.
Line 39, "$FeSO_4$.7 $H_2O$" should read -- $FeSO_4 \cdot 7H_2O$ --.
Line 42, "$CaCl_2$.2 $H_2O$" should read -- $CaCl_2 \cdot 2H_2O$ --.

Column 26,
Line 15 (Table 4), "Concentration (μg/$cm^2$) PI" should read -- Concentration (μg/$cm^2$) P1 --.

Column 27,
Line 37, "Xbal-SacI" should read -- Xbal-Sacl --.

Column 33,
Line 10 (Table 10), "CzyB cell blank" should read -- CryB cell blank --.

Column 34,
Line 62, "cryb- total" should read -- cryB- total --.

Column 35,
Line 9, "P5149B" should read -- PS149B --.

Column 36,
Lines 16-17 (Table 12), "KB6SA11-2" should read -- KB65A11-2 --.

UNITED STATES PATENT AND TRADEMARK OFFICE
CERTIFICATE OF CORRECTION

PATENT NO.       : 6,677,148 B1
APPLICATION NO.  : 09/643596
DATED            : January 13, 2004
INVENTOR(S)      : Kenneth E. Narva et al.

It is certified that error appears in the above-identified patent and that said Letters Patent is hereby corrected as shown below:

Column 39,
Line 8 (Table 13), "14.77#" should read -- 114.77$^{\#}$ --.
Line 18 (Table 13), "KB60FS-11" should read -- KB60F5-11 --.

Column 40,
Lines 16-17, ""45krev6."" should read
-- "45krev6."
        The sequences of the oligonucleotides used for PCR and sequencing follow: --.
Line 52, "201IL3" should read -- 201L3 --.

Column 42,
Line 66, "agagaCTAGT" should read -- agagaACTAGT --.

Column 43,
Line 4, "TATTTTTAATTTTTTTAG" should read -- TATTTTTTTAATTTTTTTAG --.
Line 28, "a 1.5 kb" should read -- a ~1.5 kb --.

Column 46,
Line 66, "rootworn" should read -- rootworm --.

Column 201,
Line 59 (Claim 2), "amino sequence is the amino sequence of" should read -- amino acid sequence is the amino acid sequence of --.
Line 65 (Claim 2), "selected form" should read -- selected from --.
Line 67 (Claim 2), "sequences that" should read -- sequence that --.

Column 202,
Line 41 (Claim 2), "condition with" should read -- conditions with --.
Lines 41-42 (Claim 2), "of nucleic" should read -- of a nucleic --.
Line 67 (Claim 9), "sequence SEQ ID NO:45." should read -- sequence of SEQ ID NO:45. --.

Column 203,
Line 2 (Claim 10), "said amino acid" should read -- said second amino acid --.
Line 8 (Claim 12), "according of claim" should read -- according to claim --.

UNITED STATES PATENT AND TRADEMARK OFFICE

CERTIFICATE OF CORRECTION

PATENT NO. : 6,677,148 B1
APPLICATION NO. : 09/643596
DATED : January 13, 2004
INVENTOR(S) : Kenneth E. Narva et al.

It is certified that error appears in the above-identified patent and that said Letters Patent is hereby corrected as shown below:

Column 204,
Line 6 (Claim 20), "according to claim 2," should read -- according to claim 1 --.
Line 9 (Claim 21), "according to claim 2" should read -- according to claim 1 --.
Line 13 (Claim 22), "amino aid" should read -- amino acid --.

Signed and Sealed this

Twelfth Day of May, 2009

JOHN DOLL
*Acting Director of the United States Patent and Trademark Office*

SEQUENCE LISTING

```
<160> NUMBER OF SEQ ID NOS: 166

<210> SEQ ID NO 1
<211> LENGTH: 5
<212> TYPE: PRT
<213> ORGANISM: Bacillus thuringiensis

<400> SEQUENCE: 1

Met Leu Asp Thr Asn
  1             5


<210> SEQ ID NO 2
<211> LENGTH: 25
<212> TYPE: PRT
```

-continued

<213> ORGANISM: Bacillus thuringiensis

<400> SEQUENCE: 2

```
Met Leu Asp Thr Asn Lys Val Tyr Glu Ile Ser Asn Leu Ala Asn Gly
  1               5                  10                  15

Leu Tyr Thr Ser Thr Tyr Leu Ser Leu
             20                  25
```

<210> SEQ ID NO 3
<211> LENGTH: 24
<212> TYPE: PRT
<213> ORGANISM: Bacillus thuringiensis

<400> SEQUENCE: 3

```
Ser Ala Arg Glu Val His Ile Glu Ile Asn Asn Thr Arg His Thr Leu
  1               5                  10                  15

Gln Leu Glu Ala Lys Thr Lys Leu
             20
```

<210> SEQ ID NO 4
<211> LENGTH: 25
<212> TYPE: PRT
<213> ORGANISM: Bacillus thuringiensis

<400> SEQUENCE: 4

```
Met Leu Asp Thr Asn Lys Val Tyr Glu Ile Ser Asn His Ala Asn Gly
  1               5                  10                  15

Leu Tyr Ala Ala Thr Tyr Leu Ser Leu
             20                  25
```

<210> SEQ ID NO 5
<211> LENGTH: 50
<212> TYPE: PRT
<213> ORGANISM: Bacillus thuringiensis
<220> FEATURE:
<221> NAME/KEY: MISC_FEATURE
<222> LOCATION: (35)
<223> OTHER INFORMATION: Undetermined amino acid

<400> SEQUENCE: 5

```
Ser Ala Arg Glu Val His Ile Asp Val Asn Asn Lys Thr Gly His Thr
  1               5                  10                  15

Leu Gln Leu Glu Asp Lys Thr Lys Leu Asp Gly Gly Arg Trp Arg Thr
             20                  25                  30

Ser Pro Xaa Asn Val Ala Asn Asp Gln Ile Lys Thr Phe Val Ala Glu
         35                  40                  45

Ser Asn
     50
```

<210> SEQ ID NO 6
<211> LENGTH: 25
<212> TYPE: PRT
<213> ORGANISM: Bacillus thuringiensis

<400> SEQUENCE: 6

```
Met Leu Asp Thr Asn Lys Ile Tyr Glu Ile Ser Asn Tyr Ala Asn Gly
  1               5                  10                  15

Leu His Ala Ala Thr Tyr Leu Ser Leu
             20                  25
```

<210> SEQ ID NO 7
<211> LENGTH: 25

-continued

<212> TYPE: PRT
<213> ORGANISM: Bacillus thuringiensis

<400> SEQUENCE: 7

```
Ser Ala Arg Glu Val His Ile Asp Val Asn Asn Lys Thr Gly His Thr
  1               5                  10                  15

Leu Gln Leu Glu Asp Lys Thr Lys Leu
             20                  25
```

<210> SEQ ID NO 8
<211> LENGTH: 29
<212> TYPE: DNA
<213> ORGANISM: Artificial Sequence
<220> FEATURE:
<223> OTHER INFORMATION: Description of Artificial Sequence: oligonucleotide probe for gene encoding PS80JJ1 44.3 kDa toxin; forward primer for PS149B1 and PS167H2
<221> NAME/KEY: misc_feature
<222> LOCATION: (4)
<223> OTHER INFORMATION: Any nucleotide
<221> NAME/KEY: misc_feature
<222> LOCATION: (6)
<223> OTHER INFORMATION: Any nucleotide
<221> NAME/KEY: misc_feature
<222> LOCATION: (12)
<223> OTHER INFORMATION: Any nucleotide
<221> NAME/KEY: misc_feature
<222> LOCATION: (21)
<223> OTHER INFORMATION: Any nucleotide

<400> SEQUENCE: 8

```
atgntngata cnaataaagt ntatgaaat                                      29
```

<210> SEQ ID NO 9
<211> LENGTH: 26
<212> TYPE: DNA
<213> ORGANISM: Artificial Sequence
<220> FEATURE:
<223> OTHER INFORMATION: Description of Artificial Sequence: reverse primer for PS149B1 and PS167H2

<400> SEQUENCE: 9

```
ggattatcta tctctgagtg ttcttg                                         26
```

<210> SEQ ID NO 10
<211> LENGTH: 1158
<212> TYPE: DNA
<213> ORGANISM: Bacillus thuringiensis

<400> SEQUENCE: 10

```
atgttagata ctaataaagt ttatgaaata agcaatcttg ctaatggatt atatacatca     60

acttatttaa gtcttgatga ttcaggtgtt agtttaatga gtaaaaagga tgaagatatt    120

gatgattaca atttaaaatg gtttttattt cctattgata ataatcaata tattattaca    180

agctatggag ctaataattg taaagtttgg aatgttaaaa atgataaaat aaatgtttca    240

acttattctt caacaaactc tgtacaaaaa tggcaaataa aagctaaaga ttcttcatat    300

ataatacaaa gtgataatgg aaaggtctta acagcaggag taggtcaatc tcttggaata    360

gtacgcctaa ctgatgaatt tccagagaat tctaaccaac aatggaattt aactcctgta    420

caaacaattc aactcccaca aaaacctaaa atagatgaaa aattaaaaga tcatcctgaa    480

tattcagaaa ccggaaatat aaatcctaaa acaactcctc aattaatggg atggacatta    540

gtaccttgta ttatggtaaa tgattcaaaa atagataaaa acactcaaat taaaactact    600

ccatattata tttttaaaaa atataaatac tggaatctag caaaaggaag taatgtatct    660
```

-continued

```
ttacttccac atcaaaaaag atcatatgat tatgaatggg gtacagaaaa aaatcaaaaa    720

acaactatta ttaatacagt aggattgcaa attaatatag attcaggaat gaaatttgaa    780

gtaccagaag taggaggagg tacagaagac ataaaaacac aattaactga agaattaaaa    840

gttgaatata gcactgaaac caaaataatg acgaaatatc aagaacactc agagatagat    900

aatccaacta atcaaccaat gaattctata ggacttctta tttatacttc tttagaatta    960

tatcgatata acggtacaga aattaagata atggacatag aaacttcaga tcatgatact   1020

tacactctta cttcttatcc aaatcataaa gaagcattat tacttctcac aaaccattcg   1080

tatgaagaag tagaagaaat aacaaaaata cctaagcata cacttataaa attgaaaaaa   1140

cattatttta aaaaataa                                                 1158


<210> SEQ ID NO 11
<211> LENGTH: 385
<212> TYPE: PRT
<213> ORGANISM: Bacillus thuringiensis

<400> SEQUENCE: 11

Met Leu Asp Thr Asn Lys Val Tyr Glu Ile Ser Asn Leu Ala Asn Gly
  1               5                  10                  15

Leu Tyr Thr Ser Thr Tyr Leu Ser Leu Asp Asp Ser Gly Val Ser Leu
             20                  25                  30

Met Ser Lys Lys Asp Glu Asp Ile Asp Asp Tyr Asn Leu Lys Trp Phe
         35                  40                  45

Leu Phe Pro Ile Asp Asn Asn Gln Tyr Ile Ile Thr Ser Tyr Gly Ala
     50                  55                  60

Asn Asn Cys Lys Val Trp Asn Val Lys Asn Asp Lys Ile Asn Val Ser
 65                  70                  75                  80

Thr Tyr Ser Ser Thr Asn Ser Val Gln Lys Trp Gln Ile Lys Ala Lys
                 85                  90                  95

Asp Ser Ser Tyr Ile Ile Gln Ser Asp Asn Gly Lys Val Leu Thr Ala
            100                 105                 110

Gly Val Gly Gln Ser Leu Gly Ile Val Arg Leu Thr Asp Glu Phe Pro
        115                 120                 125

Glu Asn Ser Asn Gln Gln Trp Asn Leu Thr Pro Val Gln Thr Ile Gln
    130                 135                 140

Leu Pro Gln Lys Pro Lys Ile Asp Glu Lys Leu Lys Asp His Pro Glu
145                 150                 155                 160

Tyr Ser Glu Thr Gly Asn Ile Asn Pro Lys Thr Thr Pro Gln Leu Met
                165                 170                 175

Gly Trp Thr Leu Val Pro Cys Ile Met Val Asn Asp Ser Lys Ile Asp
            180                 185                 190

Lys Asn Thr Gln Ile Lys Thr Thr Pro Tyr Tyr Ile Phe Lys Lys Tyr
        195                 200                 205

Lys Tyr Trp Asn Leu Ala Lys Gly Ser Asn Val Ser Leu Leu Pro His
    210                 215                 220

Gln Lys Arg Ser Tyr Asp Tyr Glu Trp Gly Thr Glu Lys Asn Gln Lys
225                 230                 235                 240

Thr Thr Ile Ile Asn Thr Val Gly Leu Gln Ile Asn Ile Asp Ser Gly
                245                 250                 255

Met Lys Phe Glu Val Pro Glu Val Gly Gly Gly Thr Glu Asp Ile Lys
            260                 265                 270

Thr Gln Leu Thr Glu Glu Leu Lys Val Glu Tyr Ser Thr Glu Thr Lys
```

-continued

```
        275                 280                 285

Ile Met Thr Lys Tyr Gln Glu His Ser Glu Ile Asp Asn Pro Thr Asn
    290                 295                 300

Gln Pro Met Asn Ser Ile Gly Leu Leu Ile Tyr Thr Ser Leu Glu Leu
305                 310                 315                 320

Tyr Arg Tyr Asn Gly Thr Glu Ile Lys Ile Met Asp Ile Glu Thr Ser
                325                 330                 335

Asp His Asp Thr Tyr Thr Leu Thr Ser Tyr Pro Asn His Lys Glu Ala
            340                 345                 350

Leu Leu Leu Leu Thr Asn His Ser Tyr Glu Glu Val Glu Glu Ile Thr
        355                 360                 365

Lys Ile Pro Lys His Thr Leu Ile Lys Leu Lys Lys His Tyr Phe Lys
    370                 375                 380

Lys
385


<210> SEQ ID NO 12
<211> LENGTH: 834
<212> TYPE: DNA
<213> ORGANISM: Bacillus thuringiensis

<400> SEQUENCE: 12

ggactatatg cagcaactta tttaagttta gatgattcag gtgttagttt aatgaataaa      60

aatgatgatg atattgatga ttataactta aaatggtttt tatttcctat tgatgatgat     120

caatatatta ttacaagcta tgcagcaaat aattgtaaag tttggaatgt taataatgat     180

aaaataaatg tttcgactta ttcttcaaca aattcaatac aaaaatggca aataaaagct     240

aatggttctt catatgtaat acaaagtgat aatggaaaag tcttaacagc aggaaccggt     300

caagctcttg gattgatacg tttaactgat gaatcctcaa ataatcccaa tcaacaatgg     360

aatttaactt ctgtacaaac aattcaactt ccacaaaaac ctataataga tacaaaatta     420

aaagattatc ccaaatattc accaactgga aatatagata atggaacatc tcctcaatta     480

atgggatgga cattagtacc ttgtattatg gtaaatgatc caaatataga taaaaatact     540

caaattaaaa ctactccata ttatatttta aaaaaatatc aatattggca acgagcagta     600

ggaagtaatg tagctttacg tccacatgaa aaaaaatcat atacttatga atggggcaca     660

gaaatagatc aaaaaacaac aattataaat acattaggat ttcaaatcaa tatagattca     720

ggaatgaaat ttgatatacc agaagtaggt ggaggtacag atgaaataaa aacacaacta     780

aatgaagaat taaaaataga atatagtcat gaaactaaaa taatggaaaa atat           834


<210> SEQ ID NO 13
<211> LENGTH: 278
<212> TYPE: PRT
<213> ORGANISM: Bacillus thuringiensis

<400> SEQUENCE: 13

Gly Leu Tyr Ala Ala Thr Tyr Leu Ser Leu Asp Asp Ser Gly Val Ser
  1               5                  10                  15

Leu Met Asn Lys Asn Asp Asp Asp Ile Asp Asp Tyr Asn Leu Lys Trp
             20                  25                  30

Phe Leu Phe Pro Ile Asp Asp Asp Gln Tyr Ile Ile Thr Ser Tyr Ala
         35                  40                  45

Ala Asn Asn Cys Lys Val Trp Asn Val Asn Asn Asp Lys Ile Asn Val
     50                  55                  60
```

-continued

```
Ser Thr Tyr Ser Ser Thr Asn Ser Ile Gln Lys Trp Gln Ile Lys Ala
 65                 70                  75                  80

Asn Gly Ser Ser Tyr Val Ile Gln Ser Asp Asn Gly Lys Val Leu Thr
                85                  90                  95

Ala Gly Thr Gly Gln Ala Leu Gly Leu Ile Arg Leu Thr Asp Glu Ser
            100                 105                 110

Ser Asn Asn Pro Asn Gln Gln Trp Asn Leu Thr Ser Val Gln Thr Ile
        115                 120                 125

Gln Leu Pro Gln Lys Pro Ile Ile Asp Thr Lys Leu Lys Asp Tyr Pro
    130                 135                 140

Lys Tyr Ser Pro Thr Gly Asn Ile Asp Asn Gly Thr Ser Pro Gln Leu
145                 150                 155                 160

Met Gly Trp Thr Leu Val Pro Cys Ile Met Val Asn Asp Pro Asn Ile
                165                 170                 175

Asp Lys Asn Thr Gln Ile Lys Thr Thr Pro Tyr Tyr Ile Leu Lys Lys
            180                 185                 190

Tyr Gln Tyr Trp Gln Arg Ala Val Gly Ser Asn Val Ala Leu Arg Pro
        195                 200                 205

His Glu Lys Lys Ser Tyr Thr Tyr Glu Trp Gly Thr Glu Ile Asp Gln
    210                 215                 220

Lys Thr Thr Ile Ile Asn Thr Leu Gly Phe Gln Ile Asn Ile Asp Ser
225                 230                 235                 240

Gly Met Lys Phe Asp Ile Pro Glu Val Gly Gly Gly Thr Asp Glu Ile
                245                 250                 255

Lys Thr Gln Leu Asn Glu Glu Leu Lys Ile Glu Tyr Ser His Glu Thr
            260                 265                 270

Lys Ile Met Glu Lys Tyr
        275
```

<210> SEQ ID NO 14
<211> LENGTH: 829
<212> TYPE: DNA
<213> ORGANISM: Bacillus thuringiensis

<400> SEQUENCE: 14

```
acatgcagca acttatttaa gtttagatga ttcaggtgtt agtttaatga ataaaaatga     60

tgatgatatt gatgactata atttaaggtg gtttttattt cctattgatg ataatcaata    120

tattattaca agctacgcag cgaataattg taaggtttgg aatgttaata atgataaaat    180

aaatgtttca acttattctt caacaaactc gatacagaaa tggcaaataa aagctaatgc    240

ttcttcgtat gtaatacaaa gtaataatgg gaaagttcta acagcaggaa ccggtcaatc    300

tcttggatta atacgtttaa cggatgaatc accagataat cccaatcaac aatggaattt    360

aactcctgta caaacaattc aactcccacc aaaacctaca atagatacaa agttaaaaga    420

ttaccccaaa tattcacaaa ctggcaatat agacaaggga acacctcctc aattaatggg    480

atggacatta ataccttgta ttatggtaaa tgatcccaat atagataaaa acactcaaat    540

caaaactact ccatattata ttttaaaaaa atatcaatat tggcaacaag cagtaggaag    600

taatgtagct ttacgtccgc atgaaaaaaa atcatatgct tatgagtggg gtacagaaat    660

agatcaaaaa acaactatca ttaatacatt aggatttcag attaatatag attcgggaat    720

gaaatttgat ataccagaag taggtggagg tacagatgaa ataaaaaacac aattaaacga    780

agaattaaaa atagaatata gccgtgaaac caaaataatg gaaaaatat                829
```

-continued

<210> SEQ ID NO 15
<211> LENGTH: 276
<212> TYPE: PRT
<213> ORGANISM: Bacillus thuringiensis

<400> SEQUENCE: 15

```
His Ala Ala Thr Tyr Leu Ser Leu Asp Asp Ser Gly Val Ser Leu Met
  1               5                  10                  15

Asn Lys Asn Asp Asp Asp Ile Asp Asp Tyr Asn Leu Arg Trp Phe Leu
             20                  25                  30

Phe Pro Ile Asp Asp Asn Gln Tyr Ile Ile Thr Ser Tyr Ala Ala Asn
         35                  40                  45

Asn Cys Lys Val Trp Asn Val Asn Asn Asp Lys Ile Asn Val Ser Thr
     50                  55                  60

Tyr Ser Ser Thr Asn Ser Ile Gln Lys Trp Gln Ile Lys Ala Asn Ala
 65                  70                  75                  80

Ser Ser Tyr Val Ile Gln Ser Asn Asn Gly Lys Val Leu Thr Ala Gly
                 85                  90                  95

Thr Gly Gln Ser Leu Gly Leu Ile Arg Leu Thr Asp Glu Ser Pro Asp
            100                 105                 110

Asn Pro Asn Gln Gln Trp Asn Leu Thr Pro Val Gln Thr Ile Gln Leu
        115                 120                 125

Pro Pro Lys Pro Thr Ile Asp Thr Lys Leu Lys Asp Tyr Pro Lys Tyr
    130                 135                 140

Ser Gln Thr Gly Asn Ile Asp Lys Gly Thr Pro Pro Gln Leu Met Gly
145                 150                 155                 160

Trp Thr Leu Ile Pro Cys Ile Met Val Asn Asp Pro Asn Ile Asp Lys
                165                 170                 175

Asn Thr Gln Ile Lys Thr Thr Pro Tyr Tyr Ile Leu Lys Lys Tyr Gln
            180                 185                 190

Tyr Trp Gln Gln Ala Val Gly Ser Asn Val Ala Leu Arg Pro His Glu
        195                 200                 205

Lys Lys Ser Tyr Ala Tyr Glu Trp Gly Thr Glu Ile Asp Gln Lys Thr
    210                 215                 220

Thr Ile Ile Asn Thr Leu Gly Phe Gln Ile Asn Ile Asp Ser Gly Met
225                 230                 235                 240

Lys Phe Asp Ile Pro Glu Val Gly Gly Gly Thr Asp Glu Ile Lys Thr
                245                 250                 255

Gln Leu Asn Glu Glu Leu Lys Ile Glu Tyr Ser Arg Glu Thr Lys Ile
            260                 265                 270

Met Glu Lys Tyr
        275
```

<210> SEQ ID NO 16
<211> LENGTH: 7
<212> TYPE: PRT
<213> ORGANISM: Bacillus thuringiensis

<400> SEQUENCE: 16

```
Asp Ile Asp Asp Tyr Asn Leu
  1               5
```

<210> SEQ ID NO 17
<211> LENGTH: 7
<212> TYPE: PRT
<213> ORGANISM: Bacillus thuringiensis

<400> SEQUENCE: 17

-continued

Trp Phe Leu Phe Pro Ile Asp
1 5

<210> SEQ ID NO 18
<211> LENGTH: 8
<212> TYPE: PRT
<213> ORGANISM: Bacillus thuringiensis

<400> SEQUENCE: 18

Gln Ile Lys Thr Thr Pro Tyr Tyr
1 5

<210> SEQ ID NO 19
<211> LENGTH: 6
<212> TYPE: PRT
<213> ORGANISM: Bacillus thuringiensis

<400> SEQUENCE: 19

Tyr Glu Trp Gly Thr Glu
1 5

<210> SEQ ID NO 20
<211> LENGTH: 21
<212> TYPE: DNA
<213> ORGANISM: Artificial Sequence
<220> FEATURE:
<223> OTHER INFORMATION: Description of Artificial Sequence: primer
<221> NAME/KEY: misc_feature
<222> LOCATION: (6)
<223> OTHER INFORMATION: Any nucleotide
<221> NAME/KEY: misc_feature
<222> LOCATION: (12)
<223> OTHER INFORMATION: Any nucleotide
<221> NAME/KEY: misc_feature
<222> LOCATION: (21)
<223> OTHER INFORMATION: Any nucleotide

<400> SEQUENCE: 20
gatatngatg antayaaytt n 21

<210> SEQ ID NO 21
<211> LENGTH: 21
<212> TYPE: DNA
<213> ORGANISM: Artificial Sequence
<220> FEATURE:
<223> OTHER INFORMATION: Description of Artificial Sequence: primer
<221> NAME/KEY: misc_feature
<222> LOCATION: (9)
<223> OTHER INFORMATION: Any nucleotide
<221> NAME/KEY: misc_feature
<222> LOCATION: (15)
<223> OTHER INFORMATION: Any nucleotide
<221> NAME/KEY: misc_feature
<222> LOCATION: (18)
<223> OTHER INFORMATION: Any nucleotide
<221> NAME/KEY: misc_feature
<222> LOCATION: (21)
<223> OTHER INFORMATION: Any nucleotide

<400> SEQUENCE: 21
tggtttttnt ttccnatnga n 21

<210> SEQ ID NO 22
<211> LENGTH: 24
<212> TYPE: DNA
<213> ORGANISM: Artificial Sequence
<220> FEATURE:
<223> OTHER INFORMATION: Description of Artificial Sequence: primer
<221> NAME/KEY: misc_feature -continued
<222> LOCATION: (6)
<223> OTHER INFORMATION: Any nucleotide
<221> NAME/KEY: misc_feature
<222> LOCATION: (12)
<223> OTHER INFORMATION: Any nucleotide
<221> NAME/KEY: misc_feature
<222> LOCATION: (15)
<223> OTHER INFORMATION: Any nucleotide

<400> SEQUENCE: 22
caaatnaaaa cnacnccata ttat 24

<210> SEQ ID NO 23
<211> LENGTH: 18
<212> TYPE: DNA
<213> ORGANISM: Artificial Sequence
<220> FEATURE:
<223> OTHER INFORMATION: Description of Artificial Sequence: primer
<221> NAME/KEY: misc_feature
<222> LOCATION: (3)
<223> OTHER INFORMATION: Any nucleotide
<221> NAME/KEY: misc_feature
<222> LOCATION: (6)
<223> OTHER INFORMATION: Any nucleotide
<221> NAME/KEY: misc_feature
<222> LOCATION: (12)
<223> OTHER INFORMATION: Any nucleotide

<400> SEQUENCE: 23
tangantggg gnacagaa 18

<210> SEQ ID NO 24
<211> LENGTH: 24
<212> TYPE: DNA
<213> ORGANISM: Artificial Sequence
<220> FEATURE:
<223> OTHER INFORMATION: Description of Artificial Sequence: reverse primer
<221> NAME/KEY: misc_feature
<222> LOCATION: (10)
<223> OTHER INFORMATION: Any nucleotide
<221> NAME/KEY: misc_feature
<222> LOCATION: (13)
<223> OTHER INFORMATION: Any nucleotide
<221> NAME/KEY: misc_feature
<222> LOCATION: (19)
<223> OTHER INFORMATION: Any nucleotide

<400> SEQUENCE: 24
ataatatggn gtngttttna tttg 24

<210> SEQ ID NO 25
<211> LENGTH: 18
<212> TYPE: DNA
<213> ORGANISM: Artificial Sequence
<220> FEATURE:
<223> OTHER INFORMATION: Description of Artificial Sequence: reverse primer
<221> NAME/KEY: misc_feature
<222> LOCATION: (7)
<223> OTHER INFORMATION: Any nucleotide
<221> NAME/KEY: misc_feature
<222> LOCATION: (13)
<223> OTHER INFORMATION: Any nucleotide
<221> NAME/KEY: misc_feature
<222> LOCATION: (16)
<223> OTHER INFORMATION: Any nucleotide

<400> SEQUENCE: 25
ttctgtnccc cantcnta 18

-continued

<210> SEQ ID NO 26
<211> LENGTH: 18
<212> TYPE: DNA
<213> ORGANISM: Artificial Sequence
<220> FEATURE:
<223> OTHER INFORMATION: Description of Artificial Sequence: forward primer

<400> SEQUENCE: 26
ctcaaagcgg atcaggag 18

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence: reverse primer

<400> SEQUENCE: 27
gcgtattcgg atatgcttgg 20

<210> SEQ ID NO 28
<211> LENGTH: 386
<212> TYPE: PRT
<213> ORGANISM: Artificial Sequence
<220> FEATURE:
<223> OTHER INFORMATION: Description of Artificial Sequence: generic sequence representing new class of toxins
<221> NAME/KEY: MISC_FEATURE
<222> LOCATION: (1)..(20)
<223> OTHER INFORMATION: Any amino acid
<221> NAME/KEY: MISC_FEATURE
<222> LOCATION: (34)
<223> OTHER INFORMATION: Any amino acid
<221> NAME/KEY: MISC_FEATURE
<222> LOCATION: (36)
<223> OTHER INFORMATION: Any amino acid
<221> NAME/KEY: MISC_FEATURE
<222> LOCATION: (38)
<223> OTHER INFORMATION: Any amino acid
<221> NAME/KEY: MISC_FEATURE
<222> LOCATION: (46)
<223> OTHER INFORMATION: Any amino acid
<221> NAME/KEY: MISC_FEATURE
<222> LOCATION: (54)..(55)
<223> OTHER INFORMATION: Any amino acid
<221> NAME/KEY: MISC_FEATURE
<222> LOCATION: (63)
<223> OTHER INFORMATION: Any amino acid
<221> NAME/KEY: MISC_FEATURE
<222> LOCATION: (73)
<223> OTHER INFORMATION: Any amino acid
<221> NAME/KEY: MISC_FEATURE
<222> LOCATION: (88)
<223> OTHER INFORMATION: Any amino acid
<221> NAME/KEY: MISC_FEATURE
<222> LOCATION: (96)..(97)
<223> OTHER INFORMATION: Any amino acid
<221> NAME/KEY: MISC_FEATURE
<222> LOCATION: (101)
<223> OTHER INFORMATION: Any amino acid
<221> NAME/KEY: MISC_FEATURE
<222> LOCATION: (105)
<223> OTHER INFORMATION: Any amino acid
<221> NAME/KEY: MISC_FEATURE
<222> LOCATION: (114)
<223> OTHER INFORMATION: Any amino acid
<221> NAME/KEY: MISC_FEATURE
<222> LOCATION: (117)
<223> OTHER INFORMATION: Any amino acid
<221> NAME/KEY: MISC_FEATURE
<222> LOCATION: (120)..(121)
<223> OTHER INFORMATION: Any amino acid
<221> NAME/KEY: MISC_FEATURE -continued
<222> LOCATION: (127)..(129)
<223> OTHER INFORMATION: Any amino acid
<221> NAME/KEY: MISC_FEATURE
<222> LOCATION: (131)
<223> OTHER INFORMATION: Any amino acid
<221> NAME/KEY: MISC_FEATURE
<222> LOCATION: (139)
<223> OTHER INFORMATION: Any amino acid
<221> NAME/KEY: MISC_FEATURE
<222> LOCATION: (147)
<223> OTHER INFORMATION: Any amino acid
<221> NAME/KEY: MISC_FEATURE
<222> LOCATION: (150)
<223> OTHER INFORMATION: Any amino acid
<221> NAME/KEY: MISC_FEATURE
<222> LOCATION: (153)
<223> OTHER INFORMATION: Any amino acid
<221> NAME/KEY: MISC_FEATURE
<222> LOCATION: (158)
<223> OTHER INFORMATION: Any amino acid
<221> NAME/KEY: MISC_FEATURE
<222> LOCATION: (160)
<223> OTHER INFORMATION: Any amino acid
<221> NAME/KEY: MISC_FEATURE
<222> LOCATION: (163)
<223> OTHER INFORMATION: Any amino acid
<221> NAME/KEY: MISC_FEATURE
<222> LOCATION: (168)..(170)
<223> OTHER INFORMATION: Any amino acid
<221> NAME/KEY: MISC_FEATURE
<222> LOCATION: (172)
<223> OTHER INFORMATION: Any amino acid
<221> NAME/KEY: MISC_FEATURE
<222> LOCATION: (181)
<223> OTHER INFORMATION: Any amino acid
<221> NAME/KEY: MISC_FEATURE
<222> LOCATION: (189)..(190)
<223> OTHER INFORMATION: Any amino acid
<221> NAME/KEY: MISC_FEATURE
<222> LOCATION: (205)
<223> OTHER INFORMATION: Any amino acid
<221> NAME/KEY: MISC_FEATURE
<222> LOCATION: (209)
<223> OTHER INFORMATION: Any amino acid
<221> NAME/KEY: MISC_FEATURE
<222> LOCATION: (212)..(213)
<223> OTHER INFORMATION: Any amino acid
<221> NAME/KEY: MISC_FEATURE
<222> LOCATION: (215)
<223> OTHER INFORMATION: Any amino acid
<221> NAME/KEY: MISC_FEATURE
<222> LOCATION: (220)
<223> OTHER INFORMATION: Any amino acid
<221> NAME/KEY: MISC_FEATURE
<222> LOCATION: (222)
<223> OTHER INFORMATION: Any amino acid
<221> NAME/KEY: MISC_FEATURE
<222> LOCATION: (225)
<223> OTHER INFORMATION: Any amino acid
<221> NAME/KEY: MISC_FEATURE
<222> LOCATION: (227)
<223> OTHER INFORMATION: Any amino acid
<221> NAME/KEY: MISC_FEATURE
<222> LOCATION: (230)
<223> OTHER INFORMATION: Any amino acid
<221> NAME/KEY: MISC_FEATURE
<222> LOCATION: (237)..(238)
<223> OTHER INFORMATION: Any amino acid
<221> NAME/KEY: MISC_FEATURE
<222> LOCATION: (247)
<223> OTHER INFORMATION: Any amino acid
<221> NAME/KEY: MISC_FEATURE
<222> LOCATION: (249)
<223> OTHER INFORMATION: Any amino acid
<221> NAME/KEY: MISC_FEATURE
<222> LOCATION: (260)..(261)
<223> OTHER INFORMATION: Any amino acid
<221> NAME/KEY: MISC_FEATURE
<222> LOCATION: (269)..(270)

-continued

```
<223> OTHER INFORMATION: Any amino acid
<221> NAME/KEY: MISC_FEATURE
<222> LOCATION: (276)
<223> OTHER INFORMATION: Any amino acid
<221> NAME/KEY: MISC_FEATURE
<222> LOCATION: (281)
<223> OTHER INFORMATION: Any amino acid
<221> NAME/KEY: MISC_FEATURE
<222> LOCATION: (285)
<223> OTHER INFORMATION: Any amino acid
<221> NAME/KEY: MISC_FEATURE
<222> LOCATION: (291)
<223> OTHER INFORMATION: Any amino acid
<221> NAME/KEY: MISC_FEATURE
<222> LOCATION: (294)..(386)
<223> OTHER INFORMATION: Any amino acid

<400> SEQUENCE: 28

Xaa Xaa Xaa Xaa Xaa Xaa Xaa Xaa Xaa Xaa Xaa Xaa Xaa Xaa Xaa Xaa
  1               5                  10                  15

Xaa Xaa Xaa Xaa Thr Tyr Leu Ser Leu Asp Asp Ser Gly Val Ser Leu
             20                  25                  30

Met Xaa Lys Xaa Asp Xaa Asp Ile Asp Asp Tyr Asn Leu Xaa Trp Phe
         35                  40                  45

Leu Phe Pro Ile Asp Xaa Xaa Gln Tyr Ile Ile Thr Ser Tyr Xaa Ala
     50                  55                  60

Asn Asn Cys Lys Val Trp Asn Val Xaa Asn Asp Lys Ile Asn Val Ser
 65                  70                  75                  80

Thr Tyr Ser Ser Thr Asn Ser Xaa Gln Lys Trp Gln Ile Lys Ala Xaa
                 85                  90                  95

Xaa Ser Ser Tyr Xaa Ile Gln Ser Xaa Asn Gly Lys Val Leu Thr Ala
            100                 105                 110

Gly Xaa Gly Gln Xaa Leu Gly Xaa Xaa Arg Leu Thr Asp Glu Xaa Xaa
        115                 120                 125

Xaa Asn Xaa Asn Gln Gln Trp Asn Leu Thr Xaa Val Gln Thr Ile Gln
    130                 135                 140

Leu Pro Xaa Lys Pro Xaa Ile Asp Xaa Lys Leu Lys Asp Xaa Pro Xaa
145                 150                 155                 160

Tyr Ser Xaa Thr Gly Asn Ile Xaa Xaa Xaa Thr Xaa Pro Gln Leu Met
                165                 170                 175

Gly Trp Thr Leu Xaa Pro Cys Ile Met Val Asn Asp Xaa Xaa Ile Asp
            180                 185                 190

Lys Asn Thr Gln Ile Lys Thr Thr Pro Tyr Tyr Ile Xaa Lys Lys Tyr
        195                 200                 205

Xaa Tyr Trp Xaa Xaa Ala Xaa Gly Ser Asn Val Xaa Leu Xaa Pro His
    210                 215                 220

Xaa Lys Xaa Ser Tyr Xaa Tyr Glu Trp Gly Thr Glu Xaa Xaa Gln Lys
225                 230                 235                 240

Thr Thr Ile Ile Asn Thr Xaa Gly Xaa Gln Ile Asn Ile Asp Ser Gly
                245                 250                 255

Met Lys Phe Xaa Xaa Pro Glu Val Gly Gly Gly Thr Xaa Xaa Ile Lys
            260                 265                 270

Thr Gln Leu Xaa Glu Glu Leu Lys Xaa Glu Tyr Ser Xaa Glu Thr Lys
   275                 280                 285

Ile Met Xaa Lys Tyr Xaa Xaa Xaa Xaa Xaa Xaa Xaa Xaa Xaa Xaa Xaa
          290                 295                 300

Xaa Xaa Xaa Xaa Xaa Xaa Xaa Xaa Xaa Xaa Xaa Xaa Xaa Xaa Xaa Xaa
305                 310                 315                 320
```

-continued

```
Xaa Xaa Xaa Xaa Xaa Xaa Xaa Xaa Xaa Xaa Xaa Xaa Xaa Xaa Xaa Xaa
                325                 330                 335

Xaa Xaa Xaa Xaa Xaa Xaa Xaa Xaa Xaa Xaa Xaa Xaa Xaa Xaa Xaa Xaa
            340                 345                 350

Xaa Xaa Xaa Xaa Xaa Xaa Xaa Xaa Xaa Xaa Xaa Xaa Xaa Xaa Xaa Xaa
        355                 360                 365

Xaa Xaa Xaa Xaa Xaa Xaa Xaa Xaa Xaa Xaa Xaa Xaa Xaa Xaa Xaa Xaa
    370                 375                 380

Xaa Xaa
385


<210> SEQ ID NO 29
<211> LENGTH: 28
<212> TYPE: DNA
<213> ORGANISM: Artificial Sequence
<220> FEATURE:
<223> OTHER INFORMATION: Description of Artificial Sequence:
      oligonucleotide probe
<221> NAME/KEY: misc_feature
<222> LOCATION: (2)
<223> OTHER INFORMATION: Any nucleotide
<221> NAME/KEY: misc_feature
<222> LOCATION: (8)
<223> OTHER INFORMATION: Any nucleotide
<221> NAME/KEY: misc_feature
<222> LOCATION: (14)
<223> OTHER INFORMATION: Any nucleotide
<221> NAME/KEY: misc_feature
<222> LOCATION: (20)
<223> OTHER INFORMATION: Any nucleotide

<400> SEQUENCE: 29

gngaagtnca tatngaaatn aataatac                                          28


<210> SEQ ID NO 30
<211> LENGTH: 2015
<212> TYPE: DNA
<213> ORGANISM: Bacillus thuringiensis

<400> SEQUENCE: 30

attaatttta tggaggttga tatttatgtc agctcgcgaa gtacacattg aaataaacaa     60

taaaacacgt catacattac aattagagga taaaactaaa cttagcggcg gtagatggcg    120

aacatcacct acaaatgttg ctcgtgatac aattaaaaca tttgtagcag aatcacatgg    180

ttttatgaca ggagtagaag gtattatata ttttagtgta aacggagacg cagaaattag    240

tttacatttt gacaatcctt atataggttc taataaatgt gatggttctt ctgataaacc    300

tgaatatgaa gttattactc aaagcggatc aggagataaa tctcatgtga catatactat    360

tcagacagta tctttacgat tataaggaaa atttataaaa actgtatttt ttactaaaat    420

accaaaaaat acatatttat tttttggtat tttctaatat gaaatatgaa ttataaaaat    480

attaataaaa aaggtgataa aaattatgtt agatactaat aaagtttatg aaataagcaa    540

tcttgctaat ggattatata catcaactta tttaagtctt gatgattcag gtgttagttt    600

aatgagtaaa aaggatgaag atattgatga ttacaattta aaatggtttt tatttcctat    660

tgataataat caatatatta ttacaagcta tggagctaat aattgtaaag tttggaatgt    720

taaaaatgat aaaataaatg tttcaactta ttcttcaaca aactctgtac aaaaatggca    780

aataaaagct aaagattctt catatataat acaaagtgat aatggaaagg tcttaacagc    840

aggagtaggt caatctcttg gaatagtacg cctaactgat gaatttccag agaattctaa    900

ccaacaatgg aatttaactc ctgtacaaac aattcaactc ccacaaaaac ctaaaataga    960
```

-continued

```
tgaaaaatta aaagatcatc ctgaatattc agaaaccgga aatataaatc ctaaaacaac   1020

tcctcaatta atgggatgga cattagtacc ttgtattatg gtaaatgatt caaaaataga   1080

taaaaacact caaattaaaa ctactccata ttatattttt aaaaaatata aatactggaa   1140

tctagcaaaa ggaagtaatg tatctttact tccacatcaa aaaagatcat atgattatga   1200

atggggtaca gaaaaaaatc aaaaaacaac tattattaat acagtaggat tgcaaattaa   1260

tatagattca ggaatgaaat ttgaagtacc agaagtagga ggaggtacag aagacataaa   1320

aacacaatta actgaagaat taaaagttga atatagcact gaaaccaaaa taatgacgaa   1380

atatcaagaa cactcagaga tagataatcc aactaatcaa ccaatgaatt ctataggact   1440

tcttatttat acttctttag aattatatcg atataacggt acagaaatta agataatgga   1500

catagaaact tcagatcatg atacttacac tcttacttct tatccaaatc ataaagaagc   1560

attattactt ctcacaaacc attcgtatga agaagtagaa gaaataacaa aaatacctaa   1620

gcatacactt ataaaattga aaaaacatta ttttaaaaaa taaaaaacat aatatataaa   1680

tgactgatta atatctctcg aaaaggttct ggtgcaaaaa tagtgggata tgaaaaaagc   1740

aaaagattcc taacggaatg gaacattagg ctgttaaatc aaaaagttta ttgataaaat   1800

atatctgcct ttggacagac ttctcccctt ggagagtttg tcctttttttg accatatgca   1860

tagcttctat tccggcaatc atttttgtag ctgtttgcaa ggattttaat ccaagcatat   1920

ccgaatacgc tttttgataa ccgatgtctt gttcaatgat attgtttaat attttcacac   1980

gaattggcta ctgtgcggta tcctgtctcc tttat                              2015
```

<210> SEQ ID NO 31
<211> LENGTH: 360
<212> TYPE: DNA
<213> ORGANISM: Bacillus thuringiensis

<400> SEQUENCE: 31

```
atgtcagctc gcgaagtaca cattgaaata aacaataaaa cacgtcatac attacaatta     60

gaggataaaa ctaaacttag cggcggtaga tggcgaacat cacctacaaa tgttgctcgt    120

gatacaatta aaacatttgt agcagaatca catggtttta tgacaggagt agaaggtatt    180

atatatttta gtgtaaacgg agacgcagaa attagtttac attttgacaa tccttatata    240

ggttctaata aatgtgatgg ttcttctgat aaacctgaat atgaagttat tactcaaagc    300

ggatcaggag ataaatctca tgtgacatat actattcaga cagtatcttt acgattataa    360
```

<210> SEQ ID NO 32
<211> LENGTH: 119
<212> TYPE: PRT
<213> ORGANISM: Bacillus thuringiensis

<400> SEQUENCE: 32

```
Met Ser Ala Arg Glu Val His Ile Glu Ile Asn Asn Lys Thr Arg His
  1               5                  10                  15

Thr Leu Gln Leu Glu Asp Lys Thr Lys Leu Ser Gly Gly Arg Trp Arg
             20                  25                  30

Thr Ser Pro Thr Asn Val Ala Arg Asp Thr Ile Lys Thr Phe Val Ala
         35                  40                  45

Glu Ser His Gly Phe Met Thr Gly Val Glu Gly Ile Ile Tyr Phe Ser
     50                  55                  60

Val Asn Gly Asp Ala Glu Ile Ser Leu His Phe Asp Asn Pro Tyr Ile
 65                  70                  75                  80
```

-continued

Gly Ser Asn Lys Cys Asp Gly Ser Ser Asp Lys Pro Glu Tyr Glu Val
85 90 95

Ile Thr Gln Ser Gly Ser Gly Asp Lys Ser His Val Thr Tyr Thr Ile
100 105 110

Gln Thr Val Ser Leu Arg Leu
115

<210> SEQ ID NO 33
<211> LENGTH: 24
<212> TYPE: DNA
<213> ORGANISM: Artificial Sequence
<220> FEATURE:
<223> OTHER INFORMATION: Description of Artificial Sequence: reverse oligonucleotide primer

<400> SEQUENCE: 33
catgagattt atctcctgat ccgc 24

<210> SEQ ID NO 34
<211> LENGTH: 2230
<212> TYPE: DNA
<213> ORGANISM: Bacillus thuringiensis

<400> SEQUENCE: 34
actatgacaa tgattatgac tgctgatgaa ttagctttat caataccagg atattctaaa 60
ccatcaaata taacaggaga taaaagtaaa catacattat ttactaatat aattggagat 120
attcaaataa aagatcaagc aacatttggg gttgtttttg atccccctct taatcgtatt 180
tcaggggctg aagaatcaag taagtttatt gatgtatatt atccttctga agatagtaac 240
cttaaatatt atcaatttat aaaagtagca attgattttg atattaatga agattttatt 300
aattttaata atcatgacaa tatagggata tttaattttg ttacacgaaa tttttttatta 360 aataatgaaa atgattaata aaaaatttaa tttgtataat atgtttattt tttgaaaatt 420
gaatgcatat attaatcgag tatgtgtaat aaattttaat tttatggagg ttgatattta 480
tgtcagcacg tgaagtacac attgatgtaa ataataagac aggtcataca ttacaattag 540
aagataaaac aaaacttgat ggtggtagat ggcgaacatc acctacaaat gttgctaatg 600
atcaaattaa aacatttgta gcagaatcac atggttttat gacaggtaca gaaggtacta 660
tatattatag tataaatgga gaagcagaaa ttagtttata ttttgacaat ccttattcag 720
gttctaataa atatgatggg cattccaata aaaatcaata tgaagttatt acccaaggag 780
gatcaggaaa tcaatctcat gttacgtata ctattcaaac tgtatcttca cgatatggga 840
ataattcata aaaaaatatt tttttttacg aaaataccaa aaaaattttt ttggtatttt 900
ctaatataat tcataaatat tttaataata aaattataag aaaaggtgat aaatattatg 960
ttagatacta ataaaattta tgaaataagt aattatgcta atggattaca tgcagcaact 1020
tatttaagtt tagatgattc aggtgttagt ttaatgaata aaaatgatga tgatattgat 1080
gactataatt taaggtggtt tttatttcct attgatgata atcaatatat tattacaagc 1140
tacgcagcga ataattgtaa ggtttggaat gttaataatg ataaaataaa tgtttcaact 1200
tattcttcaa caaactcgat acagaaatgg caaataaaag ctaatgcttc ttcgtatgta 1260
atacaaagta ataatgggaa agttctaaca gcaggaaccg gtcaatctct tggattaata 1320
cgtttaacgg atgaatcacc agataatccc aatcaacaat ggaatttaac tcctgtacaa 1380
acaattcaac tcccaccaaa acctacaata gatacaaagt taaaagatta ccccaaatat 1440

-continued

```
tcacaaactg gcaatataga caagggaaca cctcctcaat taatgggatg gacattaata   1500

ccttgtatta tggtaaatga tccaaatata gataaaaaca ctcaaatcaa aactactcca   1560

tattatattt taaaaaaata tcaatattgg caacaagcag taggaagtaa tgtagcttta   1620

cgtccgcatg aaaaaaaatc atatgcttat gagtggggta cagaaataga tcaaaaaaca   1680

actatcatta atacattagg atttcagatt aatatagatt cgggaatgaa atttgatata   1740

ccagaagtag gtggaggtac agatgaaata aaaacacaat taaacgaaga attaaaaata   1800

gaatatagcc gtgaaaccaa aataatggaa aaatatcagg aacaatcaga gatagataat   1860

ccaactgatc aatcaatgaa ttctatagga ttcctcacta ttacttcttt agaattatat   1920

cgatataatg gttcggaaat tagtgtaatg aaaattcaaa cttcagataa tgatacttac   1980

aatgtgacct cttatccaga tcatcaacaa gctctattac ttcttacaaa tcattcatat   2040

gaagaagtag aagaaataac aaatattccc aaaatatcac tgaaaaaatt aaaaaaatat   2100

tatttttaaa acataattat attttgatag ctttttaaaa ataaagattg ttcaaagtaa   2160

aatgaaagaa aatcttttat gaaactttaa tacaataaaa gaggaatatt ttcttataag   2220

tacttccttg                                                          2230
```

```
<210> SEQ ID NO 35
<211> LENGTH: 372
<212> TYPE: DNA
<213> ORGANISM: Bacillus thuringiensis

<400> SEQUENCE: 35

atgtcagcac gtgaagtaca cattgatgta aataataaga caggtcatac attacaatta     60

gaagataaaa caaaacttga tggtggtaga tggcgaacat cacctacaaa tgttgctaat    120

gatcaaatta aaacatttgt agcagaatca catggtttta tgacaggtac agaaggtact    180

atatattata gtataaatgg agaagcagaa attagtttat attttgacaa tccttattca    240

ggttctaata aatatgatgg gcattccaat aaaaatcaat atgaagttat tacccaagga    300

ggatcaggaa atcaatctca tgttacgtat actattcaaa ctgtatcttc acgatatggg    360

aataattcat aa                                                        372
```

```
<210> SEQ ID NO 36
<211> LENGTH: 123
<212> TYPE: PRT
<213> ORGANISM: Bacillus thuringiensis

<400> SEQUENCE: 36

Met Ser Ala Arg Glu Val His Ile Asp Val Asn Asn Lys Thr Gly His
  1               5                  10                  15

Thr Leu Gln Leu Glu Asp Lys Thr Lys Leu Asp Gly Gly Arg Trp Arg
             20                  25                  30

Thr Ser Pro Thr Asn Val Ala Asn Asp Gln Ile Lys Thr Phe Val Ala
         35                  40                  45

Glu Ser His Gly Phe Met Thr Gly Thr Glu Gly Thr Ile Tyr Tyr Ser
     50                  55                  60

Ile Asn Gly Glu Ala Glu Ile Ser Leu Tyr Phe Asp Asn Pro Tyr Ser
 65                  70                  75                  80

Gly Ser Asn Lys Tyr Asp Gly His Ser Asn Lys Asn Gln Tyr Glu Val
                 85                  90                  95

Ile Thr Gln Gly Gly Ser Gly Asn Gln Ser His Val Thr Tyr Thr Ile
            100                 105                 110
```

-continued

```
Gln Thr Val Ser Ser Arg Tyr Gly Asn Asn Ser
        115                 120


<210> SEQ ID NO 37
<211> LENGTH: 1152
<212> TYPE: DNA
<213> ORGANISM: Bacillus thuringiensis

<400> SEQUENCE: 37

atgttagata ctaataaaat ttatgaaata agtaattatg ctaatggatt acatgcagca     60

acttatttaa gtttagatga ttcaggtgtt agtttaatga ataaaaatga tgatgatatt    120

gatgactata atttaaggtg gtttttattt cctattgatg ataatcaata tattattaca    180

agctacgcag cgaataattg taaggtttgg aatgttaata atgataaaat aaatgtttca    240

acttattctt caacaaactc gatacagaaa tggcaaataa aagctaatgc ttcttcgtat    300

gtaatacaaa gtaataatgg gaaagttcta acagcaggaa ccggtcaatc tcttggatta    360

atacgtttaa cggatgaatc accagataat cccaatcaac aatggaattt aactcctgta    420

caaacaattc aactcccacc aaaacctaca atagatacaa agttaaaaga ttaccccaaa    480

tattcacaaa ctggcaatat agacaaggga acacctcctc aattaatggg atggacatta    540

ataccttgta ttatggtaaa tgatccaaat atagataaaa acactcaaat caaaactact    600

ccatattata ttttaaaaaa atatcaatat tggcaacaag cagtaggaag taatgtagct    660

ttacgtccgc atgaaaaaaa atcatatgct tatgagtggg gtacagaaat agatcaaaaa    720

acaactatca ttaatacatt aggatttcag attaatatag attcgggaat gaaatttgat    780

ataccagaag taggtggagg tacagatgaa ataaaaacac aattaaacga agaattaaaa    840

atagaatata gccgtgaaac caaaataatg gaaaaatatc aggaacaatc agagatagat    900

aatccaactg atcaatcaat gaattctata ggattcctca ctattacttc tttagaatta    960

tatcgatata atggttcgga aattagtgta atgaaaattc aaacttcaga taatgatact   1020

tacaatgtga cctcttatcc agatcatcaa caagctctat tacttcttac aaatcattca   1080

tatgaagaag tagaagaaat aacaaatatt cccaaaatat cactgaaaaa attaaaaaaa   1140

tattattttt aa                                                        1152


<210> SEQ ID NO 38
<211> LENGTH: 383
<212> TYPE: PRT
<213> ORGANISM: Bacillus thuringiensis

<400> SEQUENCE: 38

Met Leu Asp Thr Asn Lys Ile Tyr Glu Ile Ser Asn Tyr Ala Asn Gly
  1               5                  10                  15

Leu His Ala Ala Thr Tyr Leu Ser Leu Asp Asp Ser Gly Val Ser Leu
             20                  25                  30

Met Asn Lys Asn Asp Asp Asp Ile Asp Asp Tyr Asn Leu Arg Trp Phe
         35                  40                  45

Leu Phe Pro Ile Asp Asp Asn Gln Tyr Ile Ile Thr Ser Tyr Ala Ala
     50                  55                  60

Asn Asn Cys Lys Val Trp Asn Val Asn Asn Asp Lys Ile Asn Val Ser
 65                  70                  75                  80

Thr Tyr Ser Ser Thr Asn Ser Ile Gln Lys Trp Gln Ile Lys Ala Asn
                 85                  90                  95

Ala Ser Ser Tyr Val Ile Gln Ser Asn Asn Gly Lys Val Leu Thr Ala
            100                 105                 110
```

-continued

```
Gly Thr Gly Gln Ser Leu Gly Leu Ile Arg Leu Thr Asp Glu Ser Pro
        115                 120                 125

Asp Asn Pro Asn Gln Gln Trp Asn Leu Thr Pro Val Gln Thr Ile Gln
    130                 135                 140

Leu Pro Pro Lys Pro Thr Ile Asp Thr Lys Leu Lys Asp Tyr Pro Lys
145                 150                 155                 160

Tyr Ser Gln Thr Gly Asn Ile Asp Lys Gly Thr Pro Pro Gln Leu Met
                165                 170                 175

Gly Trp Thr Leu Ile Pro Cys Ile Met Val Asn Asp Pro Asn Ile Asp
            180                 185                 190

Lys Asn Thr Gln Ile Lys Thr Thr Pro Tyr Tyr Ile Leu Lys Lys Tyr
        195                 200                 205

Gln Tyr Trp Gln Gln Ala Val Gly Ser Asn Val Ala Leu Arg Pro His
    210                 215                 220

Glu Lys Lys Ser Tyr Ala Tyr Glu Trp Gly Thr Glu Ile Asp Gln Lys
225                 230                 235                 240

Thr Thr Ile Ile Asn Thr Leu Gly Phe Gln Ile Asn Ile Asp Ser Gly
                245                 250                 255

Met Lys Phe Asp Ile Pro Glu Val Gly Gly Gly Thr Asp Glu Ile Lys
            260                 265                 270

Thr Gln Leu Asn Glu Glu Leu Lys Ile Glu Tyr Ser Arg Glu Thr Lys
        275                 280                 285

Ile Met Glu Lys Tyr Gln Glu Gln Ser Glu Ile Asp Asn Pro Thr Asp
    290                 295                 300

Gln Ser Met Asn Ser Ile Gly Phe Leu Thr Ile Thr Ser Leu Glu Leu
305                 310                 315                 320

Tyr Arg Tyr Asn Gly Ser Glu Ile Ser Val Met Lys Ile Gln Thr Ser
                325                 330                 335

Asp Asn Asp Thr Tyr Asn Val Thr Ser Tyr Pro Asp His Gln Gln Ala
            340                 345                 350

Leu Leu Leu Leu Thr Asn His Ser Tyr Glu Glu Val Glu Glu Ile Thr
        355                 360                 365

Asn Ile Pro Lys Ile Ser Leu Lys Lys Leu Lys Lys Tyr Tyr Phe
    370                 375                 380
```

<210> SEQ ID NO 39
<211> LENGTH: 2132
<212> TYPE: DNA
<213> ORGANISM: Bacillus thuringiensis

<400> SEQUENCE: 39

```
gtatttcagg gggtgaagat tcaagtaagt ttattgatgt atattatcct tttgaagata     60

gtaattttaa atattatcaa tttataaaag tagcaattga ttttgatatt aatgaagatt    120

ttattaattt taataatcat gacaatatag ggatatttaa ttttgttaca cgaaattttt    180

tattaaataa tgaaaatgat gaataaaaaa tttaatttgt ttattatgtt tattttttga    240

aaattgaatg catatattaa tcgagtatgt ataataaatt ttaattttat ggaggttgat    300

atttatgtca gcacgtgaag tacacattga tgtaaataat aagacaggtc atacattaca    360

attagaagat aaaacaaaac ttgatggtgg tagatggcga acatcaccta caaatgttgc    420

taatgatcaa attaaaacat ttgtagcaga atcaaatggt tttatgacag gtacagaagg    480

tactatatat tatagtataa atggagaagc agaaattagt ttatattttg acaatccttt    540

tgcaggttct aataaatatg atggacattc caataaatct caatatgaaa ttattaccca    600
```

-continued

```
aggaggatca ggaaatcaat ctcatgttac gtatactatt caaaccacat cctcacgata    660

tgggcataaa tcataacaaa taatttttta cgaaaatacc aaaaaataaa tatttttttgg   720

tattttctaa tataaattac aaatatatta ataataaaat tataagaaaa ggtgataaag    780

attatgttag atactaataa agtttatgaa ataagcaatc atgctaatgg actatatgca    840

gcaacttatt taagtttaga tgattcaggt gttagtttaa tgaataaaaa tgatgatgat    900

attgatgatt ataacttaaa atggttttta tttcctattg atgatgatca atatattatt    960

acaagctatg cagcaaataa ttgtaaagtt tggaatgtta ataatgataa aataaatgtt   1020

tcgacttatt cttcaacaaa ttcaatacaa aaatggcaaa taaaagctaa tggttcttca   1080

tatgtaatac aaagtgataa tggaaaagtc ttaacagcag gaaccggtca agctcttgga   1140

ttgatacgtt taactgatga atcctcaaat aatcccaatc aacaatggaa tttaacttct   1200

gtacaaacaa ttcaacttcc acaaaaacct ataatagata caaaattaaa agattatccc   1260

aaatattcac caactggaaa tatagataat ggaacatctc ctcaattaat gggatggaca   1320

ttagtacctt gtattatggt aaatgatcca aatatagata aaaatactca aattaaaact   1380

actccatatt atattttaaa aaaatatcaa tattggcaac gagcagtagg aagtaatgta   1440

gctttacgtc cacatgaaaa aaaatcatat acttatgaat ggggcacaga aatagatcaa   1500

aaaacaacaa ttataaatac attaggattt caaatcaata tagattcagg aatgaaattt   1560

gatataccag aagtaggtgg aggtacagat gaaataaaaa cacaactaaa tgaagaatta   1620

aaaatagaat atagtcatga aactaaaata atggaaaaat atcaagaaca atctgaaata   1680

gataatccaa ctgatcaatc aatgaattct ataggatttc ttactattac ttccttagaa   1740

ttatatagat ataatggctc agaaattcgt ataatgcaaa ttcaaacctc agataatgat   1800

acttataatg ttacttctta tccaaatcat caacaagctt tattacttct tacaaatcat   1860

tcatatgaag aagtagaaga aataacaaat attcctaaaa gtacactaaa aaaattaaaa   1920

aaatattatt tttaaatatt gaaattagaa attatctaaa acaaaacgaa agataattta   1980

atctttaatt atttgtaaga taatcgtatt ttatttgtat taatttttat acaatataaa   2040

gtaatatctg tacgtgaaat tggtttcgct tcaatatcta atctcatctc atgtattaca   2100

tgcgtaatac cttcttgttc tgcttctaca ag                                 2132
```

<210> SEQ ID NO 40
<211> LENGTH: 372
<212> TYPE: DNA
<213> ORGANISM: Bacillus thuringiensis

<400> SEQUENCE: 40

```
atgtcagcac gtgaagtaca cattgatgta aataataaga caggtcatac attacaatta     60

gaagataaaa caaaacttga tggtggtaga tggcgaacat cacctacaaa tgttgctaat    120

gatcaaatta aaacatttgt agcagaatca aatggtttta tgacaggtac agaaggtact    180

atatattata gtataaatgg agaagcagaa attagtttat attttgacaa tccttttgca    240

ggttctaata aatatgatgg acattccaat aaatctcaat atgaaattat tacccaagga    300

ggatcaggaa atcaatctca tgttacgtat actattcaaa ccacatcctc acgatatggg    360

cataaatcat aa                                                         372
```

<210> SEQ ID NO 41
<211> LENGTH: 123
<212> TYPE: PRT

-continued

<213> ORGANISM: Bacillus thuringiensis

<400> SEQUENCE: 41

```
Met Ser Ala Arg Glu Val His Ile Asp Val Asn Asn Lys Thr Gly His
  1               5                  10                  15

Thr Leu Gln Leu Glu Asp Lys Thr Lys Leu Asp Gly Gly Arg Trp Arg
             20                  25                  30

Thr Ser Pro Thr Asn Val Ala Asn Asp Gln Ile Lys Thr Phe Val Ala
         35                  40                  45

Glu Ser Asn Gly Phe Met Thr Gly Thr Glu Gly Thr Ile Tyr Tyr Ser
     50                  55                  60

Ile Asn Gly Glu Ala Glu Ile Ser Leu Tyr Phe Asp Asn Pro Phe Ala
 65                  70                  75                  80

Gly Ser Asn Lys Tyr Asp Gly His Ser Asn Lys Ser Gln Tyr Glu Ile
                 85                  90                  95

Ile Thr Gln Gly Gly Ser Gly Asn Gln Ser His Val Thr Tyr Thr Ile
            100                 105                 110

Gln Thr Thr Ser Ser Arg Tyr Gly His Lys Ser
        115                 120
```

<210> SEQ ID NO 42
<211> LENGTH: 1241
<212> TYPE: DNA
<213> ORGANISM: Bacillus thuringiensis
<220> FEATURE:
<221> NAME/KEY: misc_feature
<222> LOCATION: (18)
<223> OTHER INFORMATION: Undetermined nucleotide
<221> NAME/KEY: misc_feature
<222> LOCATION: (53)
<223> OTHER INFORMATION: Undetermined nucleotide
<221> NAME/KEY: misc_feature
<222> LOCATION: (61)
<223> OTHER INFORMATION: Undetermined nucleotide
<221> NAME/KEY: misc_feature
<222> LOCATION: (68)
<223> OTHER INFORMATION: Undetermined nucleotide
<221> NAME/KEY: misc_feature
<222> LOCATION: (73)
<223> OTHER INFORMATION: Undetermined nucleotide
<221> NAME/KEY: misc_feature
<222> LOCATION: (81)
<223> OTHER INFORMATION: Undetermined nucleotide

<400> SEQUENCE: 42

```
wcdmtkdvrm wahkcmdndb ygtrawbmkg cwtkctgyhd cywagmawtd cvnwmhasrt      60

nchhtmsnwr manrgarcrr nwrgarhatg ttagatacta ataaagttta tgaaataagc     120

aatcatgcta atggactata tgcagcaact tatttaagtt tagatgattc aggtgttagt     180

ttaatgaata aaaatgatga tgatattgat gattataact taaaatggtt tttatttcct     240

attgatgatg atcaatatat tattacaagc tatgcagcaa ataattgtaa agtttggaat     300

gttaataatg ataaaaataa tgtttcgact tattcttcaa caaattcaat acaaaaatgg     360

caaataaaag ctaatggttc ttcatatgta atacaaagtg ataatggaaa agtcttaaca     420

gcaggaaccg gtcaagctct tggattgata cgtttaactg atgaatcctc aaataatccc     480

aatcaacaat ggaatttaac ttctgtacaa acaattcaac ttccacaaaa acctataata     540

gatacaaaat taaaagatta tcccaaatat tcaccaactg gaaatataga taatggaaca     600

tctcctcaat taatgggatg gacattagta ccttgtatta tggtaaatga tccaaatata     660

gataaaaata ctcaaattaa aactactcca tattatattt taaaaaaata tcaatattgg     720
```

-continued

```
caacgagcag taggaagtaa tgtagcttta cgtccacatg aaaaaaaatc atatacttat    780

gaatggggca cagaaataga tcaaaaaaca acaattataa atacattagg atttcaaatc    840

aatatagatt caggaatgaa atttgatata ccagaagtag gtggaggtac agatgaaata    900

aaaacacaac taaatgaaga attaaaaata gaatatagtc atgaaactaa aataatggaa    960

aaatatcaag aacaatctga aatagataat ccaactgatc aatcaatgaa ttctatagga   1020

tttcttacta ttacttcctt agaattatat agatataatg gctcagaaat tcgtataatg   1080

caaattcaaa cctcagataa tgatacttat aatgttactt cttatccaaa tcatcaacaa   1140

gctttattac ttcttacaaa tcattcatat gaagaagtag aagaaataac aaatattcct   1200

aaaagtacac taaaaaaatt aaaaaaatat tatttttaav v                       1241
```

<210> SEQ ID NO 43
<211> LENGTH: 383
<212> TYPE: PRT
<213> ORGANISM: Bacillus thuringiensis

<400> SEQUENCE: 43

```
Met Leu Asp Thr Asn Lys Val Tyr Glu Ile Ser Asn His Ala Asn Gly
  1               5                  10                  15

Leu Tyr Ala Ala Thr Tyr Leu Ser Leu Asp Asp Ser Gly Val Ser Leu
             20                  25                  30

Met Asn Lys Asn Asp Asp Asp Ile Asp Asp Tyr Asn Leu Lys Trp Phe
         35                  40                  45

Leu Phe Pro Ile Asp Asp Asp Gln Tyr Ile Ile Thr Ser Tyr Ala Ala
     50                  55                  60

Asn Asn Cys Lys Val Trp Asn Val Asn Asn Asp Lys Ile Asn Val Ser
 65                  70                  75                  80

Thr Tyr Ser Ser Thr Asn Ser Ile Gln Lys Trp Gln Ile Lys Ala Asn
                 85                  90                  95

Gly Ser Ser Tyr Val Ile Gln Ser Asp Asn Gly Lys Val Leu Thr Ala
            100                 105                 110

Gly Thr Gly Gln Ala Leu Gly Leu Ile Arg Leu Thr Asp Glu Ser Ser
        115                 120                 125

Asn Asn Pro Asn Gln Gln Trp Asn Leu Thr Ser Val Gln Thr Ile Gln
    130                 135                 140

Leu Pro Gln Lys Pro Ile Ile Asp Thr Lys Leu Lys Asp Tyr Pro Lys
145                 150                 155                 160

Tyr Ser Pro Thr Gly Asn Ile Asp Asn Gly Thr Ser Pro Gln Leu Met
                165                 170                 175

Gly Trp Thr Leu Val Pro Cys Ile Met Val Asn Asp Pro Asn Ile Asp
            180                 185                 190

Lys Asn Thr Gln Ile Lys Thr Thr Pro Tyr Tyr Ile Leu Lys Lys Tyr
        195                 200                 205

Gln Tyr Trp Gln Arg Ala Val Gly Ser Asn Val Ala Leu Arg Pro His
    210                 215                 220

Glu Lys Lys Ser Tyr Thr Tyr Glu Trp Gly Thr Glu Ile Asp Gln Lys
225                 230                 235                 240

Thr Thr Ile Ile Asn Thr Leu Gly Phe Gln Ile Asn Ile Asp Ser Gly
                245                 250                 255

Met Lys Phe Asp Ile Pro Glu Val Gly Gly Gly Thr Asp Glu Ile Lys
            260                 265                 270

Thr Gln Leu Asn Glu Glu Leu Lys Ile Glu Tyr Ser His Glu Thr Lys
        275                 280                 285
```

-continued

Ile Met Glu Lys Tyr Gln Glu Gln Ser Glu Ile Asp Asn Pro Thr Asp
    290                 295                 300

Gln Ser Met Asn Ser Ile Gly Phe Leu Thr Ile Thr Ser Leu Glu Leu
305                 310                 315                 320

Tyr Arg Tyr Asn Gly Ser Glu Ile Arg Ile Met Gln Ile Gln Thr Ser
                325                 330                 335

Asp Asn Asp Thr Tyr Asn Val Thr Ser Tyr Pro Asn His Gln Gln Ala
            340                 345                 350

Leu Leu Leu Leu Thr Asn His Ser Tyr Glu Glu Val Glu Glu Ile Thr
        355                 360                 365

Asn Ile Pro Lys Ser Thr Leu Lys Lys Leu Lys Lys Tyr Tyr Phe
    370                 375                 380

<210> SEQ ID NO 44
<211> LENGTH: 360
<212> TYPE: DNA
<213> ORGANISM: Artificial Sequence
<220> FEATURE:
<223> OTHER INFORMATION: Description of Artificial Sequence:
      maize-optimized gene sequence

<400> SEQUENCE: 44
atgtccgccc gcgaggtgca catcgagatc aacaacaaga cccgccacac cctccagctc 60
gaggacaaga ccaagctctc cggcggcagg tggcgcacct ccccgaccaa cgtggcccgc 120
gacaccatca agacgttcgt ggcggagtcc cacggcttca tgaccggcgt cgagggcatc 180
atctacttct ccgtgaacgg cgacgccgag atctccctcc acttcgacaa cccgtacatc 240
ggctccaaca agtgcgacgg ctcctccgac aagcccgagt acgaggtgat cacccagtcc 300
ggctccggcg acaagtccca cgtgacctac accatccaga ccgtgtccct ccgcctctga 360

<210> SEQ ID NO 45
<211> LENGTH: 1158
<212> TYPE: DNA
<213> ORGANISM: Artificial Sequence
<220> FEATURE:
<223> OTHER INFORMATION: Description of Artificial Sequence:
      maize-optimized gene sequence

<400> SEQUENCE: 45
atgctcgaca ccaacaaggt gtacgagatc tccaacctcg ccaacggcct ctacacctcc 60
acctacctct ccctcgacga ctccggcgtg tccctcatgt ccaagaagga cgaggacatc 120
gacgactaca acctcaagtg gttcctcttc ccgatcgaca acaaccagta catcatcacc 180
tcctacggcg ccaacaactg caaggtgtgg aacgtgaaga acgacaagat caacgtgtcc 240
acctactcct ccaccaactc cgtgcagaag tggcagatca aggccaagga ctcctcctac 300
atcatccagt ccgacaacgg caaggtgctc accgcgggcg tgggccagtc cctcggcatc 360
gtgcgcctca ccgacgagtt cccggagaac tccaaccagc aatggaacct caccccggtg 420
cagaccatcc agctcccgca gaagccgaag atcgacgaga agctcaagga ccacccggag 480
tactccgaga ccggcaacat caacccgaag accaccccgc agctcatggg ctggaccctc 540
gtgccgtgca tcatggtgaa cgactccaag atcgacaaga acacccagat caagaccacc 600
ccgtactaca tcttcaagaa atacaagtac tggaacctcg ccaagggctc caacgtgtcc 660
ctcctcccgc accagaagcg cagctacgac tacgagtggg gcaccgagaa gaaccagaag 720
accaccatca tcaacaccgt gggcctgcag atcaacatcg actcggggat gaagttcgag 780

-continued

```
gtgccggagg tgggcggcgg caccgaggac atcaagaccc agctcaccga ggagctgaag    840

gtggagtact ccaccgagac caagatcatg accaagtacc aggagcactc cgagatcgac    900

aacccgacca accagccgat gaactccatc ggcctcctca tctacacctc cctcgagctg    960

taccgctaca acggcaccga gatcaagatc atggacatcg agacctccga ccacgacacc   1020

tacaccctca cctcctaccc gaaccacaag gaggcgctgc tgctgctgac caaccactcc   1080

tacgaggagg tggaggagat caccaagatc ccgaagcaca ccctcatcaa gctcaagaag   1140

cactacttca agaagtga                                                 1158


<210> SEQ ID NO 46
<211> LENGTH: 24
<212> TYPE: DNA
<213> ORGANISM: Artificial Sequence
<220> FEATURE:
<223> OTHER INFORMATION: Description of Artificial Sequence:  reverse
      primer

<400> SEQUENCE: 46

gtagaagcag aacaagaagg tatt                                            24


<210> SEQ ID NO 47
<211> LENGTH: 25
<212> TYPE: DNA
<213> ORGANISM: Artificial Sequence
<220> FEATURE:
<223> OTHER INFORMATION: Description of Artificial Sequence:  forward
      primer

<400> SEQUENCE: 47

atgtcagcwc gygaagtwca yattg                                           25


<210> SEQ ID NO 48
<211> LENGTH: 23
<212> TYPE: DNA
<213> ORGANISM: Artificial Sequence
<220> FEATURE:
<223> OTHER INFORMATION: Description of Artificial Sequence:  reverse
      primer

<400> SEQUENCE: 48

gtytgaathg tatahgthac atg                                             23


<210> SEQ ID NO 49
<211> LENGTH: 25
<212> TYPE: DNA
<213> ORGANISM: Artificial Sequence
<220> FEATURE:
<223> OTHER INFORMATION: Description of Artificial Sequence:  forward
      primer

<400> SEQUENCE: 49

atgttagata cwaataaart wtatg                                           25


<210> SEQ ID NO 50
<211> LENGTH: 29
<212> TYPE: DNA
<213> ORGANISM: Artificial Sequence
<220> FEATURE:
<223> OTHER INFORMATION: Description of Artificial Sequence:  reverse
      primer

<400> SEQUENCE: 50

gtwatttctt cwacttcttc atahgaatg                                       29
```

<210> SEQ ID NO 51
<211> LENGTH: 341
<212> TYPE: DNA
<213> ORGANISM: Bacillus thuringiensis

<400> SEQUENCE: 51

```
atgtcaggtc gagaagtaca tattgaaata aacaataaaa cacgtcatac attacaatta     60

gaggataaaa ctaaacttag cggcggtaga tggcgaacat cacctacaaa tgttgctcgt    120

gatacaatta aaacatttgt agcagaatca catggtttta tgacaggagt agaaggtatt    180

atatatttta gtgtaaacgg agacgcagaa attagtttac attttgacaa tccttatata    240

ggttctaata aatgtgatgg ttcttctgat aaacctgaat atgaagttat tactcaaagc    300

ggatcaggag ataaatctca tgtaacatat actattcaga c                        341
```

<210> SEQ ID NO 52
<211> LENGTH: 113
<212> TYPE: PRT
<213> ORGANISM: Bacillus thuringiensis

<400> SEQUENCE: 52

```
Met Ser Gly Arg Glu Val His Ile Glu Ile Asn Asn Lys Thr Arg His
  1               5                  10                  15

Thr Leu Gln Leu Glu Asp Lys Thr Lys Leu Ser Gly Gly Arg Trp Arg
             20                  25                  30

Thr Ser Pro Thr Asn Val Ala Arg Asp Thr Ile Lys Thr Phe Val Ala
         35                  40                  45

Glu Ser His Gly Phe Met Thr Gly Val Glu Gly Ile Ile Tyr Phe Ser
     50                  55                  60

Val Asn Gly Asp Ala Glu Ile Ser Leu His Phe Asp Asn Pro Tyr Ile
 65                  70                  75                  80

Gly Ser Asn Lys Cys Asp Gly Ser Ser Asp Lys Pro Glu Tyr Glu Val
                 85                  90                  95

Ile Thr Gln Ser Gly Ser Gly Asp Lys Ser His Val Thr Tyr Thr Ile
            100                 105                 110

Gln
```

<210> SEQ ID NO 53
<211> LENGTH: 1103
<212> TYPE: DNA
<213> ORGANISM: Bacillus thuringiensis

<400> SEQUENCE: 53

```
atgttagata caaataaagt ttatgaaata agcaatcttg ctaatggatt atatacatcm     60

acttatttaa gtcttgatga ttcaggtgtt agtttaatga gtaaaaagga tgaagatatt    120

gatgattaca atttaaaatg gtttttattt cctattgata ataatcaata tattattaca    180

agctatggag ctaataattg taaagtttgg aatgttaaaa atgataaaat aaatgtttca    240

acttattctt caacaaactc tgtacaaaaa tggcaaataa aagctaaaga ttcttcatat    300

ataatacaaa gtgataatgg aaaggtctta acagcaggag taggtcaatc tcttggaata    360

gtacgcctaa ctgatgaatt tccagagaat tctaaccaac aatggaattt aactcctgta    420

caaacaattc aactcccaca aaaacctaaa atagatgaaa aattaaaaga tcatcctgaa    480

tattcagaaa ccggaaatat aaatcctaaa acaactcctc aattaatggg atggacatta    540

gtaccttgta ttatggtaaa tgattcaaaa atagataaaa acactcaaat taaaactact    600
```

-continued

```
ccatattata tttttaaaaa atataaatac tggaatctag caaaaggaag taatgtatct    660

ttacttccac atcaaaaaag atcatatgat tatgaatggg gtacagaaaa aaatcaaaaa    720

acamctatta ttaatacagt aggattgcaa attaatatag actcaggaat gaaatttgaa    780

gtaccagaag taggaggagg tacagaagac ataaaaacac aattaactga agaattaaaa    840

gttgaatata gcactgaaac caaaataatg acgaaatatc aagaacactc agagatagat    900

aatccaacta atcaaccaat gaattctata ggacttctta tttacacttc tttagaatta    960

tatcgatata acggtacaga aattaagata atggacatag aaacttcaga tcatgatact   1020

tacactctta cttcttatcc aaatcataaa gaagcattat tacttctcac aaaccattca   1080

tatgaagaag tagaagaaat aac                                            1103
```

```
<210> SEQ ID NO 54
<211> LENGTH: 367
<212> TYPE: PRT
<213> ORGANISM: Bacillus thuringiensis
<220> FEATURE:
<221> NAME/KEY: MISC_FEATURE
<222> LOCATION: (242)
<223> OTHER INFORMATION: Undetermined amino acid

<400> SEQUENCE: 54

Met Leu Asp Thr Asn Lys Val Tyr Glu Ile Ser Asn Leu Ala Asn Gly
  1               5                  10                  15

Leu Tyr Thr Ser Thr Tyr Leu Ser Leu Asp Asp Ser Gly Val Ser Leu
            20                  25                  30

Met Ser Lys Lys Asp Glu Asp Ile Asp Asp Tyr Asn Leu Lys Trp Phe
        35                  40                  45

Leu Phe Pro Ile Asp Asn Asn Gln Tyr Ile Ile Thr Ser Tyr Gly Ala
    50                  55                  60

Asn Asn Cys Lys Val Trp Asn Val Lys Asn Asp Lys Ile Asn Val Ser
 65                  70                  75                  80

Thr Tyr Ser Ser Thr Asn Ser Val Gln Lys Trp Gln Ile Lys Ala Lys
                 85                  90                  95

Asp Ser Ser Tyr Ile Ile Gln Ser Asp Asn Gly Lys Val Leu Thr Ala
            100                 105                 110

Gly Val Gly Gln Ser Leu Gly Ile Val Arg Leu Thr Asp Glu Phe Pro
        115                 120                 125

Glu Asn Ser Asn Gln Gln Trp Asn Leu Thr Pro Val Gln Thr Ile Gln
    130                 135                 140

Leu Pro Gln Lys Pro Lys Ile Asp Glu Lys Leu Lys Asp His Pro Glu
145                 150                 155                 160

Tyr Ser Glu Thr Gly Asn Ile Asn Pro Lys Thr Thr Pro Gln Leu Met
                165                 170                 175

Gly Trp Thr Leu Val Pro Cys Ile Met Val Asn Asp Ser Lys Ile Asp
            180                 185                 190

Lys Asn Thr Gln Ile Lys Thr Thr Pro Tyr Tyr Ile Phe Lys Lys Tyr
        195                 200                 205

Lys Tyr Trp Asn Leu Ala Lys Gly Ser Asn Val Ser Leu Leu Pro His
    210                 215                 220

Gln Lys Arg Ser Tyr Asp Tyr Glu Trp Gly Thr Glu Lys Asn Gln Lys
225                 230                 235                 240

Thr Xaa Ile Ile Asn Thr Val Gly Leu Gln Ile Asn Ile Asp Ser Gly
                245                 250                 255

Met Lys Phe Glu Val Pro Glu Val Gly Gly Gly Thr Glu Asp Ile Lys
```

-continued

```
            260                 265                 270

Thr Gln Leu Thr Glu Glu Leu Lys Val Glu Tyr Ser Thr Glu Thr Lys
        275                 280                 285

Ile Met Thr Lys Tyr Gln Glu His Ser Glu Ile Asp Asn Pro Thr Asn
    290                 295                 300

Gln Pro Met Asn Ser Ile Gly Leu Leu Ile Tyr Thr Ser Leu Glu Leu
305                 310                 315                 320

Tyr Arg Tyr Asn Gly Thr Glu Ile Lys Ile Met Asp Ile Glu Thr Ser
                325                 330                 335

Asp His Asp Thr Tyr Thr Leu Thr Ser Tyr Pro Asn His Lys Glu Ala
            340                 345                 350

Leu Leu Leu Leu Thr Asn His Ser Tyr Glu Glu Val Glu Glu Ile
        355                 360                 365


<210> SEQ ID NO 55
<211> LENGTH: 341
<212> TYPE: DNA
<213> ORGANISM: Bacillus thuringiensis

<400> SEQUENCE: 55

atgtcagctc gtgaagtaca tattgatgta aataataaga caggtcatac attacaatta     60

gaagataaaa caaaacttga tggtggtaga tggcgaacat cacctacaaa tgttgctaat    120

gatcaaatta aaacatttgt agcagaatca catggtttta tgacaggtac agaaggtcat    180

atatattata gtataaatgg agaagcagaa attagtttat attttgataa tccttattca    240

ggttctaata aatatgatgg ggattccaat aaacctcaat atgaagttac tacccaagga    300

ggatcaggaa atcaatctca tgtaacatat acgattcaaa c                        341


<210> SEQ ID NO 56
<211> LENGTH: 113
<212> TYPE: PRT
<213> ORGANISM: Bacillus thuringiensis

<400> SEQUENCE: 56

Met Ser Ala Arg Glu Val His Ile Asp Val Asn Asn Lys Thr Gly His
  1               5                  10                  15

Thr Leu Gln Leu Glu Asp Lys Thr Lys Leu Asp Gly Gly Arg Trp Arg
             20                  25                  30

Thr Ser Pro Thr Asn Val Ala Asn Asp Gln Ile Lys Thr Phe Val Ala
        35                  40                  45

Glu Ser His Gly Phe Met Thr Gly Thr Glu Gly His Ile Tyr Tyr Ser
    50                  55                  60

Ile Asn Gly Glu Ala Glu Ile Ser Leu Tyr Phe Asp Asn Pro Tyr Ser
 65                  70                  75                  80

Gly Ser Asn Lys Tyr Asp Gly Asp Ser Asn Lys Pro Gln Tyr Glu Val
                 85                  90                  95

Thr Thr Gln Gly Gly Ser Gly Asn Gln Ser His Val Thr Tyr Thr Ile
            100                 105                 110

Gln


<210> SEQ ID NO 57
<211> LENGTH: 1103
<212> TYPE: DNA
<213> ORGANISM: Bacillus thuringiensis
<220> FEATURE:
<221> NAME/KEY: misc_feature
<222> LOCATION: (1028)
```

-continued

<223> OTHER INFORMATION: Undetermined nucleotide

<400> SEQUENCE: 57

```
atgttagata ctaataaagt ttatgaaata agtaatcatg ctaatggact atatgcagca     60
acttatttaa gtttagatga ttcaggtgtt agtttaatga ataaaaatga tgatgatatt    120
gatgattaca acttaaaatg gtttttattt cctattgatg atgatcaata tattattaca    180
agctatgcag caaataattg taaagtttgg aatgttaata atgataaaat aaatgtttcg    240
acttattctt taacaaattc aatacaaaaa tggcaaataa aagctaatgg ttcttcatat    300
gtaatacaaa gtgataatgg aaaagtctta acagcaggaa ccggtcaagc tcttggattg    360
atacgtttaa ctgatgaatc ttcaaataat cccaatcaac aatggaattt aacttctgta    420
caaacaattc aacttccaca aaaacctata atagatacaa aattaaaaga ttatcccaaa    480
tattcaccaa ctggaaatat agataatgga acatctcctc aattaatggg atggacatta    540
gtaccttgta ttatggtaaa tgatccaaat atagataaaa atactcaaat taaaactact    600
ccatattata ttttaaaaaa atatcaatat tggcaacgag cagtaggaag taatgtagct    660
ttacgtccac atgaaaaaaa atcatatact tatgaatggg gaacagaaat agatcaaaaa    720
acaacaatca taaatacatt aggatttcaa atcaatatag attcaggaat gaaatttgat    780
ataccagaag taggtggagg tacagatgaa ataaaaacac aactaaatga agaattaaaa    840
atagaatata gtcgtgaaac taaaataatg gaaaaatatc aagaacaatc tgaaatagat    900
aatccaactg atcaaccaat gaattctata ggatttctta ctattacttc tttagaatta    960
tatagatata atggctcaga aattcgtata atgcaaattc aaacctcaga taatgatact   1020
tataatgnta cttcttatcc agatcatcaa caagctttat tacttcttac aaatcattca   1080
tatgaagaac tagaagaaat aac                                           1103
```

<210> SEQ ID NO 58
<211> LENGTH: 367
<212> TYPE: PRT
<213> ORGANISM: Bacillus thuringiensis
<220> FEATURE:
<221> NAME/KEY: MISC_FEATURE
<222> LOCATION: (343)
<223> OTHER INFORMATION: Undetermined amino acid

<400> SEQUENCE: 58

```
Met Leu Asp Thr Asn Lys Val Tyr Glu Ile Ser Asn His Ala Asn Gly
  1               5                  10                  15

Leu Tyr Ala Ala Thr Tyr Leu Ser Leu Asp Asp Ser Gly Val Ser Leu
             20                  25                  30

Met Asn Lys Asn Asp Asp Asp Ile Asp Asp Tyr Asn Leu Lys Trp Phe
         35                  40                  45

Leu Phe Pro Ile Asp Asp Asp Gln Tyr Ile Ile Thr Ser Tyr Ala Ala
     50                  55                  60

Asn Asn Cys Lys Val Trp Asn Val Asn Asn Asp Lys Ile Asn Val Ser
 65                  70                  75                  80

Thr Tyr Ser Leu Thr Asn Ser Ile Gln Lys Trp Gln Ile Lys Ala Asn
                 85                  90                  95

Gly Ser Ser Tyr Val Ile Gln Ser Asp Asn Gly Lys Val Leu Thr Ala
            100                 105                 110

Gly Thr Gly Gln Ala Leu Gly Leu Ile Arg Leu Thr Asp Glu Ser Ser
        115                 120                 125

Asn Asn Pro Asn Gln Gln Trp Asn Leu Thr Ser Val Gln Thr Ile Gln
```

-continued

```
    130                 135                 140

Leu Pro Gln Lys Pro Ile Ile Asp Thr Lys Leu Lys Asp Tyr Pro Lys
145                 150                 155                 160

Tyr Ser Pro Thr Gly Asn Ile Asp Asn Gly Thr Ser Pro Gln Leu Met
                165                 170                 175

Gly Trp Thr Leu Val Pro Cys Ile Met Val Asn Asp Pro Asn Ile Asp
            180                 185                 190

Lys Asn Thr Gln Ile Lys Thr Thr Pro Tyr Tyr Ile Leu Lys Lys Tyr
        195                 200                 205

Gln Tyr Trp Gln Arg Ala Val Gly Ser Asn Val Ala Leu Arg Pro His
    210                 215                 220

Glu Lys Lys Ser Tyr Thr Tyr Glu Trp Gly Thr Glu Ile Asp Gln Lys
225                 230                 235                 240

Thr Thr Ile Ile Asn Thr Leu Gly Phe Gln Ile Asn Ile Asp Ser Gly
                245                 250                 255

Met Lys Phe Asp Ile Pro Glu Val Gly Gly Gly Thr Asp Glu Ile Lys
            260                 265                 270

Thr Gln Leu Asn Glu Glu Leu Lys Ile Glu Tyr Ser Arg Glu Thr Lys
        275                 280                 285

Ile Met Glu Lys Tyr Gln Glu Gln Ser Glu Ile Asp Asn Pro Thr Asp
    290                 295                 300

Gln Pro Met Asn Ser Ile Gly Phe Leu Thr Ile Thr Ser Leu Glu Leu
305                 310                 315                 320

Tyr Arg Tyr Asn Gly Ser Glu Ile Arg Ile Met Gln Ile Gln Thr Ser
                325                 330                 335

Asp Asn Asp Thr Tyr Asn Xaa Thr Ser Tyr Pro Asp His Gln Gln Ala
            340                 345                 350

Leu Leu Leu Leu Thr Asn His Ser Tyr Glu Glu Leu Glu Glu Ile
        355                 360                 365


<210> SEQ ID NO 59
<211> LENGTH: 340
<212> TYPE: DNA
<213> ORGANISM: Bacillus thuringiensis

<400> SEQUENCE: 59

atgtcagcag gtgaagtaca tattgatgca aataataaga caggtcatac attacaatta      60

gaagataaaa caaaacttga tggtggtaga tggcgaacat cacctacaaa tgttgctaat     120

gatcaaatta aaacatttgt agcagaatca catggtttta tgacaggtac agaaggtcat     180

atatattata gtataaatgg agaagcagaa attagtttat attttgataa tccttattca     240

ggttctaata aatatgatgg ggattccaat aaacctcaat atgaagttac tacccaagga     300

ggatcaggaa atcaatctca tgttacttat acaattcaaa                           340


<210> SEQ ID NO 60
<211> LENGTH: 113
<212> TYPE: PRT
<213> ORGANISM: Bacillus thuringiensis

<400> SEQUENCE: 60

Met Ser Ala Gly Glu Val His Ile Asp Ala Asn Asn Lys Thr Gly His
  1               5                  10                  15

Thr Leu Gln Leu Glu Asp Lys Thr Lys Leu Asp Gly Gly Arg Trp Arg
            20                  25                  30

Thr Ser Pro Thr Asn Val Ala Asn Asp Gln Ile Lys Thr Phe Val Ala
```

-continued 35 40 45

Glu Ser His Gly Phe Met Thr Gly Thr Glu Gly His Ile Tyr Tyr Ser
50 55 60

Ile Asn Gly Glu Ala Glu Ile Ser Leu Tyr Phe Asp Asn Pro Tyr Ser
65 70 75 80

Gly Ser Asn Lys Tyr Asp Gly Asp Ser Asn Lys Pro Gln Tyr Glu Val
85 90 95

Thr Thr Gln Gly Gly Ser Gly Asn Gln Ser His Val Thr Tyr Thr Ile
100 105 110

Gln

<210> SEQ ID NO 61
<211> LENGTH: 340
<212> TYPE: DNA
<213> ORGANISM: Bacillus thuringiensis

<400> SEQUENCE: 61
tgtcagcacg tgaagtacat attgaaataa acaataaaac acgtcataca ttacaattag 60
aggataaaac taaacttagc ggcggtagat ggcgaacatc acctacaaat gttgctcgtg 120
atacaattaa aacatttgta gcagaatcac atggttttat gacaggagta gaaggtatta 180
tatattttag tgtaaacgga gacgcagaaa ttagtttaca ttttgacaat ccttatatag 240
gttctaataa atgtgatggt tcttctgata aacctgaata tgaagttatt actcaaagcg 300
gatcaggaga taaatctcat gtgacatata cgattcagac 340

<210> SEQ ID NO 62
<211> LENGTH: 112
<212> TYPE: PRT
<213> ORGANISM: Bacillus thuringiensis

<400> SEQUENCE: 62

Ser Ala Arg Glu Val His Ile Glu Ile Asn Asn Lys Thr Arg His Thr
1 5 10 15

Leu Gln Leu Glu Asp Lys Thr Lys Leu Ser Gly Gly Arg Trp Arg Thr
20 25 30

Ser Pro Thr Asn Val Ala Arg Asp Thr Ile Lys Thr Phe Val Ala Glu
35 40 45

Ser His Gly Phe Met Thr Gly Val Glu Gly Ile Ile Tyr Phe Ser Val
50 55 60

Asn Gly Asp Ala Glu Ile Ser Leu His Phe Asp Asn Pro Tyr Ile Gly
65 70 75 80

Ser Asn Lys Cys Asp Gly Ser Ser Asp Lys Pro Glu Tyr Glu Val Ile
85 90 95

Thr Gln Ser Gly Ser Gly Asp Lys Ser His Val Thr Tyr Thr Ile Gln
100 105 110

<210> SEQ ID NO 63
<211> LENGTH: 1114
<212> TYPE: DNA
<213> ORGANISM: Bacillus thuringiensis

<400> SEQUENCE: 63
atgttagata ctaataaaat ttatgaaata agcaatcttg ctaatggatt atatacatca 60
acttatttaa gtcttgatga ttcaggtgtt agtttaatga gtaaaaagga tgaagatatt 120
gatgattaca atttaaaatg gtttttattt cctattgata ataatcaata tattattaca 180

-continued

```
agctatggag ctaataattg taaagtttgg aatgttaaaa atgataaaat aaatgtttca    240

acttattctt caacaaactc tgtacaaaaa tggcaaataa aagctaaaga ttcttcatat    300

ataatacaaa gtgataatgg aaaggtctta acagcaggag taggtcaatc tcttggaata    360

gtacgcctaa ctgatgaatt tccagagaat tctaaccaac aatggaattt aactcctgta    420

caaacaattc aactcccaca aaaacctaaa atagatgaaa aattaaaaga tcatcctgaa    480

tattcagaaa ccggaaatat aaatcctaaa acaactcctc aattaatggg atggacatta    540

gtaccttgta ttatggtaaa tgattcaaaa atagataaaa acactcaaat taaaactact    600

ccatattata tttttaaaaa atataaatac tggaatctag caaaaggaag taatgtatct    660

ttacttccac atcaaaaaag atcatatgat tatgaatggg gtacagaaaa aaatcaaaaa    720

acaactatta ttaatacagt aggattgcaa attaatatag attcaggaat gaaatttgaa    780

gtaccagaag taggaggagg tacagaagac ataaaaacac aattaactga agaattaaaa    840

gttgaatata gcactgaaac caaaataatg acgaaatatc aagaacactc agagatagat    900

aatccaacta atcaaccaat gaattctata ggacttctta tttatacttc tttagaatta    960

tatcgatata acggtacaga aattaagata atggacatag aaacttcaga tcatgatact   1020

tacactctta cttcttatcc aaatcataaa gaagcattat tacttctcac aaaccattct   1080

tatgaagaac tagaacaaat tacaagggcg aatt                               1114
```

```
<210> SEQ ID NO 64
<211> LENGTH: 371
<212> TYPE: PRT
<213> ORGANISM: Bacillus thuringiensis

<400> SEQUENCE: 64

Met Leu Asp Thr Asn Lys Ile Tyr Glu Ile Ser Asn Leu Ala Asn Gly
  1               5                  10                  15

Leu Tyr Thr Ser Thr Tyr Leu Ser Leu Asp Asp Ser Gly Val Ser Leu
             20                  25                  30

Met Ser Lys Lys Asp Glu Asp Ile Asp Asp Tyr Asn Leu Lys Trp Phe
         35                  40                  45

Leu Phe Pro Ile Asp Asn Asn Gln Tyr Ile Ile Thr Ser Tyr Gly Ala
     50                  55                  60

Asn Asn Cys Lys Val Trp Asn Val Lys Asn Asp Lys Ile Asn Val Ser
 65                  70                  75                  80

Thr Tyr Ser Ser Thr Asn Ser Val Gln Lys Trp Gln Ile Lys Ala Lys
                 85                  90                  95

Asp Ser Ser Tyr Ile Ile Gln Ser Asp Asn Gly Lys Val Leu Thr Ala
            100                 105                 110

Gly Val Gly Gln Ser Leu Gly Ile Val Arg Leu Thr Asp Glu Phe Pro
        115                 120                 125

Glu Asn Ser Asn Gln Gln Trp Asn Leu Thr Pro Val Gln Thr Ile Gln
    130                 135                 140

Leu Pro Gln Lys Pro Lys Ile Asp Glu Lys Leu Lys Asp His Pro Glu
145                 150                 155                 160

Tyr Ser Glu Thr Gly Asn Ile Asn Pro Lys Thr Thr Pro Gln Leu Met
                165                 170                 175

Gly Trp Thr Leu Val Pro Cys Ile Met Val Asn Asp Ser Lys Ile Asp
            180                 185                 190

Lys Asn Thr Gln Ile Lys Thr Thr Pro Tyr Tyr Ile Phe Lys Lys Tyr
        195                 200                 205
```

-continued

```
Lys Tyr Trp Asn Leu Ala Lys Gly Ser Asn Val Ser Leu Leu Pro His
    210                 215                 220

Gln Lys Arg Ser Tyr Asp Tyr Glu Trp Gly Thr Glu Lys Asn Gln Lys
225                 230                 235                 240

Thr Thr Ile Ile Asn Thr Val Gly Leu Gln Ile Asn Ile Asp Ser Gly
                245                 250                 255

Met Lys Phe Glu Val Pro Glu Val Gly Gly Gly Thr Glu Asp Ile Lys
            260                 265                 270

Thr Gln Leu Thr Glu Glu Leu Lys Val Glu Tyr Ser Thr Glu Thr Lys
        275                 280                 285

Ile Met Thr Lys Tyr Gln Glu His Ser Glu Ile Asp Asn Pro Thr Asn
    290                 295                 300

Gln Pro Met Asn Ser Ile Gly Leu Leu Ile Tyr Thr Ser Leu Glu Leu
305                 310                 315                 320

Tyr Arg Tyr Asn Gly Thr Glu Ile Lys Ile Met Asp Ile Glu Thr Ser
                325                 330                 335

Asp His Asp Thr Tyr Thr Leu Thr Ser Tyr Pro Asn His Lys Glu Ala
            340                 345                 350

Leu Leu Leu Leu Thr Asn His Ser Tyr Glu Glu Leu Glu Gln Ile Thr
        355                 360                 365

Arg Ala Asn
    370


<210> SEQ ID NO 65
<211> LENGTH: 360
<212> TYPE: DNA
<213> ORGANISM: Bacillus thuringiensis

<400> SEQUENCE: 65

atgtcagctc gcgaagtaca cattgaaata aacaataaaa cacgtcatac attacaatta      60

gaggataaaa ctaaacttag cggcggtaga tggcgaacat cacctacaaa tgttgctcgt     120

gatacaatta aaacatttgt agcagaatca catggtttta tgacaggagt agaaggtatt     180

atatatttta gtgtaaacgg agacgcagaa attagtttac attttgacaa tccttatata     240

ggttctaata aatgtgatgg ttcttctgat aaacctgaat atgaagttat tactcaaagc     300

ggatcaggag ataaatctca tgtgacatat actattcaga cagtatcttt acgattataa     360


<210> SEQ ID NO 66
<211> LENGTH: 119
<212> TYPE: PRT
<213> ORGANISM: Bacillus thuringiensis

<400> SEQUENCE: 66

Met Ser Ala Arg Glu Val His Ile Glu Ile Asn Asn Lys Thr Arg His
  1               5                  10                  15

Thr Leu Gln Leu Glu Asp Lys Thr Lys Leu Ser Gly Gly Arg Trp Arg
             20                  25                  30

Thr Ser Pro Thr Asn Val Ala Arg Asp Thr Ile Lys Thr Phe Val Ala
         35                  40                  45

Glu Ser His Gly Phe Met Thr Gly Val Glu Gly Ile Ile Tyr Phe Ser
     50                  55                  60

Val Asn Gly Asp Ala Glu Ile Ser Leu His Phe Asp Asn Pro Tyr Ile
 65                  70                  75                  80

Gly Ser Asn Lys Cys Asp Gly Ser Ser Asp Lys Pro Glu Tyr Glu Val
                 85                  90                  95
```

-continued

```
Ile Thr Gln Ser Gly Ser Gly Asp Lys Ser His Val Thr Tyr Thr Ile
            100                 105                 110

Gln Thr Val Ser Leu Arg Leu
        115


<210> SEQ ID NO 67
<211> LENGTH: 1158
<212> TYPE: DNA
<213> ORGANISM: Bacillus thuringiensis

<400> SEQUENCE: 67

atgttagata ctaataaagt ttatgaaata agcaatcttg ctaatggatt atatacatca     60

acttatttaa gtcttgatga ttcaggtgtt agtttaatga gtaaaaagga tgaagatatt    120

gatgattaca atttaaaatg gtttttattt cctattgata ataatcaata tattattaca    180

agctatggag ctaataattg taaagtttgg aatgttaaaa atgataaaat aaatgtttca    240

acttattctt caacaaactc tgtacaaaaa tggcaaataa aagctaaaga ttcttcatat    300

ataatacaaa gtgataatgg aaaggtctta acagcaggag taggtcaatc tcttggaata    360

gtacgcctaa ctgatgaatt tccagagaat tctaaccaac aatggaattt aactcctgta    420

caaacaattc aactcccaca aaaacctaaa atagatgaaa aattaaaaga tcatcctgaa    480

tattcagaaa ccggaaatat aaatcctaaa acaactcctc aattaatggg atggacatta    540

gtaccttgta ttatggtaaa tgattcaaaa atagataaaa acactcaaat taaaactact    600

ccatattata tttttaaaaa atataaatac tggaatctag caaaaggaag taatgtatct    660

ttacttccac atcaaaaaag atcatatgat tatgaatggg gtacagaaaa aaatcaaaaa    720

acaactatta ttaatacagt aggattgcaa attaatatag attcaggaat gaaatttgaa    780

gtaccagaag taggaggagg tacagaagac ataaaaacac aattaactga agaattaaaa    840

gttgaatata gcactgaaac caaaataatg acgaaatatc aagaacactc agagatagat    900

aatccaacta atcaaccaat gaattctata ggacttctta tttatacttc tttagaatta    960

tatcgatata acggtacaga aattaagata atggacatag aaacttcaga tcatgatact   1020

tacactctta cttcttatcc aaatcataaa gaagcattat tacttctcac aaaccattcg   1080

tatgaagaag tagaagaaat aacaaaaata cctaagcata cacttataaa attgaaaaaa   1140

cattatttta aaaaataa                                                   1158


<210> SEQ ID NO 68
<211> LENGTH: 385
<212> TYPE: PRT
<213> ORGANISM: Bacillus thuringiensis

<400> SEQUENCE: 68

Met Leu Asp Thr Asn Lys Val Tyr Glu Ile Ser Asn Leu Ala Asn Gly
  1               5                  10                  15

Leu Tyr Thr Ser Thr Tyr Leu Ser Leu Asp Asp Ser Gly Val Ser Leu
             20                  25                  30

Met Ser Lys Lys Asp Glu Asp Ile Asp Asp Tyr Asn Leu Lys Trp Phe
         35                  40                  45

Leu Phe Pro Ile Asp Asn Asn Gln Tyr Ile Ile Thr Ser Tyr Gly Ala
     50                  55                  60

Asn Asn Cys Lys Val Trp Asn Val Lys Asn Asp Lys Ile Asn Val Ser
 65                  70                  75                  80

Thr Tyr Ser Ser Thr Asn Ser Val Gln Lys Trp Gln Ile Lys Ala Lys
                 85                  90                  95
```

-continued

```
Asp Ser Ser Tyr Ile Ile Gln Ser Asp Asn Gly Lys Val Leu Thr Ala
            100                 105                 110

Gly Val Gly Gln Ser Leu Gly Ile Val Arg Leu Thr Asp Glu Phe Pro
        115                 120                 125

Glu Asn Ser Asn Gln Gln Trp Asn Leu Thr Pro Val Gln Thr Ile Gln
    130                 135                 140

Leu Pro Gln Lys Pro Lys Ile Asp Glu Lys Leu Lys Asp His Pro Glu
145                 150                 155                 160

Tyr Ser Glu Thr Gly Asn Ile Asn Pro Lys Thr Thr Pro Gln Leu Met
                165                 170                 175

Gly Trp Thr Leu Val Pro Cys Ile Met Val Asn Asp Ser Lys Ile Asp
            180                 185                 190

Lys Asn Thr Gln Ile Lys Thr Thr Pro Tyr Tyr Ile Phe Lys Lys Tyr
        195                 200                 205

Lys Tyr Trp Asn Leu Ala Lys Gly Ser Asn Val Ser Leu Leu Pro His
    210                 215                 220

Gln Lys Arg Ser Tyr Asp Tyr Glu Trp Gly Thr Glu Lys Asn Gln Lys
225                 230                 235                 240

Thr Thr Ile Ile Asn Thr Val Gly Leu Gln Ile Asn Ile Asp Ser Gly
                245                 250                 255

Met Lys Phe Glu Val Pro Glu Val Gly Gly Gly Thr Glu Asp Ile Lys
            260                 265                 270

Thr Gln Leu Thr Glu Glu Leu Lys Val Glu Tyr Ser Thr Glu Thr Lys
        275                 280                 285

Ile Met Thr Lys Tyr Gln Glu His Ser Glu Ile Asp Asn Pro Thr Asn
    290                 295                 300

Gln Pro Met Asn Ser Ile Gly Leu Leu Ile Tyr Thr Ser Leu Glu Leu
305                 310                 315                 320

Tyr Arg Tyr Asn Gly Thr Glu Ile Lys Ile Met Asp Ile Glu Thr Ser
                325                 330                 335

Asp His Asp Thr Tyr Thr Leu Thr Ser Tyr Pro Asn His Lys Glu Ala
            340                 345                 350

Leu Leu Leu Leu Thr Asn His Ser Tyr Glu Glu Val Glu Glu Ile Thr
        355                 360                 365

Lys Ile Pro Lys His Thr Leu Ile Lys Leu Lys Lys His Tyr Phe Lys
    370                 375                 380

Lys
385


<210> SEQ ID NO 69
<211> LENGTH: 341
<212> TYPE: DNA
<213> ORGANISM: Bacillus thuringiensis

<400> SEQUENCE: 69

atgtcagcac gagaagtaca cattgatgta aataataaga caggtcatac attacaatta      60

gaagataaaa caaaacttga tggtggtaga tggcgaacat cacctacaaa tgttgctaat     120

gatcaaatta aaacatctgt agcagaatca aatggtttta tgacaggtac agaaggtact     180

atatattata gtataaatgg agaagcagaa attagtttat attttgacaa tccttttgca     240

ggttctaata aatatgatgg acattccaat aaatctcaat atgaaattat tacccaagga     300

ggatcaggaa atcaatctca tgttacttat acaattcaga c                         341
```

-continued

<210> SEQ ID NO 70
<211> LENGTH: 113
<212> TYPE: PRT
<213> ORGANISM: Bacillus thuringiensis

<400> SEQUENCE: 70

```
Met Ser Ala Arg Glu Val His Ile Asp Val Asn Asn Lys Thr Gly His
  1               5                  10                  15

Thr Leu Gln Leu Glu Asp Lys Thr Lys Leu Asp Gly Gly Arg Trp Arg
             20                  25                  30

Thr Ser Pro Thr Asn Val Ala Asn Asp Gln Ile Lys Thr Ser Val Ala
         35                  40                  45

Glu Ser Asn Gly Phe Met Thr Gly Thr Glu Gly Thr Ile Tyr Tyr Ser
     50                  55                  60

Ile Asn Gly Glu Ala Glu Ile Ser Leu Tyr Phe Asp Asn Pro Phe Ala
 65                  70                  75                  80

Gly Ser Asn Lys Tyr Asp Gly His Ser Asn Lys Ser Gln Tyr Glu Ile
                 85                  90                  95

Ile Thr Gln Gly Gly Ser Gly Asn Gln Ser His Val Thr Tyr Thr Ile
            100                 105                 110

Gln
```

<210> SEQ ID NO 71
<211> LENGTH: 340
<212> TYPE: DNA
<213> ORGANISM: Bacillus thuringiensis

<400> SEQUENCE: 71

```
atgtcagcag gcgaagttca tattgatgta aataataaga caggtcatac attacaatta     60

gaagataaaa caaaacttga tggtggtaga tggcgaacat cacctacaaa tgttgctaat    120

gatcaaatta aaacatttgt agcagaatca aatggtttta tgacaggtac agaaggtact    180

atatattata gtataaatgg agaagcagaa attagtttat attttgacaa tccttttgca    240

ggttctaata aatatgatgg acattccaat aaatctcaat atgaaattat tacccaagga    300

ggatcaggaa atcaatctca tgtaacgtat acaattcaaa                          340
```

<210> SEQ ID NO 72
<211> LENGTH: 113
<212> TYPE: PRT
<213> ORGANISM: Bacillus thuringiensis

<400> SEQUENCE: 72

```
Met Ser Ala Gly Glu Val His Ile Asp Val Asn Asn Lys Thr Gly His
  1               5                  10                  15

Thr Leu Gln Leu Glu Asp Lys Thr Lys Leu Asp Gly Gly Arg Trp Arg
             20                  25                  30

Thr Ser Pro Thr Asn Val Ala Asn Asp Gln Ile Lys Thr Phe Val Ala
         35                  40                  45

Glu Ser Asn Gly Phe Met Thr Gly Thr Glu Gly Thr Ile Tyr Tyr Ser
     50                  55                  60

Ile Asn Gly Glu Ala Glu Ile Ser Leu Tyr Phe Asp Asn Pro Phe Ala
 65                  70                  75                  80

Gly Ser Asn Lys Tyr Asp Gly His Ser Asn Lys Ser Gln Tyr Glu Ile
                 85                  90                  95

Ile Thr Gln Gly Gly Ser Gly Asn Gln Ser His Val Thr Tyr Thr Ile
            100                 105                 110
```

-continued

Gln

<210> SEQ ID NO 73
<211> LENGTH: 340
<212> TYPE: DNA
<213> ORGANISM: Bacillus thuringiensis

<400> SEQUENCE: 73
atgtcagctc gcgaagtwca tattgaaata aacaataaaa cacgtcatac attacaatta 60
gaggataaaa ctaaacttag cggcggtaga tggcgaacat cacctacaaa tgttgctcgt 120
gatacaatta aaacatttgt agcagaatca catggtttta tgacaggagt agaaggtatt 180
atatatttta gtgtaaacgg agacgcagaa attagtttac attttgacaa tccttatata 240
ggttctaata aatgtgatgg ttcttctgat aaacctgaat atgaagttat tactcaaagc 300
ggatcaggag ataaatctca tgtgacatat accattcaaa 340

<210> SEQ ID NO 74
<211> LENGTH: 113
<212> TYPE: PRT
<213> ORGANISM: Bacillus thuringiensis

<400> SEQUENCE: 74

Met Ser Ala Arg Glu Val His Ile Glu Ile Asn Asn Lys Thr Arg His
1 5 10 15

Thr Leu Gln Leu Glu Asp Lys Thr Lys Leu Ser Gly Gly Arg Trp Arg
20 25 30

Thr Ser Pro Thr Asn Val Ala Arg Asp Thr Ile Lys Thr Phe Val Ala
35 40 45

Glu Ser His Gly Phe Met Thr Gly Val Glu Gly Ile Ile Tyr Phe Ser
50 55 60

Val Asn Gly Asp Ala Glu Ile Ser Leu His Phe Asp Asn Pro Tyr Ile
65 70 75 80

Gly Ser Asn Lys Cys Asp Gly Ser Ser Asp Lys Pro Glu Tyr Glu Val
85 90 95

Ile Thr Gln Ser Gly Ser Gly Asp Lys Ser His Val Thr Tyr Thr Ile
100 105 110

Gln

<210> SEQ ID NO 75
<211> LENGTH: 341
<212> TYPE: DNA
<213> ORGANISM: Bacillus thuringiensis

<400> SEQUENCE: 75
atgtcagctc gcgaagttca tattgaaata aataataaaa cacgtcatac attacaatta 60
gaggataaaa ctaaacttac cagtggtaga tggcgaacat cacctacaaa tgttgctcgt 120
gatacaatta aaacatttgt agcagaatca catggtttta tgacaggaat agaaggtatt 180
atatatttta gcgtaaacgg agaagcagaa attagtttac attttgacaa tccttatgta 240
ggttctaata aatatgatgg ttcttctgat aaagctgcat acgaagttat tgctcaaggt 300
ggatcagggg atatatctca tgtaacttat acaattcaaa c 341

<210> SEQ ID NO 76
<211> LENGTH: 113
<212> TYPE: PRT
<213> ORGANISM: Bacillus thuringiensis -continued

<400> SEQUENCE: 76

```
Met Ser Ala Arg Glu Val His Ile Glu Ile Asn Asn Lys Thr Arg His
  1               5                  10                  15

Thr Leu Gln Leu Glu Asp Lys Thr Lys Leu Thr Ser Gly Arg Trp Arg
             20                  25                  30

Thr Ser Pro Thr Asn Val Ala Arg Asp Thr Ile Lys Thr Phe Val Ala
         35                  40                  45

Glu Ser His Gly Phe Met Thr Gly Ile Glu Gly Ile Ile Tyr Phe Ser
     50                  55                  60

Val Asn Gly Glu Ala Glu Ile Ser Leu His Phe Asp Asn Pro Tyr Val
 65                  70                  75                  80

Gly Ser Asn Lys Tyr Asp Gly Ser Ser Asp Lys Ala Ala Tyr Glu Val
                 85                  90                  95

Ile Ala Gln Gly Gly Ser Gly Asp Ile Ser His Val Thr Tyr Thr Ile
            100                 105                 110

Gln
```

<210> SEQ ID NO 77
<211> LENGTH: 1175
<212> TYPE: DNA
<213> ORGANISM: Bacillus thuringiensis

<400> SEQUENCE: 77

```
atgttagata ctaataaagt ttatgaaata agcaatcatg ctaatggatt atatacatca      60

acttatttaa gtctggatga ttcaggtgtt agtttaatgg gtcaaaatga tgaggatata     120

gatgaatmca atttaaagtg gttcttattt ccaatagata ataatcaata tattattaca     180

agctatggag cgaataattg taaagtttgg aatgttaaaa atgataaagt aaatgtttca     240

acgtattctc caacaaactc agtacaaaaa tggcaaataa aagctaaaaa ttcttcatat     300

ataatacaaa gtgagaatgg aaaagtctta acagcaggaa taggtcaatc tcctggaata     360

gtacgcttaa ccgatgaatc atcagagagt tctaaccaac aatggaattt aatccctgta     420

caaacaattt cactcccaca aaaacctaaa atagataaaa aattaaaaga tcatcctgaa     480

tattcagaaa ccggaaatat agctactgga acaattcctc aattaatggg atggacatta     540

gtaccttgta ttatggtaaa tgatccaaaa atagataaaa acactcaaat taaaactact     600

ccatattata tttttaaaaa atatcaatac tggaaacgag caataggaag taatgtatct     660

ttacttccac atcaaaaaaa atcatatgat tatgagtggg gtacagaaga aaatcaaaaa     720

acaactatta ttaatacagt aggatttcaa attaatgtag attcaggaat gaagtttgag     780

gtaccagaag taggaggagg tacagaagaa ataaaaacac aattaaatga agaattaaaa     840

gttgaatata gcactgacac caaaataatg aaaaaatatc aagaacactc agagatagat     900

aatccaacta atcaaacaat gaattctata ggatttctta cttttacttc tttagaatta     960

tatcgatata acggttcgga aattcgtata atgagaatgg aaacttcaga taatgatact    1020

tatactctga cctcttatcc aaatcataga gaagcattat tacttctcac aaatcattca    1080

tatcaagaag tacmagaaat tacaagggcg aattcttgca gatatccatc acactggcgg    1140

gccggtcgag ccttgcatct agaggggccc caatt                               1175
```

<210> SEQ ID NO 78
<211> LENGTH: 391
<212> TYPE: PRT
<213> ORGANISM: Bacillus thuringiensis
<220> FEATURE:

-continued

<221> NAME/KEY: MISC_FEATURE
<222> LOCATION: (43)
<223> OTHER INFORMATION: Undetermined amino acid
<221> NAME/KEY: MISC_FEATURE
<222> LOCATION: (365)
<223> OTHER INFORMATION: Undetermined amino acid

<400> SEQUENCE: 78

```
Met Leu Asp Thr Asn Lys Val Tyr Glu Ile Ser Asn His Ala Asn Gly
  1               5                  10                  15

Leu Tyr Thr Ser Thr Tyr Leu Ser Leu Asp Asp Ser Gly Val Ser Leu
             20                  25                  30

Met Gly Gln Asn Asp Glu Asp Ile Asp Glu Xaa Asn Leu Lys Trp Phe
         35                  40                  45

Leu Phe Pro Ile Asp Asn Asn Gln Tyr Ile Ile Thr Ser Tyr Gly Ala
     50                  55                  60

Asn Asn Cys Lys Val Trp Asn Val Lys Asn Asp Lys Val Asn Val Ser
 65                  70                  75                  80

Thr Tyr Ser Pro Thr Asn Ser Val Gln Lys Trp Gln Ile Lys Ala Lys
                 85                  90                  95

Asn Ser Ser Tyr Ile Ile Gln Ser Glu Asn Gly Lys Val Leu Thr Ala
            100                 105                 110

Gly Ile Gly Gln Ser Pro Gly Ile Val Arg Leu Thr Asp Glu Ser Ser
        115                 120                 125

Glu Ser Ser Asn Gln Gln Trp Asn Leu Ile Pro Val Gln Thr Ile Ser
    130                 135                 140

Leu Pro Gln Lys Pro Lys Ile Asp Lys Lys Leu Lys Asp His Pro Glu
145                 150                 155                 160

Tyr Ser Glu Thr Gly Asn Ile Ala Thr Gly Thr Ile Pro Gln Leu Met
                165                 170                 175

Gly Trp Thr Leu Val Pro Cys Ile Met Val Asn Asp Pro Lys Ile Asp
            180                 185                 190

Lys Asn Thr Gln Ile Lys Thr Thr Pro Tyr Tyr Ile Phe Lys Lys Tyr
        195                 200                 205

Gln Tyr Trp Lys Arg Ala Ile Gly Ser Asn Val Ser Leu Leu Pro His
    210                 215                 220

Gln Lys Lys Ser Tyr Asp Tyr Glu Trp Gly Thr Glu Glu Asn Gln Lys
225                 230                 235                 240

Thr Thr Ile Ile Asn Thr Val Gly Phe Gln Ile Asn Val Asp Ser Gly
                245                 250                 255

Met Lys Phe Glu Val Pro Glu Val Gly Gly Gly Thr Glu Glu Ile Lys
            260                 265                 270

Thr Gln Leu Asn Glu Glu Leu Lys Val Glu Tyr Ser Thr Asp Thr Lys
        275                 280                 285

Ile Met Lys Lys Tyr Gln Glu His Ser Glu Ile Asp Asn Pro Thr Asn
    290                 295                 300

Gln Thr Met Asn Ser Ile Gly Phe Leu Thr Phe Thr Ser Leu Glu Leu
305                 310                 315                 320

Tyr Arg Tyr Asn Gly Ser Glu Ile Arg Ile Met Arg Met Glu Thr Ser
                325                 330                 335

Asp Asn Asp Thr Tyr Thr Leu Thr Ser Tyr Pro Asn His Arg Glu Ala
            340                 345                 350

Leu Leu Leu Leu Thr Asn His Ser Tyr Gln Glu Val Xaa Glu Ile Thr
        355                 360                 365

Arg Ala Asn Ser Cys Arg Tyr Pro Ser His Trp Arg Ala Gly Arg Ala
```

-continued 370 375 380

Leu His Leu Glu Gly Pro Gln
385 390

<210> SEQ ID NO 79
<211> LENGTH: 341
<212> TYPE: DNA
<213> ORGANISM: Bacillus thuringiensis

<400> SEQUENCE: 79
atgtcagcag gtgaagttca tattgaaata aataataaaa cacgtcatac attacaatta 60
gaggataaaa ctaaacttac cagtggtaga tggcgaacat cacctacaaa tgttgctcgt 120
gatacaatta aaacatttgt agcagaatca catggtttta tgacaggaat agaaggtatt 180
atatatttta gcgtaaacgg agaagcagaa attagtttac attttgacaa tccttatgta 240
ggttctaata aatatgatgg ttcttctgat aaagctgcat acgaagttat tgctcaaggt 300
ggatcagggg atatatctca tctaacatat acaattcaaa c 341

<210> SEQ ID NO 80
<211> LENGTH: 113
<212> TYPE: PRT
<213> ORGANISM: Bacillus thuringiensis

<400> SEQUENCE: 80

Met Ser Ala Gly Glu Val His Ile Glu Ile Asn Asn Lys Thr Arg His
1 5 10 15

Thr Leu Gln Leu Glu Asp Lys Thr Lys Leu Thr Ser Gly Arg Trp Arg
20 25 30

Thr Ser Pro Thr Asn Val Ala Arg Asp Thr Ile Lys Thr Phe Val Ala
35 40 45

Glu Ser His Gly Phe Met Thr Gly Ile Glu Gly Ile Ile Tyr Phe Ser
50 55 60

Val Asn Gly Glu Ala Glu Ile Ser Leu His Phe Asp Asn Pro Tyr Val
65 70 75 80

Gly Ser Asn Lys Tyr Asp Gly Ser Ser Asp Lys Ala Ala Tyr Glu Val
85 90 95

Ile Ala Gln Gly Gly Ser Gly Asp Ile Ser His Leu Thr Tyr Thr Ile
100 105 110

Gln

<210> SEQ ID NO 81
<211> LENGTH: 1410
<212> TYPE: DNA
<213> ORGANISM: Bacillus thuringiensis

<400> SEQUENCE: 81
atgttagata ctaataaaat ttatgaaata agcaatcatg ctaatggatt atatacatca 60
acttatttaa gtctggatga ttcaggtgtt agtttaatgg gtcaaaatga tgaggatata 120
gatgaataca atttaaagtg gttcttattt ccaatagata ataatcaata tattattaca 180
agctatggag cgaataattg taaagtttgg aatgttaaaa atgataaagt aaatgtttca 240
acgtattctc caacaaactc agtacaaaaa tggcaaataa aagctaaaaa ttcttcatat 300
ataatacaaa gtgagaatgg aaaagtctta acagcaggaa taggtcaatc tcttggaata 360
gtacgcttaa ccgatgaatc atcagagagt tctaaccaac aatggaattt aatccctgta 420
caaacaattt cactcccaca aaaacctaaa atagataaaa aattaaaaga tcatcctgaa 480

-continued

```
tattcagaaa ccggaaatat agctactgga acaattcctc aattaatggg atggacatta    540

gtaccttgta ttatggtaaa tgatccaaaa ataggtaaaa acactcaaat taaaactact    600

ccatattata tttttaaaaa atatcaatac tggaaacgag caataggaag taatgtatct    660

ttacttccac atcaaaaaaa atcatatgat tatgagtggg gtacagaaga aaatcaaaaa    720

acaactatta ttaatacagt aggatttcaa attaatgtag attcaggaat gaagtttgag    780

gtaccagaag taggaggagg tacagaagaa ataaaaacac aattaaatga agaattaaaa    840

gttgaatata gcactgacac caaaataatg aaaaaatatc aagaacactc agagatagat    900

aatccaacta atcaaacaac gaattctata ggatttctta cttttacttc tttagaatta    960

tatcgatata acggttcgga aattcgtata atgagaatgg aaacttcaga taatgatact   1020

tatactctga cctcttatcc aaatcataga gaagcattat tacttctcac aaatcattct   1080

tatcaagaag taagccgaat tccagcacac tggcggccgt tactagtgga tccgagctcg   1140

gtaccaagct tggcgtaatc atggtcatag stgtttcctg tgtgaaattg ttatccgctc   1200

acaattccac acaacatacg agccggaagc ataaagtgta aagcctgggg tgcctaatga   1260

gtgagctaac tcacattaat tgcgttgcgc tcactgcccg ctttccagtc gggaaacctg   1320

tcgtgccagc tgcattaatg aatcggccaa cgcgcgggga gaggcggttt gcgtattggg   1380

cgctcttccg cttcctcgct cactgactcg                                    1410
```

<210> SEQ ID NO 82
<211> LENGTH: 462
<212> TYPE: PRT
<213> ORGANISM: Bacillus thuringiensis
<220> FEATURE:
<221> NAME/KEY: MISC_FEATURE
<222> LOCATION: (389)
<223> OTHER INFORMATION: Undetermined amino acid

<400> SEQUENCE: 82

```
Met Leu Asp Thr Asn Lys Ile Tyr Glu Ile Ser Asn His Ala Asn Gly
  1               5                  10                  15

Leu Tyr Thr Ser Thr Tyr Leu Ser Leu Asp Asp Ser Gly Val Ser Leu
             20                  25                  30

Met Gly Gln Asn Asp Glu Asp Ile Asp Glu Tyr Asn Leu Lys Trp Phe
         35                  40                  45

Leu Phe Pro Ile Asp Asn Asn Gln Tyr Ile Ile Thr Ser Tyr Gly Ala
     50                  55                  60

Asn Asn Cys Lys Val Trp Asn Val Lys Asn Asp Lys Val Asn Val Ser
 65                  70                  75                  80

Thr Tyr Ser Pro Thr Asn Ser Val Gln Lys Trp Gln Ile Lys Ala Lys
                 85                  90                  95

Asn Ser Ser Tyr Ile Ile Gln Ser Glu Asn Gly Lys Val Leu Thr Ala
            100                 105                 110

Gly Ile Gly Gln Ser Leu Gly Ile Val Arg Leu Thr Asp Glu Ser Ser
        115                 120                 125

Glu Ser Ser Asn Gln Gln Trp Asn Leu Ile Pro Val Gln Thr Ile Ser
    130                 135                 140

Leu Pro Gln Lys Pro Lys Ile Asp Lys Lys Leu Lys Asp His Pro Glu
145                 150                 155                 160

Tyr Ser Glu Thr Gly Asn Ile Ala Thr Gly Thr Ile Pro Gln Leu Met
                165                 170                 175

Gly Trp Thr Leu Val Pro Cys Ile Met Val Asn Asp Pro Lys Ile Gly
```

-continued

```
            180                 185                 190

Lys Asn Thr Gln Ile Lys Thr Thr Pro Tyr Tyr Ile Phe Lys Lys Tyr
        195                 200                 205

Gln Tyr Trp Lys Arg Ala Ile Gly Ser Asn Val Ser Leu Leu Pro His
    210                 215                 220

Gln Lys Lys Ser Tyr Asp Tyr Glu Trp Gly Thr Glu Glu Asn Gln Lys
225                 230                 235                 240

Thr Thr Ile Ile Asn Thr Val Gly Phe Gln Ile Asn Val Asp Ser Gly
                245                 250                 255

Met Lys Phe Glu Val Pro Glu Val Gly Gly Gly Thr Glu Glu Ile Lys
            260                 265                 270

Thr Gln Leu Asn Glu Glu Leu Lys Val Glu Tyr Ser Thr Asp Thr Lys
        275                 280                 285

Ile Met Lys Lys Tyr Gln Glu His Ser Glu Ile Asp Asn Pro Thr Asn
    290                 295                 300

Gln Thr Thr Asn Ser Ile Gly Phe Leu Thr Phe Thr Ser Leu Glu Leu
305                 310                 315                 320

Tyr Arg Tyr Asn Gly Ser Glu Ile Arg Ile Met Arg Met Glu Thr Ser
                325                 330                 335

Asp Asn Asp Thr Tyr Thr Leu Thr Ser Tyr Pro Asn His Arg Glu Ala
            340                 345                 350

Leu Leu Leu Leu Thr Asn His Ser Tyr Gln Glu Val Ser Arg Ile Pro
        355                 360                 365

Ala His Trp Arg Pro Leu Leu Val Asp Pro Ser Ser Val Pro Ser Leu
    370                 375                 380

Ala Ser Trp Ser Xaa Phe Pro Val Asn Cys Tyr Pro Leu Thr Ile Pro
385                 390                 395                 400

His Asn Ile Arg Ala Gly Ser Ile Lys Cys Lys Ala Trp Gly Ala Val
                405                 410                 415

Ser Leu Thr Leu Ile Ala Leu Arg Ser Leu Pro Ala Phe Gln Ser Gly
            420                 425                 430

Asn Leu Ser Cys Gln Leu His Ile Gly Gln Arg Ala Gly Arg Gly Gly
        435                 440                 445

Leu Arg Ile Gly Arg Ser Ser Ala Ser Ser Leu Thr Asp Ser
    450                 455                 460
```

<210> SEQ ID NO 83
<211> LENGTH: 340
<212> TYPE: DNA
<213> ORGANISM: Bacillus thuringiensis

<400> SEQUENCE: 83

```
tgtcagcacg tgaagtacat attgatgtaa ataataagac aggtcataca ttacaattag     60

aagataaaac aaaacttgat ggtggtagat ggcgaacatc acctacaaat gttgctaatg    120

atcaaattaa aacatttgta gcagaatcaa atggttttat gacaggtaca gaaggtacta    180

tatattatag tataaatgga gaagcagaaa ttagtttata ttttgacaat ccttttgcag    240

gttctaataa atatgatgga cattccaata aatctcaata tgaaattatt acccaaggag    300

gatcaggaaa tcaatctcat gtgacatata ctattcaaac                          340
```

<210> SEQ ID NO 84
<211> LENGTH: 112
<212> TYPE: PRT
<213> ORGANISM: Bacillus thuringiensis -continued

<400> SEQUENCE: 84

```
Ser Ala Arg Glu Val His Ile Asp Val Asn Asn Lys Thr Gly His Thr
  1               5                  10                  15

Leu Gln Leu Glu Asp Lys Thr Lys Leu Asp Gly Gly Arg Trp Arg Thr
             20                  25                  30

Ser Pro Thr Asn Val Ala Asn Asp Gln Ile Lys Thr Phe Val Ala Glu
         35                  40                  45

Ser Asn Gly Phe Met Thr Gly Thr Glu Gly Thr Ile Tyr Tyr Ser Ile
     50                  55                  60

Asn Gly Glu Ala Glu Ile Ser Leu Tyr Phe Asp Asn Pro Phe Ala Gly
 65                  70                  75                  80

Ser Asn Lys Tyr Asp Gly His Ser Asn Lys Ser Gln Tyr Glu Ile Ile
                 85                  90                  95

Thr Gln Gly Gly Ser Gly Asn Gln Ser His Val Thr Tyr Thr Ile Gln
            100                 105                 110
```

<210> SEQ ID NO 85
<211> LENGTH: 1114
<212> TYPE: DNA
<213> ORGANISM: Bacillus thuringiensis

<400> SEQUENCE: 85

```
atgttagata ctaataaagt ttatgaaata agcaatcatg ctaatggact atatgcagca     60
acttatttaa gtttagatga ttcaggtgtt agtttaatga ataaaaatga tgatgatatt    120
gatgattata acttaaaatg gtttttattt cctattgatg atgatcaata tattattaca    180
agctatgcag caaataattg taaagtttgg aatgttaata atgataaaat aaatgtttcg    240
acttattctt caacaaattc aatacaaaaa tggcaaataa aagctaatgg ttcttcatat    300
gtaatacaaa gtgataatgg aaaagtctta acagcaggaa ccggtcaagc tcttggattg    360
atacgtttaa ctgatgaatc ctcaaataat cccaatcaac aatggaattt aacttctgta    420
caaacaattc aacttccacg aaaacctata atagatacaa aattaaaaga ttatcccaaa    480
tattcaccaa ctggaaatat agataatgga acatctcctc aattaatggg atggacatta    540
gtaccttgta ttatggtaaa tgatccaaat atagataaaa atactcaaat taaaactact    600
ccatattata ttttaaaaaa atatcaatat tggcaacgag cagtaggaag taatgtagct    660
ttacgtccac atgaaaaaaa atcatatact tatgaatggg gcacagaaat agatcaaaaa    720
acaacaatta taaatacatt aggatttcaa atcaatatag attcaggaat gaaatttgat    780
ataccagaag taggtggagg tacagatgaa ataaaaacac aactaaatga agaattaaaa    840
atagaatata gtcatgaaac taaaataatg gaaaaatatc aagaacaatc tgaaatagat    900
aatccaactg atcaatcaat gaattctata ggatttctta ctattacttc cttagaatta    960
tatagatata atggctcaga aattcgtata atgcaaattc aaacctcaga taatgatact   1020
tataatgtta cttcttatcc aaatcatcaa caagctttat tacttcttac aaatcattca   1080
tatgaagaag ttgaagaaat aacaagggcg aatt                                1114
```

<210> SEQ ID NO 86
<211> LENGTH: 371
<212> TYPE: PRT
<213> ORGANISM: Bacillus thuringiensis

<400> SEQUENCE: 86

```
Met Leu Asp Thr Asn Lys Val Tyr Glu Ile Ser Asn His Ala Asn Gly
  1               5                  10                  15
```

-continued

Leu Tyr Ala Ala Thr Tyr Leu Ser Leu Asp Asp Ser Gly Val Ser Leu
            20                  25                  30

Met Asn Lys Asn Asp Asp Asp Ile Asp Asp Tyr Asn Leu Lys Trp Phe
        35                  40                  45

Leu Phe Pro Ile Asp Asp Asp Gln Tyr Ile Ile Thr Ser Tyr Ala Ala
    50                  55                  60

Asn Asn Cys Lys Val Trp Asn Val Asn Asn Asp Lys Ile Asn Val Ser
65                  70                  75                  80

Thr Tyr Ser Ser Thr Asn Ser Ile Gln Lys Trp Gln Ile Lys Ala Asn
                85                  90                  95

Gly Ser Ser Tyr Val Ile Gln Ser Asp Asn Gly Lys Val Leu Thr Ala
            100                 105                 110

Gly Thr Gly Gln Ala Leu Gly Leu Ile Arg Leu Thr Asp Glu Ser Ser
        115                 120                 125

Asn Asn Pro Asn Gln Gln Trp Asn Leu Thr Ser Val Gln Thr Ile Gln
    130                 135                 140

Leu Pro Arg Lys Pro Ile Ile Asp Thr Lys Leu Lys Asp Tyr Pro Lys
145                 150                 155                 160

Tyr Ser Pro Thr Gly Asn Ile Asp Asn Gly Thr Ser Pro Gln Leu Met
                165                 170                 175

Gly Trp Thr Leu Val Pro Cys Ile Met Val Asn Asp Pro Asn Ile Asp
            180                 185                 190

Lys Asn Thr Gln Ile Lys Thr Thr Pro Tyr Tyr Ile Leu Lys Lys Tyr
        195                 200                 205

Gln Tyr Trp Gln Arg Ala Val Gly Ser Asn Val Ala Leu Arg Pro His
    210                 215                 220

Glu Lys Lys Ser Tyr Thr Tyr Glu Trp Gly Thr Glu Ile Asp Gln Lys
225                 230                 235                 240

Thr Thr Ile Ile Asn Thr Leu Gly Phe Gln Ile Asn Ile Asp Ser Gly
                245                 250                 255

Met Lys Phe Asp Ile Pro Glu Val Gly Gly Gly Thr Asp Glu Ile Lys
            260                 265                 270

Thr Gln Leu Asn Glu Glu Leu Lys Ile Glu Tyr Ser His Glu Thr Lys
        275                 280                 285

Ile Met Glu Lys Tyr Gln Glu Gln Ser Glu Ile Asp Asn Pro Thr Asp
    290                 295                 300

Gln Ser Met Asn Ser Ile Gly Phe Leu Thr Ile Thr Ser Leu Glu Leu
305                 310                 315                 320

Tyr Arg Tyr Asn Gly Ser Glu Ile Arg Ile Met Gln Ile Gln Thr Ser
                325                 330                 335

Asp Asn Asp Thr Tyr Asn Val Thr Ser Tyr Pro Asn His Gln Gln Ala
            340                 345                 350

Leu Leu Leu Leu Thr Asn His Ser Tyr Glu Glu Val Glu Glu Ile Thr
        355                 360                 365

Arg Ala Asn
    370

<210> SEQ ID NO 87
<211> LENGTH: 341
<212> TYPE: DNA
<213> ORGANISM: Bacillus thuringiensis

<400> SEQUENCE: 87
atgtcagctg gcgaagttca tattgaaata aacaataaaa cacgtcatac attacaatta     60

-continued

```
gaggataaaa ctaaacttag cggcggtaga tggcgaacat cacctacaaa tgttgctcgt    120

gatacaatta aaacatttgt agcagaatca catggtttta tgacaggagt agaaggtatt    180

atatatttta gtgtaaacgg agacgcagaa attagtttac attttgacaa tccttatata    240

ggttctaata aatgtgatgg ttcttctgat aaacctgaat atgaagttat tactcaaagc    300

ggatcaggag ataaatctca tgtcacttat acaattcaaa c                        341
```

<210> SEQ ID NO 88
<211> LENGTH: 113
<212> TYPE: PRT
<213> ORGANISM: Bacillus thuringiensis

<400> SEQUENCE: 88

```
Met Ser Ala Gly Glu Val His Ile Glu Ile Asn Asn Lys Thr Arg His
  1               5                  10                  15

Thr Leu Gln Leu Glu Asp Lys Thr Lys Leu Ser Gly Gly Arg Trp Arg
             20                  25                  30

Thr Ser Pro Thr Asn Val Ala Arg Asp Thr Ile Lys Thr Phe Val Ala
         35                  40                  45

Glu Ser His Gly Phe Met Thr Gly Val Glu Gly Ile Ile Tyr Phe Ser
     50                  55                  60

Val Asn Gly Asp Ala Glu Ile Ser Leu His Phe Asp Asn Pro Tyr Ile
 65                  70                  75                  80

Gly Ser Asn Lys Cys Asp Gly Ser Ser Asp Lys Pro Glu Tyr Glu Val
                 85                  90                  95

Ile Thr Gln Ser Gly Ser Gly Asp Lys Ser His Val Thr Tyr Thr Ile
            100                 105                 110

Gln
```

<210> SEQ ID NO 89
<211> LENGTH: 1186
<212> TYPE: DNA
<213> ORGANISM: Bacillus thuringiensis

<400> SEQUENCE: 89

```
atgttagata caaataaagt ttatgaaata agcaatcttg ctaatggatt atatacatca     60

acttatttaa gtcttgatga ttcaggtgtt agtttaatga gtaaaaagga tgaagatatt    120

gatgattaca atttaaaatg gtttttattt cctattgata ataatcaata tattattaca    180

agctatggag ctaataattg taaagtttgg aatgttaaaa atgataaaat aaatgtttca    240

acttattctt caacaaactc tgtacaaaaa tggcaaataa aagctaaaga ttcttcatat    300

ataatacaaa gtgataatgg aaaggtctta acagcaggag taggtcaatc tcttggaata    360

gtacgcctaa ctgatgaatt tccagagaat tctaaccaac aatggaattt aactcctgta    420

caaacaattc aactcccaca aaaacctaaa atagatgaaa aattaaaaga tcatcctgaa    480

tattcagaaa ccggaaatat aaatcctaaa acaactcctc aattaatggg atggacatta    540

gtaccttgta ttatggtaaa tgattcaaaa atagataaaa acactcaaat taaaactact    600

ccatattata tttttaaaaa atataaatac tggaatctag caaaaggaag taatgtatct    660

ttacttccac atcaaaaaag atcatatgat tatgaatggg gtacagaaaa aaatcaaaaa    720

acaactatta ttaatacagt aggattgcaa attaatatag attcaggaat gaaatttgaa    780

gtaccagaag taggaggagg tacagaagac ataaaaacac aattaactga agaattaaaa    840

gttgaatata gcactgaaac caaaataatg acgaaatatc aagaacactc agagatagat    900
```

-continued

```
aatccaacta atcaaccaat gaattctata ggacttctta tttatacttc tttagaatta    960

tatcgatata acggrcagaa attaagataa tggacataga aacttcagat catgatactt   1020

acactcttac ttcttatcca aatcataaag aagcattatt acttctcaca aaccattctt   1080

atgaagaagt agaagaaatt acaagggcga attccagcac actggcggcc gttactagtg   1140

gatccgagct cggtaccaag cttggcgtgt caggtcaaag ggttca                  1186


<210> SEQ ID NO 90
<211> LENGTH: 392
<212> TYPE: PRT
<213> ORGANISM: Bacillus thuringiensis

<400> SEQUENCE: 90

Met Leu Asp Thr Asn Lys Val Tyr Glu Ile Ser Asn Leu Ala Asn Gly
  1               5                  10                  15

Leu Tyr Thr Ser Thr Tyr Leu Ser Leu Asp Asp Ser Gly Val Ser Leu
             20                  25                  30

Met Ser Lys Lys Asp Glu Asp Ile Asp Asp Tyr Asn Leu Lys Trp Phe
         35                  40                  45

Leu Phe Pro Ile Asp Asn Asn Gln Tyr Ile Ile Thr Ser Tyr Gly Ala
     50                  55                  60

Asn Asn Cys Lys Val Trp Asn Val Lys Asn Asp Lys Ile Asn Val Ser
 65                  70                  75                  80

Thr Tyr Ser Ser Thr Asn Ser Val Gln Lys Trp Gln Ile Lys Ala Lys
                 85                  90                  95

Asp Ser Ser Tyr Ile Ile Gln Ser Asp Asn Gly Lys Val Leu Thr Ala
            100                 105                 110

Gly Val Gly Gln Ser Leu Gly Ile Val Arg Leu Thr Asp Glu Phe Pro
        115                 120                 125

Glu Asn Ser Asn Gln Gln Trp Asn Leu Thr Pro Val Gln Thr Ile Gln
    130                 135                 140

Leu Pro Gln Lys Pro Lys Ile Asp Glu Lys Leu Lys Asp His Pro Glu
145                 150                 155                 160

Tyr Ser Glu Thr Gly Asn Ile Asn Pro Lys Thr Thr Pro Gln Leu Met
                165                 170                 175

Gly Trp Thr Leu Val Pro Cys Ile Met Val Asn Asp Ser Lys Ile Asp
            180                 185                 190

Lys Asn Thr Gln Ile Lys Thr Thr Pro Tyr Tyr Ile Phe Lys Lys Tyr
        195                 200                 205

Lys Tyr Trp Asn Leu Ala Lys Gly Ser Asn Val Ser Leu Leu Pro His
    210                 215                 220

Gln Lys Arg Ser Tyr Asp Tyr Glu Trp Gly Thr Glu Lys Asn Gln Lys
225                 230                 235                 240

Thr Thr Ile Ile Asn Thr Val Gly Leu Gln Ile Asn Ile Asp Ser Gly
                245                 250                 255

Met Lys Phe Glu Val Pro Glu Val Gly Gly Gly Thr Glu Asp Ile Lys
            260                 265                 270

Thr Gln Leu Thr Glu Glu Leu Lys Val Glu Tyr Ser Thr Glu Thr Lys
        275                 280                 285

Ile Met Thr Lys Tyr Gln Glu His Ser Glu Ile Asp Asn Pro Thr Asn
    290                 295                 300

Gln Pro Met Asn Ser Ile Gly Leu Leu Ile Tyr Thr Ser Leu Glu Leu
305                 310                 315                 320
```

-continued

```
Tyr Arg Tyr Asn Gly Gln Lys Leu Arg Trp Thr Lys Leu Gln Ile Met
                325                 330                 335

Ile Leu Thr Leu Leu Leu Leu Ile Gln Ile Ile Lys Lys His Tyr Tyr
            340                 345                 350

Phe Ser Gln Thr Ile Leu Met Lys Lys Lys Lys Leu Gln Gly Arg Ile
        355                 360                 365

Pro Ala His Trp Arg Pro Leu Leu Val Asp Pro Ser Ser Val Pro Ser
    370                 375                 380

Leu Ala Cys Gln Val Lys Gly Phe
385                 390


<210> SEQ ID NO 91
<211> LENGTH: 341
<212> TYPE: DNA
<213> ORGANISM: Bacillus thuringiensis

<400> SEQUENCE: 91

atgtcagcag ccgaagtaca tattgaaata ataaatcata caggtcatac cttacaaatg     60

gataaaagaa ctagacttgc acatggtgaa tggattatta cacccgtgaa tgttccaaat    120

aattcttctg atttatttca agcaggttct gatggagttt tgacaggagt agaaggaata    180

ataatttata ctataaatgg agaaatagaa attaccttac attttgacaa tccttatgca    240

ggttctaata aatattctgg acgttctagt gatgatgatt ataaagttat aactgaagca    300

agagcagaac atagagctaa taatcatgat catgtaactt a                        341


<210> SEQ ID NO 92
<211> LENGTH: 113
<212> TYPE: PRT
<213> ORGANISM: Bacillus thuringiensis

<400> SEQUENCE: 92

Met Ser Ala Ala Glu Val His Ile Glu Ile Ile Asn His Thr Gly His
  1               5                  10                  15

Thr Leu Gln Met Asp Lys Arg Thr Arg Leu Ala His Gly Glu Trp Ile
             20                  25                  30

Ile Thr Pro Val Asn Val Pro Asn Asn Ser Ser Asp Leu Phe Gln Ala
         35                  40                  45

Gly Ser Asp Gly Val Leu Thr Gly Val Glu Gly Ile Ile Ile Tyr Thr
     50                  55                  60

Ile Asn Gly Glu Ile Glu Ile Thr Leu His Phe Asp Asn Pro Tyr Ala
 65                  70                  75                  80

Gly Ser Asn Lys Tyr Ser Gly Arg Ser Ser Asp Asp Asp Tyr Lys Val
                 85                  90                  95

Ile Thr Glu Ala Arg Ala Glu His Arg Ala Asn Asn His Asp His Val
            100                 105                 110

Thr


<210> SEQ ID NO 93
<211> LENGTH: 341
<212> TYPE: DNA
<213> ORGANISM: Bacillus thuringiensis

<400> SEQUENCE: 93

atgtcagatc gcgaagtaca tattgaaata ataaatcata caggtcatac cttacaaatg     60

gataaaagaa ctagacttgc acatggtgaa tggattatta cacccgtgaa tgttccaaat    120

aattcttctg atttatttca agcaggttct gatggagttt tgacaggagt agaaggaata    180
```

-continued

```
ataatttata ctataaatgg agaaatagaa attaccttac attttgacaa tccttatgca    240

ggttctaata aatattctgg acgttctagt gatgatgatt ataaagttat aactgaagca    300

agagcagaac atagagctaa taatcatgat catgtaactt a                        341
```

<210> SEQ ID NO 94
<211> LENGTH: 113
<212> TYPE: PRT
<213> ORGANISM: Bacillus thuringiensis

<400> SEQUENCE: 94

```
Met Ser Asp Arg Glu Val His Ile Glu Ile Ile Asn His Thr Gly His
  1               5                  10                  15

Thr Leu Gln Met Asp Lys Arg Thr Arg Leu Ala His Gly Glu Trp Ile
             20                  25                  30

Ile Thr Pro Val Asn Val Pro Asn Asn Ser Ser Asp Leu Phe Gln Ala
         35                  40                  45

Gly Ser Asp Gly Val Leu Thr Gly Val Glu Gly Ile Ile Ile Tyr Thr
     50                  55                  60

Ile Asn Gly Glu Ile Glu Ile Thr Leu His Phe Asp Asn Pro Tyr Ala
 65                  70                  75                  80

Gly Ser Asn Lys Tyr Ser Gly Arg Ser Ser Asp Asp Asp Tyr Lys Val
                 85                  90                  95

Ile Thr Glu Ala Arg Ala Glu His Arg Ala Asn Asn His Asp His Val
            100                 105                 110

Thr
```

<210> SEQ ID NO 95
<211> LENGTH: 353
<212> TYPE: DNA
<213> ORGANISM: Bacillus thuringiensis

<400> SEQUENCE: 95

```
atgtcagcac gtgaagtaca tattgaaata ataaatcata caggtcatac cttacaaatg     60

gataaaagaa ctagacttgc acatggtgaa tggattatta cacccgtgaa tgttccaaat    120

aattcttctg atttatttca agcaggttct gatggagttt tgacaggagt agaaggaata    180

ataatttata ctataaatgg agaaatagaa attaccttac attttgacaa tccttatgca    240

ggttctaata aatattctgg acgttctagt gatgatgatt ataaagttat aactgaagca    300

agagcagaac atagagctaa taatcatgat catgtaacat atacgattca aac          353
```

<210> SEQ ID NO 96
<211> LENGTH: 117
<212> TYPE: PRT
<213> ORGANISM: Bacillus thuringiensis

<400> SEQUENCE: 96

```
Met Ser Ala Arg Glu Val His Ile Glu Ile Ile Asn His Thr Gly His
  1               5                  10                  15

Thr Leu Gln Met Asp Lys Arg Thr Arg Leu Ala His Gly Glu Trp Ile
             20                  25                  30

Ile Thr Pro Val Asn Val Pro Asn Asn Ser Ser Asp Leu Phe Gln Ala
         35                  40                  45

Gly Ser Asp Gly Val Leu Thr Gly Val Glu Gly Ile Ile Ile Tyr Thr
     50                  55                  60

Ile Asn Gly Glu Ile Glu Ile Thr Leu His Phe Asp Asn Pro Tyr Ala
```

-continued

```
 65                  70                  75                  80

Gly Ser Asn Lys Tyr Ser Gly Arg Ser Ser Asp Asp Asp Tyr Lys Val
                 85                  90                  95

Ile Thr Glu Ala Arg Ala Glu His Arg Ala Asn Asn His Asp His Val
            100                 105                 110

Thr Tyr Thr Ile Gln
        115


<210> SEQ ID NO 97
<211> LENGTH: 353
<212> TYPE: DNA
<213> ORGANISM: Bacillus thuringiensis

<400> SEQUENCE: 97

atgtcagctc gtgaagtaca tattgaaata ataaatcata caggtcatac cttacaaatg     60

gataaaagaa ctagacttgc acatggtgaa tggattatta cacccgtgaa tgttccaaat    120

aattcttctg atttatttca agcaggttct gatggagttt tgacaggagt agaaggaata    180

ataatttata ctataaatgg agaaatagaa attaccttac attttgacaa tccttatgca    240

ggttctaata aatattctgg acgttctagt gatgatgatt ataaagttat aactgaagca    300

agagcagaac atagagctaa taatcatgat catgtgacat atacaattca aac           353


<210> SEQ ID NO 98
<211> LENGTH: 117
<212> TYPE: PRT
<213> ORGANISM: Bacillus thuringiensis

<400> SEQUENCE: 98

Met Ser Ala Arg Glu Val His Ile Glu Ile Ile Asn His Thr Gly His
  1               5                  10                  15

Thr Leu Gln Met Asp Lys Arg Thr Arg Leu Ala His Gly Glu Trp Ile
             20                  25                  30

Ile Thr Pro Val Asn Val Pro Asn Asn Ser Ser Asp Leu Phe Gln Ala
         35                  40                  45

Gly Ser Asp Gly Val Leu Thr Gly Val Glu Gly Ile Ile Ile Tyr Thr
     50                  55                  60

Ile Asn Gly Glu Ile Glu Ile Thr Leu His Phe Asp Asn Pro Tyr Ala
 65                  70                  75                  80

Gly Ser Asn Lys Tyr Ser Gly Arg Ser Ser Asp Asp Asp Tyr Lys Val
                 85                  90                  95

Ile Thr Glu Ala Arg Ala Glu His Arg Ala Asn Asn His Asp His Val
            100                 105                 110

Thr Tyr Thr Ile Gln
        115


<210> SEQ ID NO 99
<211> LENGTH: 353
<212> TYPE: DNA
<213> ORGANISM: Bacillus thuringiensis

<400> SEQUENCE: 99

atgtcaggtc gcgaagttca tattgaaata ataaatcata caggtcatac cttacaaatg     60

gataaaagaa ctagacttgc acatggtgaa tggattatta cacccgtgaa tgttccaaat    120

aattcttctg atttatttca agcaggttct gatggagttt tgacaggagt agaaggaata    180

ataatttata ctataaatgg agaaatagaa attaccttac attttgacaa tccttatgca    240
```

-continued

```
ggttctaata aatattctgg acgttctagt gatgatgatt ataaagttat aactgaagca    300

agagcagaac atagagctaa taatcatgat catgtaacat atacgattca aac           353


<210> SEQ ID NO 100
<211> LENGTH: 117
<212> TYPE: PRT
<213> ORGANISM: Bacillus thuringiensis

<400> SEQUENCE: 100

Met Ser Gly Arg Glu Val His Ile Glu Ile Ile Asn His Thr Gly His
  1               5                  10                  15

Thr Leu Gln Met Asp Lys Arg Thr Arg Leu Ala His Gly Glu Trp Ile
             20                  25                  30

Ile Thr Pro Val Asn Val Pro Asn Asn Ser Ser Asp Leu Phe Gln Ala
         35                  40                  45

Gly Ser Asp Gly Val Leu Thr Gly Val Glu Gly Ile Ile Ile Tyr Thr
     50                  55                  60

Ile Asn Gly Glu Ile Glu Ile Thr Leu His Phe Asp Asn Pro Tyr Ala
 65                  70                  75                  80

Gly Ser Asn Lys Tyr Ser Gly Arg Ser Ser Asp Asp Asp Tyr Lys Val
                 85                  90                  95

Ile Thr Glu Ala Arg Ala Glu His Arg Ala Asn Asn His Asp His Val
            100                 105                 110

Thr Tyr Thr Ile Gln
        115


<210> SEQ ID NO 101
<211> LENGTH: 353
<212> TYPE: DNA
<213> ORGANISM: Bacillus thuringiensis

<400> SEQUENCE: 101

atgtcagctc gtgaagtaca tattgaaata ataaatcata caggtcatac cttacaaatg     60

gataaaagaa ctagacttgc acatggtgaa tggattatta cacccgtgaa tgttccaaat    120

aattcttctg atttatttca agcaggttct gatggagttt tgacaggagt agaaggaata    180

ataatttata ctataaatgg agaaatagaa attaccttac attttgacaa tccttatgca    240

ggttctaata aatattctgg acgttctagt gatgatgatt ataaagttat aactgaagca    300

agagcagaac atagagctaa taatcatgat catgttacgt atacaattca aac           353


<210> SEQ ID NO 102
<211> LENGTH: 117
<212> TYPE: PRT
<213> ORGANISM: Bacillus thuringiensis

<400> SEQUENCE: 102

Met Ser Ala Arg Glu Val His Ile Glu Ile Ile Asn His Thr Gly His
  1               5                  10                  15

Thr Leu Gln Met Asp Lys Arg Thr Arg Leu Ala His Gly Glu Trp Ile
             20                  25                  30

Ile Thr Pro Val Asn Val Pro Asn Asn Ser Ser Asp Leu Phe Gln Ala
         35                  40                  45

Gly Ser Asp Gly Val Leu Thr Gly Val Glu Gly Ile Ile Ile Tyr Thr
     50                  55                  60

Ile Asn Gly Glu Ile Glu Ile Thr Leu His Phe Asp Asn Pro Tyr Ala
 65                  70                  75                  80
```

-continued

```
Gly Ser Asn Lys Tyr Ser Gly Arg Ser Ser Asp Asp Asp Tyr Lys Val
                 85                  90                  95

Ile Thr Glu Ala Arg Ala Glu His Arg Ala Asn Asn His Asp His Val
            100                 105                 110

Thr Tyr Thr Ile Gln
        115
```

<210> SEQ ID NO 103
<211> LENGTH: 353
<212> TYPE: DNA
<213> ORGANISM: Bacillus thuringiensis

<400> SEQUENCE: 103

```
atgtcaggtc gcgaagtaga tattgaaata ataaatcata caggtcatac cttacaaatg     60

gataaaagaa ctagacttgc acatggtgaa tggattatta cacccgtgaa tgttccaaat    120

aattcttctg atttatttca agcaggttct gatggagttt tgacaggagt agaaggaata    180

ataatttata ctataaatgg agaaatagaa attaccttac attttgacaa tccttatgca    240

ggttctaata aatattctgg acgttctagt gatgatgatt ataaagttat aactgaagcg    300

agagcagaac atagagctaa taatcatgat catgtaacat atactattca gac           353
```

<210> SEQ ID NO 104
<211> LENGTH: 117
<212> TYPE: PRT
<213> ORGANISM: Bacillus thuringiensis

<400> SEQUENCE: 104

```
Met Ser Gly Arg Glu Val Asp Ile Glu Ile Ile Asn His Thr Gly His
  1               5                  10                  15

Thr Leu Gln Met Asp Lys Arg Thr Arg Leu Ala His Gly Glu Trp Ile
             20                  25                  30

Ile Thr Pro Val Asn Val Pro Asn Asn Ser Ser Asp Leu Phe Gln Ala
         35                  40                  45

Gly Ser Asp Gly Val Leu Thr Gly Val Glu Gly Ile Ile Ile Tyr Thr
     50                  55                  60

Ile Asn Gly Glu Ile Glu Ile Thr Leu His Phe Asp Asn Pro Tyr Ala
 65                  70                  75                  80

Gly Ser Asn Lys Tyr Ser Gly Arg Ser Ser Asp Asp Asp Tyr Lys Val
                 85                  90                  95

Ile Thr Glu Ala Arg Ala Glu His Arg Ala Asn Asn His Asp His Val
            100                 105                 110

Thr Tyr Thr Ile Gln
        115
```

<210> SEQ ID NO 105
<211> LENGTH: 353
<212> TYPE: DNA
<213> ORGANISM: Bacillus thuringiensis

<400> SEQUENCE: 105

```
atgtcagcac gtgaagtaca tattgaaata ataaatcata caggtcatac cttacaaatg     60

gataaaagaa ctagacttgc acatggtgaa tggattatta cacccgtgaa tgttccaaat    120

aattcttctg atttatttca agcaggttct gatggagttt tgacaggagt agaaggaata    180

ataatttata ctataaatgg agaaatagaa attaccttac attttgacaa tccttatgca    240

ggttctaata aatattctgg acgttctagt gatgatgatt ataaagttat aactgaagca    300
```

-continued

```
agagcagaac atagagctaa taatcatgat catgtaacat ataccattca aac          353


<210> SEQ ID NO 106
<211> LENGTH: 117
<212> TYPE: PRT
<213> ORGANISM: Bacillus thuringiensis

<400> SEQUENCE: 106

Met Ser Ala Arg Glu Val His Ile Glu Ile Ile Asn His Thr Gly His
  1               5                  10                  15

Thr Leu Gln Met Asp Lys Arg Thr Arg Leu Ala His Gly Glu Trp Ile
             20                  25                  30

Ile Thr Pro Val Asn Val Pro Asn Asn Ser Ser Asp Leu Phe Gln Ala
         35                  40                  45

Gly Ser Asp Gly Val Leu Thr Gly Val Glu Gly Ile Ile Ile Tyr Thr
     50                  55                  60

Ile Asn Gly Glu Ile Glu Ile Thr Leu His Phe Asp Asn Pro Tyr Ala
 65                  70                  75                  80

Gly Ser Asn Lys Tyr Ser Gly Arg Ser Ser Asp Asp Asp Tyr Lys Val
                 85                  90                  95

Ile Thr Glu Ala Arg Ala Glu His Arg Ala Asn Asn His Asp His Val
            100                 105                 110

Thr Tyr Thr Ile Gln
        115


<210> SEQ ID NO 107
<211> LENGTH: 341
<212> TYPE: DNA
<213> ORGANISM: Bacillus thuringiensis

<400> SEQUENCE: 107

atgtcaggtc gcgaagttca tattgatgta aataataaga caggtcatac attacaatta     60

gaagataaaa caagacttga tggtggtaga tggcgaacat cacctacaaa tgttgctaat    120

gatcaaatta aaacatttgt agcagaatca catggtttta tgacaggtac agaaggtact    180

atatattata gtataaatgg agaagcagaa attagtttat attttgacaa tccttattca    240

ggttctaata aatatgatgg gcattccaat aaaaatcaat atgaagttat tacccaagga    300

ggatcaggaa atcaatctca tctgacgtat acaattcaaa c                        341


<210> SEQ ID NO 108
<211> LENGTH: 113
<212> TYPE: PRT
<213> ORGANISM: Bacillus thuringiensis

<400> SEQUENCE: 108

Met Ser Gly Arg Glu Val His Ile Asp Val Asn Asn Lys Thr Gly His
  1               5                  10                  15

Thr Leu Gln Leu Glu Asp Lys Thr Arg Leu Asp Gly Gly Arg Trp Arg
             20                  25                  30

Thr Ser Pro Thr Asn Val Ala Asn Asp Gln Ile Lys Thr Phe Val Ala
         35                  40                  45

Glu Ser His Gly Phe Met Thr Gly Thr Glu Gly Thr Ile Tyr Tyr Ser
     50                  55                  60

Ile Asn Gly Glu Ala Glu Ile Ser Leu Tyr Phe Asp Asn Pro Tyr Ser
 65                  70                  75                  80

Gly Ser Asn Lys Tyr Asp Gly His Ser Asn Lys Asn Gln Tyr Glu Val
                 85                  90                  95
```

-continued

```
Ile Thr Gln Gly Gly Ser Gly Asn Gln Ser His Leu Thr Tyr Thr Ile
            100                 105                 110

Gln


<210> SEQ ID NO 109
<211> LENGTH: 1114
<212> TYPE: DNA
<213> ORGANISM: Bacillus thuringiensis

<400> SEQUENCE: 109

atgttagata ctaataaagt atatgaaata agtaattatg ctaatggatt acatgcagca      60

acttatttaa gtttagatga ttcaggtgtt agtttaatga ataaaaatga tgatgatatt     120

gatgactata atttaaggtg gtttttattt cctattgatg ataatcaata tattattaca     180

agctacgcag cgaataattg taaggtttgg aatgttaata atgataaaat aaatgtttca     240

acttattctt caacaaactc gatacagaaa tggcaaataa aagctaatgc ttcttcgtat     300

gtaatacaaa gtaataatgg gaaagttcta acagcaggaa ccggtcaatc tcttggatta     360

atacgtttaa cggatgaatc accagataat cccaatcaac aatggaattt aactcctgta     420

caaacaattc aactcccacc aaaacctaca atagatacaa agttaaaaga ttaccccaaa     480

tattcacaaa ctggcaatat agacaaggga acacctcctc aattaatggg atggacatta     540

ataccttgta ttatggtaaa tgatccaaat atagataaaa acactcaaat caaaactact     600

ccatattata ttttaaaaaa atatcaatat tggcaacaag cagtaggaag taatgtagct     660

ttacgtccgc atgaaaaaaa atcatatgct tatgagtggg gtacagaaat agatcaaaaa     720

acaactatca ttaatacatt aggatttcag attaatatag attcgggaat ggaatttgat     780

ataccagaag taggtggagg tacagatgaa ataaaaacac aattaaacga agaattaaaa     840

atagaatata gccgtgaaac caaaataatg gaaaaatatc aggaacaatc agagatagat     900

aatccaactg atcaatcaat gaattctata ggattcctca ctattacttc tttagaatta     960

tatcgatata atggttcgga aattagtgta atgaaaattc aaacttcaga taatgatact    1020

tacaatgtga cctcttatcc agatcatcaa caagctctat tacttcttac aaatcattca    1080

tatgaacaag tacaagaaat aacaagggcg aatt                                1114


<210> SEQ ID NO 110
<211> LENGTH: 371
<212> TYPE: PRT
<213> ORGANISM: Bacillus thuringiensis

<400> SEQUENCE: 110

Met Leu Asp Thr Asn Lys Val Tyr Glu Ile Ser Asn Tyr Ala Asn Gly
  1               5                  10                  15

Leu His Ala Ala Thr Tyr Leu Ser Leu Asp Asp Ser Gly Val Ser Leu
            20                  25                  30

Met Asn Lys Asn Asp Asp Asp Ile Asp Asp Tyr Asn Leu Arg Trp Phe
        35                  40                  45

Leu Phe Pro Ile Asp Asp Asn Gln Tyr Ile Ile Thr Ser Tyr Ala Ala
     50                  55                  60

Asn Asn Cys Lys Val Trp Asn Val Asn Asn Asp Lys Ile Asn Val Ser
 65                  70                  75                  80

Thr Tyr Ser Ser Thr Asn Ser Ile Gln Lys Trp Gln Ile Lys Ala Asn
                 85                  90                  95

Ala Ser Ser Tyr Val Ile Gln Ser Asn Asn Gly Lys Val Leu Thr Ala
```

-continued

```
            100                 105                 110

Gly Thr Gly Gln Ser Leu Gly Leu Ile Arg Leu Thr Asp Glu Ser Pro
        115                 120                 125

Asp Asn Pro Asn Gln Gln Trp Asn Leu Thr Pro Val Gln Thr Ile Gln
    130                 135                 140

Leu Pro Pro Lys Pro Thr Ile Asp Thr Lys Leu Lys Asp Tyr Pro Lys
145                 150                 155                 160

Tyr Ser Gln Thr Gly Asn Ile Asp Lys Gly Thr Pro Pro Gln Leu Met
                165                 170                 175

Gly Trp Thr Leu Ile Pro Cys Ile Met Val Asn Asp Pro Asn Ile Asp
            180                 185                 190

Lys Asn Thr Gln Ile Lys Thr Thr Pro Tyr Tyr Ile Leu Lys Lys Tyr
        195                 200                 205

Gln Tyr Trp Gln Gln Ala Val Gly Ser Asn Val Ala Leu Arg Pro His
    210                 215                 220

Glu Lys Lys Ser Tyr Ala Tyr Glu Trp Gly Thr Glu Ile Asp Gln Lys
225                 230                 235                 240

Thr Thr Ile Ile Asn Thr Leu Gly Phe Gln Ile Asn Ile Asp Ser Gly
                245                 250                 255

Met Glu Phe Asp Ile Pro Glu Val Gly Gly Gly Thr Asp Glu Ile Lys
            260                 265                 270

Thr Gln Leu Asn Glu Glu Leu Lys Ile Glu Tyr Ser Arg Glu Thr Lys
        275                 280                 285

Ile Met Glu Lys Tyr Gln Glu Gln Ser Glu Ile Asp Asn Pro Thr Asp
    290                 295                 300

Gln Ser Met Asn Ser Ile Gly Phe Leu Thr Ile Thr Ser Leu Glu Leu
305                 310                 315                 320

Tyr Arg Tyr Asn Gly Ser Glu Ile Ser Val Met Lys Ile Gln Thr Ser
                325                 330                 335

Asp Asn Asp Thr Tyr Asn Val Thr Ser Tyr Pro Asp His Gln Gln Ala
            340                 345                 350

Leu Leu Leu Leu Thr Asn His Ser Tyr Glu Gln Val Gln Glu Ile Thr
        355                 360                 365

Arg Ala Asn
    370


<210> SEQ ID NO 111
<211> LENGTH: 341
<212> TYPE: DNA
<213> ORGANISM: Bacillus thuringiensis

<400> SEQUENCE: 111

atgtcagctc gtgaagtaca tattgaaata aacaataaaa cacgtcatac attacaatta      60

gaggataaaa ctaaacttag cggcggtaga tggcgaacat cacctacaaa tgttgctcgt     120

gatacaatta aaacatttgt agcagaatca catggtttta tgacaggagt agaaggtatt     180

atatatttta gtgtaaacgg agacgcagaa attagtttac attttgacaa tccttatata     240

ggttctaata aatgtgatgg ttcttctgat aaacctgaat atgaagttat tactcaaagc     300

ggatcaggag ataaatctca tgttacatat acaattcaga c                         341


<210> SEQ ID NO 112
<211> LENGTH: 113
<212> TYPE: PRT
<213> ORGANISM: Bacillus thuringiensis
```

-continued

<400> SEQUENCE: 112

```
Met Ser Ala Arg Glu Val His Ile Glu Ile Asn Asn Lys Thr Arg His
  1               5                  10                  15

Thr Leu Gln Leu Glu Asp Lys Thr Lys Leu Ser Gly Gly Arg Trp Arg
             20                  25                  30

Thr Ser Pro Thr Asn Val Ala Arg Asp Thr Ile Lys Thr Phe Val Ala
         35                  40                  45

Glu Ser His Gly Phe Met Thr Gly Val Glu Gly Ile Ile Tyr Phe Ser
     50                  55                  60

Val Asn Gly Asp Ala Glu Ile Ser Leu His Phe Asp Asn Pro Tyr Ile
 65                  70                  75                  80

Gly Ser Asn Lys Cys Asp Gly Ser Ser Asp Lys Pro Glu Tyr Glu Val
                 85                  90                  95

Ile Thr Gln Ser Gly Ser Gly Asp Lys Ser His Val Thr Tyr Thr Ile
            100                 105                 110

Gln
```

<210> SEQ ID NO 113
<211> LENGTH: 360
<212> TYPE: DNA
<213> ORGANISM: Bacillus thuringiensis

<400> SEQUENCE: 113

```
atgtcagctc gcgaagtaca cattgaaata aacaataaaa cacgtcatac attacaatta     60

gaggataaaa ctaaacttag cggcggtaga tggcgaacat cacctacaaa tgttgctcgt    120

gatacaatta aaacatttgt agcagaatca catggtttta tgacaggagt agaaggtatt    180

atatatttta gtgtaaacgg agacgcagaa attagtttac attttgacaa tccttatata    240

ggttctaata aatgtgatgg ttcttctgat aaacctgaat atgaagttat tactcaaagc    300

ggatcaggag ataaatctca tgtgacatat actattcaga cagtatcttt acgattataa    360
```

<210> SEQ ID NO 114
<211> LENGTH: 119
<212> TYPE: PRT
<213> ORGANISM: Bacillus thuringiensis

<400> SEQUENCE: 114

```
Met Ser Ala Arg Glu Val His Ile Glu Ile Asn Asn Lys Thr Arg His
  1               5                  10                  15

Thr Leu Gln Leu Glu Asp Lys Thr Lys Leu Ser Gly Gly Arg Trp Arg
             20                  25                  30

Thr Ser Pro Thr Asn Val Ala Arg Asp Thr Ile Lys Thr Phe Val Ala
         35                  40                  45

Glu Ser His Gly Phe Met Thr Gly Val Glu Gly Ile Ile Tyr Phe Ser
     50                  55                  60

Val Asn Gly Asp Ala Glu Ile Ser Leu His Phe Asp Asn Pro Tyr Ile
 65                  70                  75                  80

Gly Ser Asn Lys Cys Asp Gly Ser Ser Asp Lys Pro Glu Tyr Glu Val
                 85                  90                  95

Ile Thr Gln Ser Gly Ser Gly Asp Lys Ser His Val Thr Tyr Thr Ile
            100                 105                 110

Gln Thr Val Ser Leu Arg Leu
        115
```

<210> SEQ ID NO 115

-continued

<211> LENGTH: 1158
<212> TYPE: DNA
<213> ORGANISM: Bacillus thuringiensis

<400> SEQUENCE: 115
atgttagata ctaataaagt ttatgaaata agcaatcttg ctaatggatt atatacatca 60
acttatttaa gtcttgatga ttcaggtgtt agtttaatga gtaaaaagga tgaagatatt 120
gatgattaca atttaaaatg gtttttattt cctattgata ataatcaata tattattaca 180
agctatggag ctaataattg taaagtttgg aatgttaaaa atgataaaat aaatgtttca 240
acttattctt caacaaactc tgtacaaaaa tggcaaataa aagctaaaga ttcttcatat 300
ataatacaaa gtgataatgg aaaggtctta acagcaggag taggtgaatc tcttggaata 360
gtacgcctaa ctgatgaatt tccagagaat tctaaccaac aatggaattt aactcctgta 420
caaacaattc aactcccaca aaaacctaaa atagatgaaa aattaaaaga tcatcctgaa 480
tattcagaaa ccggaaatat aaatcctaaa acaactcctc aattaatggg atggacatta 540
gtaccttgta ttatggtaaa tgattcagga atagataaaa acactcaaat taaaactact 600
ccatattata tttttaaaaa atataaatac tggaatctag caaaaggaag taatgtatct 660
ttacttccac atcaaaaaag atcatatgat tatgaatggg gtacagaaaa aaatcaaaaa 720
acatctatta ttaatacagt aggattgcaa attaatatag attcaggaat gaaatttgaa 780
gtaccagaag taggaggagg tacagaagac ataaaaacac aattaactga agaattaaaa 840
gttgaatata gcactgaaac caaaataatg acgaaatatc aagaacactc agagatagat 900
aatccaacta atcaaccaat gaattctata ggacttctta tttatacttc tttagaatta 960
tatcgatata acggtacaga aattaagata atggacatag aaacttcaga tcatgatact 1020
tacactctta cttcttatcc aaatcataaa gaagcattat tacttctcac aaaccattcg 1080
tatgaagaag tagaagaaat aacaaaaata cctaagcata cacttataaa attgaaaaaa 1140
cattatttta aaaaataa 1158

<210> SEQ ID NO 116
<211> LENGTH: 385
<212> TYPE: PRT
<213> ORGANISM: Bacillus thuringiensis

<400> SEQUENCE: 116

Met Leu Asp Thr Asn Lys Val Tyr Glu Ile Ser Asn Leu Ala Asn Gly
1 5 10 15

Leu Tyr Thr Ser Thr Tyr Leu Ser Leu Asp Asp Ser Gly Val Ser Leu
20 25 30

Met Ser Lys Lys Asp Glu Asp Ile Asp Asp Tyr Asn Leu Lys Trp Phe
35 40 45

Leu Phe Pro Ile Asp Asn Asn Gln Tyr Ile Ile Thr Ser Tyr Gly Ala
50 55 60

Asn Asn Cys Lys Val Trp Asn Val Lys Asn Asp Lys Ile Asn Val Ser
65 70 75 80

Thr Tyr Ser Ser Thr Asn Ser Val Gln Lys Trp Gln Ile Lys Ala Lys
85 90 95

Asp Ser Ser Tyr Ile Ile Gln Ser Asp Asn Gly Lys Val Leu Thr Ala
100 105 110

Gly Val Gly Glu Ser Leu Gly Ile Val Arg Leu Thr Asp Glu Phe Pro
115 120 125

Glu Asn Ser Asn Gln Gln Trp Asn Leu Thr Pro Val Gln Thr Ile Gln

-continued

```
    130                 135                 140

Leu Pro Gln Lys Pro Lys Ile Asp Glu Lys Leu Lys Asp His Pro Glu
145                 150                 155                 160

Tyr Ser Glu Thr Gly Asn Ile Asn Pro Lys Thr Thr Pro Gln Leu Met
                165                 170                 175

Gly Trp Thr Leu Val Pro Cys Ile Met Val Asn Asp Ser Gly Ile Asp
            180                 185                 190

Lys Asn Thr Gln Ile Lys Thr Thr Pro Tyr Tyr Ile Phe Lys Lys Tyr
        195                 200                 205

Lys Tyr Trp Asn Leu Ala Lys Gly Ser Asn Val Ser Leu Leu Pro His
    210                 215                 220

Gln Lys Arg Ser Tyr Asp Tyr Glu Trp Gly Thr Glu Lys Asn Gln Lys
225                 230                 235                 240

Thr Ser Ile Ile Asn Thr Val Gly Leu Gln Ile Asn Ile Asp Ser Gly
                245                 250                 255

Met Lys Phe Glu Val Pro Glu Val Gly Gly Gly Thr Glu Asp Ile Lys
            260                 265                 270

Thr Gln Leu Thr Glu Glu Leu Lys Val Glu Tyr Ser Thr Glu Thr Lys
        275                 280                 285

Ile Met Thr Lys Tyr Gln Glu His Ser Glu Ile Asp Asn Pro Thr Asn
    290                 295                 300

Gln Pro Met Asn Ser Ile Gly Leu Leu Ile Tyr Thr Ser Leu Glu Leu
305                 310                 315                 320

Tyr Arg Tyr Asn Gly Thr Glu Ile Lys Ile Met Asp Ile Glu Thr Ser
                325                 330                 335

Asp His Asp Thr Tyr Thr Leu Thr Ser Tyr Pro Asn His Lys Glu Ala
            340                 345                 350

Leu Leu Leu Leu Thr Asn His Ser Tyr Glu Glu Val Glu Glu Ile Thr
        355                 360                 365

Lys Ile Pro Lys His Thr Leu Ile Lys Leu Lys Lys His Tyr Phe Lys
    370                 375                 380

Lys
385


<210> SEQ ID NO 117
<211> LENGTH: 341
<212> TYPE: DNA
<213> ORGANISM: Bacillus thuringiensis

<400> SEQUENCE: 117

atgtcagcac gccaacttca tattgatgta aataataaga caggtcatac attacaatta     60

gaagataaaa caaaacttga tggtggtaga tggcgaacat cacctacaaa tgttgctaat    120

gatcaaatta aaacatttgt agcagaatca catggtttta tgacaggtac agaaggtact    180

atatattata gtataaatgg agaagcagaa attagtttat attttgacaa tccttattca    240

ggttctaata aatatgatgg gcattctaat aaaaatcaat atgaagttat tacccaagga    300

ggatcaggaa atcaatctca tgtgacttat acgattcaca c                        341


<210> SEQ ID NO 118
<211> LENGTH: 113
<212> TYPE: PRT
<213> ORGANISM: Bacillus thuringiensis

<400> SEQUENCE: 118

Met Ser Ala Arg Gln Leu His Ile Asp Val Asn Asn Lys Thr Gly His
```

-continued

```
  1               5                  10                  15

Thr Leu Gln Leu Glu Asp Lys Thr Lys Leu Asp Gly Gly Arg Trp Arg
            20                  25                  30

Thr Ser Pro Thr Asn Val Ala Asn Asp Gln Ile Lys Thr Phe Val Ala
        35                  40                  45

Glu Ser His Gly Phe Met Thr Gly Thr Glu Gly Thr Ile Tyr Tyr Ser
    50                  55                  60

Ile Asn Gly Glu Ala Glu Ile Ser Leu Tyr Phe Asp Asn Pro Tyr Ser
 65                  70                  75                  80

Gly Ser Asn Lys Tyr Asp Gly His Ser Asn Lys Asn Gln Tyr Glu Val
                 85                  90                  95

Ile Thr Gln Gly Gly Ser Gly Asn Gln Ser His Val Thr Tyr Thr Ile
            100                 105                 110

His


<210> SEQ ID NO 119
<211> LENGTH: 341
<212> TYPE: DNA
<213> ORGANISM: Bacillus thuringiensis

<400> SEQUENCE: 119

atgtcaggtc gtgaagttca tattgatgta aataataaga caggtcatac attacaatta      60

gaagataaaa caaaacttga tggtggtaga tggcgaacat cacctacaaa tgttgctaat     120

gatcaaatta aaacatttgt agcagaatca catggtttta tgacaggtac agaaggtact     180

atatattata gtataaatgg agaagcagaa attagtttat attttgataa tccttattca     240

ggttctaata aatatgatgg gcattccaat aaacctcaat atgaagttac tacccaagga     300

ggatcaggaa atcaatctca tgtaacgtat actattcaaa c                         341


<210> SEQ ID NO 120
<211> LENGTH: 113
<212> TYPE: PRT
<213> ORGANISM: Bacillus thuringiensis

<400> SEQUENCE: 120

Met Ser Gly Arg Glu Val His Ile Asp Val Asn Asn Lys Thr Gly His
  1               5                  10                  15

Thr Leu Gln Leu Glu Asp Lys Thr Lys Leu Asp Gly Gly Arg Trp Arg
            20                  25                  30

Thr Ser Pro Thr Asn Val Ala Asn Asp Gln Ile Lys Thr Phe Val Ala
        35                  40                  45

Glu Ser His Gly Phe Met Thr Gly Thr Glu Gly Thr Ile Tyr Tyr Ser
    50                  55                  60

Ile Asn Gly Glu Ala Glu Ile Ser Leu Tyr Phe Asp Asn Pro Tyr Ser
 65                  70                  75                  80

Gly Ser Asn Lys Tyr Asp Gly His Ser Asn Lys Pro Gln Tyr Glu Val
                 85                  90                  95

Thr Thr Gln Gly Gly Ser Gly Asn Gln Ser His Val Thr Tyr Thr Ile
            100                 105                 110

Gln


<210> SEQ ID NO 121
<211> LENGTH: 341
<212> TYPE: DNA
<213> ORGANISM: Bacillus thuringiensis
```

-continued

<400> SEQUENCE: 121

```
atgtcaggtc gcgaagttga cattgatgta aataataaga caggtcatac attacaatta     60

gaagataaaa caaaacttga tggtggtaga tggcgaacat cacctacaaa tgttgctaat    120

gatcaaatta aaacatttgt agcagaatca catggtttta tgacaggtac agaaggtact    180

atatattata gtataaatgg agaagcagaa attagtttat attttgataa tccttattca    240

ggttctaata aatatgatgg gcattccaat aaacctcaat atgaagttac tacccaagga    300

ggatcaggaa atcaatctca tgtcacatat acgattcaaa c                        341
```

<210> SEQ ID NO 122
<211> LENGTH: 113
<212> TYPE: PRT
<213> ORGANISM: Bacillus thuringiensis

<400> SEQUENCE: 122

```
Met Ser Gly Arg Glu Val Asp Ile Asp Val Asn Asn Lys Thr Gly His
  1               5                  10                  15

Thr Leu Gln Leu Glu Asp Lys Thr Lys Leu Asp Gly Gly Arg Trp Arg
             20                  25                  30

Thr Ser Pro Thr Asn Val Ala Asn Asp Gln Ile Lys Thr Phe Val Ala
         35                  40                  45

Glu Ser His Gly Phe Met Thr Gly Thr Glu Gly Thr Ile Tyr Tyr Ser
     50                  55                  60

Ile Asn Gly Glu Ala Glu Ile Ser Leu Tyr Phe Asp Asn Pro Tyr Ser
 65                  70                  75                  80

Gly Ser Asn Lys Tyr Asp Gly His Ser Asn Lys Pro Gln Tyr Glu Val
                 85                  90                  95

Thr Thr Gln Gly Gly Ser Gly Asn Gln Ser His Val Thr Tyr Thr Ile
            100                 105                 110

Gln
```

<210> SEQ ID NO 123
<211> LENGTH: 341
<212> TYPE: DNA
<213> ORGANISM: Bacillus thuringiensis

<400> SEQUENCE: 123

```
atgtcagcac gtgaagtaga tattgatgta aataataaga caggtcatac attacaatta     60

gaagataaaa caaaacttga tggtggtaga tggcgaacat cacctacaaa tgttgctaat    120

gatcaaatta aaacatttgt agcagaatca catggtttta tgacaggtac agaaggtact    180

atatattata gtataaatgg agaagcagaa attagtttat attttgataa tccttattca    240

ggttctaata aatatgatgg gcattccaat aaacctcaat atgaagttac tacccaagga    300

ggatcaggaa atcaatctca tgtaacgtat acgattcaaa c                        341
```

<210> SEQ ID NO 124
<211> LENGTH: 113
<212> TYPE: PRT
<213> ORGANISM: Bacillus thuringiensis

<400> SEQUENCE: 124

```
Met Ser Ala Arg Glu Val Asp Ile Asp Val Asn Asn Lys Thr Gly His
  1               5                  10                  15

Thr Leu Gln Leu Glu Asp Lys Thr Lys Leu Asp Gly Gly Arg Trp Arg
             20                  25                  30
```

-continued

```
Thr Ser Pro Thr Asn Val Ala Asn Asp Gln Ile Lys Thr Phe Val Ala
         35                  40                  45

Glu Ser His Gly Phe Met Thr Gly Thr Glu Gly Thr Ile Tyr Tyr Ser
     50                  55                  60

Ile Asn Gly Glu Ala Glu Ile Ser Leu Tyr Phe Asp Asn Pro Tyr Ser
 65                  70                  75                  80

Gly Ser Asn Lys Tyr Asp Gly His Ser Asn Lys Pro Gln Tyr Glu Val
                 85                  90                  95

Thr Thr Gln Gly Gly Ser Gly Asn Gln Ser His Val Thr Tyr Thr Ile
            100                 105                 110

Gln


<210> SEQ ID NO 125
<211> LENGTH: 1103
<212> TYPE: DNA
<213> ORGANISM: Bacillus thuringiensis

<400> SEQUENCE: 125

atgttagata ctaataaagt ttatgaaata agtaatcatg ctaatggact atatgcagca     60

acttatttaa gtttagatga ttcaggtgtt agtttaatga ataaaaatga tgatgatatt    120

gatgattata acttaaaatg gtttttattt cctattgatg atgatcaata tattattaca    180

agctatgcag caaataattg taaagtttgg aatgttaata atgataaaat aaatgtttcg    240

acttattctt caacaaattc aatacaaaaa tggcaaataa aagctaatgg ttcttcatat    300

gtaatacaaa gtgataatgg aaaagtctta acagcaggaa ccggtcaagc tcttggattg    360

atacgtttaa ctgatgaatc ctcaaataat cccaatcaac aatggaattt aacttctgta    420

caaacaattc aacttccaca aaaacctata atagatacaa aattaaaaga ttatcccaaa    480

tattcaccaa ctggaaatat agataatgga acatctcctc aattaatggg atggacatta    540

gtaccttgta ttatggtaaa tgatccaaat atagataaaa atactcaaat taaaactact    600

ccatattata ttttaaaaaa atatcaatat tggcaacgag cagtaggaag taatgtagct    660

ttacgtccac atgaagaaaa atcatatact tatgaatggg gaacagaaat agatcaaaaa    720

acaacaatca taaatacatt aggatttcaa atcaatatag attcaggaat gaaatttgat    780

ataccagaag taggtggagg tacagatgaa ataaaaacac aactaaatga agaattaaaa    840

atagaatata gtcgtgaaac taaaataatg gaaaaatatc aagaacaatc tgaaatagat    900

aatccaactg atcaaccaat gaattctata ggatttctta ctattacttc tttagaatta    960

tatagatata atggctcaga aattcgtata atgcaaattc aaacctcaga taatgatact   1020

tataatgtta cttcttatcc agatcatcaa caagctttat tacttcttac aaatcattca   1080

tatgaagaac ttgaagaaat tag                                            1103


<210> SEQ ID NO 126
<211> LENGTH: 367
<212> TYPE: PRT
<213> ORGANISM: Bacillus thuringiensis

<400> SEQUENCE: 126

Met Leu Asp Thr Asn Lys Val Tyr Glu Ile Ser Asn His Ala Asn Gly
  1               5                  10                  15

Leu Tyr Ala Ala Thr Tyr Leu Ser Leu Asp Asp Ser Gly Val Ser Leu
             20                  25                  30

Met Asn Lys Asn Asp Asp Asp Ile Asp Asp Tyr Asn Leu Lys Trp Phe
         35                  40                  45
```

-continued

```
Leu Phe Pro Ile Asp Asp Asp Gln Tyr Ile Ile Thr Ser Tyr Ala Ala
     50                  55                  60

Asn Asn Cys Lys Val Trp Asn Val Asn Asn Asp Lys Ile Asn Val Ser
 65                  70                  75                  80

Thr Tyr Ser Ser Thr Asn Ser Ile Gln Lys Trp Gln Ile Lys Ala Asn
                 85                  90                  95

Gly Ser Ser Tyr Val Ile Gln Ser Asp Asn Gly Lys Val Leu Thr Ala
            100                 105                 110

Gly Thr Gly Gln Ala Leu Gly Leu Ile Arg Leu Thr Asp Glu Ser Ser
        115                 120                 125

Asn Asn Pro Asn Gln Gln Trp Asn Leu Thr Ser Val Gln Thr Ile Gln
    130                 135                 140

Leu Pro Gln Lys Pro Ile Ile Asp Thr Lys Leu Lys Asp Tyr Pro Lys
145                 150                 155                 160

Tyr Ser Pro Thr Gly Asn Ile Asp Asn Gly Thr Ser Pro Gln Leu Met
                165                 170                 175

Gly Trp Thr Leu Val Pro Cys Ile Met Val Asn Asp Pro Asn Ile Asp
            180                 185                 190

Lys Asn Thr Gln Ile Lys Thr Thr Pro Tyr Tyr Ile Leu Lys Lys Tyr
        195                 200                 205

Gln Tyr Trp Gln Arg Ala Val Gly Ser Asn Val Ala Leu Arg Pro His
    210                 215                 220

Glu Glu Lys Ser Tyr Thr Tyr Glu Trp Gly Thr Glu Ile Asp Gln Lys
225                 230                 235                 240

Thr Thr Ile Ile Asn Thr Leu Gly Phe Gln Ile Asn Ile Asp Ser Gly
                245                 250                 255

Met Lys Phe Asp Ile Pro Glu Val Gly Gly Gly Thr Asp Glu Ile Lys
            260                 265                 270

Thr Gln Leu Asn Glu Glu Leu Lys Ile Glu Tyr Ser Arg Glu Thr Lys
        275                 280                 285

Ile Met Glu Lys Tyr Gln Glu Gln Ser Glu Ile Asp Asn Pro Thr Asp
    290                 295                 300

Gln Pro Met Asn Ser Ile Gly Phe Leu Thr Ile Thr Ser Leu Glu Leu
305                 310                 315                 320

Tyr Arg Tyr Asn Gly Ser Glu Ile Arg Ile Met Gln Ile Gln Thr Ser
                325                 330                 335

Asp Asn Asp Thr Tyr Asn Val Thr Ser Tyr Pro Asp His Gln Gln Ala
            340                 345                 350

Leu Leu Leu Leu Thr Asn His Ser Tyr Glu Glu Leu Glu Glu Ile
        355                 360                 365
```

<210> SEQ ID NO 127
<211> LENGTH: 369
<212> TYPE: DNA
<213> ORGANISM: Artificial Sequence
<220> FEATURE:
<223> OTHER INFORMATION: Description of Artificial Sequence: gene sequence optimized for expression in Zea mays

<400> SEQUENCE: 127

```
atgtccgccc gcgaggtgca catcgacgtg aacaacaaga ccggccacac cctccagctg     60

gaggacaaga ccaagctcga cggcggcagg tggcgcacct ccccgaccaa cgtggccaac    120

gaccagatca agaccttcgt ggccgaatcc aacggcttca tgaccggcac cgagggcacc    180

atctactact ccatcaacgg cgaggccgag atcagcctct acttcgacaa cccgttcgcc    240
```

-continued

```
ggctccaaca aatacgacgg ccactccaac aagtcccagt acgagatcat cacccagggc    300

ggctccggca accagtccca cgtgacctac accatccaga ccacctcctc ccgctacggc    360

cacaagtcc                                                            369
```

<210> SEQ ID NO 128
<211> LENGTH: 1149
<212> TYPE: DNA
<213> ORGANISM: Artificial Sequence
<220> FEATURE:
<223> OTHER INFORMATION: Description of Artificial Sequence: gene sequence optimized for expression in Zea mays

<400> SEQUENCE: 128

```
atgctcgaca ccaacaaggt gtacgagatc agcaaccacg ccaacggcct ctacgccgcc     60

acctacctct ccctcgacga ctccggcgtg tccctcatga acaagaacga cgacgacatc    120

gacgactaca acctcaagtg gttcctcttc ccgatcgacg acgaccagta catcatcacc    180

tcctacgccg ccaacaactg caaggtgtgg aacgtgaaca acgacaagat caacgtgtcc    240

acctactcct ccaccaactc catccagaag tggcagatca aggccaacgg ctcctcctac    300

gtgatccagt ccgacaacgg caaggtgctc accgccggca ccggccaggc cctcggcctc    360

atccgcctca ccgacgagtc ctccaacaac ccgaaccagc aatggaacct gacgtccgtg    420

cagaccatcc agctcccgca gaagccgatc atcgacacca agctcaagga ctacccgaag    480

tactccccga ccggcaacat cgacaacggc acctccccgc agctcatggg ctggaccctc    540

gtgccgtgca tcatggtgaa cgacccgaac atcgacaaga acacccagat caagaccacc    600

ccgtactaca tcctcaagaa gtaccagtac tggcagaggg ccgtgggctc caacgtcgcg    660

ctccgcccgc acgagaagaa gtcctacacc tacgagtggg gcaccgagat cgaccagaag    720

accaccatca tcaacaccct cggcttccag atcaacatcg acagcggcat gaagttcgac    780

atcccggagg tgggcggcgg taccgacgag atcaagaccc agctcaacga ggagctcaag    840

atcgagtact cccacgagac gaagatcatg gagaagtacc aggagcagtc cgagatcgac    900

aacccgaccg accagtccat gaactccatc ggcttcctca ccatcacctc cctggagctc    960

taccgctaca acggctccga gatccgcatc atgcagatcc agacctccga caacgacacc   1020

tacaacgtga cctcctaccc gaaccaccag caggccctgc tgctgctgac caaccactcc   1080

tacgaggagg tggaggagat caccaacatc ccgaagtcca ccctcaagaa gctcaagaag   1140

tactacttc                                                           1149
```

<210> SEQ ID NO 129
<211> LENGTH: 357
<212> TYPE: DNA
<213> ORGANISM: Artificial Sequence
<220> FEATURE:
<223> OTHER INFORMATION: Description of Artificial Sequence: maize-optimized gene sequence

<400> SEQUENCE: 129

```
atgtccgccc gcgaggtgca catcgagatc aacaacaaga cccgccacac cctccagctc     60

gaggacaaga ccaagctctc cggcggcagg tggcgcacct ccccgaccaa cgtggcccgc    120

gacaccatca agacgttcgt ggcggagtcc cacggcttca tgaccggcgt cgagggcatc    180

atctacttct ccgtgaacgg cgacgccgag atctccctcc acttcgacaa cccgtacatc    240

ggctccaaca agtccgacgg ctcctccgac aagcccgagt acgaggtgat cacccagtcc    300
```

-continued ggctccggcg acaagtccca cgtgacctac accatccaga ccgtgtccct ccgcctc 357

<210> SEQ ID NO 130
<211> LENGTH: 119
<212> TYPE: PRT
<213> ORGANISM: Artificial Sequence
<220> FEATURE:
<223> OTHER INFORMATION: Description of Artificial Sequence: protein encoded by maize-optimized gene

<400> SEQUENCE: 130

Met Ser Ala Arg Glu Val His Ile Glu Ile Asn Asn Lys Thr Arg His
1 5 10 15

Thr Leu Gln Leu Glu Asp Lys Thr Lys Leu Ser Gly Gly Arg Trp Arg
20 25 30

Thr Ser Pro Thr Asn Val Ala Arg Asp Thr Ile Lys Thr Phe Val Ala
35 40 45

Glu Ser His Gly Phe Met Thr Gly Val Glu Gly Ile Ile Tyr Phe Ser
50 55 60

Val Asn Gly Asp Ala Glu Ile Ser Leu His Phe Asp Asn Pro Tyr Ile
65 70 75 80

Gly Ser Asn Lys Ser Asp Gly Ser Ser Asp Lys Pro Glu Tyr Glu Val
85 90 95

Ile Thr Gln Ser Gly Ser Gly Asp Lys Ser His Val Thr Tyr Thr Ile
100 105 110

Gln Thr Val Ser Leu Arg Leu
115

<210> SEQ ID NO 131
<211> LENGTH: 21
<212> TYPE: DNA
<213> ORGANISM: Artificial Sequence
<220> FEATURE:
<223> OTHER INFORMATION: Description of Artificial Sequence: oligonucleotide primer

<400> SEQUENCE: 131
atgtcagctc gcgaagtaca c 21

<210> SEQ ID NO 132
<211> LENGTH: 22
<212> TYPE: DNA
<213> ORGANISM: Artificial Sequence
<220> FEATURE:
<223> OTHER INFORMATION: Description of Artificial Sequence: oligonucleotide primer

<400> SEQUENCE: 132
gtccatccca ttaattgagg ag 22

<210> SEQ ID NO 133
<211> LENGTH: 399
<212> TYPE: DNA
<213> ORGANISM: Bacillus thuringiensis

<400> SEQUENCE: 133
atgtcagcac gtgaagtaca cattgaaata ataaatcata caggtcatac cttacaaatg 60
gataaaagaa ctagacttgc acatggtgaa tggattatta cacccgtgaa tgttccaaat 120
aattcttctg atttatttca agcaggttct gatggagttt tgacaggagt agaaggaata 180
ataatttata ctataaatgg agaaatagaa attcccttac attttgacaa tccttatgca 240

-continued

```
ggttctaata aatattctgg acgttctagt gatgatgatt ataaagttat aactgaagca    300

agagcagaac atagagctaa taatcatgat catgtaacat atacagttca aagaaacata    360

tcacgatata ccaataaatt atgttctaat aactcctaa                           399


<210> SEQ ID NO 134
<211> LENGTH: 132
<212> TYPE: PRT
<213> ORGANISM: Bacillus thuringiensis

<400> SEQUENCE: 134

Met Ser Ala Arg Glu Val His Ile Glu Ile Ile Asn His Thr Gly His
  1               5                  10                  15

Thr Leu Gln Met Asp Lys Arg Thr Arg Leu Ala His Gly Glu Trp Ile
             20                  25                  30

Ile Thr Pro Val Asn Val Pro Asn Asn Ser Ser Asp Leu Phe Gln Ala
         35                  40                  45

Gly Ser Asp Gly Val Leu Thr Gly Val Glu Gly Ile Ile Ile Tyr Thr
     50                  55                  60

Ile Asn Gly Glu Ile Glu Ile Pro Leu His Phe Asp Asn Pro Tyr Ala
 65                  70                  75                  80

Gly Ser Asn Lys Tyr Ser Gly Arg Ser Ser Asp Asp Asp Tyr Lys Val
                 85                  90                  95

Ile Thr Glu Ala Arg Ala Glu His Arg Ala Asn Asn His Asp His Val
            100                 105                 110

Thr Tyr Thr Val Gln Arg Asn Ile Ser Arg Tyr Thr Asn Lys Leu Cys
        115                 120                 125

Ser Asn Asn Ser
    130


<210> SEQ ID NO 135
<211> LENGTH: 1164
<212> TYPE: DNA
<213> ORGANISM: Bacillus thuringiensis

<400> SEQUENCE: 135

atgatagaaa ctaataagat atatgaaata agcaataaag ctaatggatt atatgcaact     60

acttatttaa gttttgataa ttcaggtgtt agtttattaa ataaaaatga atctgatatt    120

aatgattata atttgaaatg gtttttattt cctattgata ataatcagta tattattaca    180

agttatggag taaataaaaa taaggtttgg actgctaatg gtaataaaat aaatgttaca    240

acatattccg cagaaaattc agcacaacaa tggcaaataa gaaacagttc ttctggatat    300

ataatagaaa ataataatgg gaaaatttta acggcaggaa caggccaatc attaggttta    360

ttatatttaa ctgatgaaat acctgaagat tctaatcaac aatggaattt aacttcaata    420

caaacaattt cacttccttc acaaccaata attgatacaa cattagtaga ttaccctaaa    480

tattcaacga ccggtagtat aaattataat ggtacagcac ttcaattaat gggatggaca    540

ctcataccat gtattatggt atacgataaa acgatagctt ctacacacac tcaaattaca    600

acaacccctt attatatttt gaaaaaatat caacgttggg tacttgcaac aggaagtggt    660

ctatctgtac ctgcacatgt caaatcaact ttcgaatacg aatggggaac agacacagat    720

caaaaaacca gtgtaataaa tacattaggt tttcaaatta atacagatac aaaattaaaa    780

gctactgtac cagaagtagg tggaggtaca acagatataa gaacacaaat cactgaagaa    840

cttaaagtag aatatagtag tgaaaataaa gaaatgcgaa aatataaaca aagctttgac    900
```

-continued

```
gtagacaact taaattatga tgaagcacta aatgctgtag gatttattgt tgaaacttca    960

ttcgaattat atcgaatgaa tggaaatgtc cttataacaa gtataaaaac tacaaataaa   1020

gacacctata atacagttac ttatccaaat cataaagaag ttttattact tcttacaaat   1080

cattcttatg aagaagtaac agcactaact ggcatttcca aagaaagact tcaaaatctt   1140

aaaaacaatt ggaaaaaaag ataa                                          1164


<210> SEQ ID NO 136
<211> LENGTH: 387
<212> TYPE: PRT
<213> ORGANISM: Bacillus thuringiensis

<400> SEQUENCE: 136

Met Ile Glu Thr Asn Lys Ile Tyr Glu Ile Ser Asn Lys Ala Asn Gly
  1               5                  10                  15

Leu Tyr Ala Thr Thr Tyr Leu Ser Phe Asp Asn Ser Gly Val Ser Leu
             20                  25                  30

Leu Asn Lys Asn Glu Ser Asp Ile Asn Asp Tyr Asn Leu Lys Trp Phe
         35                  40                  45

Leu Phe Pro Ile Asp Asn Asn Gln Tyr Ile Ile Thr Ser Tyr Gly Val
     50                  55                  60

Asn Lys Asn Lys Val Trp Thr Ala Asn Gly Asn Lys Ile Asn Val Thr
 65                  70                  75                  80

Thr Tyr Ser Ala Glu Asn Ser Ala Gln Gln Trp Gln Ile Arg Asn Ser
                 85                  90                  95

Ser Ser Gly Tyr Ile Ile Glu Asn Asn Asn Gly Lys Ile Leu Thr Ala
            100                 105                 110

Gly Thr Gly Gln Ser Leu Gly Leu Leu Tyr Leu Thr Asp Glu Ile Pro
        115                 120                 125

Glu Asp Ser Asn Gln Gln Trp Asn Leu Thr Ser Ile Gln Thr Ile Ser
    130                 135                 140

Leu Pro Ser Gln Pro Ile Ile Asp Thr Thr Leu Val Asp Tyr Pro Lys
145                 150                 155                 160

Tyr Ser Thr Thr Gly Ser Ile Asn Tyr Asn Gly Thr Ala Leu Gln Leu
                165                 170                 175

Met Gly Trp Thr Leu Ile Pro Cys Ile Met Val Tyr Asp Lys Thr Ile
            180                 185                 190

Ala Ser Thr His Thr Gln Ile Thr Thr Thr Pro Tyr Tyr Ile Leu Lys
        195                 200                 205

Lys Tyr Gln Arg Trp Val Leu Ala Thr Gly Ser Gly Leu Ser Val Pro
    210                 215                 220

Ala His Val Lys Ser Thr Phe Glu Tyr Glu Trp Gly Thr Asp Thr Asp
225                 230                 235                 240

Gln Lys Thr Ser Val Ile Asn Thr Leu Gly Phe Gln Ile Asn Thr Asp
                245                 250                 255

Thr Lys Leu Lys Ala Thr Val Pro Glu Val Gly Gly Gly Thr Thr Asp
            260                 265                 270

Ile Arg Thr Gln Ile Thr Glu Glu Leu Lys Val Glu Tyr Ser Ser Glu
        275                 280                 285

Asn Lys Glu Met Arg Lys Tyr Lys Gln Ser Phe Asp Val Asp Asn Leu
    290                 295                 300

Asn Tyr Asp Glu Ala Leu Asn Ala Val Gly Phe Ile Val Glu Thr Ser
305                 310                 315                 320

Phe Glu Leu Tyr Arg Met Asn Gly Asn Val Leu Ile Thr Ser Ile Lys
```

-continued

```
            325                 330                 335

Thr Thr Asn Lys Asp Thr Tyr Asn Thr Val Thr Tyr Pro Asn His Lys
            340                 345                 350

Glu Val Leu Leu Leu Leu Thr Asn His Ser Tyr Glu Glu Val Thr Ala
        355                 360                 365

Leu Thr Gly Ile Ser Lys Glu Arg Leu Gln Asn Leu Lys Asn Asn Trp
    370                 375                 380

Lys Lys Arg
385


<210> SEQ ID NO 137
<211> LENGTH: 341
<212> TYPE: DNA
<213> ORGANISM: Bacillus thuringiensis

<400> SEQUENCE: 137

atgtcagcag gtgaagttca tattgaaata aataataaaa cacgtcatac attacaatta      60

gaggataaaa ctaaacttac cagtggtaga tggcgaacat cacctacaaa tgttgctcgt     120

gatacaatta aaacatttgt agcagaatca catggtttta tgacaggaat agaaggtatt     180

atatatttta gcgtaaacgg agaagcagaa attagtttac attttgacaa tccttatgta     240

ggttctaata aatatgatgg ttcttctgat aaagctgcat acgaagttat tgctcaaggt     300

ggatcagggg atatatctca tctaacatat acaattcaaa c                         341


<210> SEQ ID NO 138
<211> LENGTH: 113
<212> TYPE: PRT
<213> ORGANISM: Bacillus thuringiensis

<400> SEQUENCE: 138

Met Ser Ala Gly Glu Val His Ile Glu Ile Asn Asn Lys Thr Arg His
  1               5                  10                  15

Thr Leu Gln Leu Glu Asp Lys Thr Lys Leu Thr Ser Gly Arg Trp Arg
             20                  25                  30

Thr Ser Pro Thr Asn Val Ala Arg Asp Thr Ile Lys Thr Phe Val Ala
         35                  40                  45

Glu Ser His Gly Phe Met Thr Gly Ile Glu Gly Ile Ile Tyr Phe Ser
     50                  55                  60

Val Asn Gly Glu Ala Glu Ile Ser Leu His Phe Asp Asn Pro Tyr Val
 65                  70                  75                  80

Gly Ser Asn Lys Tyr Asp Gly Ser Ser Asp Lys Ala Ala Tyr Glu Val
                 85                  90                  95

Ile Ala Gln Gly Gly Ser Gly Asp Ile Ser His Leu Thr Tyr Thr Ile
            100                 105                 110

Gln


<210> SEQ ID NO 139
<211> LENGTH: 1158
<212> TYPE: DNA
<213> ORGANISM: Bacillus thuringiensis

<400> SEQUENCE: 139

atgttagata ctaataaaat ttatgaaata agcaatcatg ctaatggatt atatacatca      60

acttatttaa gtctggatga ttcaggtgtt agtttaatgg gtcaaaatga tgaggatata     120

gatgaataca atttaaagtg gttcttattt ccaatagata ataatcaata tattattaca     180
```

-continued

```
agctatggag cgaataattg taaagtttgg aatgttaaaa atgataaagt aaatgtttca    240

acgtattctc caacaaactc agtacaaaaa tggcaaataa aagctaaaaa ttcttcatat    300

ataatacaaa gtgagaatgg aaaagtctta acagcaggaa taggtcaatc tcttggaata    360

gtacgcttaa ccgatgaatc atcagagagt tctaaccaac aatggaattt aatccctgta    420

caaacaattt cactcccaca aaaacctaaa atagataaaa aattaaaaga tcatcctgaa    480

tattcagaaa ccggaaatat agctactgga acaattcctc aattaatggg atggacatta    540

gtaccttgta ttatggtaaa tgatccaaaa ataggtaaaa acactcaaat taaaactact    600

ccatattata tttttaaaaa atatcaatac tggaaacgag caataggaag taatgtatct    660

ttacttccac atcaaaaaaa atcatatgat tatgagtggg gtacagaaga aaatcaaaaa    720

acaactatta ttaatacagt aggatttcaa attaatgtag attcaggaat gaagtttgag    780

gtaccagaag taggaggagg tacagaagaa ataaaaacac aattaaatga agaattaaaa    840

gttgaatata gcactgacac caaaataatg aaaaaatatc aagaacactc agagatagat    900

aatccaacta atcaaacaac gaattctata ggatttctta cttttacttc tttagaatta    960

tatcgatata acggttcgga aattcgtata atgagaatgg aaacttcaga taatgatact   1020

tatactctga cctcttatcc aaatcataga gaagcattat tacttctcac aaatcattct   1080

tatcaagaag taagccgaat tccagcacac tggcggccgt tactagtgga tccgagctcg   1140

gtaccaagct tggcgtaa                                                 1158
```

<210> SEQ ID NO 140
<211> LENGTH: 385
<212> TYPE: PRT
<213> ORGANISM: Bacillus thuringiensis

<400> SEQUENCE: 140

```
Met Leu Asp Thr Asn Lys Ile Tyr Glu Ile Ser Asn His Ala Asn Gly
  1               5                  10                  15

Leu Tyr Thr Ser Thr Tyr Leu Ser Leu Asp Asp Ser Gly Val Ser Leu
             20                  25                  30

Met Gly Gln Asn Asp Glu Asp Ile Asp Glu Tyr Asn Leu Lys Trp Phe
         35                  40                  45

Leu Phe Pro Ile Asp Asn Asn Gln Tyr Ile Ile Thr Ser Tyr Gly Ala
     50                  55                  60

Asn Asn Cys Lys Val Trp Asn Val Lys Asn Asp Lys Val Asn Val Ser
 65                  70                  75                  80

Thr Tyr Ser Pro Thr Asn Ser Val Gln Lys Trp Gln Ile Lys Ala Lys
                 85                  90                  95

Asn Ser Ser Tyr Ile Ile Gln Ser Glu Asn Gly Lys Val Leu Thr Ala
            100                 105                 110

Gly Ile Gly Gln Ser Leu Gly Ile Val Arg Leu Thr Asp Glu Ser Ser
        115                 120                 125

Glu Ser Ser Asn Gln Gln Trp Asn Leu Ile Pro Val Gln Thr Ile Ser
    130                 135                 140

Leu Pro Gln Lys Pro Lys Ile Asp Lys Lys Leu Lys Asp His Pro Glu
145                 150                 155                 160

Tyr Ser Glu Thr Gly Asn Ile Ala Thr Gly Thr Ile Pro Gln Leu Met
                165                 170                 175

Gly Trp Thr Leu Val Pro Cys Ile Met Val Asn Asp Pro Lys Ile Gly
            180                 185                 190

Lys Asn Thr Gln Ile Lys Thr Thr Pro Tyr Tyr Ile Phe Lys Lys Tyr
```

-continued 195 200 205

Gln Tyr Trp Lys Arg Ala Ile Gly Ser Asn Val Ser Leu Leu Pro His
210 215 220

Gln Lys Lys Ser Tyr Asp Tyr Glu Trp Gly Thr Glu Glu Asn Gln Lys
225 230 235 240

Thr Thr Ile Ile Asn Thr Val Gly Phe Gln Ile Asn Val Asp Ser Gly
245 250 255

Met Lys Phe Glu Val Pro Glu Val Gly Gly Gly Thr Glu Glu Ile Lys
260 265 270

Thr Gln Leu Asn Glu Glu Leu Lys Val Glu Tyr Ser Thr Asp Thr Lys
275 280 285

Ile Met Lys Lys Tyr Gln Glu His Ser Glu Ile Asp Asn Pro Thr Asn
290 295 300

Gln Thr Thr Asn Ser Ile Gly Phe Leu Thr Phe Thr Ser Leu Glu Leu
305 310 315 320

Tyr Arg Tyr Asn Gly Ser Glu Ile Arg Ile Met Arg Met Glu Thr Ser
325 330 335

Asp Asn Asp Thr Tyr Thr Leu Thr Ser Tyr Pro Asn His Arg Glu Ala
340 345 350

Leu Leu Leu Leu Thr Asn His Ser Tyr Gln Glu Val Ser Arg Ile Pro
355 360 365

Ala His Trp Arg Pro Leu Leu Val Asp Pro Ser Ser Val Pro Ser Leu
370 375 380

Ala
385

<210> SEQ ID NO 141
<211> LENGTH: 399
<212> TYPE: DNA
<213> ORGANISM: Bacillus thuringiensis

<400> SEQUENCE: 141
atgtcagatc gcgaagtaca tattgaaata ataaatcata caggtcatac cttacaaatg 60
gataaaagaa ctagacttgc acatggtgaa tggattatta cacccgtgaa tgttccaaat 120
aattcttctg atttatttca agcaggttct gatggagttt tgacaggagt agaaggaata 180
ataatttata ctataaatgg agaaatagaa attaccttac attttgacaa tccttatgca 240
ggttctaata aatattctgg acgttctagt gatgatgatt ataaagttat aactgaagca 300
agagcagaac atagagctaa taatcatgat catgtaacat atacagttca aagaaacata 360
tcacgatata ccaataaatt atgttctaat aactcctaa 399

<210> SEQ ID NO 142
<211> LENGTH: 132
<212> TYPE: PRT
<213> ORGANISM: Bacillus thuringiensis

<400> SEQUENCE: 142

Met Ser Asp Arg Glu Val His Ile Glu Ile Ile Asn His Thr Gly His
1 5 10 15

Thr Leu Gln Met Asp Lys Arg Thr Arg Leu Ala His Gly Glu Trp Ile
20 25 30

Ile Thr Pro Val Asn Val Pro Asn Asn Ser Ser Asp Leu Phe Gln Ala
35 40 45

Gly Ser Asp Gly Val Leu Thr Gly Val Glu Gly Ile Ile Ile Tyr Thr
50 55 60

-continued

```
Ile Asn Gly Glu Ile Glu Ile Thr Leu His Phe Asp Asn Pro Tyr Ala
 65                  70                  75                  80

Gly Ser Asn Lys Tyr Ser Gly Arg Ser Ser Asp Asp Asp Tyr Lys Val
                 85                  90                  95

Ile Thr Glu Ala Arg Ala Glu His Arg Ala Asn Asn His Asp His Val
            100                 105                 110

Thr Tyr Thr Val Gln Arg Asn Ile Ser Arg Tyr Thr Asn Lys Leu Cys
        115                 120                 125

Ser Asn Asn Ser
    130


<210> SEQ ID NO 143
<211> LENGTH: 871
<212> TYPE: DNA
<213> ORGANISM: Bacillus thuringiensis

<400> SEQUENCE: 143

atgatagaaa ctaataagat atatgaaata agcaataaag ctaatggatt atatgcaact     60

acttatttaa gttttgataa ttcaggtgtt agtttattaa ataaaaatga atctgatatt    120

aatgattata atttgaaatg gtttttattt cctattgata ataatcagta tattattaca    180

agttatggag taaataaaaa taaggtttgg actgctaatg gtaataaaat aaatgttaca    240

acatattccg cagaaaattc agcacaacaa tggcaaataa gaaacagttc ttctggatat    300

ataatagaaa ataataatgg gaaaatttta acggcaggaa caggccaatc attaggttta    360

ttatatttaa ctgatgaaat acctgaagat tctaatcaac aatggaattt aacttcaata    420

caaacaattt cacttccttc acaaccaata attgatacaa cattagtaga ttaccctaaa    480

tattcaacga ccggtagtat aaattataat ggtacagcac ttcaattaat gggatggaca    540

ctcataccat gtattatggt atacgataaa acgatagctt ctacacacac tcaaattaca    600

acaacccctt attatatttt gaaaaaatat caacgttggg tacttgcaac aggaagtggt    660

ctatctgtac ctgcacatgt caaatcaact ttcgaatacg aatggggaac agacacagat    720

caaaaaacca gtgtaataaa tacattaggt tttcaaatta atacagatac aaaattaaaa    780

gctactgtac cagaagtagg tggaggtaca acagatataa gaacacaaat cactgaagaa    840

cttaaagtag aatatagtag tgaaaataaa g                                   871


<210> SEQ ID NO 144
<211> LENGTH: 290
<212> TYPE: PRT
<213> ORGANISM: Bacillus thuringiensis

<400> SEQUENCE: 144

Met Ile Glu Thr Asn Lys Ile Tyr Glu Ile Ser Asn Lys Ala Asn Gly
  1               5                  10                  15

Leu Tyr Ala Thr Thr Tyr Leu Ser Phe Asp Asn Ser Gly Val Ser Leu
             20                  25                  30

Leu Asn Lys Asn Glu Ser Asp Ile Asn Asp Tyr Asn Leu Lys Trp Phe
         35                  40                  45

Leu Phe Pro Ile Asp Asn Asn Gln Tyr Ile Ile Thr Ser Tyr Gly Val
     50                  55                  60

Asn Lys Asn Lys Val Trp Thr Ala Asn Gly Asn Lys Ile Asn Val Thr
 65                  70                  75                  80

Thr Tyr Ser Ala Glu Asn Ser Ala Gln Gln Trp Gln Ile Arg Asn Ser
                 85                  90                  95
```

-continued

```
Ser Ser Gly Tyr Ile Ile Glu Asn Asn Asn Gly Lys Ile Leu Thr Ala
            100                 105                 110

Gly Thr Gly Gln Ser Leu Gly Leu Leu Tyr Leu Thr Asp Glu Ile Pro
        115                 120                 125

Glu Asp Ser Asn Gln Gln Trp Asn Leu Thr Ser Ile Gln Thr Ile Ser
    130                 135                 140

Leu Pro Ser Gln Pro Ile Ile Asp Thr Thr Leu Val Asp Tyr Pro Lys
145                 150                 155                 160

Tyr Ser Thr Thr Gly Ser Ile Asn Tyr Asn Gly Thr Ala Leu Gln Leu
                165                 170                 175

Met Gly Trp Thr Leu Ile Pro Cys Ile Met Val Tyr Asp Lys Thr Ile
            180                 185                 190

Ala Ser Thr His Thr Gln Ile Thr Thr Thr Pro Tyr Tyr Ile Leu Lys
        195                 200                 205

Lys Tyr Gln Arg Trp Val Leu Ala Thr Gly Ser Gly Leu Ser Val Pro
    210                 215                 220

Ala His Val Lys Ser Thr Phe Glu Tyr Glu Trp Gly Thr Asp Thr Asp
225                 230                 235                 240

Gln Lys Thr Ser Val Ile Asn Thr Leu Gly Phe Gln Ile Asn Thr Asp
                245                 250                 255

Thr Lys Leu Lys Ala Thr Val Pro Glu Val Gly Gly Gly Thr Thr Asp
            260                 265                 270

Ile Arg Thr Gln Ile Thr Glu Glu Leu Lys Val Glu Tyr Ser Ser Glu
        275                 280                 285

Asn Lys
    290


<210> SEQ ID NO 145
<211> LENGTH: 372
<212> TYPE: DNA
<213> ORGANISM: Bacillus thuringiensis

<400> SEQUENCE: 145

atgtcagcac gtgaagtaca cattgatgta aataataaga caggtcatac attacaatta      60

gaagataaaa caaaacttga tggtggtaga tggcgaacat cacctacaaa tgttgctaat     120

gatcaaatta aaacatttgt agcagaatca catggtttta tgacaggtac agaaggtact     180

atatattata gtataaatgg agaagcagaa attagtttat attttgataa tccttattca     240

ggttctaata aatatgatgg gcattccaat aaacctcaat atgaagttac tacccaagga     300

ggatcaggaa atcaatctca tgttacgtat actattcaaa ctgcatcttc acgatatggg     360

aataactcat aa                                                         372


<210> SEQ ID NO 146
<211> LENGTH: 123
<212> TYPE: PRT
<213> ORGANISM: Bacillus thuringiensis

<400> SEQUENCE: 146

Met Ser Ala Arg Glu Val His Ile Asp Val Asn Asn Lys Thr Gly His
  1               5                  10                  15

Thr Leu Gln Leu Glu Asp Lys Thr Lys Leu Asp Gly Gly Arg Trp Arg
            20                  25                  30

Thr Ser Pro Thr Asn Val Ala Asn Asp Gln Ile Lys Thr Phe Val Ala
         35                  40                  45
```

-continued

Glu Ser His Gly Phe Met Thr Gly Thr Glu Gly Thr Ile Tyr Tyr Ser
50 55 60

Ile Asn Gly Glu Ala Glu Ile Ser Leu Tyr Phe Asp Asn Pro Tyr Ser
65 70 75 80

Gly Ser Asn Lys Tyr Asp Gly His Ser Asn Lys Pro Gln Tyr Glu Val
85 90 95

Thr Thr Gln Gly Gly Ser Gly Asn Gln Ser His Val Thr Tyr Thr Ile
100 105 110

Gln Thr Ala Ser Ser Arg Tyr Gly Asn Asn Ser
115 120

<210> SEQ ID NO 147
<211> LENGTH: 1152
<212> TYPE: DNA
<213> ORGANISM: Bacillus thuringiensis

<400> SEQUENCE: 147
atgttagata ctaataaagt ttatgaaata agtaatcatg ctaatggact atatgcagca 60
acttatttaa gtttagatga ttcaggtgtt agtttaatga ataaaaatga tgatgatatt 120
gatgattata acttaaaatg gtttttattt cctattgatg atgatcaata tattattaca 180
agctatgcag caaataattg taaagtttgg aatgttaata atgataaaat aaatgtttcg 240
acttattctt caacaaattc aatacaaaaa tggcaaataa aagctaatgg ttcttcatat 300
gtaatacaaa gtgataatgg aaaagtctta acagcaggaa ccggtcaagc tcttggattg 360
atacgtttaa ctgatgaatc ctcaaataat cccaatcaac aatggaattt aacttctgta 420
caaacaattc aacttccaca aaaacctata atagatacaa aattaaaaga ttatcccaaa 480
tattcaccaa ctggaaatat agataatgga acatctcctc aattaatggg atggacatta 540
gtaccttgta ttatggtaaa tgatccaaat atagataaaa atactcaaat taaaactact 600
ccatattata ttttaaaaaa atatcaatat tggcaacgag cagtaggaag taatgtagct 660
ttacgtccac atgaaaaaaa atcatatact tatgaatggg gaacagaaat agatcaaaaa 720
acaacaatca taaatacatt aggatttcaa atcaatatag attcaggaat gaaatttgat 780
ataccagaag taggtggagg tacagatgaa ataaaaacac aactaaatga agaattaaaa 840
atagaatata gtcgtgaaac taaaataatg gaaaaatatc aagaacaatc tgaaatagat 900
aatccaactg atcaaccaat gaattctata ggatttctta ctattacttc tttagaatta 960
tatagatata atggctcaga aattcgtata atgcaaattc aaacctcaga taatgatact 1020
tataatgtta cttcttatcc agatcatcaa caagctttat tacttcttac aaatcattca 1080
tatgaagaag tagaagaaat aacaaatatt cctaaaagta cactaaaaaa attaaaaaaa 1140
tattattttt aa 1152

<210> SEQ ID NO 148
<211> LENGTH: 383
<212> TYPE: PRT
<213> ORGANISM: Bacillus thuringiensis

<400> SEQUENCE: 148

Met Leu Asp Thr Asn Lys Val Tyr Glu Ile Ser Asn His Ala Asn Gly
1 5 10 15

Leu Tyr Ala Ala Thr Tyr Leu Ser Leu Asp Asp Ser Gly Val Ser Leu
20 25 30

Met Asn Lys Asn Asp Asp Asp Ile Asp Asp Tyr Asn Leu Lys Trp Phe
35 40 45

-continued

```
Leu Phe Pro Ile Asp Asp Asp Gln Tyr Ile Ile Thr Ser Tyr Ala Ala
     50                  55                  60

Asn Asn Cys Lys Val Trp Asn Val Asn Asn Asp Lys Ile Asn Val Ser
 65                  70                  75                  80

Thr Tyr Ser Ser Thr Asn Ser Ile Gln Lys Trp Gln Ile Lys Ala Asn
                 85                  90                  95

Gly Ser Ser Tyr Val Ile Gln Ser Asp Asn Gly Lys Val Leu Thr Ala
            100                 105                 110

Gly Thr Gly Gln Ala Leu Gly Leu Ile Arg Leu Thr Asp Glu Ser Ser
        115                 120                 125

Asn Asn Pro Asn Gln Gln Trp Asn Leu Thr Ser Val Gln Thr Ile Gln
    130                 135                 140

Leu Pro Gln Lys Pro Ile Ile Asp Thr Lys Leu Lys Asp Tyr Pro Lys
145                 150                 155                 160

Tyr Ser Pro Thr Gly Asn Ile Asp Asn Gly Thr Ser Pro Gln Leu Met
                165                 170                 175

Gly Trp Thr Leu Val Pro Cys Ile Met Val Asn Asp Pro Asn Ile Asp
            180                 185                 190

Lys Asn Thr Gln Ile Lys Thr Thr Pro Tyr Tyr Ile Leu Lys Lys Tyr
        195                 200                 205

Gln Tyr Trp Gln Arg Ala Val Gly Ser Asn Val Ala Leu Arg Pro His
    210                 215                 220

Glu Lys Lys Ser Tyr Thr Tyr Glu Trp Gly Thr Glu Ile Asp Gln Lys
225                 230                 235                 240

Thr Thr Ile Ile Asn Thr Leu Gly Phe Gln Ile Asn Ile Asp Ser Gly
                245                 250                 255

Met Lys Phe Asp Ile Pro Glu Val Gly Gly Gly Thr Asp Glu Ile Lys
            260                 265                 270

Thr Gln Leu Asn Glu Glu Leu Lys Ile Glu Tyr Ser Arg Glu Thr Lys
        275                 280                 285

Ile Met Glu Lys Tyr Gln Glu Gln Ser Glu Ile Asp Asn Pro Thr Asp
    290                 295                 300

Gln Pro Met Asn Ser Ile Gly Phe Leu Thr Ile Thr Ser Leu Glu Leu
305                 310                 315                 320

Tyr Arg Tyr Asn Gly Ser Glu Ile Arg Ile Met Gln Ile Gln Thr Ser
                325                 330                 335

Asp Asn Asp Thr Tyr Asn Val Thr Ser Tyr Pro Asp His Gln Gln Ala
            340                 345                 350

Leu Leu Leu Leu Thr Asn His Ser Tyr Glu Glu Val Glu Glu Ile Thr
        355                 360                 365

Asn Ile Pro Lys Ser Thr Leu Lys Lys Leu Lys Lys Tyr Tyr Phe
    370                 375                 380


<210> SEQ ID NO 149
<211> LENGTH: 354
<212> TYPE: DNA
<213> ORGANISM: Bacillus thuringiensis

<400> SEQUENCE: 149

atgtcagctc gcgaagttca tattgaaata ataaatcata caggtcatac cttacaaatg     60

gataaaagaa ctagacttgc acatggtgaa tggattatta cacccgtgaa tgttccaaat    120

aattcttctg atttatttca agcaggttct gatggagttt tgacaggagt agaaggaata    180

ataatttata ctataaatgg agaaatagaa attaccttac attttgacaa tccttatgca    240
```

-continued

```
ggttctaata aatattctgg acgttctagt gatgatgatt ataaagttat aactgaagca    300

agagcagaac atagagctaa taatcatgat catgtgacat atacaattca aaca          354


<210> SEQ ID NO 150
<211> LENGTH: 113
<212> TYPE: PRT
<213> ORGANISM: Bacillus thuringiensis

<400> SEQUENCE: 150

Met Ser Ala Arg Glu Val His Ile Glu Ile Ile Asn His Thr Gly His
  1               5                  10                  15

Thr Leu Gln Met Asp Lys Arg Thr Arg Leu Ala His Gly Glu Trp Ile
             20                  25                  30

Ile Thr Pro Val Asn Val Pro Asn Asn Ser Ser Asp Leu Phe Gln Ala
         35                  40                  45

Gly Ser Asp Gly Val Leu Thr Gly Val Glu Gly Ile Ile Ile Tyr Thr
     50                  55                  60

Ile Asn Gly Glu Ile Glu Ile Thr Leu His Phe Asp Asn Pro Tyr Ala
 65                  70                  75                  80

Gly Ser Asn Lys Tyr Ser Gly Arg Ser Ser Asp Asp Asp Tyr Lys Val
                 85                  90                  95

Ile Thr Glu Ala Arg Ala Glu His Arg Ala Asn Asn His Asp His Val
            100                 105                 110

Thr


<210> SEQ ID NO 151
<211> LENGTH: 353
<212> TYPE: DNA
<213> ORGANISM: Bacillus thuringiensis

<400> SEQUENCE: 151


atgtcagctc gtgaagttca tattgaaata ataaatcata caggtcatac cttacaaatg     60

gataaaagaa ctagacttgc acatggtgaa tggattatta cacccgtgaa tgttccaaat    120

aattcttctg atttatttca agcaggttct gatggagttt tgacaggagt agaaggaata    180

ataatttata ctataaatgg agaaatagaa attaccttac attttgacaa tccttatgca    240

ggttctaata aatattctgg acgttctagt gatgatgatt ataaagttat aactgaagca    300

agagcagaac atagagctaa taatcatgat catgtaacat atacaattca aac           353


<210> SEQ ID NO 152
<211> LENGTH: 113
<212> TYPE: PRT
<213> ORGANISM: Bacillus thuringiensis

<400> SEQUENCE: 152

Met Ser Ala Arg Glu Val His Ile Glu Ile Ile Asn His Thr Gly His
  1               5                  10                  15

Thr Leu Gln Met Asp Lys Arg Thr Arg Leu Ala His Gly Glu Trp Ile
             20                  25                  30

Ile Thr Pro Val Asn Val Pro Asn Asn Ser Ser Asp Leu Phe Gln Ala
         35                  40                  45

Gly Ser Asp Gly Val Leu Thr Gly Val Glu Gly Ile Ile Ile Tyr Thr
     50                  55                  60

Ile Asn Gly Glu Ile Glu Ile Thr Leu His Phe Asp Asn Pro Tyr Ala
 65                  70                  75                  80
```

-continued

Gly Ser Asn Lys Tyr Ser Gly Arg Ser Ser Asp Asp Asp Tyr Lys Val
85 90 95

Ile Thr Glu Ala Arg Ala Glu His Arg Ala Asn Asn His Asp His Val
100 105 110

Thr

<210> SEQ ID NO 153
<211> LENGTH: 353
<212> TYPE: DNA
<213> ORGANISM: Bacillus thuringiensis

<400> SEQUENCE: 153
atgtcagcac gcgaagtaga tattgaaata ataaatcata caggtcatac cttacaaatg 60
gataaaagaa ctagacttgc acatggtgaa tggattatta cacccgtgaa tgttccaaat 120
aattcttctg atttatttca agcaggttct gatggagttt tgacaggagt agaaggaata 180
ataatttata ctataaatgg agaaatagaa attaccttac attttgacaa tccttatgca 240
ggttctaata aatattctgg acgttctagt gatgatgatt ataaagttat aactgaagca 300
agagcagaac atagagctaa taatcatgat catgtgactt atacaattca aac 353

<210> SEQ ID NO 154
<211> LENGTH: 113
<212> TYPE: PRT
<213> ORGANISM: Bacillus thuringiensis

<400> SEQUENCE: 154

Met Ser Ala Arg Glu Val Asp Ile Glu Ile Ile Asn His Thr Gly His
1 5 10 15

Thr Leu Gln Met Asp Lys Arg Thr Arg Leu Ala His Gly Glu Trp Ile
20 25 30

Ile Thr Pro Val Asn Val Pro Asn Asn Ser Ser Asp Leu Phe Gln Ala
35 40 45

Gly Ser Asp Gly Val Leu Thr Gly Val Glu Gly Ile Ile Ile Tyr Thr
50 55 60

Ile Asn Gly Glu Ile Glu Ile Thr Leu His Phe Asp Asn Pro Tyr Ala
65 70 75 80

Gly Ser Asn Lys Tyr Ser Gly Arg Ser Ser Asp Asp Asp Tyr Lys Val
85 90 95

Ile Thr Glu Ala Arg Ala Glu His Arg Ala Asn Asn His Asp His Val
100 105 110

Thr

<210> SEQ ID NO 155
<211> LENGTH: 37
<212> TYPE: DNA
<213> ORGANISM: Artificial Sequence
<220> FEATURE:
<223> OTHER INFORMATION: Description of Artificial Sequence:
oligonucleotide primer

<400> SEQUENCE: 155
aaatattatt ttatgtcagc acgtgaagta cacattg 37

<210> SEQ ID NO 156
<211> LENGTH: 40
<212> TYPE: DNA
<213> ORGANISM: Artificial Sequence
<220> FEATURE:

<223> OTHER INFORMATION: Description of Artificial Sequence:
      oligonucleotide primer

<400> SEQUENCE: 156
tctctggtac cttattatga tttatgccca tatcgtgagg 40

<210> SEQ ID NO 157
<211> LENGTH: 45
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 157
agagaactag taaaaaggag ataaccatgt tagatactaa taaag 45

<210> SEQ ID NO 158
<211> LENGTH: 46
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 158
cgtgctgaca taaaataata tttttttaat ttttttagtg tacttt 46

<210> SEQ ID NO 159
<211> LENGTH: 506
<212> TYPE: PRT
<213> ORGANISM: Artificial Sequence
<220> FEATURE:
<223> OTHER INFORMATION: Description of Artificial Sequence: fusion
      protein

<400> SEQUENCE: 159

```
Met Leu Asp Thr Asn Lys Val Tyr Glu Ile Ser Asn His Ala Asn Gly
  1               5                  10                  15

Leu Tyr Ala Ala Thr Tyr Leu Ser Leu Asp Asp Ser Gly Val Ser Leu
             20                  25                  30

Met Asn Lys Asn Asp Asp Asp Ile Asp Asp Tyr Asn Leu Lys Trp Phe
         35                  40                  45

Leu Phe Pro Ile Asp Asp Asp Gln Tyr Ile Ile Thr Ser Tyr Ala Ala
     50                  55                  60

Asn Asn Cys Lys Val Trp Asn Val Asn Asn Asp Lys Ile Asn Val Ser
 65                  70                  75                  80

Thr Tyr Ser Ser Thr Asn Ser Ile Gln Lys Trp Gln Ile Lys Ala Asn
                 85                  90                  95

Gly Ser Ser Tyr Val Ile Gln Ser Asp Asn Gly Lys Val Leu Thr Ala
            100                 105                 110

Gly Thr Gly Gln Ala Leu Gly Leu Ile Arg Leu Thr Asp Glu Ser Ser
        115                 120                 125

Asn Asn Pro Asn Gln Gln Trp Asn Leu Thr Ser Val Gln Thr Ile Gln
    130                 135                 140

Leu Pro Gln Lys Pro Ile Ile Asp Thr Lys Leu Lys Asp Tyr Pro Lys
145                 150                 155                 160

Tyr Ser Pro Thr Gly Asn Ile Asp Asn Gly Thr Ser Pro Gln Leu Met
                165                 170                 175

Gly Trp Thr Leu Val Pro Cys Ile Met Val Asn Asp Pro Asn Ile Asp
            180                 185                 190
```

-continued

Lys Asn Thr Gln Ile Lys Thr Thr Pro Tyr Tyr Ile Leu Lys Lys Tyr
195 200 205

Gln Tyr Trp Gln Arg Ala Val Gly Ser Asn Val Ala Leu Arg Pro His
210 215 220

Glu Lys Lys Ser Tyr Thr Tyr Glu Trp Gly Thr Glu Ile Asp Gln Lys
225 230 235 240

Thr Thr Ile Ile Asn Thr Leu Gly Phe Gln Ile Asn Ile Asp Ser Gly
245 250 255

Met Lys Phe Asp Ile Pro Glu Val Gly Gly Gly Thr Asp Glu Ile Lys
260 265 270

Thr Gln Leu Asn Glu Glu Leu Lys Ile Glu Tyr Ser His Glu Thr Lys
275 280 285

Ile Met Glu Lys Tyr Gln Glu Gln Ser Glu Ile Asp Asn Pro Thr Asp
290 295 300

Gln Ser Met Asn Ser Ile Gly Phe Leu Thr Ile Thr Ser Leu Glu Leu
305 310 315 320

Tyr Arg Tyr Asn Gly Ser Glu Ile Arg Ile Met Gln Ile Gln Thr Ser
325 330 335

Asp Asn Asp Thr Tyr Asn Val Thr Ser Tyr Pro Asn His Gln Gln Ala
340 345 350

Leu Leu Leu Leu Thr Asn His Ser Tyr Glu Glu Val Glu Glu Ile Thr
355 360 365

Asn Ile Pro Lys Ser Thr Leu Lys Lys Leu Lys Lys Tyr Tyr Phe Met
370 375 380

Ser Ala Arg Glu Val His Ile Asp Val Asn Asn Lys Thr Gly His Thr
385 390 395 400

Leu Gln Leu Glu Asp Lys Thr Lys Leu Asp Gly Gly Arg Trp Arg Thr
405 410 415

Ser Pro Thr Asn Val Ala Asn Asp Gln Ile Lys Thr Phe Val Ala Glu
420 425 430

Ser Asn Gly Phe Met Thr Gly Thr Glu Gly Thr Ile Tyr Tyr Ser Ile
435 440 445

Asn Gly Glu Ala Glu Ile Ser Leu Tyr Phe Asp Asn Pro Phe Ala Gly
450 455 460

Ser Asn Lys Tyr Asp Gly His Ser Asn Lys Ser Gln Tyr Glu Ile Ile
465 470 475 480

Thr Gln Gly Gly Ser Gly Asn Gln Ser His Val Thr Tyr Thr Ile Gln
485 490 495

Thr Thr Ser Ser Arg Tyr Gly His Lys Ser
500 505

<210> SEQ ID NO 160
<211> LENGTH: 1521
<212> TYPE: DNA
<213> ORGANISM: Artificial Sequence
<220> FEATURE:
<223> OTHER INFORMATION: Description of Artificial Sequence: fusion gene

<400> SEQUENCE: 160
atgttagata ctaataaagt ttatgaaata agcaatcatg ctaatggact atatgcagca 60
acttatttaa gtttagatga ttcaggtgtt agtttaatga ataaaaatga tgatgatatt 120
gatgattata acttaaaatg gtttttattt cctattgatg atgatcaata tattattaca 180
agctatgcag caaataattg taaagtttgg aatgttaata atgataaaat aaatgtttcg 240

-continued

```
acttattctt caacaaattc aatacaaaaa tggcaaataa aagctaatgg ttcttcatat    300

gtaatacaaa gtgataatgg aaaagtctta acagcaggaa ccggtcaagc tcttggattg    360

atacgtttaa ctgatgaatc ctcaaataat cccaatcaac aatggaattt aacttctgta    420

caaacaattc aacttccaca aaaacctata atagatacaa aattaaaaga ttatcccaaa    480

tattcaccaa ctggaaatat agataatgga acatctcctc aattaatggg atggacatta    540

gtaccttgta ttatggtaaa tgatccaaat atagataaaa atactcaaat taaaactact    600

ccatattata ttttaaaaaa atatcaatat tggcaacgag cagtaggaag taatgtagct    660

ttacgtccac atgaaaaaaa atcatatact tatgaatggg gcacagaaat agatcaaaaa    720

acaacaatta taaatacatt aggatttcaa atcaatatag attcaggaat gaaatttgat    780

ataccagaag taggtggagg tacagatgaa ataaaaacac aactaaatga agaattaaaa    840

atagaatata gtcatgaaac taaaataatg gaaaaatatc aagaacaatc tgaaatagat    900

aatccaactg atcaatcaat gaattctata ggatttctta ctattacttc cttagaatta    960

tatagatata atggctcaga aattcgtata atgcaaattc aaacctcaga taatgatact   1020

tataatgtta cttcttatcc aaatcatcaa caagctttat tacttcttac aaatcattca   1080

tatgaagaag tagaagaaat aacaaatatt cctaaaagta cactaaaaaa attaaaaaaa   1140

tattatttta tgtcagcacg tgaagtacac attgatgtaa ataataagac aggtcataca   1200

ttacaattag aagataaaac aaaacttgat ggtggtagat ggcgaacatc acctacaaat   1260

gttgctaatg atcaaattaa aacatttgta gcagaatcaa atggttttat gacaggtaca   1320

gaaggtacta tatattatag tataaatgga gaagcagaaa ttagtttata ttttgacaat   1380

ccttttgcag gttctaataa atatgatgga cattccaata aatctcaata tgaaattatt   1440

acccaaggag gatcaggaaa tcaatctcat gttacgtata ctattcaaac cacatcctca   1500

cgatatgggc ataaatcata a                                             1521


<210> SEQ ID NO 161
<211> LENGTH: 23
<212> TYPE: DNA
<213> ORGANISM: Artificial Sequence
<220> FEATURE:
<223> OTHER INFORMATION: Description of Artificial Sequence:  primer
      45kD5'

<400> SEQUENCE: 161

gatratratc aatatattat tac                                             23


<210> SEQ ID NO 162
<211> LENGTH: 20
<212> TYPE: DNA
<213> ORGANISM: Artificial Sequence
<220> FEATURE:
<223> OTHER INFORMATION: Description of Artificial Sequence:  primer
      45kD3'rc

<400> SEQUENCE: 162

caaggtarta atgtccatcc                                                 20


<210> SEQ ID NO 163
<211> LENGTH: 24
<212> TYPE: DNA
<213> ORGANISM: Artificial Sequence
<220> FEATURE:
<223> OTHER INFORMATION: Description of Artificial Sequence:  primer
      45kD5'01
```

-continued

```
<400> SEQUENCE: 163

gatgatgrtm rakwwattat trca                                   24


<210> SEQ ID NO 164
<211> LENGTH: 24
<212> TYPE: DNA
<213> ORGANISM: Artificial Sequence
<220> FEATURE:
<223> OTHER INFORMATION: Description of Artificial Sequence:  primer
      45kD5'02

<400> SEQUENCE: 164

gatgatgrtm ratatattat trca                                   24


<210> SEQ ID NO 165
<211> LENGTH: 23
<212> TYPE: DNA
<213> ORGANISM: Artificial Sequence
<220> FEATURE:
<223> OTHER INFORMATION: Description of Artificial Sequence:  primer
      45kD3'03

<400> SEQUENCE: 165

ggawgkrcdy twdtmccwtg tat                                    23


<210> SEQ ID NO 166
<211> LENGTH: 23
<212> TYPE: DNA
<213> ORGANISM: Artificial Sequence
<220> FEATURE:
<223> OTHER INFORMATION: Description of Artificial Sequence:  primer
      45kD3'04

<400> SEQUENCE: 166

ggawgkacry tadtaccttg tat                                    23
```